(12) United States Patent
Dutta et al.

(10) Patent No.: US 11,347,965 B2
(45) Date of Patent: May 31, 2022

(54) TRAINING DATA GENERATION FOR ARTIFICIAL INTELLIGENCE-BASED SEQUENCING

(71) Applicant: Illumina, Inc., San Diego, CA (US)

(72) Inventors: Anindita Dutta, San Francisco, CA (US); Dorna Kashefhaghighi, Menlo Park, CA (US); Amirali Kia, San Mateo, CA (US)

(73) Assignee: Illumina, Inc., San Diego, CA (US)

( * ) Notice: Subject to any disclaimer, the term of this patent is extended or adjusted under 35 U.S.C. 154(b) by 78 days.

(21) Appl. No.: 16/825,987

(22) Filed: Mar. 20, 2020

(65) Prior Publication Data

US 2020/0302225 A1   Sep. 24, 2020

Related U.S. Application Data

(60) Provisional application No. 62/821,602, filed on Mar. 21, 2019, provisional application No. 62/821,618, (Continued)

(51) Int. Cl.
*G06K 9/62*  (2022.01)
*G06N 3/08*  (2006.01)
(Continued)

(52) U.S. Cl.
CPC ......... *G06K 9/6218* (2013.01); *G06F 16/907* (2019.01); *G06K 9/628* (2013.01);
(Continued)

(58) Field of Classification Search
CPC .. G06K 9/6218; G06K 9/6262; G06K 9/6277; G06K 9/628; G06K 9/6222;
(Continued)

(56) References Cited

U.S. PATENT DOCUMENTS 8,182,993 B2  5/2012  Tomaney et al.
8,241,573 B2  8/2012  Banerjee et al.
(Continued)

FOREIGN PATENT DOCUMENTS

CA  2894317 A1  12/2016
EP  3130681 A1   2/2017
(Continued)

OTHER PUBLICATIONS

Lutteropp, Error-Profile-Aware Correction of Next Generation Sequencing Reads, Karlsruhe Institute of Technology, dated Mar. 31, 2017, 96 pages.

(Continued)

*Primary Examiner* — Juan A Torres
(74) *Attorney, Agent, or Firm* — Haynes Beffel & Wolfeld, LLP; Ernest J. Beffel, Jr.

(57) ABSTRACT

The technology disclosed relates to generating ground truth training data to train a neural network-based template generator for cluster metadata determination task. In particular, it relates to accessing sequencing images, obtaining, from a base caller, a base call classifying each subpixel in the sequencing images as one of four bases (A, C, T, and G), generating a cluster map that identifies clusters as disjointed regions of contiguous subpixels which share a substantially matching base call sequence, determining cluster metadata based on the disjointed regions in the cluster map, and using the cluster metadata to generate the ground truth training data for training the neural network-based template generator for the cluster metadata determination task.

14 Claims, 88 Drawing Sheets
(69 of 88 Drawing Sheet(s) Filed in Color)

Related U.S. Application Data filed on Mar. 21, 2019, provisional application No. 62/821,681, filed on Mar. 21, 2019, provisional application No. 62/821,724, filed on Mar. 21, 2019, provisional application No. 62/821,766, filed on Mar. 21, 2019.

(51) Int. Cl.

| G16B 40/00 | (2019.01) |
|---|---|
| G06N 3/04 | (2006.01) |
| G06F 16/907 | (2019.01) |
| G06N 7/00 | (2006.01) |
| G06V 10/75 | (2022.01) |
| G06N 5/04 | (2006.01) |

(52) U.S. Cl.
CPC ......... *G06K 9/6222* (2013.01); *G06K 9/6232* (2013.01); *G06K 9/6256* (2013.01); *G06K 9/6262* (2013.01); *G06K 9/6267* (2013.01); *G06K 9/6277* (2013.01); *G06N 3/04* (2013.01); *G06N 3/08* (2013.01); *G06N 3/084* (2013.01); *G06N 7/005* (2013.01); *G06V 10/751* (2022.01); *G16B 40/00* (2019.02); *G06N 5/046* (2013.01)

(58) Field of Classification Search
CPC .. G06K 9/6232; G06K 9/6202; G06K 9/6256; G06K 9/6267; G06K 9/4628; G06K 9/036; G06K 9/6263; G06K 9/6272; G06N 3/084; G06N 7/005; G06N 3/04; G06N 3/08; G06N 5/046; G06N 3/0445; G06N 3/0454; G06F 16/907; G06F 16/58; G16B 40/00; G16B 30/20; G16B 40/20
USPC ......................................................... 382/225
See application file for complete search history.

(56) References Cited

U.S. PATENT DOCUMENTS

| 8,392,126 | B2 | 3/2013 | Mann |
|---|---|---|---|
| 8,401,258 | B2 | 3/2013 | Hargrove et al. |
| 8,594,439 | B2 | 11/2013 | Staelin et al. |
| 8,725,425 | B2 | 5/2014 | Heiner et al. |
| 8,795,971 | B2 | 8/2014 | Kersey et al. |
| 8,965,076 | B2 | 2/2015 | Garcia et al. |
| 9,708,656 | B2 | 7/2017 | Turner et al. |
| 10,023,911 | B2 | 7/2018 | Tomaney et al. |
| 10,068,054 | B2 | 9/2018 | Van Rooyen et al. |
| 10,241,075 | B2 | 3/2019 | Davey et al. |
| 10,423,861 | B2 | 9/2019 | Gao et al. |
| 10,540,591 | B2 | 1/2020 | Gao et al. |
| 10,648,027 | B2 | 5/2020 | Mannion et al. |
| 10,711,299 | B2 | 7/2020 | Rothberg et al. |
| 10,963,673 | B2 | 3/2021 | Schaumberg et al. |
| 2006/0064248 | A1 | 3/2006 | Saidi et al. |
| 2006/0269130 | A1 | 11/2006 | Maroy et al. |
| 2009/0081775 | A1 | 3/2009 | Hodneland et al. |
| 2010/0046830 | A1 | 2/2010 | Wang et al. |
| 2010/0111370 | A1 | 5/2010 | Black et al. |
| 2010/0157086 | A1 | 6/2010 | Segale et al. |
| 2011/0286628 | A1 | 11/2011 | Goncalves et al. |
| 2012/0020537 | A1 | 1/2012 | Garcia et al. |
| 2013/0079232 | A1 | 3/2013 | Kain et al. |
| 2013/0124100 | A1* | 5/2013 | Drmanac ............. C12Q 1/6869 702/20 |
| 2013/0188866 | A1 | 7/2013 | Obrador et al. |
| 2013/0250407 | A1 | 9/2013 | Schaffer et al. |
| 2015/0079596 | A1 | 3/2015 | Eltoukhy et al. |
| 2015/0117784 | A1 | 4/2015 | Lin et al. |
| 2015/0169824 | A1 | 6/2015 | Kermani et al. |
| 2016/0042511 | A1 | 2/2016 | Chukka et al. |
| 2016/0078272 | A1 | 3/2016 | Hammoud |
| 2016/0110498 | A1 | 4/2016 | Bruand et al. |
| 2016/0196479 | A1 | 7/2016 | Chertok et al. |
| 2016/0356715 | A1 | 12/2016 | Zhong et al. |
| 2016/0357903 | A1 | 12/2016 | Shendure et al. |
| 2016/0371431 | A1 | 12/2016 | Haque et al. |
| 2017/0169313 | A1 | 6/2017 | Choi et al. |
| 2017/0249421 | A1 | 8/2017 | Eberle et al. |
| 2017/0249744 | A1 | 8/2017 | Wang et al. |
| 2018/0075279 | A1 | 3/2018 | Gertych et al. |
| 2018/0107927 | A1 | 4/2018 | Frey |
| 2018/0114337 | A1 | 4/2018 | Li et al. |
| 2018/0189613 | A1 | 7/2018 | Wolf et al. |
| 2018/0195953 | A1 | 7/2018 | Langlois et al. |
| 2018/0201992 | A1 | 7/2018 | Wu et al. |
| 2018/0211001 | A1* | 7/2018 | Gopalan ................ G16B 40/00 |
| 2018/0274023 | A1 | 9/2018 | Belitz et al. |
| 2018/0305751 | A1 | 10/2018 | Vermaas et al. |
| 2018/0322327 | A1 | 11/2018 | Smith et al. |
| 2018/0330824 | A1 | 11/2018 | Athey |
| 2018/0334711 | A1 | 11/2018 | Kelley et al. |
| 2018/0334712 | A1 | 11/2018 | Singer et al. |
| 2018/0340234 | A1* | 11/2018 | Scafe ..................... G16B 30/10 |
| 2019/0080450 | A1 | 3/2019 | Arar et al. |
| 2019/0107642 | A1 | 4/2019 | Farhadi Nia et al. |
| 2019/0114544 | A1 | 4/2019 | Sundaram et al. |
| 2019/0156915 | A1 | 5/2019 | Zhang et al. |
| 2019/0164010 | A1 | 5/2019 | Ma et al. |
| 2019/0170680 | A1 | 6/2019 | Sikora et al. |
| 2019/0213473 | A1 | 7/2019 | Dutta et al. |
| 2019/0237160 | A1 | 8/2019 | Rothberg et al. |
| 2019/0237163 | A1 | 8/2019 | Wang et al. |
| 2019/0272638 | A1 | 9/2019 | Mouton et al. |
| 2019/0332118 | A1 | 10/2019 | Wang et al. |
| 2019/0392578 | A1 | 12/2019 | Chukka et al. |
| 2020/0027002 | A1 | 1/2020 | Hickson et al. |
| 2020/0057838 | A1* | 2/2020 | Yekhanin .............. G06F 40/166 |
| 2020/0065675 | A1 | 2/2020 | Sundaram et al. |
| 2020/0176082 | A1 | 6/2020 | Massingham |
| 2020/0302603 | A1 | 9/2020 | Barnes et al. |
| 2020/0320294 | A1 | 10/2020 | Mangal et al. |
| 2020/0388029 | A1 | 12/2020 | Saltz et al. |
| 2021/0027462 | A1 | 1/2021 | Bredno et al. |
| 2021/0056287 | A1 | 2/2021 | Schaumburg et al. |
| 2021/0072391 | A1 | 3/2021 | Li et al. |
| 2021/0089827 | A1 | 3/2021 | Kumagai et al. |

FOREIGN PATENT DOCUMENTS

| EP | 3373238 A1 | 9/2018 |
|---|---|---|
| JP | 2007199397 A | 8/2007 |
| WO | 2008154317 A1 | 12/2008 |
| WO | 2014142921 A1 | 9/2014 |
| WO | 2015084985 A2 | 6/2015 |
| WO | 2016145516 A1 | 9/2016 |
| WO | 2016201564 A1 | 12/2016 |
| WO | 2017184997 A1 | 10/2017 |
| WO | 2018129314 A1 | 7/2018 |
| WO | 2018165099 A1 | 9/2018 |
| WO | 2018203084 A1 | 11/2018 |
| WO | 2019027767 A1 | 2/2019 |
| WO | 2019028047 A1 | 2/2019 |
| WO | 2019055856 A1 | 3/2019 |
| WO | 2019079182 A1 | 4/2019 |
| WO | 2019079202 A1 | 4/2019 |
| WO | 2019090251 A2 | 5/2019 |
| WO | 2019136284 A1 | 7/2019 |
| WO | 2019136388 A1 | 7/2019 |
| WO | 2019140402 A1 | 7/2019 |
| WO | 2019147904 A1 | 8/2019 |
| WO | 2020014280 A1 | 1/2020 |
| WO | 2020123552 A1 | 6/2020 |

OTHER PUBLICATIONS

Illumina, HCS 1.4/RTA 1.12 Theory of Operation, 2010, 32 pages.
Cacho, Base-Calling of High-throughput Sequencing Data Using a Random Effects Mixture Model, UC Riverside, Dec. 2016, 102 pages.

(56) References Cited

OTHER PUBLICATIONS

Zhou et. al., Incorporating Side-Channel Information into Convolutional Neural Networks for Robotic Tasks, 2017, 7 pages.
Linder, Modeling the intronic regulation of Alternative Splicing using Deep Convolutional Neural Nets, KTH Institute of Technology, dated Jun. 14, 2015, 53 pages.
Bentley et. al., Accurate Whole Human Genome Sequencing using Reversible Terminator Chemistry, Nature, Nov. 2008, 21 pages.
Illumina, Calculating Percent Passing Filter for Patterned and Nonpatterned Flow Cells, 2017, 2 pages.
Fritzilas, An Overview of Illumina's Sequencing Technology and its Applications, University of Primorska, dated Mar. 4, 2011, 47 pages.
Python Implementation of the color map function for the Pascal VOC data set, Github, 4 pages, retrieved on Jul. 23, 2021. Retrieved from [URL: https://gist.github.com/wllhf/a4533e0adebe57e3ed06d4b50c8419ae ].
Illumina, Quality Score Encoding, 2 pages, retrieved on Jul. 23, 2021. Retrieved from [URL: https://support.illumina.com/help/BaseSpace_OLH_009008/Content/Source/Informatics/BS/QualityScoreEncoding_swBS.htm ].
Illumina, Reducing Whole-Genome Data Storage Footprint, Illumina Whitepaper, 2010-2014, 4 pages.
Badrinarayanan et. al., SegNet: A Deep Convolutional Encoder-Decoder Architecture for Image Segmentation, dated Oct. 10, 2016, 14 pages.
Li et. al., CS231 Lecture 13 Segmentation and Attention, Stanford University, dated Feb. 24, 2016, 133 pages.
Whiteford et. al., Swift: Primary data analysis for the Illumina Solexa sequencing platform, Bioinformatics, vol. 25, No. 17, 2009, pp. 2194-2199, 7 pages.
Schilling, The Effect of Batch Normalization on Deep Convolutional Neural Networks, KTH Royal Institute of Technology, 2016, 113 pages.
Tutorial Image Segmentation, BoofCV, 6 pages, retrieved on Jul. 23, 2021. Retrieved from [URL: https://boofcv.org/index.php?title=Tutorial_Image_Segmentation ].
Illumina, Understanding Illumina Quality Scores, dated Apr. 23, 2014, 2 pages.
Yue et. al., Deep Learning for Genomics: A Concise Overview, dated May 8, 2018, 40 pages.
Zhang et. al., Estimating Phred scores of Illumina base calls by logistic regression and sparse modeling, Bio Med Central Bioinformatics, 2017, 14 pages.
Renaud et. al., freelbis: an efficient base caller with calibrated quality scores for Illumina sequencers, dated Mar. 6, 2013, 2 pages.
Kircher, Improving data quality of the Illumina Genome Analyzer platform, Max Planck Institute for Evolutionary Anthropology, dated Oct. 24, 2009, 46 pages.
Mitra et. al., Strategies for Achieving High Sequencing Accuracy for Low Diversity Samples and Avoiding Sample Bleeding Using Illumina Platform, PLOS One, published Apr. 10, 2015, 21 pages.
Datta et. al., Statistical Analyses of Next Generation Sequence Data: A Partial Overview, Journal of Proteomics and Bioinformatics, vol. 3, Issue 6, 2010, 8 pages.
Erlich et. al., Alta-Cyclic: a self-optimizing base-caller for next generation sequencing, Nature Methods, Aug. 2008, 7 pages.
Kao et. al., Algorithms for Next-Generation High-Throughput Sequencing Technologies, University of California, Berkeley, 2011, 106 pages.
Kircher et. al., Addressing challenges in the production and analysis of Illumina sequencing data, published Jul. 29, 2011, retrieved on Jul. 24, 2021, 25 pages. Retrieved from [URL: https://www.ncbi.nlm.nih.gov/pmc/articles/PMC3163567/ ].
Teng et. al., Chiron: translating nanopore raw signal directly into nucleotide sequence using deep learning, GigaScience, 7, 2018, 9 pages.
Ratkovic, Deep Learning Model for Base Calling of MinION Nanopore Reads, dated Jun. 2017, 48 pages.
Teng et. al., Chiron: translating nanopore raw signal directly into nucleotide sequence using deep learning, dated Aug. 23, 2017, 10 pages.
Stoiber et. al., BasecRAWller: Streaming Nanopore Basecalling Directly from Raw Signal, dated May 1, 2017, 15 pages.
Li et. al., DeepSimulator: a deep simulator for Nanopore sequencing, Bioinformatics 34(17), 2018, pp. 2899-2908, 10 pages.
Wick et. al., Performance of neural network basecalling tools for Oxford Nanopore sequencing, dated Feb. 7, 2019, 14 pages.
Ledergerber et. al., Base-calling for next-generation sequencing platforms, Briefings in Bioinformatics vol. 12, No. 5, pp. 489-497, dated Jan. 18, 2011, 9 pages.
Sheikh et. al., Chapter 5 Base-Calling for Bioinformaticians, 2012, 17 pages.
Kriseman et. al., BING: Biomedical informatics pipeline for Next Generation Sequencing, Journal of Biomedical Informatics, vol. 43, 2010, pp. 428-434, 7 pages.
Das et. al., Model-based sequential base calling for Illumina sequencing, IEEE, 2010, 4 pages.
Shamaiah et. al., Base calling error rates in next-generation DNA sequencing, IEEE Statistical Signal Processing Workshop, 2012, 4 pages.
Ye et. al., BlindCall: ultra-fast base-calling of high-throughput sequencing data by blind deconvolution, Bioinformatics, vol. 30, No. 9, 2014, pp. 1214-1219, 6 pages.
Wolowski, High-quality, high-throughput measurement of protein-DNA binding using HiTS-FLIP, Ludwig Maxmilian University, 2016, 251 pages.
Bravo et. al., Model-Based Quality Assessment and Base-Calling for Second-Generation Sequencing Data, Biometrics, 2009, 10 pages.
Illumina, RTA Theory of Operation, 2009, 8 pages.
Dash et. al., Artificial Intelligence and Evolutionary Computations in Engineering Systems, Advances in Intelligent Systems and Computing, vol. 1056, Springer 2020, 781 pages.
Ahmed, Signet: A Neural Network Architecture for Predicting Protein-Protein Interactions, The University of Western Ontario, dated May 7, 2017, 84 pages.
Deepa J, Development of Fully Automated Image Analysis Method for High Density cDNA and array CGH Microarray based genomic studies, Cochin University of Science and Technology, Mar. 2013, 232 pages.
Zhang et. al., Nanopore basecalling from a perspective of instance segmentation, BMC Bioinformatics, 2020, 9 pages.
Kao et. al., naiveBayesCall: An Efficient Model-Based Base-Calling Algorithm for High-Throughput Sequencing, Journal of Computational Biology, dated Mar. 2011, 16 pages.
Wick et. al., Performance of neural network basecalling tools for Oxford Nanopore sequencing, Genome Biology, 2019, 10 pages.
Angermueller, Christof, et. al., "Deep learning for computational biology", Jun. 6, 2016, 16 pages.
PCT/US2021/018258 International Search Report and Written Opinion, dated May 26, 2021, 17 pages.
Smith et. al., Barcoding and demultiplexing Oxford nanopore native RNA sequencing reads with deep residual learning, bioRxiv, dated Dec. 5, 2019, 18 pages.
PCT/US2021/018910 Partial Search Report and Invitation to pay fee, dated May 31, 2021, 14 pages.
PCT/US2021/018422 International Search Report and Written Opinion, dated Jun. 10, 2021, 12 pages.
Aggarwal, Neural Networks and Deep Learning: A Textbook, Springer, dated Aug. 26, 2018, 512 pages.
Wang et. al., Deep Neural Netwotk Approximation for Custom Hardware: Where We've Been, Where We're Going, Cornell University, dated Jan. 21, 2019, 37 pages.
Lavin et. al., Fast Algorithms for Convolutional Neural Networks, dated Nov. 10, 2015, 9 pages.
Liu et. al., A Uniform Architecture Design for Accelerating 2D and 3D CNNs on FPGAs, published Jan. 7, 2019, 19 pages.
PCT/US2021/018427 International Search Report and Written Opinion, dated Jun. 1, 2021, 15 pages.
PCT/US2021/018913 International Search Report and Written Opinion, dated Jun. 10, 2021, 11 pages.

(56) References Cited

OTHER PUBLICATIONS

Zeng et. al., Causalcall: Nanopore Basecalling Using a Temporal Convolutional Network, dated Jan. 20, 2020, 11 pages.
PCT/US2021/018915 International Search Report and Written Opinion, dated Jun. 15, 2021, 13 pages.
Kwon et. al., Understanding Reuse, Performance, and Hardware Cost of DNN Dataflow—A Data-Centric Approach, Proceedings of the 52nd Annual IEEE/ACM International Symposium on Microarchitecture, dated Oct. 12, 2019, 13 pages.
Sze et. al., Efficient Processing of Deep Neural Networks: A Tutorial and Survey, Cornell University Library, dated Mar. 27, 2017, 21 pages.
Sundaram, L. et. al., "Predicitng the clinical impact of human mutation with deep neural networks", Nat. Genet. 50, 1161-1170 (2018).
Jaganathan, K. et. al., "Predicting splicing from primary sequence with deep learning", Cell 176, 535-548, (2019).
Kircher, Martin, et al. "A general framework for estimating the relative pathogenicity of human genetic variants." Nature genetics 46.3 (2014): 310. (Year:2014).
Henikoff, S. & Henikoff, J. G. Amino acid substitution matrices from protein blocks. Proc. Natl. Acad. Sci. USA 89, 10915-10919 (1992).
Li, W. H., Wu, C. I. & Luo, C. C. Nonrandomness of point mutation as reflected in nucleotide substitutions in pseudogenes and its evolutionary implications. J. Molec. Evol. 21, 58-71 (1984).
Grantham, R. Amino acid difference formula to help explain protein evolution. Science 185, 862-864 (1974).
LeCun, Y., Botlou, L., Bengio, Y., & Haffner, P. Gradient based learning applied to document recognition. Proc. IEEE 86, 2278-2324 (1998).
Vissers, L. E., Gilissen, C., & Veltman, J. A. Genetic studies in intellectual disability and related disorders. Nat. Rev. Genet. 17, 9-18 (2016).
Neale, B. M. et al. Patterns and rates of exonicde novo mutations in autism spectrum disorders. Nature 485, 242-245 (2012).
Sanders, S. J. et al. De novo mutations revealed by whole-exome sequencing are strongly associated with autism. Nature 485, 237-241 (2012).
De Rubeis, S. et al. Synaptic, transcriptional and chromatin genes disrupted in autism. Nature 515, 209-215 (2014).
Deciphering Developmental Disorders Study. Large-scale discovery of novel genetic causes of developmental disorders. Nature 519, 223-228 (2015).
Deciphering Developmental Disorders Study. Prevalence and architecture of de novo mutations in developmental disorders. Nature 542, 433-438 (2017).
Iossifov, I. et al. The contribution of de novo coding mutations to autism spectrum disorder. Nature 515, 216-221 (2014).
Zhu, X. Need, A. C., Petrovski, S. & Goldstein, D. B. One gene, many neuropsychiatric disorders: lessons from Mendelian diseases. Nat. Neurosci. 17, 773-781, (2014).
Leffler, E. M. et al. Revisiting an old riddle: what determines genetic diversity levels within species? PLoS Biol. 10, e1001388 (2012), 9pages.
Estrada, A. et al. Impending extinction crisis of the world's primates—why primates matter. Sc. Adv. 3, e1600946 (2017), 17 pages.
Kent, W. J. et al. The human genome browser at UCSC. Genome Res. 12, 996-1006 (2002).
Tyner, C. et al. The UCSC Genome Browser database—2017 update. Nucleic Acids Res. 45, D626-D634 (2017).
Kabsch, W., & Sander, C. Dictionary of protein secondary structure-pattern recognition of hydrogen-bonded and geometrical features. Biopolymers 22, 2577-2637 (1983).
Joosten, R. P. et al. A series of PDB related databases for everyday needs. Nucleic Acids Res. 39, 411-419 (2011).
He, K, Zhang, X., Ren, S., & Sun, J. Identity mappings in deep residual networks, in 14th European Conference on Computer Vision—ECCV 2016. ECCV 2016. Lecture Notes in Computer Science, vol. 9908; 630 6,15 (Springer, Cham, Switzerland; 2016).

Ionita-Laza, I., McCallum, K., Xu, B., & Buxbaum, J. D. A spectral approach integrating functional genomic annotations for coding and noncoding variants. Nat. Genet. 48, 214-220 (2016).
Li, B. et al. Automated inference of molecular mechanisms of disease from amino acid substitutions. Bioinformatics 25, 2744-2750 (2009).
Lu, Q. et al. A statistical framework to predict functional non-coding regions in the human genome through integrated analysis of annotation data. Sci. Rep. 5, 10576 (2015), 13pgs.
Shihab, H. A. et al. Predicting the functional, molecular, and phenotypic consequences of amino acid substitutions using hidden Markov models. Human. Mutat. 34, 57-65 (2013).
Davydov, E. V. et al. Identifying a high fraction of the human genome to be under selective constraint using GERP++. PLoS Comput. Biol. 6, Dec. 2, 2010, 13 pages.
Liu, X., Wu, C., Li, C., & Boerwinkle, E. dbNSFPv3.0 a one-stop database of functional predictions and annotations for human nonsynonymous and splice-site SNVs. Human. Mutat. 37, 235-241 (2016).
Jain, S., White, M., Radivojac, P. Recovering true classifier performance in positive-unlabeled learning. in Proceedings Thirty-First AAAI Conference on Artificial Intelligence. 2066-2072 (AAAI Press, San Francisco; 2017).
de Ligt, J. et al. Diagnostic exome sequencing in persons with severe intellectual disability. N. Engl. J. Med. 367, 1921-1929 (2012).
Iossifov, I. et al. De novo gene disruptions in children on the autistic spectrum. Neuron 74, 285-299 (2012).
O'Roak, B. J. et al. Sporadic autism exomes reveal a highly interconnected protein network of de novo mutations. Nature 485, 246-250 (2012).
Rauch, A. et al. Range of genetic mutations associated with severe non-syndromic sporadic intellectual disability—an exome sequencing study. Lancet 380, 1674-1682 (2012).
Epi, K. C. et al. De novo mutations in epileptic encephalopathies. Nature 501, 217-221 (2013).
EuroEpinomics-Res Consortium, Epilepsy Phenome/Genome Project, Epi4K Consortium. De novo mutations in synaptic transmission genes including DNM1 cause epileptic encephalopathies. Am. J. Hum. Genet. 95, 360-370 (2014).
Baek et. al., LncRNAnet: long non-coding RNA identification using deep learning, Bioinformatics, vol. 34 (22), 2018, pp. 3889-3897, 9 pages.
Evans et. al., Estimating Change-Points in Biological Sequences via the Cross-Entropy Method, dated Sep. 20, 2010, 17 pages.
Shen et. al., ParticleCall: A particle filter for base calling in next-generation sequencing systems, BMC Bioinformatics, 2012, 10 pages.
Peresini et. al., Nanopore Base Calling on the Edge, dated Nov. 9, 2020, 15 pages.
Liang et. al., Bayesian Basecalling for DNA Sequence Analysis Using Hidden Markov Models, IEEE Transactions on Computational Biology and Bioinformatics, vol. 4, No. 3, Jul.-Sep. 2007, 11 pages.
Wang et. al., DeepDNA: a hybrid convolutional and recurrent neural network for compressing human mitochondrial genomes, IEEE International Conference on Bioinformatics and Biomedicine, 2018, 5 pages.
PCT/US2020/024092, International Preliminary Report on Patentability (IPRP), dated Jun. 30, 2021, 30 pages.
PCT/US2020/024091 International Preliminary Report and Patentability (IPRP), dated Jun. 30, 2021, 32 pages.
PCT/US2020/024088 International Preliminary Report on Patentability (IPRP), dated Jun. 30, 2021, 35 pages.
PCT/US2020/024087 International Preliminary Report on Patentability (IPRP), dated Jun. 30, 2021, 26 pages.
PCT/US2021/018917 Internation Search Report and Written Opinion, dated Jul. 1, 2021, 15 pages.
Anonymous, Vanishing Gradient Problem, Wikipedia, dated Jun. 16, 2018, retrieved on Jan. 12, 2020. Retrieved from [URL: https://en.wikipedia.org/w/index.php?title=Vanishing_gradient_problem&oldid=846115335 ].

(56) References Cited

OTHER PUBLICATIONS

PCT/US2020/033281, Second Article 34 Amendment Letter in response to Second Written Opinion, dated Jul. 10, 2021, 4 pages.
NL 2023310 NL Search Report, dated Mar. 5, 2020, 17 pages.
NL 2023311 NL Search Report, dated Mar. 24, 2020, 15 pages.
NL 2023312, NL Search Report, dated Mar. 24, 2020, 22 pages.
NL 2023317, NL Search Report, dated Mar. 24, 2020, 16 pages.
NL 2023316, NL Search Report, dated Mar. 23, 2020, 15 pages.
MX/a/2020/014288 First Office Action, dated Mar. 10, 2021, 2 pages.
MX/a/2020/014288 Response to First Office Action, dated May 5, 2021, 390 pages.
Despois, Julien, "Memorizing is not learning!—6 tricks to prevent overfitting in machine learning", Mar. 20, 2018, 17 pages.
Bhande, Anup What is underfitting and overfitting in machine learning and how to deal with it, Mar. 11, 2018, 10pages.
PCT/US2019031621—International Search Report and Written Opinion dated Aug. 7, 2019, 17 pages.
Carter et al., "Cancer-specific high-throughput annotation of somatic mutations—computational prediction of driver missense mutations," Cancer research 69, No. 16 (2009) pp. 6660-6667.
Min, et. al., "Deep Learning in Bioinformatics", Jun. 19, 2016, 46pgs.
Jiminez et. al., DeepSite—protein binding site predictor using 3D CNNs, dated Oct. 1, 2017, 7 pages.
Pu et. al., "DeepDrug3D: Classification of ligand-binding pockets in proteins with a convolutional neural network", dated Feb. 4, 2019, 23 pages.
Adam, "Deep learning, 3D technology to improve structure modeling for protein interactions, create better drugs", dated Jan. 9, 2020, 4 pages.
Varela, "Ligvoxel: A Deep Learning Pharmacore-Field Predictor", dated Mar. 19, 2019, 5 pages.
Li et. al., "Predicting changes in protein thermostability upon mutation with deep 3D convolutional neural networks", dated Feb. 28, 2020, 21 pages.
Raschka et. al., "Machine Learning and AI-based approaches for bioactive ligand discovery and GPCR-ligand recognition", dated Jun. 6, 2020, 33 pages.
Torng et. al., "3D deep convolutional neural networks for amino acid environment similarity analysis", dated 2017, 23 pages.
Morrone et. al., "Combining docking pose rank and structure with deep learning improves protein-ligand binding mode prediction", dated Oct. 7, 2019, 13 pages.
Li, "Machine Learning Methods for Medical and Biological Image Computing", dated Summer 2016, 113 pages.
Rivera et. al., "A Deep Learning Approach to Protein Structure Prediction", dated Apr. 24, 2019, 22 pages.
Aritake et. al., "Single-molecule localization by voxel-wise regression using convolutional neural network", dated Nov. 3, 2020, 11 pages.
Townshend et. al., "End-to-End Learning on 3D Protein Structure for Interface Prediction", dated 2019, 10 pages.
Amidi et. al., "EnzyNet: enzyme classification using 3D convolutional neural networks on spatial representation", dated Jul. 25, 2017, 18 pages.
Luna, "Machine Learning in structural biology and chemoinformatics", dated 2019, 106 pages.
Eraslan et. al., "Deep Learning: New computational modelling techniques for genomics", dated Jul. 2019, 15 pages.
Dias et. al., "Artificial intelligence in clinical and genomic diagnostics", dated 2019, 12 pages.
Luna et. al., "A Deep-Learning Approach toward Rational Molecular Docking Protocol Selection", dated May 27, 2020, 12 pages.
Li et. al., "DeepAtom: A Framework for Protein-Ligand Binding Affinity Prediction", dated 2019, 8 pages.
Zhang et. al., "Template-based prediction of protein structure with deep learning", dated Jun. 2, 2020, 16 pages.
Wallach et. al., AtomNet: A Deep Convolutional Neural Network for Bioactivity Prediction in Structure-based Drug Discovery, dated Oct. 10, 2015, 11 pages.
Illumina, Two-Channel SBS Sequencing Technology, 2016, 2 pages.
Illumina, Low-diversity sequencing on the Illumina HiSeq Platform, 2014, 2 pages.
Hedegaard, An introduction to "Next Generation" DNA Sequencing, dated Nov. 26, 2017, 63 pages.
Jordan, An overview of semantic image segmentation, dated May 21, 2018, 28 pages retrieved on Jul. 21, 2021. Retrieved from the internet [URL: https://www.jeremyjordan.me/semantic-segmentation/].
Lanchantin, Deep Motif Dashboard: Visualizing and Understanding Genomic Sequences Using Deep Neural Networks, Oct. 18, 2016, 11 pages.
Thalles Silva, Deeplab Image Semantic Segmentation Network, dated Jan. 29, 2018, 19 pages, retrieved on Jul. 21, 2021. Retrieved from [URL: https://sthalles.github.io/deep_segmentation_network/].
James Le, How to do Semantic Segmentation using Deep Learning, dated May 3, 2018, 17 pages, retrieved on Jul. 21, 2021. Retrieved from [URL: https://medium.com/nanonets/how-to-do-image-segmentation-using-deep-learning-c673cc5862ef].
Townley, Illumina Primary and Secondary Analysis, Illumina UK, 2010, 33 pages.
Silver, Literature Review: Fully Convolutional Networks, dated Jun. 12, 2017, 5 pages, retrieved on Jul. 21, 2021. Retrieved from [URL: https://medium.com/self-driving-cars/literature-review-fully-convolutional-networks-d0a11fe0a7aa].
Bowen, Nanotechnology for a Genomic Revolution, Illumina, dated Dec. 14, 2016, 40 pages.
Han, Deconvolutions in Convolutional Neural Networks, Postech Computer Vision Lab, 2015, 20 pages.
Illumina, Illumina's Genotyping Data Normalization Methods, 2006, 6 pages.
Illumina, Quality Scores for Next-Generation Sequencing—Assessing sequencing accuracy using Phred quality scoring, 2011, 2 pages.
Restrepo, A Gentle Introduction to Semantic Segmentation—Inputs, Labels and Outputs, 2 pages, retrieved on Jul. 21, 2021. Retrieved from [URL: http://ronny.rest/tutorials/module/seg_01/segmentation_03_inputs_outputs/].
Illumina, An Introduction to Next-Generation Sequencing Technology, 2017, 16 pages.
Belanovic, Library of Parameterized Hardware Modules for Floating-Point Arithmetic with an Example Application, Northeastern University, Boston, MA, May 2002, 83 pages.
Massingham, Base Calling: methods, problems and alternatives, EMBL Advanced Course in Analysis of Short Read Sequencing Data, Jun. 8, 2009-Jun. 10, 2009, 84 pages.
Thoma, A Survey of Semantic Segmentation, dated May 11, 2016, 16 pages.
Rodriguez-Ezpeleta, Bioinformatics for High Throughput Sequencing, Springer, 2012, 266 pages.
Illumina, Optimizing Cluster Density on Illumina Sequencing Systems, 2016, 12 pages.
Boza et. al., DeepNano: Deep recurrent neural networks for base calling in MinION nanopore reads, PLOS One, dated Jun. 5, 2017, 13 pages.
Kircher, Understanding and Improving high-throughput sequencing data production and analysis, Leipzig University, 2011, 216 pages.
Gilissen, C. et al. Genome sequencing identifies major causes of severe intellectual disability. Nature 511, 344-347 (2014).
Lelieveld, S. H. et al. Meta-analysis of 2,104 trios provides support for 10 new genes for intellectual disability. Nat. Neurosci. 19, 1194-1196 (2016).
Famiglietti, M. L. et al. Genetic variations and diseases in UniProtKB Swiss-Prot—the ins and outs of expert manual curation Human. Mutat. 35, 927-935 (2014).
Horaitis, O., Talbot, C. C.Jr., Phommarinh, M., Phillips, K. M., & Cotton, R. G. A database of locus-specific databases. Nat. Genet. 39, 425 (2007).

(56) References Cited

OTHER PUBLICATIONS

Stenson, P. D. et al. The Human Gene Mutation Database—building a comprehensive mutation repository for clinical and molecular genetics, diagnostic testing and personalized genomic medicine. Hum. Genet 133, 1-9 (2014).
Alipanahi, et. al., "Predicting the Sequence Specificities of DNA and RNA Binding Proteins by Deep Learning", Aug. 2015, 9pgs.
Angermueller, et. al., "Accurate Prediction of Single Cell DNA Methylation States Using Deep Learning", Apr. 11, 2017, 13pgs.
Ching, et. al., "Opportunities and Obstacles for Deep Learning in Biology and Medicine", Jan. 19, 2018, 123pgs.
Ching, et. al., "Opportunities and Obstacles for Deep Learning in Biology and Medicine", May 26, 2017, 47pgs.
Gu, et. al., "Recent Advances in Convolutional Neural Networks", Jan. 5, 2017, 37pgs.
Leung, et. al., "Deep learning of the tissue regulated splicing code", 2014, 9pgs.
Leung, et. al., "Inference of the Human Polyadenylation Code", Apr. 27, 2017, 13pgs.
Leung, et. al., "Machine Learning in Genomic Medicine", Jan. 1, 2016, 22pgs.
Park, et. al., "Deep Learning for Regulatory Genomics", Aug. 2015, 2pgs.
MacArthur, D. G. et al. Guidelines for investigating causality of sequence variants in human disease. Nature 508, 469-476 (2014).
Rehm, H. L. et al. ClinGen—the Clinical Genome Resource. N. Engl. J. Med. 372, 2235-2242 (2015).
Bamshad, M. J. et al. Exome sequencing as a tool for Mendelian disease gene discovery. Nat. Rev. Genet. 12, 745-755 (2011).
Rehm, H. L. Evolving health care through personal genomics. Nat. Rev. Genet. 18, 259-267 (2017).
Richards, S. et al. Standards and guidelines for the interpretation of sequence variants—a joint consensus recommendation of the American College of Medical Genetics and Genomics and the Association for Molecular Pathology. Genet. Med. 17, 405-424 (2015).
Lek, M. et al. Analysis of protein-coding genetic variation in 60,706 humans. Nature 536, 285-291 (2016).
Mallick, S. et al. The Simons Genome Diversity Project—300 genomes from 142 diverse populations. Nature 538, 201-206 (2016).
Genomes Project Consortium, et al. A global reference for human genetic variation. Nature 526, 68-74 (2015).
Liu, X., Jian, X. & Boerwinkle, E. dbNSFP—a lightweight database of human nonsynonymous SNPs and their functional predictions. Human. Mutat. 32, 894-899 (2011).
Chimpanzee Sequencing Analysis Consortium. Initial sequence of the chimpanzee genome and comparison with the human genome. Nature 437, 69-87 (2005).
Takahata, N. Allelic genealogy and human evolution. Mol. Biol. Evol. 10, 2-22 (1993).
Asthana, S., Schmidt, S., & Sunyaev, S. A limited role for balancing selection. Trends Genet. 21, 30-32 (2005).
Leffler, E. M. et al. Multiple instances of ancient balancing selection shared between humans and chimpanzees. Science 339, 12 pages (2013).
Samocha, K. E. et al. A framework for the interpretation of de novo mutation in human disease. Nat. Genet. 46, 944-950 (2014).
Ohta, T. Slightly deleterious mutant substitutions in evolution. Nature 246, 96-98 (1973).
Reich, D. E. & Lander, E. S. On the allelic spectrum of human disease. Trends Genet. 17, 502-510 (2001).
Whiffin, N. et al. Using high-resolution variant frequencies to empower clinical genome interpretation. Genet. Med. 19, 1151-1158(2017).
Prado-Martinez, J. et al. Great ape genome diversity and population history. Nature 499, 471-475 (2013).
Klein, J., Satta, Y., O'HUigin, C., & Takahata, N. The molecular descent of the major histocompatibility complex. Annu. Rev. Immunol. 11, 269-295 (1993).
de Manuel, M. et al. Chimpanzee genomic diversity reveals ancient admixture with bonobos. Science 354, 477-481 (2016).
Locke, D. P. et al. Comparative and demographic analysis of orang-utan genomes. Nature 469, 529-533 (2011).
Rhesus Macaque Genome Sequencing Analysis Consortium. Evolutionary and biomedical insights from the rhesus macaque genome. Science 316, 222-234 (2007).
Worley, K. C. et al. The common marmoset genome provides insight into primate biology and evolution. Nat. Genet. 46, 850-857 (2014).
Sherry, S. T. et al. dbSNP—the NCBI database of genetic variation. Nucleic Acids Res. 29, 308-211 (2001).
Schrago, C. G., & Russo, C. A. Timing the origin of New World monkeys. Mol. Biol. Evol. 20, 1620-1625 (2003).
Landrum, M. J. et al. ClinVar—public archive of interpretations of clinically relevant variants. Nucleic Acids Res. 44, D862-868 (2016).
Brandon, E. P., Idzerda, R. L. & McKnight, G. S. Targeting the mouse genome—a compendium of knockouts (Part II). Curr. Biol. 5, 758-765 (1995).
Lieschke, J. G. & Currie, P. D. Animal models of human disease—zebrafish swim into view. Nat. Rev. Genet. 8, 353-367 (2007).
Sittig, L. J. et al. Genetic background limits generalizability of genotype-phenotype relationships. Neuron 91, 1253-1259 (2016).
Bazykin, G. A. et al. Extensive parallelism in protein evolution. Biol. Direct 2, 20, 13 pages (2007).
Ng, P. C., & Henikoff, S. Predicting deleterious amino acid substitutions. Genome Res. 11, 863-874 (2001).
Adzhubei, I. A. et al. A method and server for predicting damaging missense mutations. Nat. Methods 7, 248-249 (2010).
Chun, S. & Fay, J. C. Identification of deleterious mutations within three human genomes. Genome Res. 19, 1553-1561 (2009).
Schwarz, J. M., Rodelsperger, C., Schuelke, M. & Seelow, D. MutationTaster evaluates disease-causing potential of sequence alterations. Nat. Methods 7, 575-576 (2010).
Reva, B., Antipin, Y., & Sander, C. Predicting the functional impact of protein mutations-application to cancer genomics. Nucleic Acids Res 39, e118 (2011), 14pgs.
Dong, C. et al. Comparison and integration of deleteriousness prediction methods for nonsynonymous SNVs in whole exome sequencing studies. Hum. Mol. Genet. 24, 2125-2137 (2015).
Carter, H., Douville, C., Stenson, P. D., Cooper, D. N., & Karchin, R. Identifying Mendelian disease genes with the variant effect scoring tool. BMC Genom, (2013), 13 pages.
Choi, Y., Sims, G. E., Murphy, S., Miller, J. R., & Chan, A. P. Predicting the functional effect of amino acid substitutions and indels PLoS One 7, e46688 (2012).
Gulko, B., Hubisz, M. J., Gronau, I., & Siepel, A. A method for calculating probabilities of fitness consequences for point mutations across the human genome. Nat. Genet. 47, 276-283 (2015).
Shihab, H. A. et al. An integrative approach to predicting the functional effects of non-coding and coding sequence variation. Bioinformatics 31, 1536-1543 (2015).
Bell, C. J. et al. Comprehensive carrier testing for severe childhood recessive diseases by next generation sequencing. Sci. Transl. Med. 3, Jan. 12, 2011, 28 pages.
Smedley, D. et al. A whole-genome analysis framework for effective identification of pathogenic regulatory variants in mendelian disease. Am. J. Hum. Genet. 99, 595-606 (2016).
Jagadeesh, K. A. et al. M-CAP eliminates a majority of variants of uncertain significance in clinical exomes at high sensitivity. Nat. Genet. 48, 1581-1586 (2016).
Grimm, D. G. The evaluation of tools used to predict the impact of missense variants is hindered by two types of circularity. Human. Mutat. 36, 513-523 (2015).
Heffernan, R. et al. Improving prediction of secondary structure, local backbone angles, and solvent accessible surface area of proteins by iterative deep learning. Sci. Rep. 5, 11476 (2015) 11 pages.
Wang, S., Peng, J., Ma, J. & Xu, J. Protein secondary structure prediction using deep convolutional neural fields. Sci. Rep. 6, 18962-18962 (2016).
Harpak, A., Bhaskar, A., & Pritchard, J. K. Mutation rate variation is a primary determinant of the distribution of allele frequencies in humans. PLoS Genet. Dec. 15, 2016, 22pgs.

(56) References Cited

OTHER PUBLICATIONS

Payandeh, J., Scheuer, T., Zheng, N. & Catterall, W. A. The crystal structure of a voltage-gated sodium channel. Nature 475, 353-358 (2011).
Shen, H. et al. Structure of a eukaryotic voltage-gated sodium channel at near-atomic resolution. Science 355, eaal4326 (2017), 19 pages.
Makamura, K. et al. Clinical spectrum of SCN2A mutations expanding to Ohtahara syndrome. Neurology 81, 992-998 (2013).
Ioannidis, Nilah M., et al., "REVEL—An Ensemble Method for Predicting the Pathogenicity of Rare Missense Variants", Oct. 5, 2016, 9 pages.
Quang Daniel, et. al., "DANN—a deep learning approach for annotating the pathogenicity of genetic variants", Oct. 22, 2014, 3 pages.
Sundaram, et. al., "Predicting the clinical impact of human mutation with deep neural networks", Aug. 2018, 15pgs.
Xiong, et. al., "The human splicing code reveals new insights into the genetic determinants of disease", Jan. 9, 2015, 20pgs.
Yue, et. al., "Deep Learning for Genomics—A Concise Overview from internet", May 8, 2018, 40pgs.
Yuen, et. al., "Genome wide characteristics of de novo mutations in autism", Jun. 1, 2016, 10pgs.
Libbrecht, et. al., "Machine learning in genetics and genomics", Jan. 2, 2017, 30pgs.
Min, et. al., "Deep Learning in Bioinformatics", Jul. 25, 2016, 19 pgs.
Torng, Wen, et al., "3D deep convolutional neural networks for amino acid environment similarity analysis", 2017, 23pages.
Chen, Kathleen M., et. al., "Selene—a PyTorch based deep learning library for sequence level data", Oct. 10, 2018, 15pages.
Grob, C., et. al., "Predicting variant deleteriousness in non human species Applying the CADD approach in mouse", 2018, 11 pages.
Li, et. al., "FoldingZero—Protein Folding from Scratch in Hydrophobic Polar Model", Dec. 3, 2018, 10 pages.
Rentzsch, et. al., "CADD—predicting the deleteriousness of variants throughout the human genome", Oct. 11, 2018, 9 pages.
Zou, etal, "A primer on deep learning in genomics", Nov. 26, 2018, 7pages.
Alberts, Bruce, et al., "Molecular biology of the cell", Sixth Edition, 2015, 3 pages.
PCT/US2018/055840—International Search Report and Written Opinion dated Jan. 25, 2019, 18 pages.
Wei etal_The Role of Balanced Training and Testing Data Sets for Binary Classifiers in Bioinformatics dated Jul. 9, 2013 12 pages.
PCT/US2018/055878—International Search Report and Written Opinion dated Jan. 22, 2019, 20 pages.
PCT/US2018/055881—International Search Report and Written Opinion dated Jan. 25, 2019, 17 pages.
Duggirala, Ravindranath, et.al., "Genome Mapping and Genomics in Human and Non Human Primate", 2015, 306pgs.
Brookes, Anthony J., "The essence of SNPs", 1999, pp. 177-186.
UniProtKB P04217 A1BG Human [retrieved on Mar. 13, 2019 from (www.uniprot.org/uniprot/P04217), 12pages.
Bahar, Protein Actions Principles and Modeling, Chapter 7, 2017 pp. 165-166.
Dunbrack, Roland L., Re Question about your Paper titled "The Role of Balanced Training and Testing Data Sets for Binary Classifiers in Bioinformatics", Message to Sikander Mohammed Khan, Feb. 3, 2019, E-mailm, 3pgs.
dbSNP rs2241788 [Retrieved on Mar. 13, 2019], Retrieved from the Internet<www.ncbi.nlm.nih.gov/snp/rs2241788>, 5 pages.
Wei, et. al., "Prediction of phenotypes of missense mutations in human proteins from biological assemblies", Feb. 2013, 28 pages.
Zhang, Jun, and Bin Liu. "PSFM-DBT—identifying DNA-binding proteins by combing position specific frequency matrix and distance-bigram transformation" International journal of molecular sciences 18.9 (2017) 1856.
Gao, Tingting, et al. "Identifying translation initiation sites in prokaryotes using support vector machine." Journal of theoretical biology 262.4 (2010) 644-649. (Year 2010).
Bi, Yingtao, et al. "Tree-based position weight matrix approach to model transcription factor binding site profiles." PloS one6.9(2011) e24210.
Korhonen, Janne H., et al. "Fast motif matching revisited—high-order PWMs, SNPs and indels." Bioinformatics 33.4 (2016) 514-521.
Wong, Sebastien C., et al. "Understanding data augmentation for classification—when to warp?." 2016 international conference on digital image computing—techniques and applications (DICTA) IEEE, 2016.
Chang, Chia-Yun, et al. "Oversampling to overcome overfitting—exploring the relationship between data set composition, molecular descriptors, and predictive modeling methods." Journal of chemical information and modeling 53.4 (2013) 958-971.
Li, Gangmin, and Bei Yao. "Classification of Genetic Mutations for Cancer Treatment with Machine Learning Approaches." International Journal of Design, Analysis and Tools for Integrated Circuits and Systems 7.1 (2018) pp. 63-67.
Martin-Navarro, Antonio, et al. "Machine learning classifier for identification of damaging missense mutations exclusive to human mitochondrial DNA-encoded polypeptides." BMC bioinformatics 18.1 (2017) p. 158.
Krizhevsky, Alex, et al., ImageNet Classification with Deep Convolutional Neural Networks, 2012, 9 Pages.
Geeks for Geeks, "Underfitting and Overfitting in Machine Learning", [retrieved on Aug. 26, 2019]. Retrieved from the Internet <www.geeksforgeeks.org/underfitting-and-overfitting-in-machine-learning/>, 2 pages.
PCT/US2020/024090 Article 34 Amendment, dated Dec. 4, 2020, 6 pages.
PCT/US2020/024090 Article 34 Amendment, dated Mar. 18, 2021, 3 pages.
Albrecht et. al., Deep learning for single-molecule science, Nanotechnology (28), dated 2017, 423001, 11 pages.
MiSeq: Imaging and Base Calling: Illumina, Inc. Online Training Course, dated Jan. 1, 2013 [retrieved on Jul. 13, 2020], Retrieved from <URL: https://support.illumina.com/training.html >, 13 pages.
MiSeq: Imaging and Base Calling Script, retrieved on [Jun. 14, 2021], Retrieved from the internet <URL: https://support.illumina.com/content/dam/illumina-support/courses/MiSeq_Imaging_and_Base_Calling/story_content/extemal_files/MiSeq%20Imaging%20and%20Base%20Calling%20Script.pdf >.
PCT/US2020/024087 PCT Direct Letter, dated Mar. 21, 2020, 5 pages.
PCT/US2020/024087 International Search Report and Written Opinion, dated Aug. 28, 2020, 24 pages.
PCT/US2020/024087 Article 34 Amendment, filed Mar. 21, 2020, 7 pages.
PCT/US2020/024087 Second Written Opinion, dated Apr. 7, 2021, 12 pages.
PCT/US2020/024087 Article 34 Letter Response to Second Written Opinion, dated May 7, 2021, 7 pages.
Zhao et. al., Object detection with Deep Learning: A Review, dated Jul. 15, 2018, 22 pages.
Lee et. al., Fast Object Localization Using a CNN Feature Map Based Multi-Scale Search, dated Apr. 12, 2016, 16 pages.
PCT/US2020/24088 PCT Direct Letter, filed Mar. 21, 2020,4 pages.
PCT/US2020/024088 Article 34 Letter in response to Second Written Opinion, dated May 28, 2021, 9 pages.
PCT/US2020/024088 Second Written Opinion, dated Apr. 20, 2021, 17 pages.
PCT/US2020/024088 International Search Report and Written Opinion, dated Sep. 7, 2020, 29 pages.
PCT/US2020/024088 Article 34 Letter in Response to Written Opinion, dated Mar. 9, 2021, 11 pages.
PCT/US2020/024088 Partial Search Report and Invitation to Pay Fees, dated Jul. 8, 2020, 22 pages.
Misiunas et. al., QuipuNet: convolutional neural network for single-molecule nanopore sensing, dated May 30, 2018, 7 pages.

(56) References Cited

OTHER PUBLICATIONS

Boza et. al., Deep Recurrent Neural Networks for Base Calling in MinION Nanopore Reads, dated Mar. 30, 2016, 12 pages.
Kao et. al., BayesCall: A model-based base-calling algorithm for high-throughput short-read sequencing, Genome Research (19), pp. 1884-1895, dated 2009.
Rang et. al., From squiggle to basepair: computational approaches for improving nanopore sequencing read accuracy, Genome Biology 2018, (19), 30.
Wang et. al., An adaptive decorrelation method removes Illumina DNA base-calling errors caused by crosstalk between adjacent clusters, Scientific Reports, published Feb. 20, 2017, 11 pages.
Cacho et. al., A comparison of Base Calling Algorithms for Illumina Sequencing Technology, dated Oct. 5, 2015, Briefings in Bioinformatics 2016 (17), 786-795.
PCT/US2020/024091 PCT Direct Letter, dated Mar. 21, 2020, 5 pages.
PCT/US2020/024091 Partial Search Report and Invitation to Pay Fee, dated Jul. 3, 2020, 17 pages.
PCT/US2020/024091 International Search Report and Written Opinion, dated Oct. 23, 2020, 24 pages.
PCT/US2020/024091 Article 34 Letter in Reponse to International Search Report and Written Opinion, filed Mar. 8, 2021, 10 pages.
PCT/US2020/024091 Second Article 34 Amendment Letter, dated Mar. 22, 2021, 10 pages.
PCT/US2020/024091 Written Opinion of the International Preliminary Examining Authority (Second Written Opinon), dated Apr. 20, 2021, 14 pages.
PCT/US2020/024091 Second Article 34 Amendment in response to Second Written Opinion, dated May 30, 2021, 9 pages.
Luo et. al., G-softmax: Improving Intra-class Compactness and Inter-class Separability of Features, dated Apr. 8, 2019, 15 pages.
Luo et. al., A multi-task convolutional deep neural network for variant calling in single molecule sequencing, Nature Communications (10), No. 1, dated Mar. 1, 2019.
Kingma et. al., Adam: A method for Stochastic Optimization, ICLR 2015, dated Jul. 23, 2015.
Luo et. al., Skyhawk: An Artificial Neural Network-based discriminator for reviewing clinically significant genomic variants, dated Jan. 28, 2019, 8 pages.
MiSeq: Imaging and Base Calling: Illumina, Inc. Online Training Course, colored version, [retrieved on Oct. 11, 2020], Retrieved from <URL: https://support.illumina.com/training.html >, 9 pages.
PCT/US2020/024092 PCT Direct Letter, dated Mar. 21, 2020, 5 pages.
PCT/US2020/024092 Partial Search Report and Invitation to Pay Fees, dated Sep. 11, 2020, 22 pages.
PCT/US2020/024092 International Search Report and Written Opinion, dated Nov. 2, 2020, 24 pages.
PCT/US2020/024092 Article 34 Amendment in Response to International Search Report and Written Opinion, dated Mar. 4, 20221, 7 pages.
PCT/US2020/024092 Second Written Opinion dated Apr. 7, 2021, 13 pages.
PCT/US2020/024092 Article 34 Amendment Response to Second Written Opinion, dated May 7, 2021, 10 pages.
PCT/US2021/018910—Partial Search Report and Invitation to Pay Fees dated May 31, 2021, 14 pgs.
PCT/US2020/033280 International Search Report and Written Opinion, dated Jul. 22, 2020, 18 pages.
PCT/US2020/033280 Article 34 Amendment, dated Apr. 19, 2021, 10 pages.
PCT/US2020/033281 International Search Report and Written Opinion, dated Aug. 14, 2020, 15 pages.
Kircher et. al., Improved base-calling for the Illumina Genome Analyzer using Machine Learning Strategies, Genome Biology, published Aug. 14, 2009, 9 pages.
PCT/US2020/033281 Article 34 Amendment, dated Apr. 19, 2021, 8 pages.
PCT/US2020/033281 Second Written Opinion, dated May 10, 2021, 8 pages.
Ramesh, Nisha, et. al., "Cell Segmentation Using a Similarity Interface With a Multi-Task Convolutional Neural Network"; IEEE Journal of Biomedical and Health Informatics, vol. 23, No. 4, Jul. 2019, 12 pages.
U.S. Appl. No. 16/825,991—Notice of Allowance dated Apr. 19, 2021, 12 pages.
Arpali et. al., High-throughput screening of large volumes of whole blood using structured illumination and fluoresecent on-chip imaging, Lab on a Chip, United Kingdom, Royal Society of Chemistry, Sep. 12, 2012, vol. 12, pp. 4968-4971.
Liu et. al., 3D Stacked Many Core Architecture for Biological Sequence Analysis Problems, 2017, Int J Parallel Prog, 45:1420-1460.
Wu et. al., FPGA-Based DNA Basecalling Hardware Acceleration, in Proc. IEEE 61st Int. Midwest Symp. Circuits Syst., Aug. 2018, pp. 1098-1101.
Wu et. al., FPGA-Accelerated 3rd Generation DNA Sequencing, in IEEE Transactions on Biomedical Circuits and Systems, vol. 14, Issue 1, Feb. 2020, pp. 65-74.
Prabhakar et. al., Plasticine: A Reconfigurable Architecture for Parallel Patterns, ISCA '17, Jun. 24-28, 2017, Toronto, ON, Canada.
Lin et. al., Network in Network, in Proc. of ICLR, 2014.
Sifre, Rigid-motion Scattering for Image Classification, Ph.D. thesis, 2014.
Sifre et. al., Rotation, Scaling and Deformation Invariant Scattering for Texture Discrimination, in Proc. of CVPR, 2013.
Chollet, Xception: Deep Learning with Depthwise Separable Convolutions, in Proc. of CVPR, 2017. 8 pages.
Zhang et. al., ShuffleNet: An Extremely Efficient Convolutional Neural Network for Mobile Devices, 2017.
He et. al., Deep Residual Learning for Image Recognition, in Proc. of CVPR, 2016.
Xie et. al., Aggregated Residual Transformations for Deep Neural Networks, in Proc. of CVPR, 2017.
Howard et. al., Mobilenets: Efficient Convolutional Neural Networks for Mobile Vision Applications, 2017.
Sandler et. al., MobileNetV2: Inverted Residuals and Linear Bottlenecks, 2018.
Qin et. al., FD-MobileNet: Improved MobileNet with a Fast Downsampling Strategy, 2018.
Chen et. al., Rethinking atrous convolution for semantic image segmentation, 2017.
Huang et. al., Speed/accuracy trade-offs for modern convolutional detectors, 2016.
Oord, Dieleman et. al., WaveNet: A Generative Model for Raw Audio, 2016.
Arik et. al., Deep Voice: Real-time Neural Text-to-Speech, 2017.
Yu et. al., Multi-Scale Context Aggregation by Dilated Convolutions, 2016.
He et. al., Deep Residual Learning for Image Recognition, 2015.
Srivastava et. al., Highway Networks, 2015.
Huang et. al., Densely Connected Convolutional Networks, 2017.
Szegedy et. al., Going Deeper with Convolutions, 2014.
Ioffe et. al., Batch Normalization Accelerating Deep Network Training by Reducing Internal Covariate Shift, 2015.
Wolterink et. al., Dilated Convolutional Neural Networks for Cardiovascular MR Segmentation in Congenital Heart Disease, 2017.
Piqueras, Autoregressive Model Based on a Deep Convolutional Neural Network for Audio Generation, Tampere University of Technology, 2016.
Wu, Introduction to Convolutional Neural Networks, Nanjing University, 2017.
Illumina CMOS Chip and One-Channel SBS Chemistry, Illumina Inc, 2018, 4 pages.
scikit-image/peak.py at master, Github, retrieved on Jun. 8, 2021, 10 pages, Retrieved from the internet <URL: https://github.com/scikit-image/scikit-image/blob/main/skimage/feature/peak.py>.
3.3.9.11.Watershed and random walker for segmentation, Scipy lecture notes, 2 pages, [retrieved on Jun. 8, 2021] Retrieved from the internet <URL: http:scipy-lectures.org/packages/scikit-image/auto_examples/plot_segmentations.html>.

(56) References Cited

OTHER PUBLICATIONS

Mordvintsev et. al., Image Segmentation with Watershed Algorithm, Revision 43532856, 2013, 6 pages, [retrieved on Jun. 8, 2021] Retrieved from the Internet <URL: https://opencv-python-tutroals.readthedocs.io/en/latest/py_tutorials/py_imgproc/py_watershed/py_watershed.html>.
Mzur, Watershed.py, Github, 3 pages, [retrieved on Jun. 8, 2021] Retrieved from the internet <URL: https://github.com/mzur/watershed/blob/master/Watershed.py>.
Thakur et. al., A Survey of Image Segmentation Techniques, International Journal of Research in Computer Applications and Robotics, vol. 2, Issue 4, Apr. 2014, p. 158-165.
Long et. al., Fully Convolutional Networks for Semantic Segmentation, IEEE Transactions on Pattern Analysis and Machine Intelligence, vol. 39, Issue 4, Apr. 1, 2017, 12 pages.
Ronneberger et. al., U-net: Convolutional networks for biomedical image segmentation, in International Conference on Medical Image computing and computer assisted intervention, May 18, 2015, 8 pages.
Xie et. al., Microscopy cell counting and detection with fully convolutional regression networks, Computer methods in biomechanics and biomedical engineering, Imaging and Visualization, 6(3), pp. 283-292, 2018.
Xie, Y., et. al., Beyond classification: structured regression for robust cell detection using convolutional neural network International conference on medical image computing and computer assisted intervention, Oct. 2015, 12 pages.
Snuverink, Deep Learning for Pixelwise Classification of Hyperspectral Images, Master of Science Thesis, Delft University of Technology, Nov. 23, 2017, 128 pages.
Shevchenko, Keras weighted categorical_crossentropy, Github, [retrieved on Jun. 12, 2021], Retrieved from the internet <URL: https://gist.github.com/skeeet/cad06d584548fb45eece1d4e28cfa98b >, 2 pages.
Assem, Predicting periodic and chaotic signals using Wavenets, Master of Science thesis, Delft University of Technology, Aug. 18, 2017, pp. 3-38.
Goodfellow et. al., Convolutional Networks, Deep Learning, MIT Press, 2016.
Gu et. al., Recent Advances in Convolutional Neural Networks, 2017.
Illumina, "Indexed Sequencing Overview Guide", Document No. 15057455, v. 5, Mar. 2019.
PCT/US2020/024090 International Preliminary Report on Patentability, dated Apr. 13, 2021, 20 pages.
PCT/US2020/024090 Written Opinion of the International Preliminary Examining Authority, dated Dec. 22, 2020, 11 pages.
PCT/US2020/024090 PCT Direct Letter, filed Mar. 21, 2020, 5 pages.
PCT/US2020/024090 International Search Report, dated Aug. 31, 2020, 8 pages.
Anonymous, "Transferrable end-to-end learning for protein interface prediction", dated 2019, 12 pages.
Semantic Segmentation Examples—MATLAB and Simuiink, 22 pages, [retrieved on Jul. 21, 2021], Retrieved from the internet [URL: https://www.mathworks.com/help/vision/ug/semantic-segmentation-examples.html ].
Grange, NGS: the basics, Institut Jacques Monod, dated Jun. 26, 2000, 59 pages.
Massingham et. al., All Your Base: a fast and accurate probabilistic approach to base calling, European Bioinformatics Institute, 22 pages, [retrieved on Jul. 22, 2021], Retrieved from the internet [URL: https://www.ebi.ac.uk/goldman-srv/AYB/references/ayb.pdf].

* cited by examiner

Cluster Centers (RTA) and Origin Subpixels

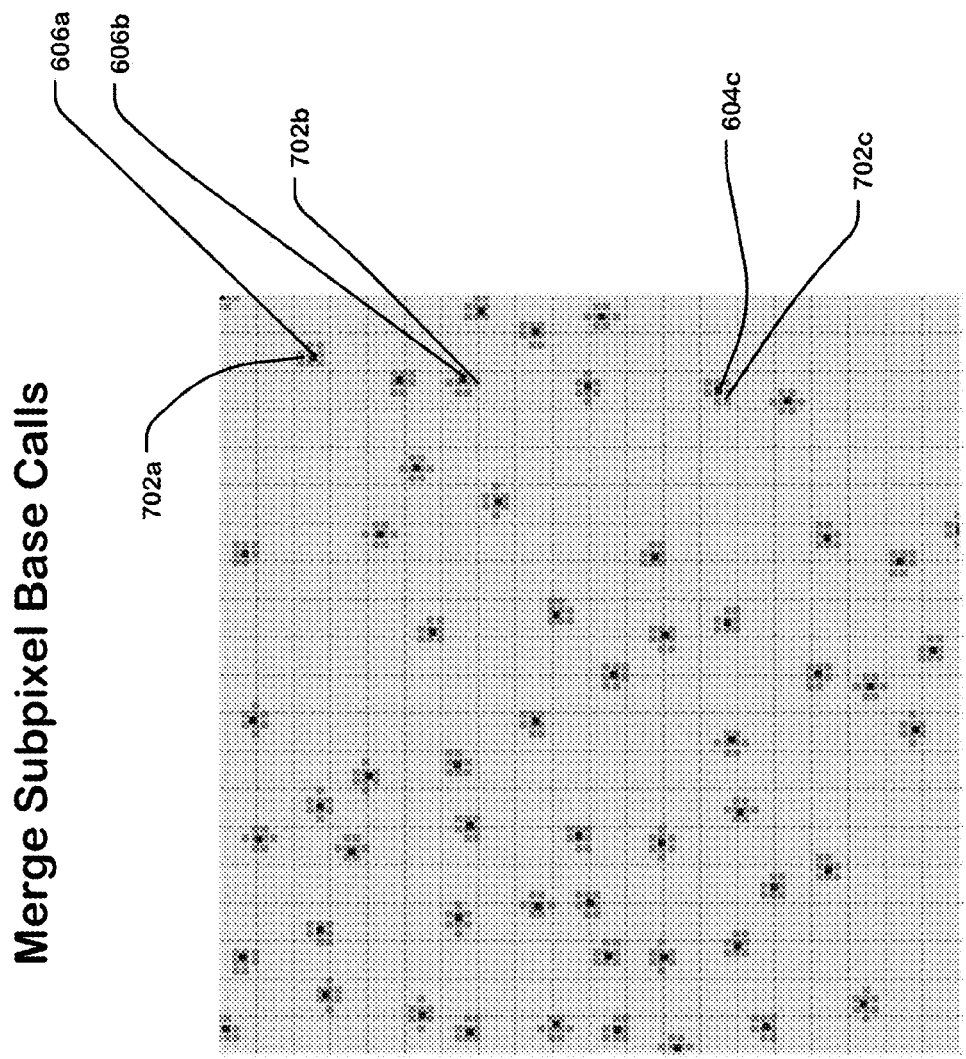

Regression Model 2600

| Layer (type) | Output Shape | Param # | Connected to |
|---|---|---|---|
| input_1 (InputLayer) | (None, None, None, 28) | 0 | |
| batch_normalization_1 (BatchNormali | (None, None, None, 28) | 112 | input_1[0][0] |
| conv2d_1 (Conv2D) | (None, None, None, 32) | 8064 | batch_normalization_1[0][0] |
| batch_normalization_2 (BatchNormali | (None, None, None, 32) | 128 | conv2d_1[0][0] |
| conv2d_2 (Conv2D) | (None, None, None, 32) | 9216 | batch_normalization_2[0][0] |
| batch_normalization_3 (BatchNormali | (None, None, None, 32) | 128 | conv2d_2[0][0] |
| max_pooling2d_1 (MaxPooling2D) | (None, None, None, 32) | 0 | batch_normalization_3[0][0] |
| conv2d_3 (Conv2D) | (None, None, None, 64) | 18432 | max_pooling2d_1[0][0] |
| batch_normalization_4 (BatchNormali | (None, None, None, 64) | 256 | conv2d_3[0][0] |
| conv2d_4 (Conv2D) | (None, None, None, 64) | 36864 | batch_normalization_4[0][0] |
| batch_normalization_5 (BatchNormali | (None, None, None, 64) | 256 | conv2d_4[0][0] |
| max_pooling2d_2 (MaxPooling2D) | (None, None, None, 64) | 0 | batch_normalization_5[0][0] |
| conv2d_5 (Conv2D) | (None, None, None, 128) | 73728 | max_pooling2d_2[0][0] |
| batch_normalization_6 (BatchNormali | (None, None, None, 128) | 512 | conv2d_5[0][0] |
| conv2d_6 (Conv2D) | (None, None, None, 128) | 147456 | batch_normalization_6[0][0] |
| batch_normalization_7 (BatchNormali | (None, None, None, 128) | 512 | conv2d_6[0][0] |
| dropout_1 (Dropout) | (None, None, None, 128) | 0 | batch_normalization_7[0][0] |
| max_pooling2d_3 (MaxPooling2D) | (None, None, None, 128) | 0 | dropout_1[0][0] |
| conv2d_7 (Conv2D) | (None, None, None, 256) | 294912 | max_pooling2d_3[0][0] |
| batch_normalization_8 (BatchNormali | (None, None, None, 256) | 1024 | conv2d_7[0][0] |
| conv2d_8 (Conv2D) | (None, None, None, 256) | 589824 | batch_normalization_8[0][0] |
| batch_normalization_9 (BatchNormali | (None, None, None, 256) | 1024 | conv2d_8[0][0] |
| dropout_2 (Dropout) | (None, None, None, 256) | 0 | batch_normalization_9[0][0] |
| up_sampling2d_1 (UpSampling2D) | (None, None, None, 256) | 0 | dropout_2[0][0] |
| concatenate_1 (Concatenate) | (None, None, None, 384) | 0 | up_sampling2d_1[0][0]<br>batch_normalization_7[0][0] |
| conv2d_9 (Conv2D) | (None, None, None, 128) | 442368 | concatenate_1[0][0] |
| batch_normalization_10 (BatchNormal | (None, None, None, 128) | 512 | conv2d_9[0][0] |
| conv2d_10 (Conv2D) | (None, None, None, 128) | 147456 | batch_normalization_10[0][0] |
| batch_normalization_11 (BatchNormal | (None, None, None, 128) | 512 | conv2d_10[0][0] |
| dropout_3 (Dropout) | (None, None, None, 128) | 0 | batch_normalization_11[0][0] |
| up_sampling2d_2 (UpSampling2D) | (None, None, None, 128) | 0 | dropout_3[0][0] |
| concatenate_2 (Concatenate) | (None, None, None, 192) | 0 | up_sampling2d_2[0][0]<br>batch_normalization_5[0][0] |
| conv2d_11 (Conv2D) | (None, None, None, 64) | 110592 | concatenate_2[0][0] |
| batch_normalization_12 (BatchNormal | (None, None, None, 64) | 256 | conv2d_11[0][0] |
| conv2d_12 (Conv2D) | (None, None, None, 64) | 36864 | batch_normalization_12[0][0] |
| batch_normalization_13 (BatchNormal | (None, None, None, 64) | 256 | conv2d_12[0][0] |
| up_sampling2d_3 (UpSampling2D) | (None, None, None, 64) | 0 | batch_normalization_13[0][0] |
| concatenate_3 (Concatenate) | (None, None, None, 96) | 0 | up_sampling2d_3[0][0]<br>batch_normalization_3[0][0] |
| conv2d_13 (Conv2D) | (None, None, None, 32) | 27648 | concatenate_3[0][0] |
| batch_normalization_14 (BatchNormal | (None, None, None, 32) | 128 | conv2d_13[0][0] |
| conv2d_14 (Conv2D) | (None, None, None, 32) | 9216 | batch_normalization_14[0][0] |
| batch_normalization_15 (BatchNormal | (None, None, None, 32) | 128 | conv2d_14[0][0] |
| pred (Conv2D) | (None, None, None, 1) | 32 | batch_normalization_15[0][0] |

Total params: 1,958,816
Trainable params: 1,955,944
Non-trainable params: 2,872

Figure 32

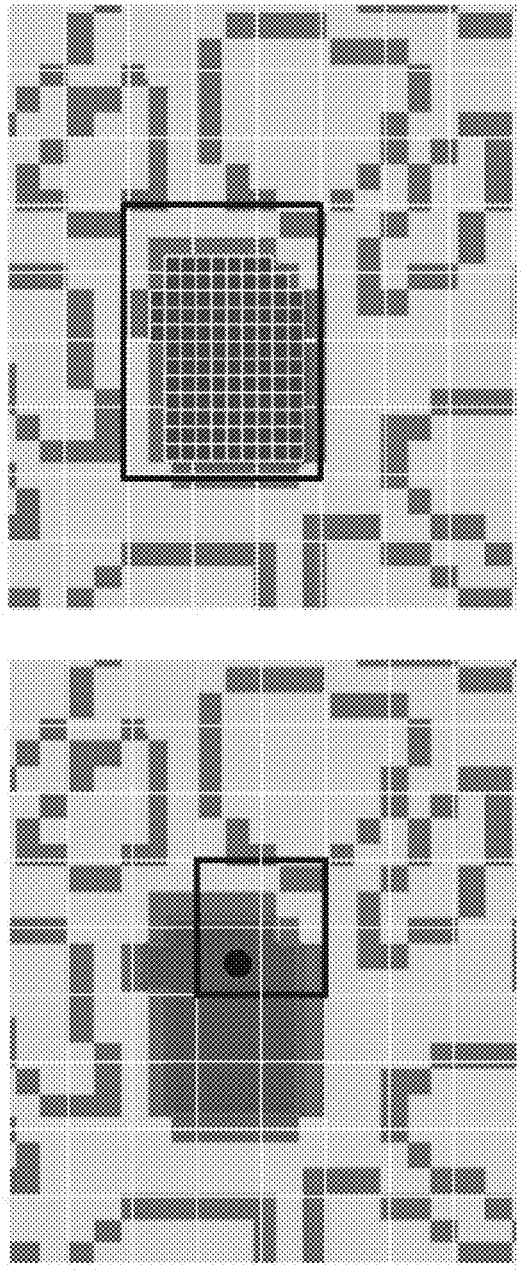

Intensity Extraction using Cluster Shapes

Approach 1 $\quad \dfrac{\sum_{subpixels} Bilinear\ Interpolated\ Intensity\ from\ Original\ Image}{No.\ of\ Subpixels\ in\ Cluster}$

Approach 2 $\quad \dfrac{\sum_{pixels} intensity * \dfrac{no\ of.\ subpixels}{16}}{\sum_{pixels} \dfrac{no\ of.\ subpixels}{16}}$

Approach 3 $\quad \dfrac{\sum_{pixels*} Intensity\ from\ Upsampled\ Image}{No.\ of\ pixels\ in\ Cluster}$

Figure 33

\* These pixels are in upsampled space. Upsampled image obtained by bicubic interpolation.

Centers of Mass vs. RTA centers

Centers of Mass

```
956048 + 0 in total (QC-passed reads + QC-
failed reads)
158 + 0 secondary
0 + 0 supplementary
841 + 0 duplicates
936609 + 0 mapped (97.97% : N/A)
955890 + 0 paired in sequencing
477945 + 0 read1
477945 + 0 read2
928926 + 0 properly paired (97.18% : N/A)
930732 + 0 with itself and mate mapped
5719 + 0 singletons (0.60% : N/A)
0 + 0 with mate mapped to a different chr
0 + 0 with mate mapped to a different chr
(mapQ>=5)
```

```
bases mapped: 141404101  # ignores clipping
bases mapped (cigar):  140673703
bases trimmed: 0
bases duplicated:     126991
mismatches:    498799  # from NM fields
error rate: 3.545787e-03   # mismatches /
bases mapped (cigar)
```

RTA centers

```
956054 + 0 in total (QC-passed reads + QC-
failed reads)
164 + 0 secondary
0 + 0 supplementary
1045 + 0 duplicates
932910 + 0 mapped (97.58% : N/A)
955890 + 0 paired in sequencing
477945 + 0 read1
477945 + 0 read2
923322 + 0 properly paired (96.59% : N/A)
925276 + 0 with itself and mate mapped
7470 + 0 singletons (0.78% : N/A)
0 + 0 with mate mapped to a different chr
0 + 0 with mate mapped to a different chr
(mapQ>=5)
```

```
bases mapped: 140844646  # ignores clipping
bases mapped (cigar): 139683478
bases trimmed: 0
bases duplicated: 157795
mismatches: 821045  # from NM fields
error rate: 5.877897e-03   # mismatches /
bases mapped (cigar)
```

Figure 35

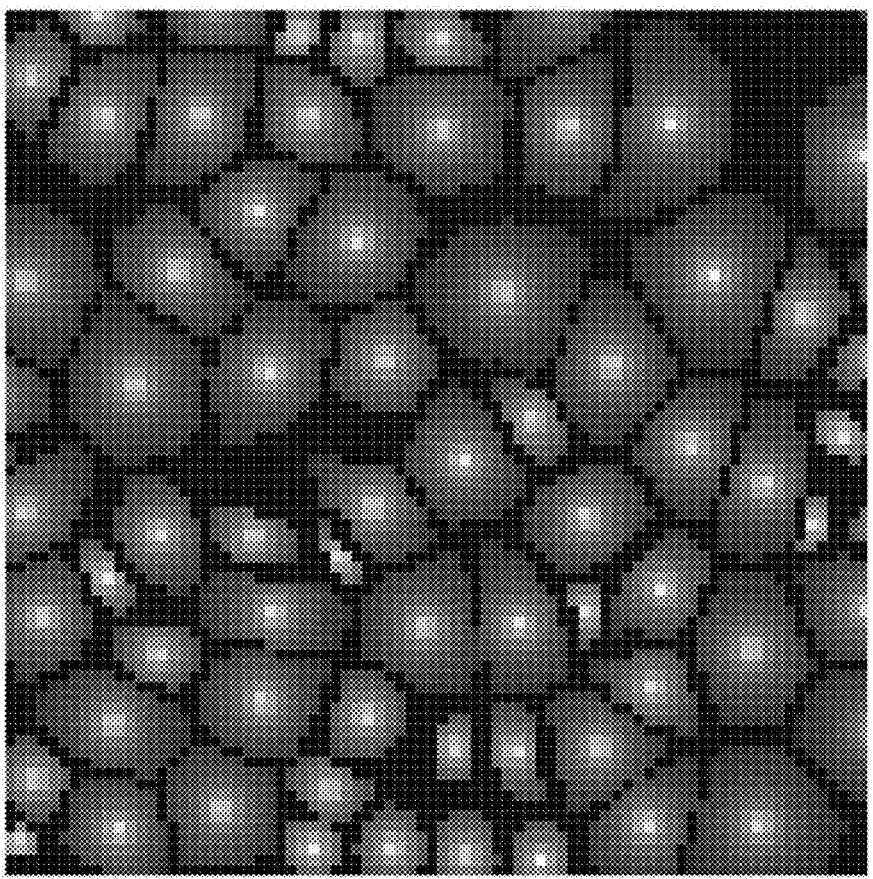
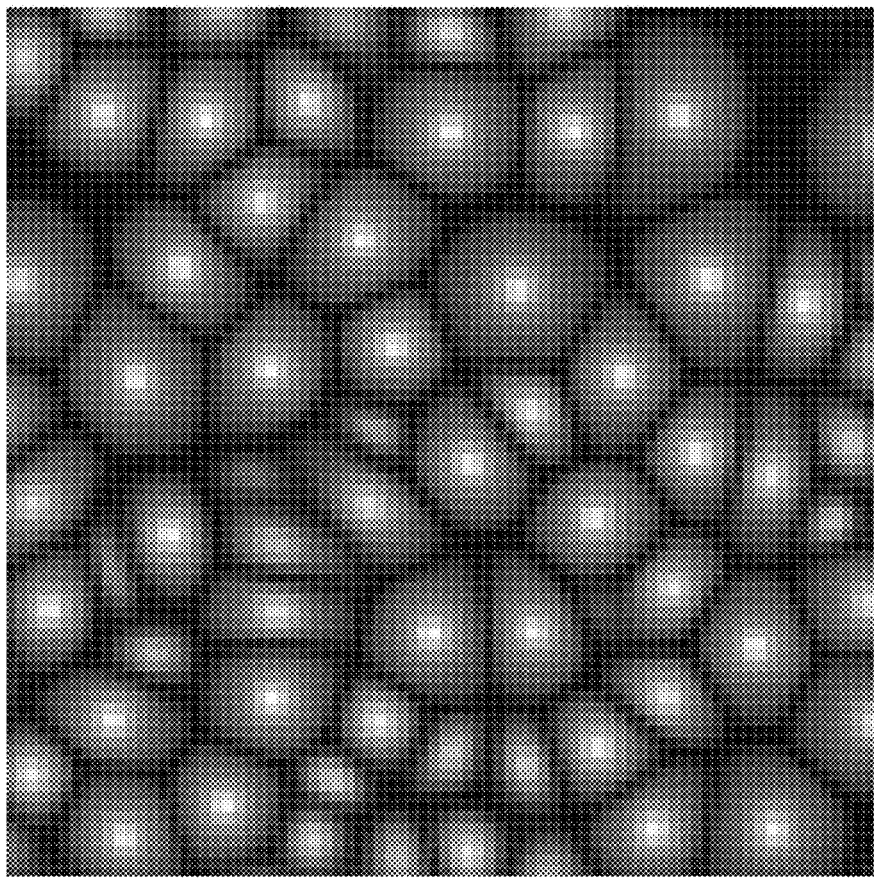
Figure 36

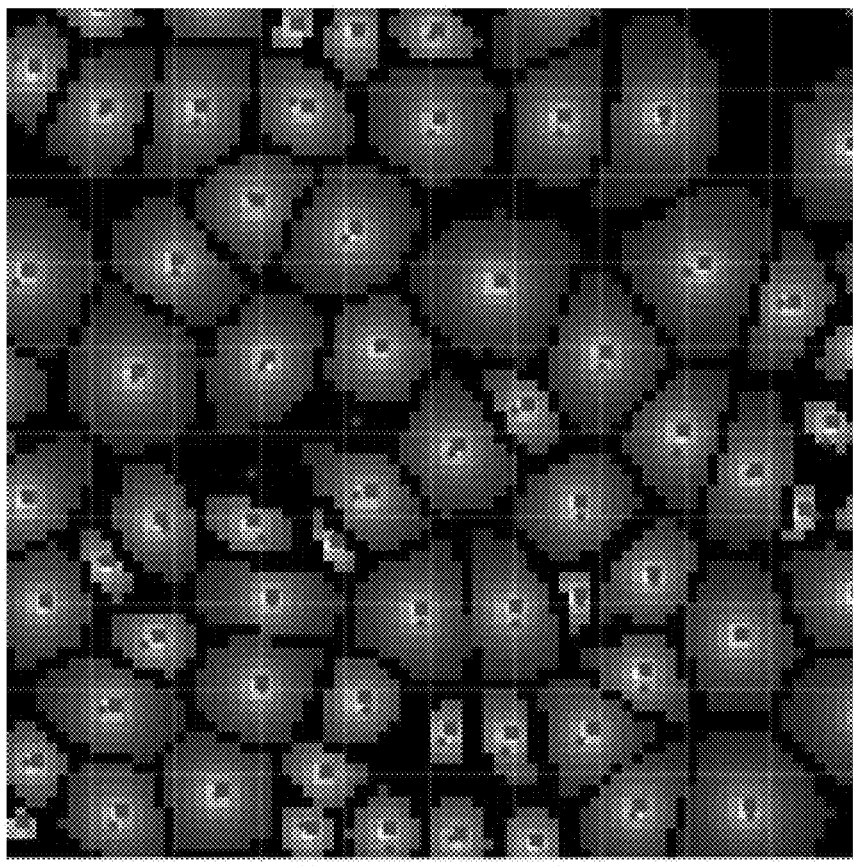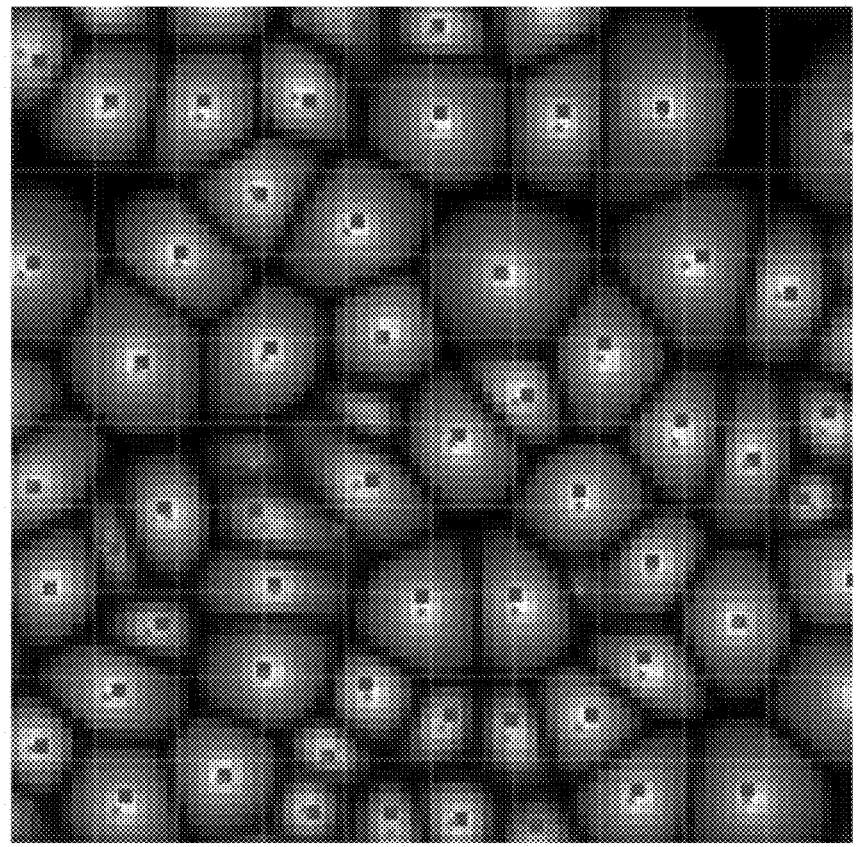
Figure 38

NORMAL RUN 20pM Tile: 1102 (7 cycles)

| | RTA | Within Boundary +/- 10 (Unet) |
|---|---|---|
| # clusters | 903,040 | 988,884 |
| % PF | 88.55% (799,684) | 84.54% (836,197) |
| % Aligned | 97.50% | 97.47% |
| % Duplicate | 0.05% | 0.12% |
| % Mismatch | 0.37% | 0.34% |
| % soft clipped | 2.07% | 2.05% |
| % Q30 bases | 90.59% | 91.42% |
| Non-duplicate proper read pairs | 769,150 | 803,473 (4.46%, 34,323) |

Figure 40

DENSE RUN 30pM Tile: 2103 (7 cycles)

| | RTA | Within Boundary +/- 10 (Unet) |
|---|---|---|
| # clusters | 1,157,285 | 1,351,588 |
| % PF | 78.58% (909,340) | 71.62% (968,066) |
| % Aligned | 97.69% | 97.62% |
| % Duplicate | 0.05% | 0.07% |
| % Mismatch | 0.65% | 0.63% |
| % soft clipped | 2.60% | 2.57% |
| % Q30 bases | 83.45% | 83.88% |
| Non-duplicate proper read pairs | 874,000 | 928,787 (6.27%) |

Figure 41

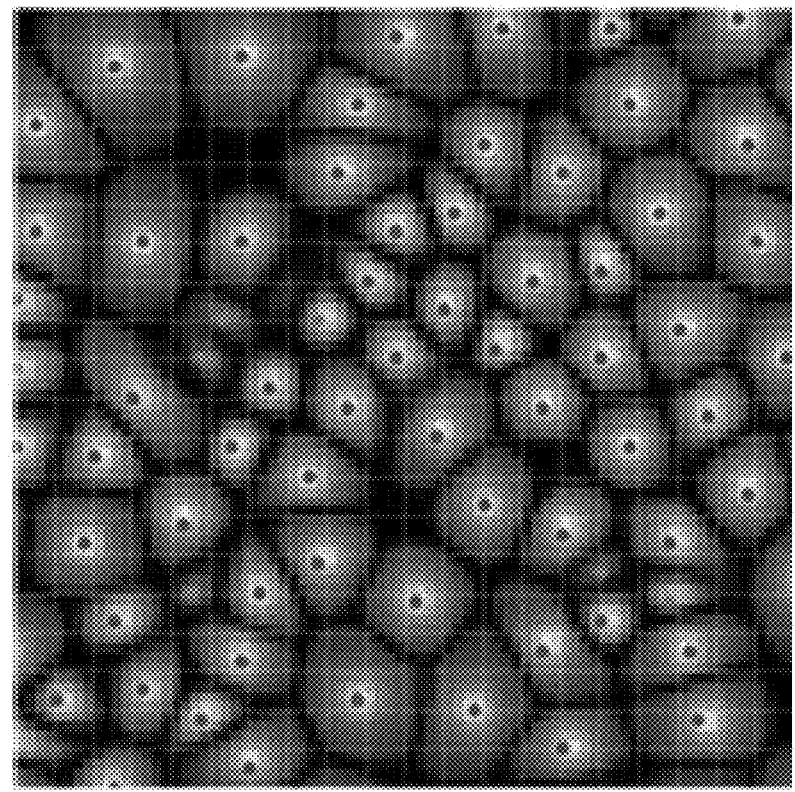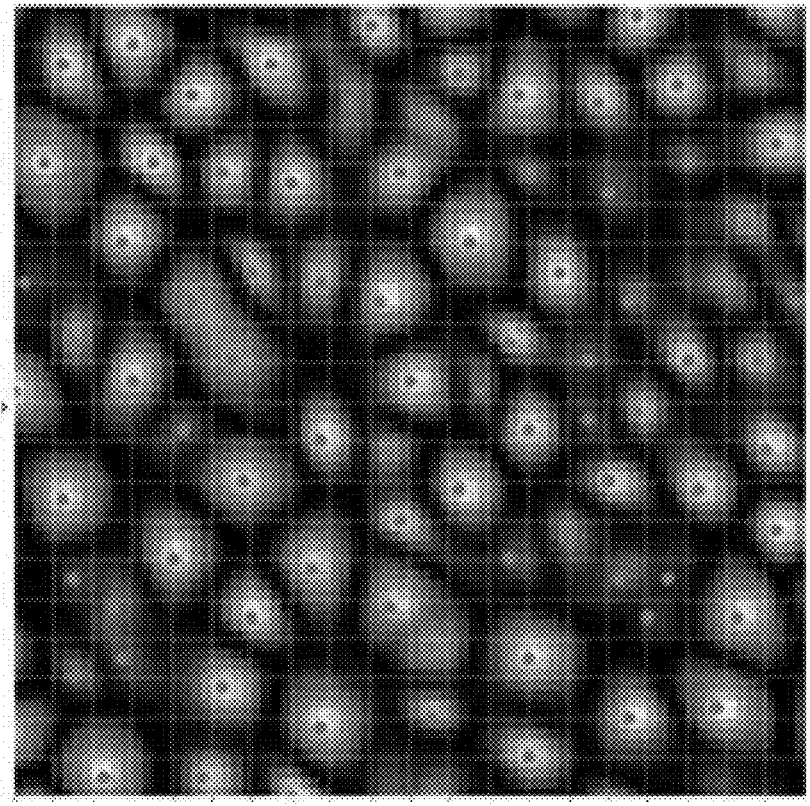
Figure 43

DENSE RUN 40pM Tile: 1101 (7 cycles)

| | RTA | Within Boundary +/- 10 (Unet) |
|---|---|---|
| # clusters | 1,089,460 | 1,509,395 |
| % PF | 42.60% (464,095) | 54.00% (815,168) |
| % Aligned | 93.00% | 96.58% |
| % Duplicate | 0.25% | 0.04% |
| % Mismatch | 2.93% | 2.02% |
| % soft clipped | 4.79% | 11.83% |
| % Q30 bases | 60.10% | 65.33% |
| Non-duplicate proper read pairs | 415,877 | 771,851 (85.6%) |
| Total aligned bases | 117,893,944 | 207,335,632 |

Figure 44

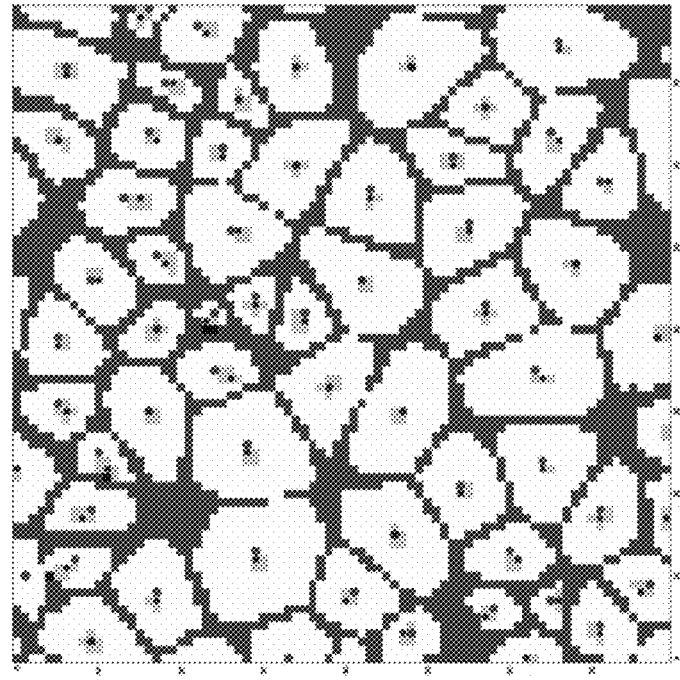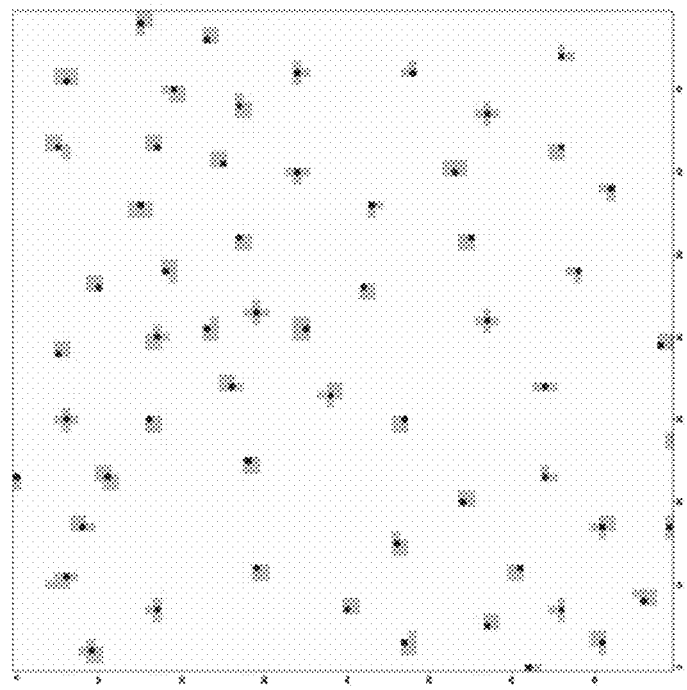
Figure 52b

| Layer (type) | Output Shape | Param # |
|---|---|---|
| input_1 (InputLayer) | (None, 80, 80, 28) | 0 |
| conv2d_1 (Conv2D) | (None, 80, 80, 32) | 8064 |
| batch_normalization_1 (Batch | (None, 80, 80, 32) | 128 |
| conv2d_2 (Conv2D) | (None, 80, 80, 32) | 9216 |
| batch_normalization_2 (Batch | (None, 80, 80, 32) | 128 |
| max_pooling2d_1 (MaxPooling2 | (None, 40, 40, 32) | 0 |
| conv2d_3 (Conv2D) | (None, 40, 40, 64) | 18432 |
| batch_normalization_3 (Batch | (None, 40, 40, 64) | 256 |
| conv2d_4 (Conv2D) | (None, 40, 40, 64) | 36864 |
| batch_normalization_4 (Batch | (None, 40, 40, 64) | 256 |
| max_pooling2d_2 (MaxPooling2 | (None, 20, 20, 64) | 0 |
| conv2d_5 (Conv2D) | (None, 20, 20, 128) | 73728 |
| batch_normalization_5 (Batch | (None, 20, 20, 128) | 512 |
| conv2d_6 (Conv2D) | (None, 20, 20, 128) | 147456 |
| batch_normalization_6 (Batch | (None, 20, 20, 128) | 512 |
| dropout_1 (Dropout) | (None, 20, 20, 128) | 0 |
| max_pooling2d_3 (MaxPooling2 | (None, 10, 10, 128) | 0 |
| conv2d_7 (Conv2D) | (None, 10, 10, 512) | 589824 |
| batch_normalization_7 (Batch | (None, 10, 10, 512) | 2048 |
| dropout_2 (Dropout) | (None, 10, 10, 512) | 0 |
| up_sampling2d_1 (UpSampling2 | (None, 20, 20, 512) | 0 |
| conv2d_8 (Conv2D) | (None, 20, 20, 128) | 589824 |
| batch_normalization_8 (Batch | (None, 20, 20, 128) | 512 |
| conv2d_9 (Conv2D) | (None, 20, 20, 128) | 147456 |
| batch_normalization_9 (Batch | (None, 20, 20, 128) | 512 |
| dropout_3 (Dropout) | (None, 20, 20, 128) | 0 |
| up_sampling2d_2 (UpSampling2 | (None, 40, 40, 128) | 0 |
| conv2d_10 (Conv2D) | (None, 40, 40, 64) | 73728 |
| batch_normalization_10 (Batc | (None, 40, 40, 64) | 256 |
| conv2d_11 (Conv2D) | (None, 40, 40, 64) | 36864 |
| batch_normalization_11 (Batc | (None, 40, 40, 64) | 256 |
| up_sampling2d_3 (UpSampling2 | (None, 80, 80, 64) | 0 |
| conv2d_12 (Conv2D) | (None, 80, 80, 32) | 18432 |
| batch_normalization_12 (Batc | (None, 80, 80, 32) | 128 |
| conv2d_13 (Conv2D) | (None, 80, 80, 32) | 9216 |
| batch_normalization_13 (Batc | (None, 80, 80, 32) | 128 |
| pred (Conv2D) | (None, 80, 80, 2) | 64 |

Total params: 1,764,800
Trainable params: 1,761,984
Non-trainable params: 2,816

Three-Category Classification: Predictions
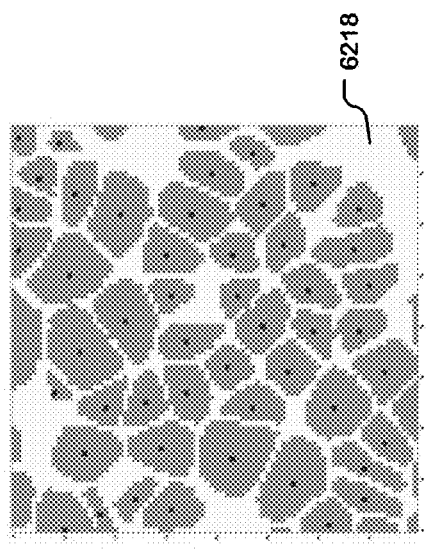
Truth map
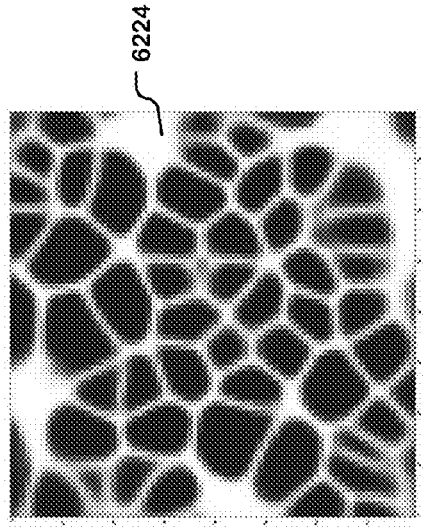
Background
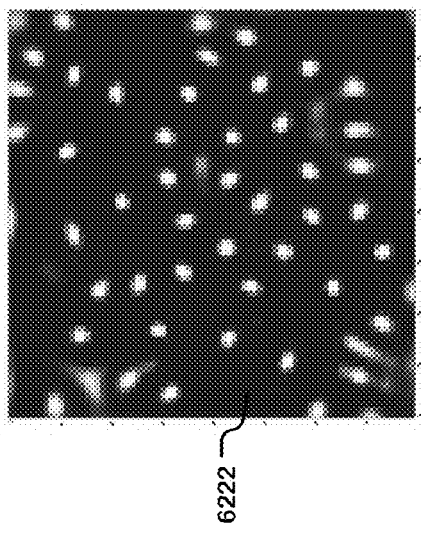
Cluster centers
Figure 62c
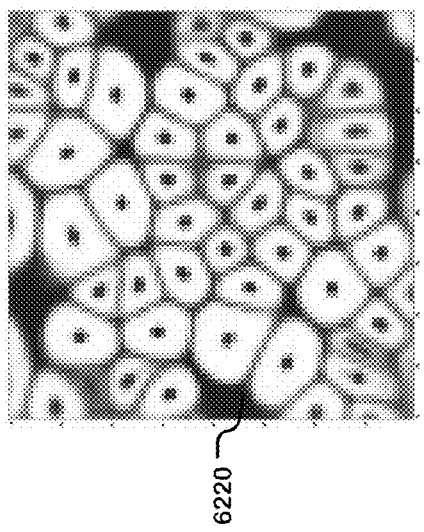
Cluster interiors
Model predictions

Basecall comparisons (using RTA 1.18)

| | RTA | DL binary classification | DL regression |
|---|---|---|---|
| # clusters | 493,944 | 519,100 | 543,348 |
| % PF | 88.8% | 86.99% | 85.86% |
| % Aligned | 97.63% | 97.68% | 97.67% |
| % Duplicate | 0.02% | 0.2% | 0.14% |
| % Mismatch | 0.34% | 0.29% | 0.29% |
| % soft clipped | 2.02% | 1.97% | 1.97% |
| % Q30 bases | 91.94% | 92.76% | 92.81% |
| Total proper read pairs | 422,907 | 435,737 | 449,993 |
| Non-duplicate proper read pairs | 424,665 | 434,869 | 449,344 |

Figure 64

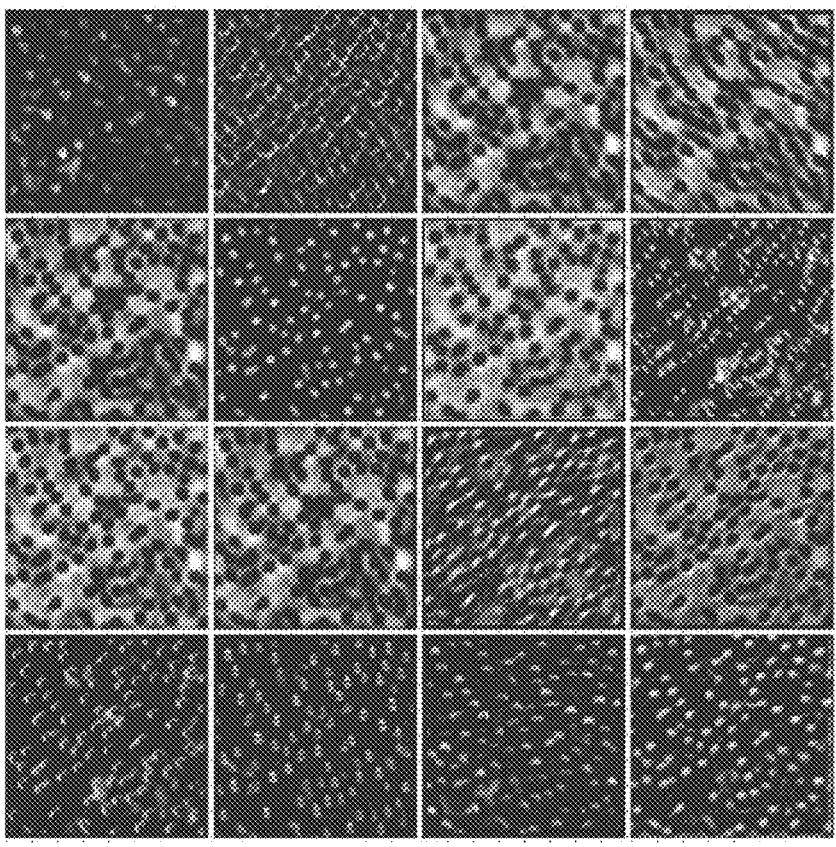
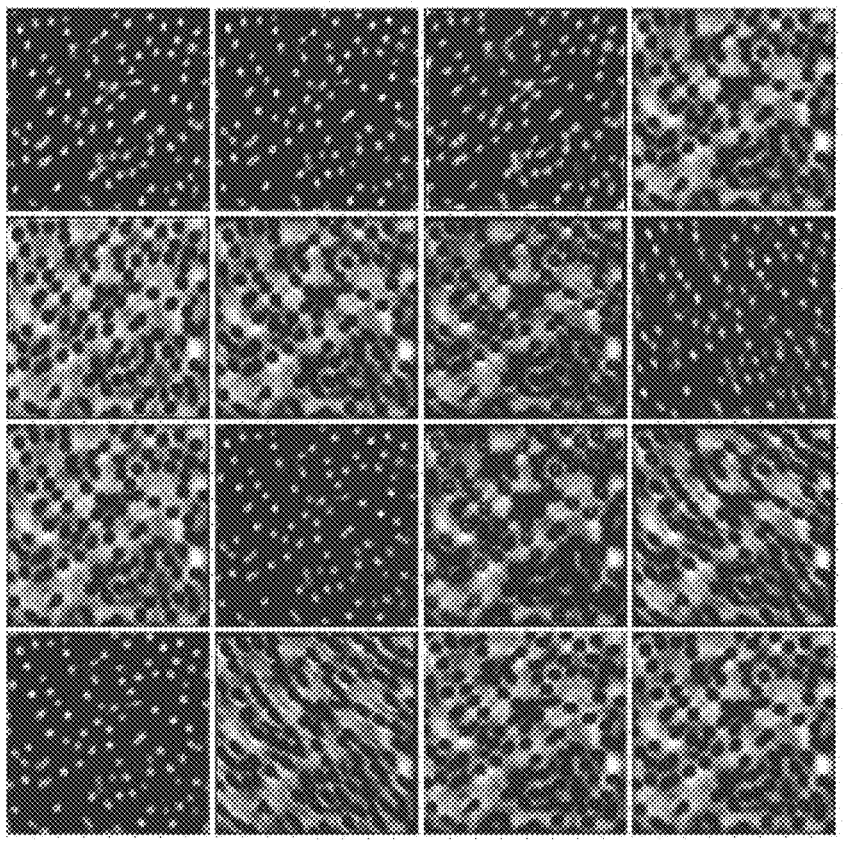
Figure 70

Probe imaging data
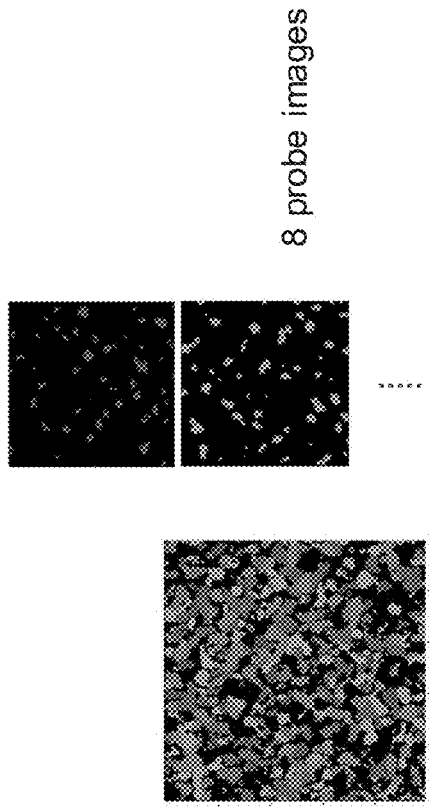
Probe imaging using STORM probes
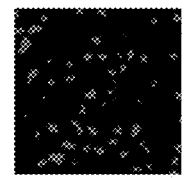
STORM probes – 8 oligos labelled with Alexa-Fluor 647, designed to hybridise to the i7 index region
8 probe images
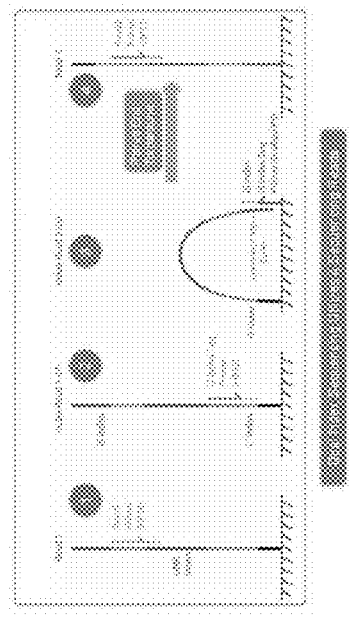
Datasets
Miseq, Human 40pM
Miseq, Human 80pM
Miseq, E. Coli 40pM
101 cycles of read 1 + i7 index cycles
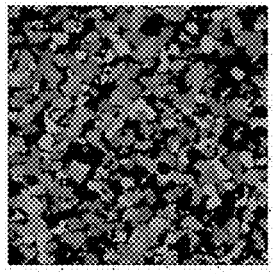
Figure 71

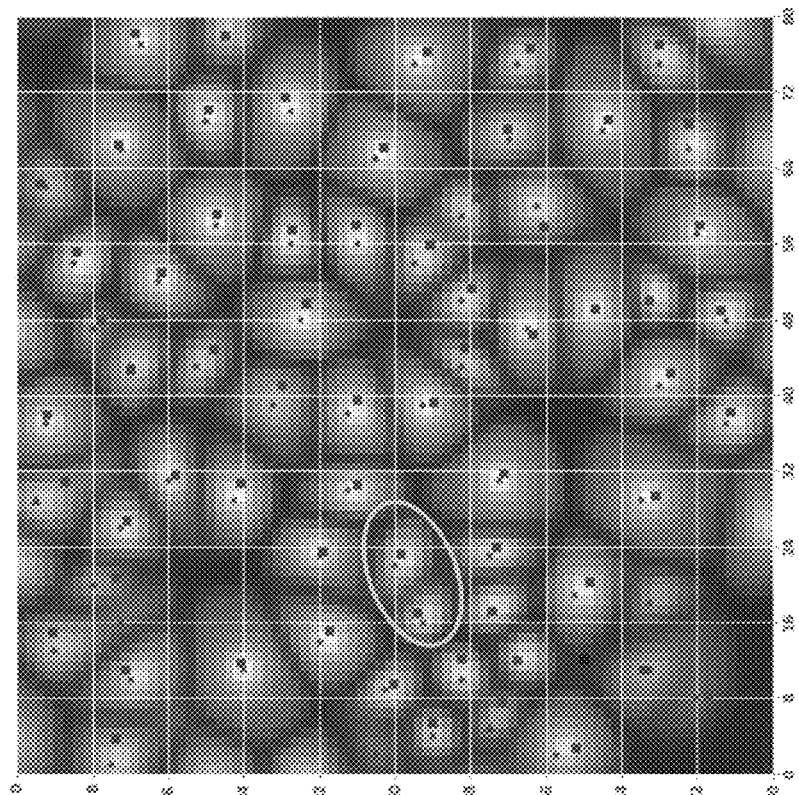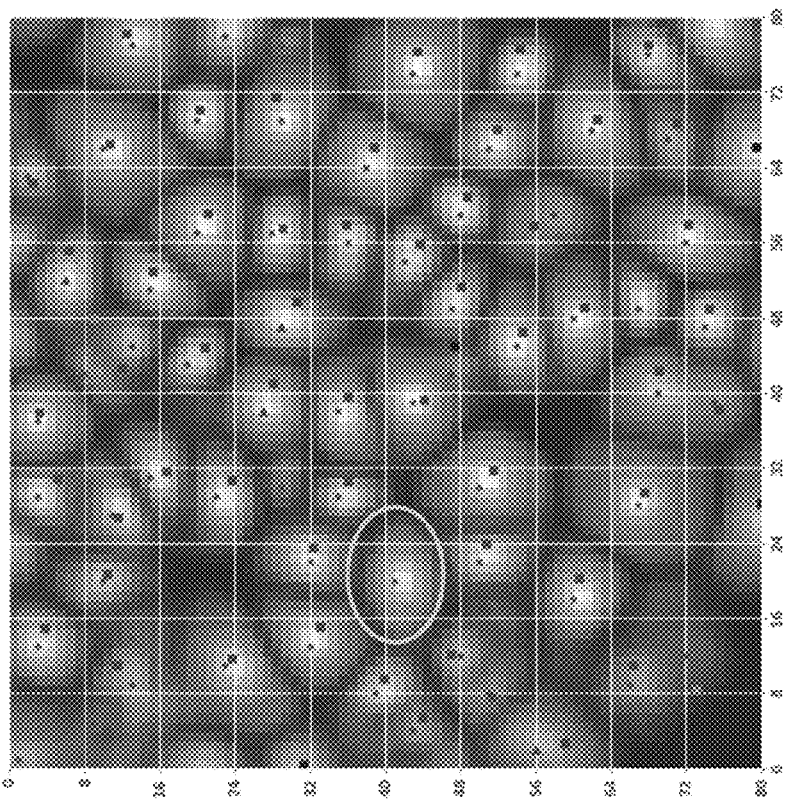
Figure 74

RTA centers vs. mass centers

Mass centers

956048 + 0 in total (QC-passed reads + QC-failed reads)
158 + 0 secondary
0 + 0 supplementary
841 + 0 duplicates
936609 + 0 mapped (97.97% : N/A)
955890 + 0 paired in sequencing
477945 + 0 read1
477945 + 0 read2
928926 + 0 properly paired (97.18% : N/A)
930732 + 0 with itself and mate mapped
5719 + 0 singletons (0.60% : N/A)
0 + 0 with mate mapped to a different chr
0 + 0 with mate mapped to a different chr (mapQ>=5)

bases mapped: 141404101  # ignores clipping
bases mapped (cigar): 140673703
bases trimmed: 0
bases duplicated:    126991
mismatches:    498799  # from NM fields
error rate: 3.545787e-03  # mismatches / bases mapped (cigar)

RTA centers

956054 + 0 in total (QC-passed reads + QC-failed reads)
164 + 0 secondary
0 + 0 supplementary
1045 + 0 duplicates
932910 + 0 mapped (97.58% : N/A)
955890 + 0 paired in sequencing
477945 + 0 read1
477945 + 0 read2
923322 + 0 properly paired (96.59% : N/A)
925276 + 0 with itself and mate mapped
7470 + 0 singletons (0.78% : N/A)
0 + 0 with mate mapped to a different chr
0 + 0 with mate mapped to a different chr (mapQ>=5)

bases mapped: 140844646  # ignores clipping
bases mapped (cigar): 139683478
bases trimmed: 0
bases duplicated: 157795
mismatches: 821045  # from NM fields
error rate: 5.877897e-03  # mismatches / bases mapped (cigar)

Figure 75

Extra grown clusters

```
102777 + 0 in total (QC-passed reads + QC-failed reads)
27 + 0 secondary
0 + 0 supplementary
129 + 0 duplicates
99134 + 0 mapped (96.46% : N/A)
102750 + 0 paired in sequencing
51375 + 0 read1
51375 + 0 read2
96742 + 0 properly paired (94.15% : N/A)
97296 + 0 with itself and mate mapped
1811 + 0 singletons (1.76% : N/A)
0 + 0 with mate mapped to a different chr
0 + 0 with mate mapped to a different chr (mapQ>=5)
```

```
bases mapped: 14965157    # ignores clipping
bases mapped (cigar): 14637927
bases trimmed: 0
bases duplicated: 19479
mismatches: 285579    # from NM fields
error rate: 1.950952e-02    # mismatches / bases mapped (cigar)
```

Figure 76

Data sets

Miseq

| Library | Density | RTA PF% |
|---|---|---|
| 20pM | 1254 K/mm2 | 85% |
| 30pM | 1524 K/mm2 | 72% |
| 40pM | 1529 K/mm2 | 31% |

Nextseq

| Library | RTA PF% |
|---|---|
| 1.3pM | 61% |
| 1.3pM | 42% |
| 3pM | 14% |

Figure 77

TRAINING DATA GENERATION FOR ARTIFICIAL INTELLIGENCE-BASED SEQUENCING

PRIORITY APPLICATIONS

This application claims priority to or the benefit of the following applications:

U.S. Provisional Patent Application No. 62/821,602, entitled "Training Data Generation for Artificial Intelligence-Based Sequencing," filed 21 Mar. 2019;

U.S. Provisional Patent Application No. 62/821,618, entitled "Artificial Intelligence-Based Generation of Sequencing Metadata," filed 21 Mar. 2019;

U.S. Provisional Patent Application No. 62/821,681, entitled "Artificial Intelligence-Based Base Calling," filed 21 Mar. 2019;

U.S. Provisional Patent Application No. 62/821,724, entitled "Artificial Intelligence-Based Quality Scoring," filed 21 Mar. 2019;

U.S. Provisional Patent Application No. 62/821,766, entitled "Artificial Intelligence-Based Sequencing," filed 21 Mar. 2019;

The priority applications are hereby incorporated by reference for all purposes as if fully set forth herein.

INCORPORATIONS

The following are incorporated by reference for all purposes as if fully set forth herein:

U.S. patent application Ser. No. 16/825,991, entitled "Artificial Intelligence-Based Generation of Sequencing Metadata," filed contemporaneously on 20 Mar. 2020;

U.S. patent application Ser. No. 16/826,126, entitled "Artificial Intelligence-Based Base Calling," filed contemporaneously on 20 Mar. 2020;

U.S. patent application Ser. No. 16/826,134, entitled "Artificial Intelligence-Based Quality Scoring," filed contemporaneously on 20 Mar. 2020;

U.S. patent application Ser. No. 16/826,168, entitled "Artificial Intelligence-Based Sequencing," filed contemporaneously on 20 Mar. 2020;

U.S. Provisional Patent Application No. 62/849,091, entitled, "Systems and Devices for Characterization and Performance Analysis of Pixel-Based Sequencing," filed May 16, 2019;

U.S. Provisional Patent Application No. 62/849,132, entitled, "Base Calling Using Convolutions," filed May 16, 2019;

U.S. Provisional Patent Application No. 62/849,133, entitled, "Base Calling Using Compact Convolutions," filed May 16, 2019;

U.S. Provisional Patent Application No. 62/979,384, entitled, "Artificial Intelligence-Based Base Calling of Index Sequences," filed Feb. 20, 2020;

U.S. Provisional Patent Application No. 62/979,414, entitled, "Artificial Intelligence-Based Many-To-Many Base Calling," filed Feb. 20, 2020;

U.S. Provisional Patent Application No. 62/979,385, entitled, "Knowledge Distillation-Based Compression of Artificial Intelligence-Based Base Caller," filed Feb. 20, 2020;

U.S. Provisional Patent Application No. 62/979,412, entitled, "Multi-Cycle Cluster Based Real Time Analysis System," filed Feb. 20, 2020;

U.S. Provisional Patent Application No. 62/979,411, entitled, "Data Compression for Artificial Intelligence-Based Base Calling," filed Feb. 20, 2020;

U.S. Provisional Patent Application No. 62/979,399, entitled, "Squeezing Layer for Artificial Intelligence-Based Base Calling," filed Feb. 20, 2020;

Liu P, Hemani A, Paul K, Weis C, Jung M, Wehn N. 3D-Stacked Many-Core Architecture for Biological Sequence Analysis Problems. Int J Parallel Prog. 2017; 45(6):1420-60;

Z. Wu, K. Hammad, R Mittmann, S. Magierowski, E. Ghafar-Zadeh, and X. Zhong, "FPGA-Based DNA Basecalling Hardware Acceleration," in Proc. IEEE 61st Int. Midwest Symp. Circuits Syst., August 2018, pp. 1098-1101;

Z. Wu, K. Hammad, E Ghafar-Zadeh, and S. Magierowski, "FPGA-Accelerated 3rd Generation DNA Sequencing," in IEEE Transactions on Biomedical Circuits and Systems, Volume 14, Issue 1, February 2020, pp. 65-74;

Prabhakar et al., "Plasticine: A Reconfigurable Architecture for Parallel Patterns," ISCA '17, Jun. 24-28, 2017, Toronto, ON, Canada;

M. Lin, Q. Chen, and S. Yan, "Network in Network," in Proc. of ICLR, 2014;

L. Sifre, "Rigid-motion Scattering for Image Classification, Ph.D. thesis, 2014;

L. Sifre and S. Mallat, "Rotation, Scaling and Deformation Invariant Scattering for Texture Discrimination," in Proc. of CVPR, 2013;

F. Chollet, "Xception: Deep Learning with Depthwise Separable Convolutions," in Proc. of CVPR, 2017;

X. Zhang, X. Zhou, M. Lin, and J. Sun, "ShuffleNet: An Extremely Efficient Convolutional Neural Network for Mobile Devices," in arXiv:1707.01083, 2017;

K. He, X. Zhang, S. Ren, and J. Sun, "Deep Residual Learning for Image Recognition," in Proc. of CVPR, 2016;

S. Xie, R. Girshick, P. Dollar, Z. Tu, and K. He, "Aggregated Residual Transformations for Deep Neural Networks," in Proc. of CVPR, 2017;

A. G. Howard, M. Zhu, B. Chen, D. Kalenichenko, W. Wang, T. Weyand, M. Andreetto, and H. Adam, "Mobilenets: Efficient Convolutional Neural Networks for Mobile Vision Applications," in arXiv:1704.04861, 2017;

M. Sandler, A. Howard, M. Zhu, A. Zhmoginov, and L. Chen, "MobileNetV2: Inverted Residuals and Linear Bottlenecks," in arXiv:1801.04381v3, 2018;

Z. Qin, Z. Zhang, X. Chen, and Y. Peng, "FD-MobileNet: Improved MobileNet with a Fast Downsampling Strategy," in arXiv:1802.03750, 2018;

Liang-Chieh Chen, George Papandreou, Florian Schroff, and Hartwig Adam. Rethinking atrous convolution for semantic image segmentation. CoRR, abs/1706.05587, 2017;

J. Huang, V. Rathod, C. Sun, M. Zhu, A. Korattikara, A. Fathi, I. Fischer, Z. Wojna, Y. Song, S. Guadarrama, et al. Speed/accuracy trade-offs for modern convolutional object detectors. arXiv preprint arXiv:1611.10012, 2016;

S. Dieleman, H. Zen, K. Simonyan, O. Vinyals, A. Graves, N. Kalchbrenner, A. Senior, and K. Kavukcuoglu, "WAVENET: A GENERATIVE MODEL FOR RAW AUDIO," arXiv:1609.03499, 2016;

S. Ö. Arik, M. Chrzanowski, A. Coates, G. Diamos, A. Gibiansky, Y. Kang, X. Li, J. Miller, A. Ng, J. Raiman, S Sengupta and M. Shoeybi, "DEEP VOICE: REAL-TIME NEURAL TEXT-TO-SPEECH," arXiv:1702.07825, 2017;

F. Yu and V. Koltun, "MULTI-SCALE CONTEXT AGGREGATION BY DILATED CONVOLUTIONS," arXiv: 1511.07122, 2016;

K. He, X. Zhang, S. Ren, and J. Sun, "DEEP RESIDUAL LEARNING FOR IMAGE RECOGNITION," arXiv: 1512.03385, 2015;

R. K. Srivastava, K. Greff, and J. Schmidhuber, "HIGHWAY NETWORKS," arXiv: 1505.00387, 2015;

G. Huang, Z. Liu, L. van der Maaten and K. Q. Weinberger, "DENSELY CONNECTED CONVOLUTIONAL NETWORKS," arXiv:1608.06993, 2017;

C. Szegedy, W. Liu, Y. Jia, P. Sermanet, S. Reed, D. Anguelov, D. Erhan, V. Vanhoucke, and A. Rabinovich, "GOING DEEPER WITH CONVOLUTIONS," arXiv: 1409.4842, 2014;

S. Ioffe and C. Szegedy, "BATCH NORMALIZATION: ACCELERATING DEEP NETWORK TRAINING BY REDUCING INTERNAL COVARIATE SHIFT," arXiv: 1502.03167, 2015;

J. M. Wolterink, T. Leiner, M. A. Viergever, and I. Išgum, "DILATED CONVOLUTIONAL NEURAL NETWORKS FOR CARDIOVASCULAR MR SEGMENTATION IN CONGENITAL HEART DISEASE," arXiv: 1704.03669, 2017;

L. C. Piqueras, "AUTOREGRESSIVE MODEL BASED ON A DEEP CONVOLUTIONAL NEURAL NETWORK FOR AUDIO GENERATION," Tampere University of Technology, 2016;

J. Wu, "Introduction to Convolutional Neural Networks," Nanjing University, 2017;

"Illumina CMOS Chip and One-Channel SBS Chemistry", Illumina, Inc. 2018, 2 pages;

"skikit-image/peak.py at master", GitHub, 5 pages, [retrieved on 2018-11-16]. Retrieved from the Internet <URL: (https://)github.com/scikit-image/scikit-image/blob/master/skimage/feature/peak.py#L25>;

"3.3.9.11. Watershed and random walker for segmentation", Scipy lecture notes, 2 pages, [retrieved on 2018-11-13]. Retrieved from the Internet <URL: (http://)scipy-lectures.org/packages/scikit-image/auto_examples/plot_segmentations.html>;

Mordvintsev, Alexander and Revision, Abid K., "Image Segmentation with Watershed Algorithm", Revision 43532856, 2013, 6 pages [retrieved on 2018-11-13]. Retrieved from the Internet <URL:(https://)opencv-python-tutroals.readthedocs.io/en/latest/py_tutorials/py_imgproc/py_watershed/py_watershed.html>;

Mzur, "Watershed.py", 25 Oct. 2017, 3 pages, [retrieved on 2018-November 2013]. Retrieved from the Internet <URL: (https://)github.com/mzur/watershed/blob/master/Watershed.py>;

Thakur, Pratibha, et. al. "A Survey of Image Segmentation Techniques", International Journal of Research in Computer Applications and Robotics, Vol. 2, Issue. 4, April 2014, Pg.: 158-165;

Long, Jonathan, et. al., "Fully Convolutional Networks for Semantic Segmentation", IEEE Transactions on Pattern Analysis and Machine Intelligence, Vol 39, Issue 4, 1 Apr. 2017, 10 pages;

Ronneberger, Olaf, et. al., "U-net: Convolutional networks for biomedical image segmentation." In *International Conference on Medical image computing and computer-assisted intervention,* 18 May 2015, 8 pages;

Xie, W., et. al., "Microscopy cell counting and detection with fully convolutional regression networks", *Computer methods in biomechanics and biomedical engineering: Imaging & Visualization,* 6(3), pp. 283-292, 2018;

Xie, Yuanpu, et al., "Beyond classification: structured regression for robust cell detection using convolutional neural network", *International Conference on Medical Image Computing and Computer-Assisted Intervention.* October 2015, 12 pages;

Snuverink, I. A. F., "Deep Learning for Pixelwise Classification of Hyperspectral Images", Master of Science Thesis, Delft University of Technology, 23 Nov. 2017, 19 pages;

Shevchenko, A., "Keras weighted categorical_crossentropy", 1 page, [retrieved on 2019-01-15]. Retrieved from the Internet <URL: (https://)gist.github.com/skeeet/cad06d584548fb45eece1d4e28cfa98b>, van den Assem, D. C. F., "Predicting periodic and chaotic signals using Wavenets", Master of Science Thesis, Delft University of Technology, 18 Aug. 2017, pages 3-38;

I. J. Goodfellow, D. Warde-Farley, M. Mirza, A. Courville, and Y. Bengio, "CONVOLUTIONAL NETWORKS", Deep Learning, MIT Press, 2016; and J. Gu, Z. Wang, J. Kuen, L. Ma, A. Shahroudy, B. Shuai, T. Liu, X. Wang, and G. Wang, "RECENT ADVANCES IN CONVOLUTIONAL NEURAL NETWORKS," arXiv: 1512.07108, 2017.

FIELD OF THE TECHNOLOGY DISCLOSED

The technology disclosed relates to artificial intelligence type computers and digital data processing systems and corresponding data processing methods and products for emulation of intelligence (i.e., knowledge based systems, reasoning systems, and knowledge acquisition systems); and including systems for reasoning with uncertainty (e.g., fuzzy logic systems), adaptive systems, machine learning systems, and artificial neural networks. In particular, the technology disclosed relates to using deep neural networks such as deep convolutional neural networks for analyzing data.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

Deep neural networks are a type of artificial neural networks that use multiple nonlinear and complex transforming layers to successively model high-level features. Deep neural networks provide feedback via backpropagation which carries the difference between observed and predicted output to adjust parameters. Deep neural networks have evolved with the availability of large training datasets, the power of parallel and distributed computing, and sophisticated training algorithms. Deep neural networks have facilitated major advances in numerous domains such as computer vision, speech recognition, and natural language processing.

Convolutional neural networks (CNNs) and recurrent neural networks (RNNs) are components of deep neural networks. Convolutional neural networks have succeeded particularly in image recognition with an architecture that comprises convolution layers, nonlinear layers, and pooling layers. Recurrent neural networks are designed to utilize sequential information of input data with cyclic connections among building blocks like perceptrons, long short-term memory units, and gated recurrent units. In addition, many other emergent deep neural networks have been proposed for limited contexts, such as deep spatio-temporal neural networks, multi-dimensional recurrent neural networks, and convolutional auto-encoders.

The goal of training deep neural networks is optimization of the weight parameters in each layer, which gradually combines simpler features into complex features so that the most suitable hierarchical representations can be learned from data. A single cycle of the optimization process is organized as follows. First, given a training dataset, the forward pass sequentially computes the output in each layer and propagates the function signals forward through the network. In the final output layer, an objective loss function measures error between the inferenced outputs and the given labels. To minimize the training error, the backward pass uses the chain rule to backpropagate error signals and compute gradients with respect to all weights throughout the neural network. Finally, the weight parameters are updated using optimization algorithms based on stochastic gradient descent. Whereas batch gradient descent performs parameter updates for each complete dataset, stochastic gradient descent provides stochastic approximations by performing the updates for each small set of data examples. Several optimization algorithms stem from stochastic gradient descent. For example, the Adagrad and Adam training algorithms perform stochastic gradient descent while adaptively modifying learning rates based on update frequency and moments of the gradients for each parameter, respectively.

Another core element in the training of deep neural networks is regularization, which refers to strategies intended to avoid overfitting and thus achieve good generalization performance. For example, weight decay adds a penalty term to the objective loss function so that weight parameters converge to smaller absolute values. Dropout randomly removes hidden units from neural networks during training and can be considered an ensemble of possible subnetworks. To enhance the capabilities of dropout, a new activation function, maxout, and a variant of dropout for recurrent neural networks called rnnDrop have been proposed. Furthermore, batch normalization provides a new regularization method through normalization of scalar features for each activation within a mini-batch and learning each mean and variance as parameters.

Given that sequenced data are multi- and high-dimensional, deep neural networks have great promise for bioinformatics research because of their broad applicability and enhanced prediction power. Convolutional neural networks have been adapted to solve sequence-based problems in genomics such as motif discovery, pathogenic variant identification, and gene expression inference. Convolutional neural networks use a weight-sharing strategy that is especially useful for studying DNA because it can capture sequence motifs, which are short, recurring local patterns in DNA that are presumed to have significant biological functions. A hallmark of convolutional neural networks is the use of convolution filters.

Unlike traditional classification approaches that are based on elaborately-designed and manually-crafted features, convolution filters perform adaptive learning of features, analogous to a process of mapping raw input data to the informative representation of knowledge. In this sense, the convolution filters serve as a series of motif scanners, since a set of such filters is capable of recognizing relevant patterns in the input and updating themselves during the training procedure. Recurrent neural networks can capture long-range dependencies in sequential data of varying lengths, such as protein or DNA sequences.

Therefore, an opportunity arises to use a principled deep learning-based framework for template generation and base calling.

In the era of high-throughput technology, amassing the highest yield of interpretable data at the lowest cost per effort remains a significant challenge. Cluster-based methods of nucleic acid sequencing, such as those that utilize bridge amplification for cluster formation, have made a valuable contribution toward the goal of increasing the throughput of nucleic acid sequencing. These cluster-based methods rely on sequencing a dense population of nucleic acids immobilized on a solid support, and typically involve the use of image analysis software to deconvolve optical signals generated in the course of simultaneously sequencing multiple clusters situated at distinct locations on a solid support.

However, such solid-phase nucleic acid cluster-based sequencing technologies still face considerable obstacles that limit the amount of throughput that can be achieved. For example, in cluster-based sequencing methods, determining the nucleic acid sequences of two or more clusters that are physically too close to one another to be resolved spatially, or that in fact physically overlap on the solid support, can pose an obstacle. For example, current image analysis software can require valuable time and computational resources for determining from which of two overlapping clusters an optical signal has emanated. As a consequence, compromises are inevitable for a variety of detection platforms with respect to the quantity and/or quality of nucleic acid sequence information that can be obtained.

High density nucleic acid cluster-based genomics methods extend to other areas of genome analysis as well. For example, nucleic acid cluster-based genomics can be used in sequencing applications, diagnostics and screening, gene expression analysis, epigenetic analysis, genetic analysis of polymorphisms, and the like. Each of these nucleic acid cluster-based genomics technologies, too, is limited when there is an inability to resolve data generated from closely proximate or spatially overlapping nucleic acid clusters.

Clearly there remains a need for increasing the quality and quantity of nucleic acid sequencing data that can be obtained rapidly and cost-effectively for a wide variety of uses, including for genomics (e.g., for genome characterization of any and all animal, plant, microbial or other biological species or populations), pharmacogenomics, transcriptomics, diagnostics, prognostics, biomedical risk assessment, clinical and research genetics, personalized medicine, drug efficacy and drug interactions assessments, veterinary medicine, agriculture, evolutionary and biodiversity studies, aquaculture, forestry, oceanography, ecological and environmental management, and other purposes.

The technology disclosed provides neural network-based methods and systems that address these and similar needs, including increasing the level of throughput in high-throughput nucleic acid sequencing technologies, and offers other related advantages.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The color drawings also may be available in PAIR via the Supplemental Content tab.

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIG. 7 depicts one example of merging subpixel base calls produced over the plurality of sequencing cycles to generate the so-called "cluster maps" that contain the cluster metadata.

FIG. 32 is a table that shows an example U-Net architecture of the regression model.

FIG. 33 illustrates different approaches of extracting cluster intensity using cluster shape information identified in a template image.

FIG. 35 illustrates the difference in base calling performance when the RTA base caller uses ground truth center of mass (COM) location as the cluster center, as opposed to using a non-COM location as the cluster center. The results show that using COM improves base calling.

FIG. 36 shows, on the left, an example decay map produced the regression model. On the right, FIG. 36 also shows an example ground truth decay map that the regression model approximates during the training.

FIG. 38 compares peaks detected by the peak locator in a decay map produced by the regression model with peaks in a corresponding ground truth decay map.

FIG. 40 compares performance of the regression model with the RTA base caller for 20 pM library concentration (normal run).

FIG. 41 compares performance of the regression model with the RTA base caller for 30 pM library concentration (dense run).

FIG. 43 shows, on the right, a first decay map produced by the regression model. On the left, FIG. 43 shows a second decay map produced by the regression model.

FIG. 44 compares performance of the regression model with the RTA base caller for 40 pM library concentration (highly dense run).

FIG. 45 shows the results of the thresholding, the peak locating, and the watershed segmentation technique applied to the first decay map.

FIG. 52b illustrates performance of the binary classification model using a precision statistic.

FIG. 53 is a table that shows an example architecture of the binary classification model.

FIG. 57 is a table that shows an example architecture of the ternary classification model.

FIG. 62c shows yet other example predictions of the ternary classification model.

FIG. 63 depicts one implementation of deriving the cluster centers and cluster shapes from the output of the ternary classification model in FIG. 62a.

FIG. 64 compares base calling performance of the binary classification model, the regression model, and the RTA base caller.

FIG. 70 overlays cluster center predictions made by the RTA base caller (in pink) onto visualization of the trained convolution filters of the penultimate layer of the binary classification model.

FIG. 71 illustrates one implementation of training data used to train the neural network-based template generator.

FIG. 74 shows how the neural network-based template generator's ability to distinguish between adjacent clusters improves when the number of initial sequencing cycles for which the input image data is used increases from five to seven.

FIG. 75 illustrates the difference in base calling performance when a RTA base caller uses ground truth center of mass (COM) location as the cluster center, as opposed to when a non-COM location is used as the cluster center.

FIG. 76 portrays the performance of the neural network-based template generator on extra detected clusters.

FIG. 77 shows different datasets used for training the neural network-based template generator.

DETAILED DESCRIPTION

Figure 1:
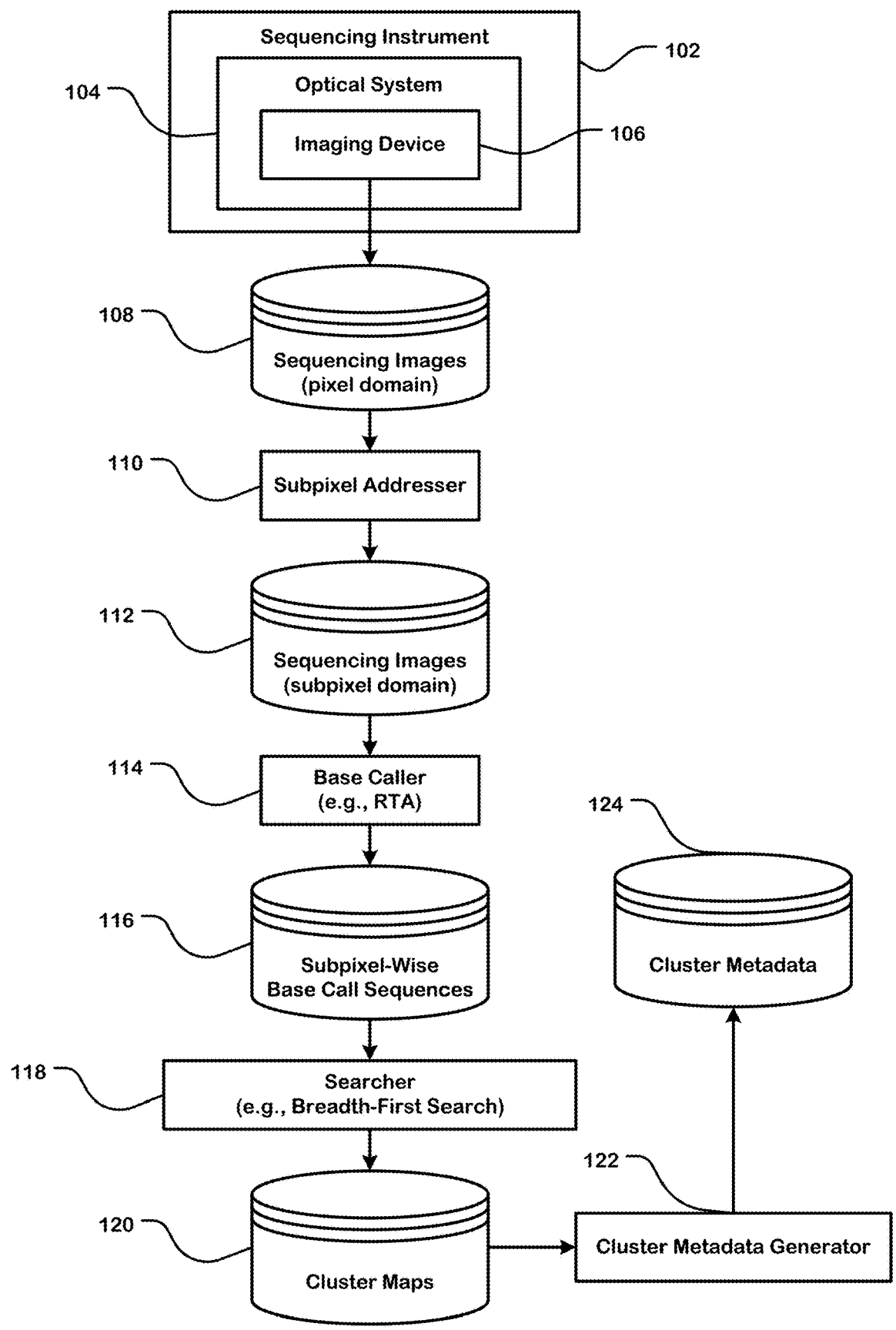
FIG. 1 shows one implementation of a processing pipeline that determines cluster metadata using subpixel base calling.

The following discussion is presented to enable any person skilled in the art to make and use the technology disclosed, and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown, but is to be accorded the widest scope consistent with the principles and features disclosed herein.

Introduction

Base calling from digital images is massively parallel and computationally intensive. This presents numerous technical challenges that we identify before introducing our new technology.

The signal from an image set being evaluated is increasingly faint as classification of bases proceeds in cycles, especially over increasingly long strands of bases. The signal-to-noise ratio decreases as base classification extends over the length of a strand, so reliability decreases. Updated estimates of reliability are expected as the estimated reliability of base classification changes.

Digital images are captured from amplified clusters of sample strands. Samples are amplified by duplicating strands using a variety of physical structures and chemistries. During sequencing by synthesis, tags are chemically attached in cycles and stimulated to glow. Digital sensors collect photons from the tags that are read out of pixels to produce images.

Interpreting digital images to classify bases requires resolving positional uncertainty, handicapped by limited image resolution. At a greater resolution than collected during base calling, it is apparent imaged clusters have irregular shapes and indeterminate center positions. Cluster positions are not mechanically regulated, so cluster centers are not aligned with pixel centers. A pixel center can be the integer coordinate assigned to a pixel. In other implementations, it can be the top-left corner of the pixel. In yet other implementations, it can be the centroid or center-of-mass of the pixel. Amplification does not produce uniform cluster shapes. Distribution of cluster signals in the digital image is, therefore, a statistical distribution rather than a regular pattern. We call this positional uncertainty.

One of the signal classes may produce no detectable signal and be classified at a particular position based on a "dark" signal. Thus, templates are necessary for classification during dark cycles. Production of templates resolves initial positional uncertainty using multiple imaging cycles to avoid missing dark signals.

Trade-offs in image sensor size, magnification, and stepper design lead to pixel sizes that are relatively large, that are too large to treat cluster centers as coincident with sensor pixel centers. This disclosure uses pixel in two senses. The physical, sensor pixel is a region of an optical sensor that reports detected photons. A logical pixel, simply referred to as a pixel, is data corresponding to at least one physical pixel, data read from the sensor pixel. The pixel can be subdivided or "up sampled" into sub pixels, such as 4×4 sub pixels. To take into account the possibility that all the photons are hitting one side of the physical pixel and not the opposite side, values can be assigned to sub pixels by interpolation, such as bilinear interpolation or area weighting. Interpolation or bilinear interpolation also is applied when pixels are re-framed by applying an affine transformation to data from physical pixels.

Larger physical pixels are more sensitive to faint signals than smaller pixels. While digital sensors improve with time, the physical limitation of collector surface area is unavoidable. Taking design trade-offs into consideration, legacy systems have been designed to collect and analyze image data from a three-by-three patch of sensor pixels, with the center of the cluster somewhere in the center pixel of the patch.

High resolution sensors capture only part of an imaged media at a time. The sensor is stepped over the imaged media to cover the whole field. Thousands of digital images can be collected during one processing cycle.

Sensor and illumination design are combined to distinguish among at least four illumination response values that are used to classify bases. If a traditional RGB camera with a Bayer color filter array were used, four sensor pixels would be combined into a single RGB value. This would reduce the effective sensor resolution by four-fold. Alternatively, multiple images can be collected at a single position using different illumination wavelengths and/or different filters rotated into position between the imaged media and the sensor. The number of images required to distinguish among four base classifications varies between systems. Some systems use one image with four intensity levels for different classes of bases. Other systems use two images with different illumination wavelengths (red and green, for instance) and/or filters with a sort of truth table to classify bases. Systems also can use four images with different illumination wavelengths and/or filters tuned to specific base classes.

Massively parallel processing of digital images is practically necessary to align and combine relatively short strands, on the order of 30 to 2000 base pairs, into longer sequences, potentially millions or even billions of bases in length. Redundant samples are desirable over an imaged media, so a part of a sequence may be covered by dozens of sample reads. Millions or at least hundreds of thousands of sample clusters are imaged from a single imaged media. Massively parallel processing of so many clusters has increased in sequencing capacity while decreasing cost.

The capacity for sequencing has increased at a pace that rivals Moore's law. While the first sequencing cost billions of dollars, in 2018 services such as Illumina™ are delivering results for hundred(s) of dollars. As sequencing goes mainstream and unit prices drop, less computing power is available for classification, which increases the challenge of near real time classification. With these technical challenges in mind, we turn to the technology disclosed.

The technology disclosed improves processing during both template generation to resolve positional uncertainty and during base classification of clusters at resolved positions. Applying the technology disclosed, less expensive hardware can be used to reduce the cost of machines. Near real time analysis can become cost effective, reducing the lag between image collection and base classification.

The technology disclosed can use upsampled images produced by interpolating sensor pixels into subpixels and then producing templates that resolve positional uncertainty. A resulting subpixel is submitted to a base caller for classification that treats the subpixel as if it were at the center of a cluster. Clusters are determined from groups of adjoining subpixels that repeatedly receive the same base classification. This aspect of the technology leverages existing base calling technology to determine shapes of clusters and to hyper-locate cluster centers with a subpixel resolution.

Another aspect of the technology disclosed is to create ground truth, training data sets that pair images with confidently determined cluster centers and/or cluster shapes. Deep learning systems and other machine learning approaches require substantial training sets. Human curated data is expensive to compile. The technology disclosed can be used to leverage existing classifiers, in a non-standard mode of operation, to generate large sets of confidently classified training data without intervention or the expense of a human curator. The training data correlates raw images with cluster centers and/or cluster shapes available from existing classifiers, in a non-standard mode of operation, such as CNN-based deep learning systems, which can then directly process image sequences. One training image can be rotated and reflected to produce additional, equally valid examples. Training examples can focus on regions of a predetermined size within an overall image. The context evaluated during base calling determines the size of example training regions, rather than the size of an image from or overall imaged media.

The technology disclosed can produce different types of maps, usable as training data or as templates for base classification, which correlate cluster centers and/or cluster shapes with digital images. First, a subpixel can be classified as a cluster center, thereby localizing a cluster center within a physical sensor pixel. Second, a cluster center can be calculated as the centroid of a cluster shape. This location can be reported with a selected numeric precision. Third, a cluster center can be reported with surrounding subpixels in a decay map, either at subpixel or pixel resolution. A decay map reduces weight given to photons detected in regions as separation of the regions from the cluster center increase, attenuating signals from more distant positions. Fourth, binary or ternary classifications can be applied to subpixels or pixels in clusters of adjoining regions. In binary classification, a region is classified as belonging to a cluster center or as background. In ternary classification, the third class type is assigned to the region that contains the cluster interior, but not the cluster center. Subpixel classification of cluster center locations could be substituted for real valued cluster center coordinates within a larger optical pixel.

The alternative styles of maps can initially be produced as ground truth data sets, or, with training, they can be produced using a neural network. For instance, clusters can be depicted as disjoint regions of adjoining subpixels with appropriate classifications. Intensity mapped clusters from a neural network can be post-processed by a peak detector filter, to calculate cluster centers, if the centers have not already been determined. Applying a so-called watershed analysis, abutting regions can be assigned to separate clusters. When produced by a neural network inference engine, the maps can be used as templates for evaluating a sequence of digital images and classifying bases over cycles of base calling.

Neural Network-Based Template Generation

The first step of template generation is determining cluster metadata. Cluster metadata identifies spatial distribution of clusters, including their centers, shapes, sizes, background, and/or boundaries.

Determining Cluster Metadata

FIG. 1 shows one implementation of a processing pipeline that determines cluster metadata using subpixel base calling.

Figure 2:
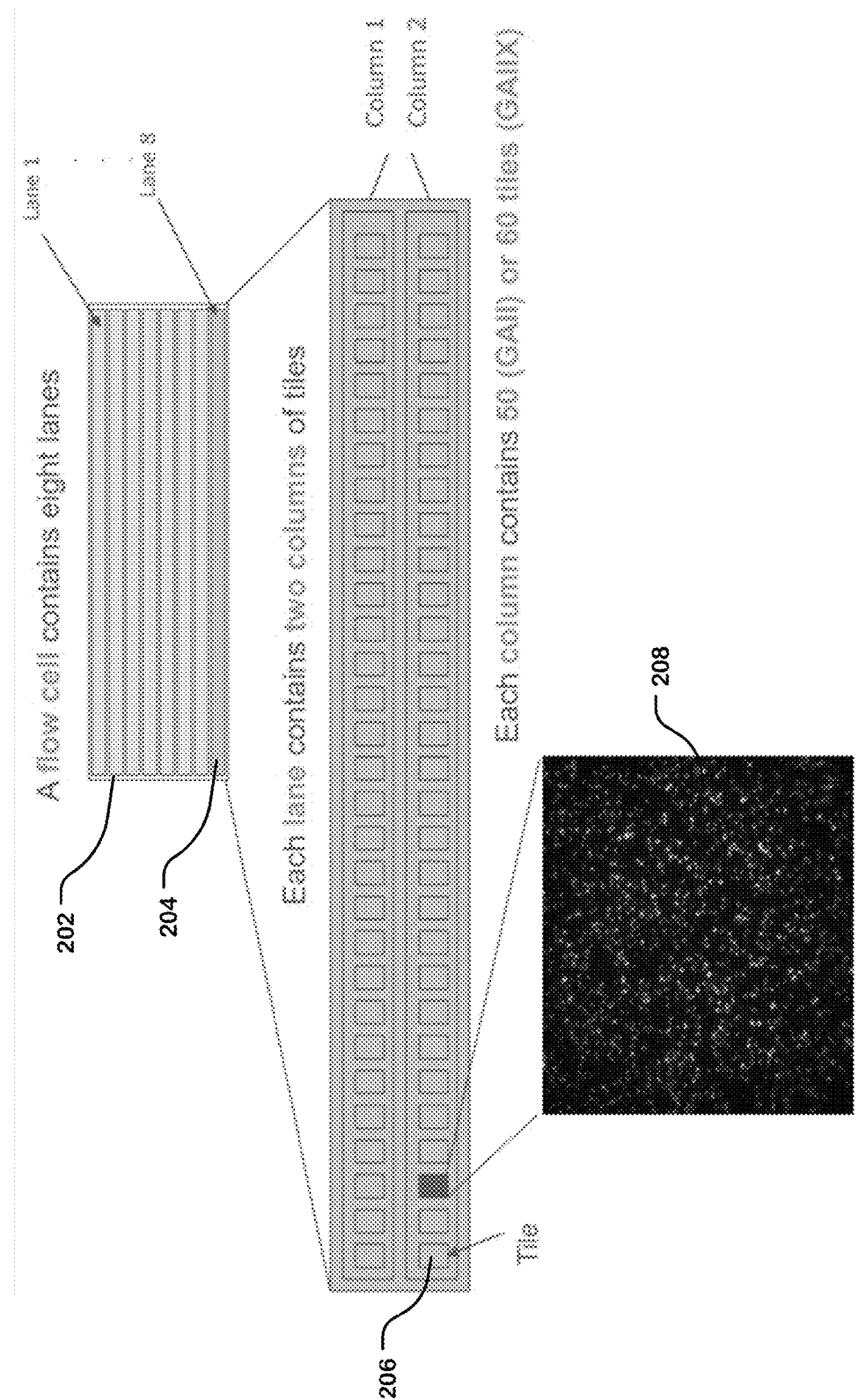
FIG. 2 depicts one implementation of a flow cell that contains clusters in its tiles.

FIG. 2 depicts one implementation of a flow cell that contains clusters in its tiles. The flow cell is partitioned into lanes. The lanes are further partitioned into non-overlapping regions called "tiles". During the sequencing procedure, the clusters and their surrounding background on the tiles are imaged.

Figure 3:
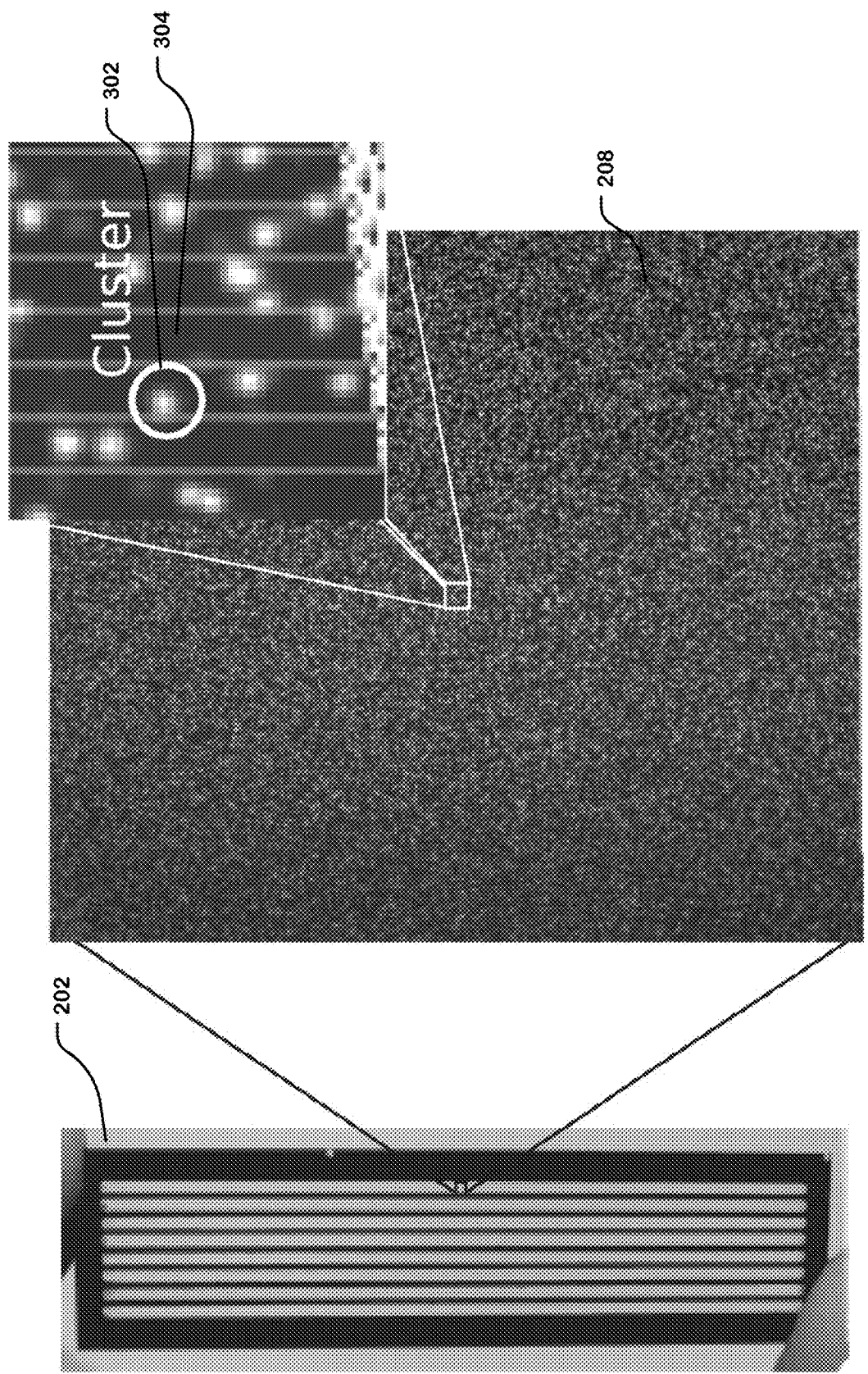
FIG. 3 illustrates one example of the Illumina GA-IIx flow cell with eight lanes.

FIG. 3 illustrates an example Illumina GA-IIx™ flow cell with eight lanes. FIG. 3 also shows a zoom-in on one tile and its clusters and their surrounding background.

Figure 4:
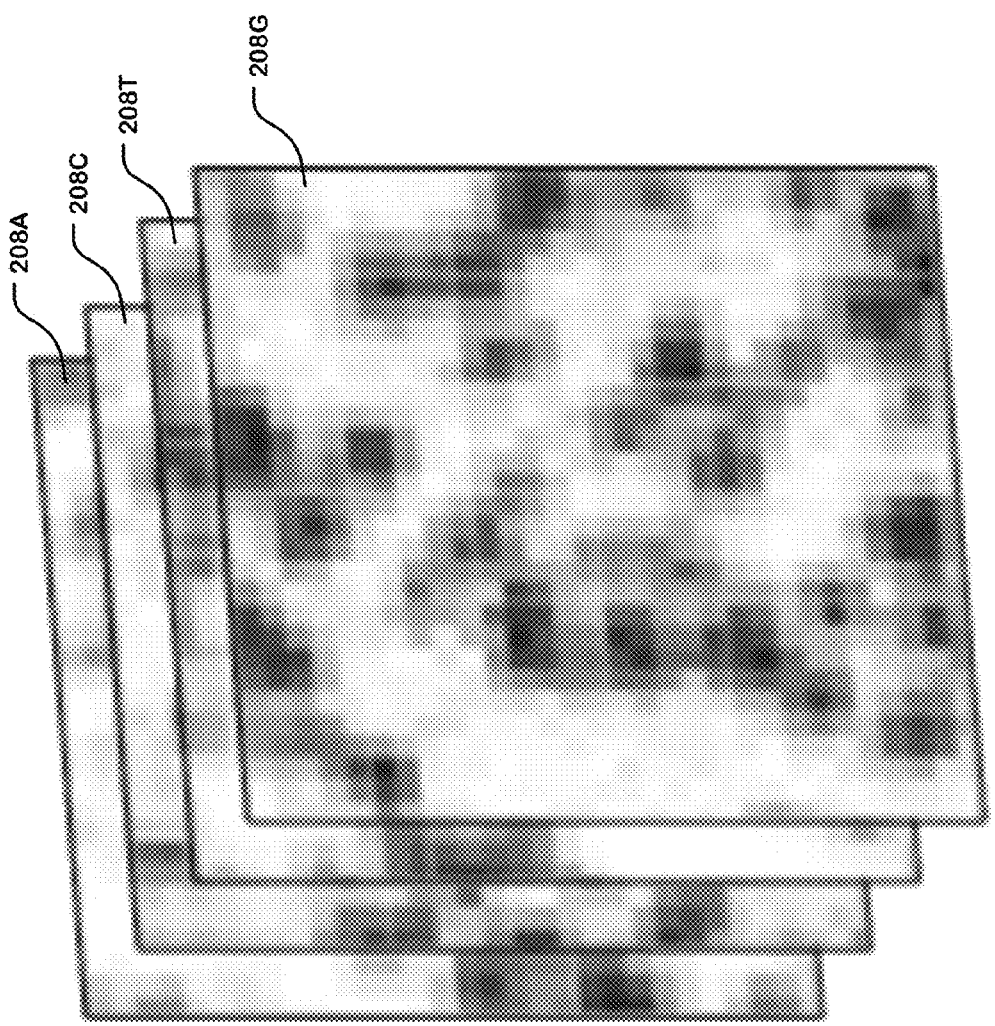
FIG. 4 depicts an image set of sequencing images for four-channel chemistry, i.e., the image set has four sequencing images, captured using four different wavelength bands (image/imaging channel) in the pixel domain.

FIG. 4 depicts an image set of sequencing images for four-channel chemistry, i.e., the image set has four sequencing images, captured using four different wavelength bands (image/imaging channel) in the pixel domain. Each image in the image set covers a tile of a flow cell and depicts intensity emissions of clusters on the tile and their surrounding background captured for a particular image channel at a particular one of a plurality of sequencing cycles of a sequencing run performed on the flow cell. In one implementation, each imaged channel corresponds to one of a plurality of filter wavelength bands. In another implementation, each imaged channel corresponds to one of a plurality of imaging events at a sequencing cycle. In yet another implementation, each imaged channel corresponds to a combination of illumination with a specific laser and imaging through a specific optical filter. The intensity emissions of a cluster comprise signals detected from an analyte that can be used to classify a base associated with the analyte. For example, the intensity emissions may be signals indicative of photons emitted by tags that are chemically attached to an analyte during a cycle when the tags are stimulated and that may be detected by one or more digital sensors, as described above.

Figure 5:
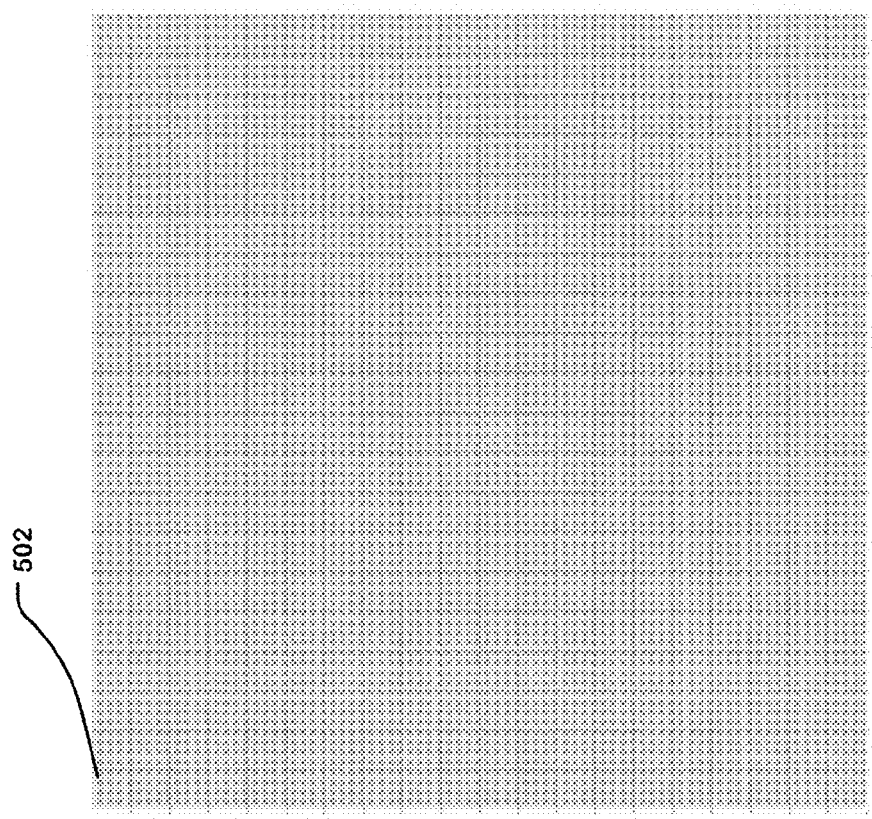
FIG. 5 is one implementation of dividing a sequencing image into subpixels (or subpixel regions).

FIG. 5 is one implementation of dividing a sequencing image into subpixels (or subpixel regions). In the illustrated implementation, quarter (0.25) subpixels are used, which results in each pixel in the sequencing image being divided into sixteen subpixels. Given that the illustrated sequencing image has a resolution of 20×20 pixels, i.e., 400 pixels, the division produces 6400 subpixels. Each of the subpixels is treated by a base caller as a region center for subpixel base calling. In some implementations, this base caller does not use neural network-based processing. In other implementations, this base caller is a neural network-based base caller.

For a given sequencing cycle and a particular subpixel, the base caller is configured with logic to produce a base call for the given sequencing cycle particular subpixel by performing image processing steps and extracting intensity data for the subpixel from the corresponding image set of the sequencing cycle. This is done for each of the subpixels and for each of a plurality of sequencing cycles. Experiments have also been carried out with quarter subpixel division of 1800×1800 pixel resolution tile images of the Illumina MiSeq sequencer. Subpixel base calling was performed for fifty sequencing cycles and for ten tiles of a lane.

Figure 6:
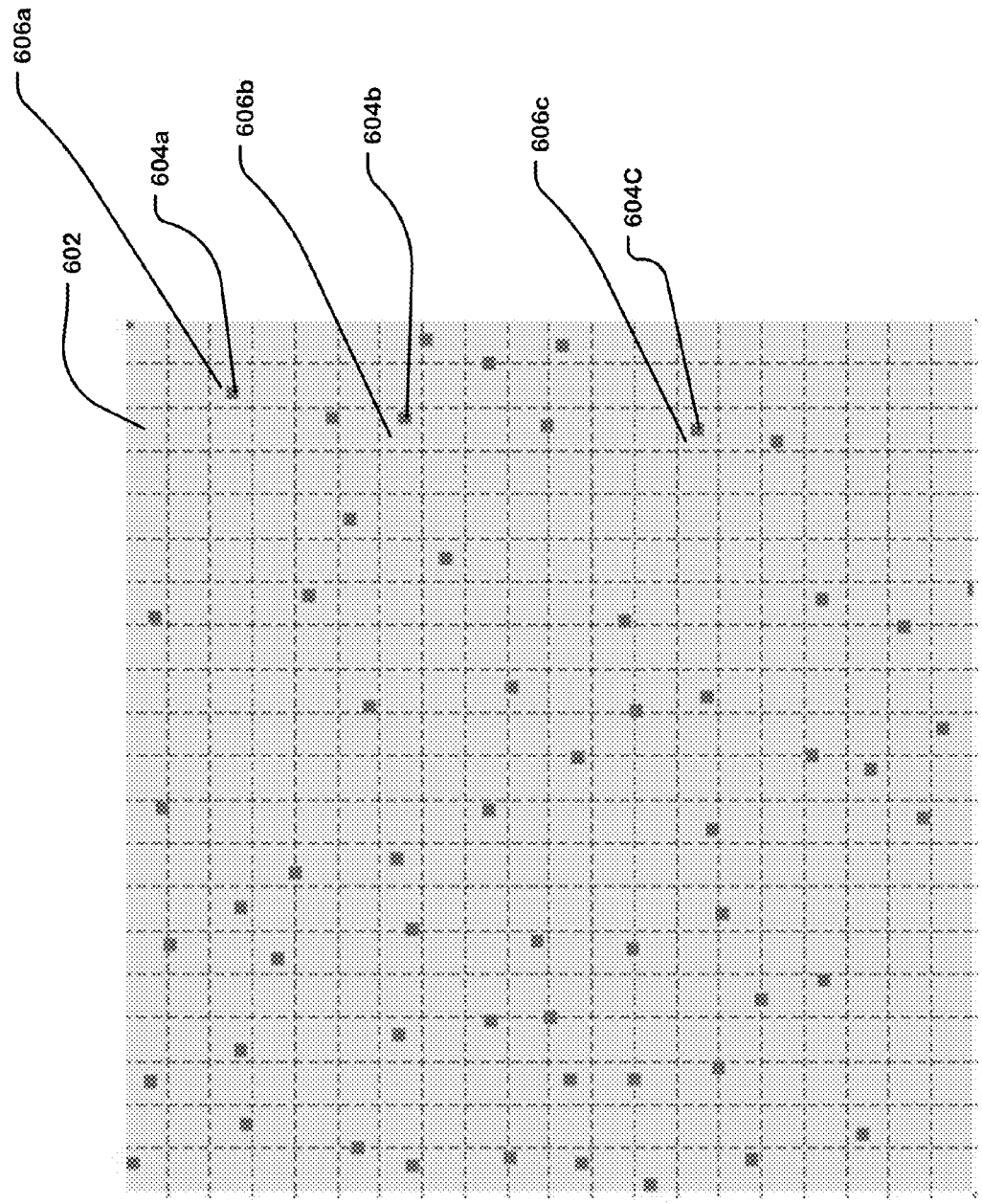
FIG. 6 shows preliminary center coordinates of the clusters identified by the base caller during the subpixel base calling.

FIG. 6 shows preliminary center coordinates of the clusters identified by the base caller during the subpixel base calling. FIG. 6 also shows "origin subpixels" or "center subpixels" that contain the preliminary center coordinates.

FIG. 7 depicts one example of merging subpixel base calls produced over the plurality of sequencing cycles to generate the so-called "cluster maps" that contain the cluster metadata. In the illustrated implementation, the subpixel base calls are merged using a breadth-first search approach.

Figure 8A:
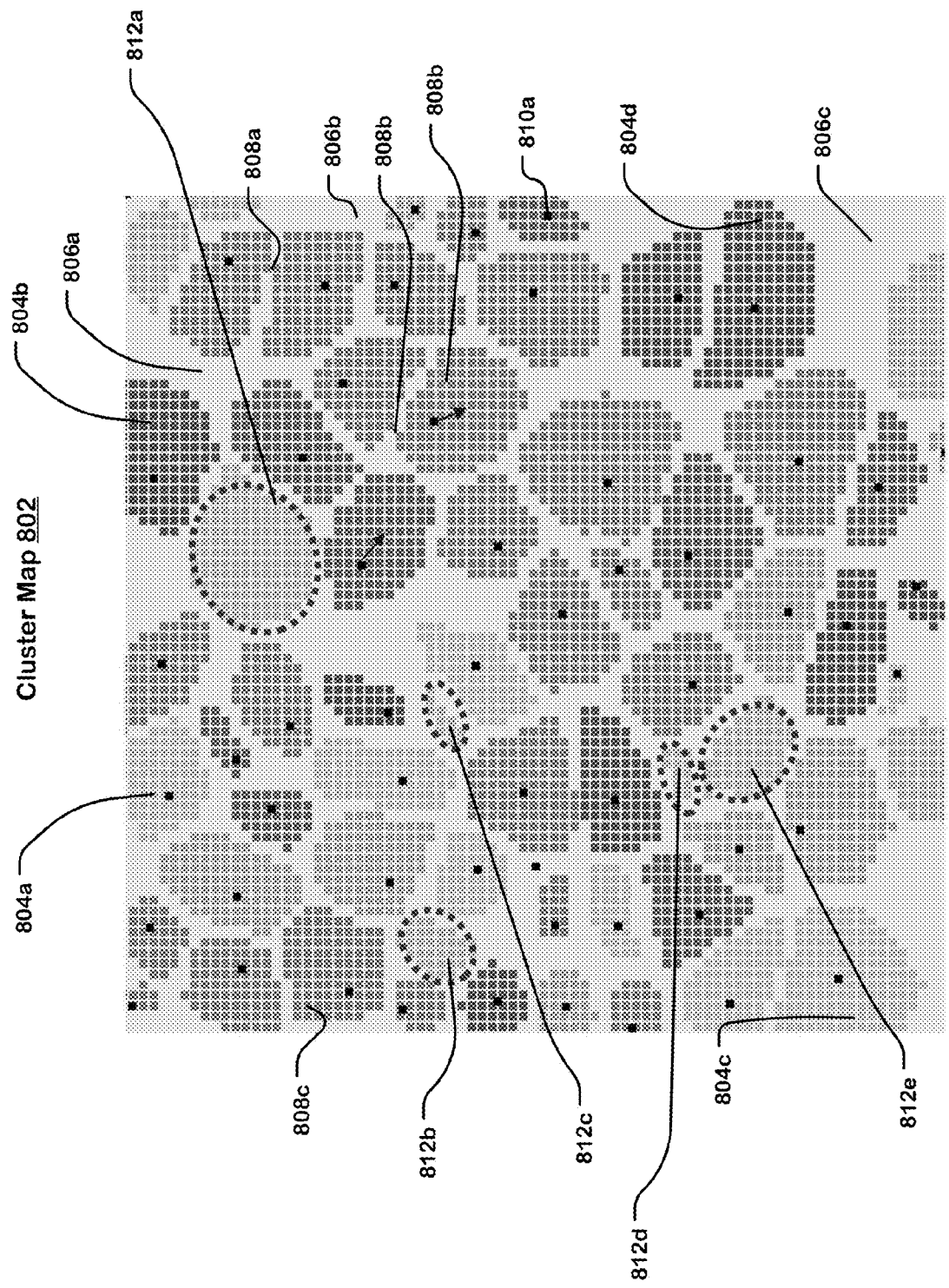
FIG. 8a illustrates one example of a cluster map generated by the merging of the subpixel base calls.
Figure 8B:
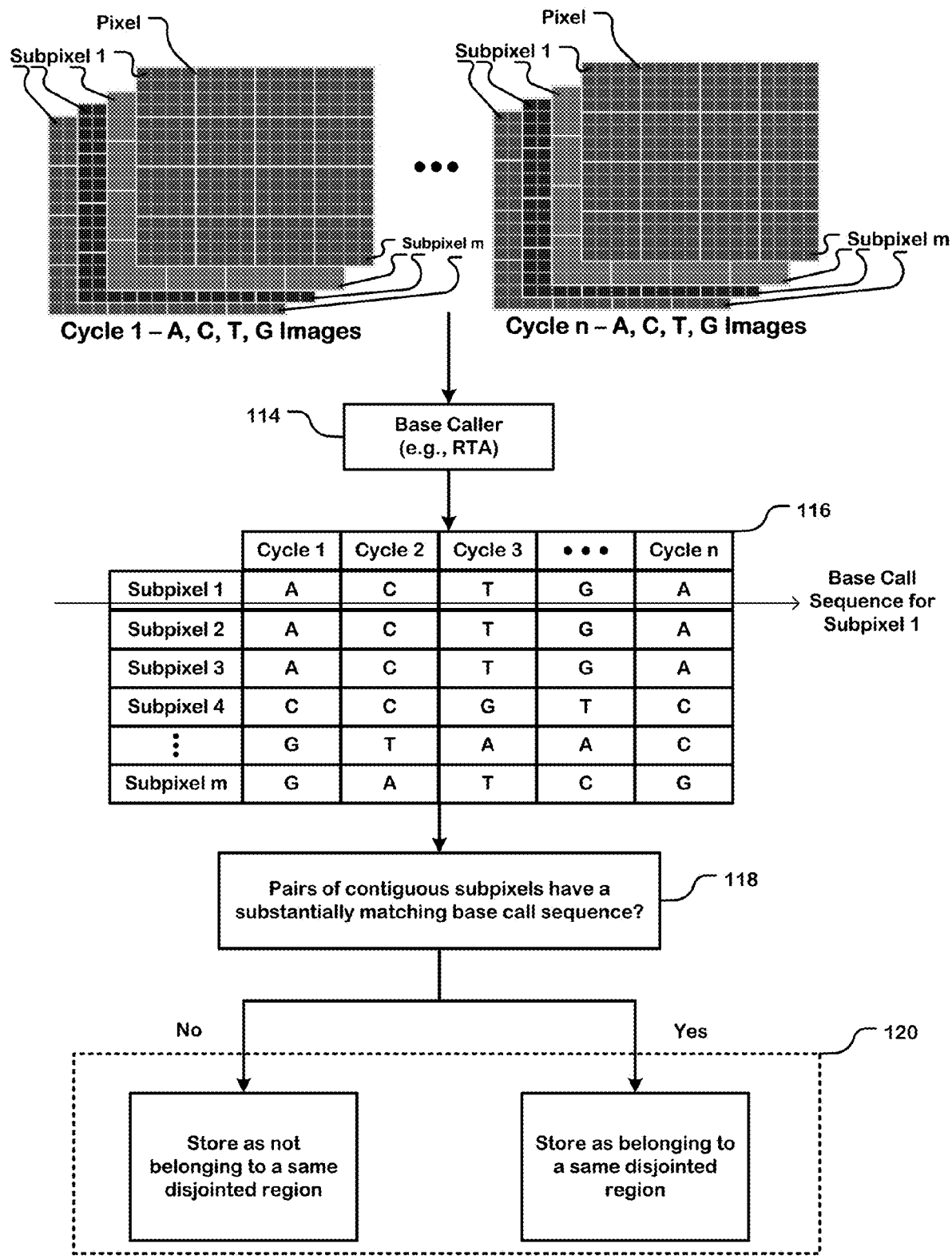
FIG. 8b depicts one implementation of subpixel base calling.

FIG. 8a illustrates one example of a cluster map generated by the merging of the subpixel base calls. FIG. 8b depicts one example of subpixel base calling. FIG. 8b also shows one implementation of analyzing subpixel-wise base call sequences produced from the subpixel base calling to generate a cluster map.

Sequencing Images

Cluster metadata determination involves analyzing image data produced by a sequencing instrument 102 (e.g., Illumina's iSeq, HiSeqX, HiSeq3000, HiSeq4000, HiSeq2500, NovaSeq 6000, NextSeq, NextSeqDx, MiSeq and MiSeqDx). The following discussion outlines how the image data is generated and what it depicts, in accordance with one implementation.

Base calling is the process in which the raw signal of the sequencing instrument 102, i.e., intensity data extracted from images, is decoded into DNA sequences and quality scores. In one implementation, the Illumina platforms employ cyclic reversible termination (CRT) chemistry for base calling. The process relies on growing nascent DNA strands complementary to template DNA strands with modified nucleotides, while tracking an emitted signal of each newly added nucleotide. The modified nucleotides have a 3' removable block that anchors a fluorophore signal of the nucleotide type.

Sequencing occurs in repetitive cycles, each comprising three steps: (a) extension of a nascent strand by adding a modified nucleotide; (b) excitation of the fluorophores using one or more lasers of the optical system 104 and imaging through different filters of the optical system 104, yielding sequencing images 108; and (c) cleavage of the fluorophores and removal of the 3' block in preparation for the next sequencing cycle. Incorporation and imaging cycles are repeated up to a designated number of sequencing cycles, defining the read length of all clusters. Using this approach, each cycle interrogates a new position along the template strands.

The tremendous power of the Illumina platforms stems from their ability to simultaneously execute and sense millions or even billions of clusters undergoing CRT reactions. The sequencing process occurs in a flow cell 202—a small glass slide that holds the input DNA fragments during the sequencing process. The flow cell 202 is connected to the high-throughput optical system 104, which comprises microscopic imaging, excitation lasers, and fluorescence filters. The flow cell 202 comprises multiple chambers called lanes 204. The lanes 204 are physically separated from each other and may contain different tagged sequencing libraries, distinguishable without sample cross contamination. The imaging device 106 (e.g., a solid-state imager such as a charge-coupled device (CCD) or a complementary metal-oxide-semiconductor (CMOS) sensor) takes snapshots at multiple locations along the lanes 204 in a series of non-overlapping regions called tiles 206.

For example, there are a hundred tiles per lane in Illumina Genome Analyzer II and sixty-eight tiles per lane in Illumina HiSeq2000. A tile 206 holds hundreds of thousands to millions of clusters. An image generated from a tile with clusters shown as bright spots is shown at 208. A cluster 302 comprises approximately one thousand identical copies of a template molecule, though clusters vary in size and shape. The clusters are grown from the template molecule, prior to the sequencing run, by bridge amplification of the input library. The purpose of the amplification and cluster growth is to increase the intensity of the emitted signal since the imaging device 106 cannot reliably sense a single fluorophore. However, the physical distance of the DNA fragments within a cluster 302 is small, so the imaging device 106 perceives the cluster of fragments as a single spot 302.

The output of a sequencing run is the sequencing images 108, each depicting intensity emissions of clusters on the tile in the pixel domain for a specific combination of lane, tile, sequencing cycle, and fluorophore (208A, 208C, 208T, 208G).

In one implementation, a biosensor comprises an array of light sensors. A light sensor is configured to sense information from a corresponding pixel area (e.g., a reaction site/well/nanowell) on the detection surface of the biosensor. An analyte disposed in a pixel area is said to be associated with the pixel area, i.e., the associated analyte. At a sequencing cycle, the light sensor corresponding to the pixel area is configured to detect/capture/sense emissions/photons from the associated analyte and, in response, generate a pixel signal for each imaged channel In one implementation, each imaged channel corresponds to one of a plurality of filter wavelength bands. In another implementation, each imaged channel corresponds to one of a plurality of imaging events at a sequencing cycle. In yet another implementation, each imaged channel corresponds to a combination of illumination with a specific laser and imaging through a specific optical filter.

Pixel signals from the light sensors are communicated to a signal processor coupled to the biosensor (e.g., via a communication port). For each sequencing cycle and each imaged channel, the signal processor produces an image whose pixels respectively depict/contain/denote/represent/characterize pixel signals obtained from the corresponding light sensors. This way, a pixel in the image corresponds to: (i) a light sensor of the biosensor that generated the pixel signal depicted by the pixel, (ii) an associated analyte whose emissions were detected by the corresponding light sensor and converted into the pixel signal, and (iii) a pixel area on the detection surface of the biosensor that holds the associated analyte.

Consider, for example, that a sequencing run uses two different imaged channels: a red channel and a green channel. Then, at each sequencing cycle, the signal processor produces a red image and a green image. This way, for a series of k sequencing cycles of the sequencing run, a sequence with k pairs of red and green images is produced as output.

Pixels in the red and green images (i.e., different imaged channels) have one-to-one correspondence within a sequencing cycle. This means that corresponding pixels in a pair of the red and green images depict intensity data for the same associated analyte, albeit in different imaged channels. Similarly, pixels across the pairs of red and green images have one-to-one correspondence between the sequencing cycles. This means that corresponding pixels in different pairs of the red and green images depict intensity data for the same associated analyte, albeit for different acquisition events/timesteps (sequencing cycles) of the sequencing run.

Corresponding pixels in the red and green images (i.e., different imaged channels) can be considered a pixel of a "per-cycle image" that expresses intensity data in a first red channel and a second green channel A per-cycle image whose pixels depict pixel signals for a subset of the pixel areas, i.e., a region (tile) of the detection surface of the biosensor, is called a "per-cycle tile image." A patch extracted from a per-cycle tile image is called a "per-cycle image patch." In one implementation, the patch extraction is performed by an input preparer.

The image data comprises a sequence of per-cycle image patches generated for a series of k sequencing cycles of a sequencing run. The pixels in the per-cycle image patches contain intensity data for associated analytes and the intensity data is obtained for one or more imaged channels (e.g., a red channel and a green channel) by corresponding light sensors configured to detect emissions from the associated analytes. In one implementation, when a single target cluster is to be base called, the per-cycle image patches are centered at a center pixel that contains intensity data for a target associated analyte and non-center pixels in the per-cycle image patches contain intensity data for associated analytes adjacent to the target associated analyte. In one implementation, the image data is prepared by an input preparer.

Subpixel Base Calling

The technology disclosed accesses a series of image sets generated during a sequencing run. The image sets comprise the sequencing images 108. Each image set in the series is captured during a respective sequencing cycle of the sequencing run. Each image (or sequencing image) in the series captures clusters on a tile of a flow cell and their surrounding background.

In one implementation, the sequencing run utilizes four-channel chemistry and each image set has four images. In another implementation, the sequencing run utilizes two-channel chemistry and each image set has two images. In yet another implementation, the sequencing run utilizes one-channel chemistry and each image set has two images. In yet other implementations, each image set has only one image.

The sequencing images 108 in the pixel domain are first converted into the subpixel domain by a subpixel addresser 110 to produce sequencing images 112 in the subpixel domain. In one implementation, each pixel in the sequencing images 108 is divided into sixteen subpixels 502. Thus, in one implementation, the subpixels 502 are quarter subpixels. In another implementation, the subpixels 502 are half subpixels. As a result, each of the sequencing images 112 in the subpixel domain has a plurality of subpixels 502.

The subpixels are then separately fed as input to a base caller 114 to obtain, from the base caller 114, a base call classifying each of the subpixels as one of four bases (A, C, T, and G). This produces a base call sequence 116 for each of the subpixels across a plurality of sequencing cycles of the sequencing run. In one implementation, the subpixels 502 are identified to the base caller 114 based on their integer or non-integer coordinates. By tracking the emission signal from the subpixels 502 across image sets generated during the plurality of sequencing cycles, the base caller 114 recovers the underlying DNA sequence for each subpixel. An example of this is illustrated in FIG. 8b.

In other implementations, the technology disclosed obtains, from the base caller 114, the base call classifying each of the subpixels as one of five bases (A, C, T, G, and N). In such implementations, N base call denotes an undecided base call, usually due to low levels of extracted intensity.

Some examples of the base caller 114 include non-neural network-based Illumina offerings such as the RTA (Real Time Analysis), the Firecrest program of the Genome Analyzer Analysis Pipeline, the IPAR (Integrated Primary Analysis and Reporting) machine, and the OLB (Off-Line Basecaller). For example, the base caller 114 produces the base call sequences by interpolating intensity of the subpixels, including at least one of nearest neighbor intensity extraction, Gaussian based intensity extraction, intensity extraction based on average of 2×2 subpixel area, intensity extraction based on brightest of 2×2 subpixel area, intensity extraction based on average of 3×3 subpixel area, bilinear intensity extraction, bicubic intensity extraction, and/or intensity extraction based on weighted area coverage. These techniques are described in detail in Appendix entitled "Intensity Extraction Methods".

In other implementations, the base caller 114 can be a neural network-based base caller, such as the neural network-based base caller 1514 disclosed herein.

The subpixel-wise base call sequences 116 are then fed as input to a searcher 118. The searcher 118 searches for substantially matching base call sequences of contiguous subpixels. Base call sequences of contiguous subpixels are "substantially matching" when a predetermined portion of base calls match on an ordinal position-wise basis (e.g., >=41 matches in 45 cycles, <=4 mismatches in 45 cycles, <=4 mismatches in 50 cycles, or <=2 mismatches in 34 cycles).

The searcher 118 then generates a cluster map 802 that identifies clusters as disjointed regions, e.g., 804a-d, of contiguous subpixels that share a substantially matching base call sequence. This application uses "disjointed", "disjoint", and "non-overlapping" interchangeably. The search involves base calling the subpixels that contain parts of clusters to allow linking the called subpixels to contiguous subpixels with which they share a substantially matching base call sequence. In some implementations, the searcher 118 requires that at least some of the disjointed regions have a predetermined minimum number of subpixels (e.g., more than 4, 6, or 10 subpixels) to be processed as a cluster.

In some implementations, the base caller 114 also identifies preliminary center coordinates of the clusters. Subpixels that contain the preliminary center coordinates are referred to as origin subpixels. Some example preliminary center coordinates (604a-c) identified by the base caller 114 and corresponding origin subpixels (606a-c) are shown in FIG. 6. However, identification of the origin subpixels (preliminary center coordinates of the clusters) is not needed, as explained below. In some implementations, the searcher 118 uses breadth-first search for identifying substantially matching base call sequences of the subpixels by beginning with the origin subpixels 606a-c and continuing with successively contiguous non-origin subpixels 702a-c. This again is optional, as explained below.

Cluster Map

FIG. 8a illustrates one example of a cluster map 802 generated by the merging of the subpixel base calls. The cluster map identifies a plurality of disjointed regions (depicted in various colors in FIG. 8a). Each disjointed region comprises a non-overlapping group of contiguous subpixels that represents a respective cluster on a tile (from whose sequencing images and for which the cluster map is generated via the subpixel base calling). The region between the disjointed regions represents the background on the tile. The subpixels in the background region are called "background subpixels". The subpixels in the disjointed regions are called "cluster subpixels" or "cluster interior subpixels". In this discussion, origin subpixels are those subpixels in which preliminary center cluster coordinates determined by the RTA or another base caller, are located.

The origin subpixels contain the preliminary center cluster coordinates. This means that the area covered by an origin subpixel includes a coordinate location that coincides with a preliminary center cluster coordinate location. Since the cluster map 802 is an image of logical subpixels, the origin subpixels are some of the subpixels in the cluster map.

The search to identify clusters with substantially matching base call sequences of the subpixels does not need to begin with identification of the origin subpixels (preliminary center coordinates of the clusters) because the search can be done for all the subpixels and can start from any subpixel (e.g., 0,0 subpixel or any random subpixel). Thus, since each subpixel is evaluated to determine whether it shares a substantially matching base call sequence with another contiguous subpixel, the search does not depend on origin subpixels; the search can start with any subpixel.

Irrespective of whether origin subpixels are used or not, certain clusters are identified that do not contain the origin subpixels (preliminary center coordinates of the clusters) predicted by the base caller 114. Some examples of clusters identified by the merging of the subpixel base calls and not containing an origin subpixel are clusters 812*a*, 812*b*, 812*c*, 812*d*, and 812*e* in FIG. 8*a*. Thus, the technology disclosed identifies additional or extra clusters for which the centers may not have been identified by the base caller 114. Therefore, use of the base caller 114 for identification of origin subpixels (preliminary center coordinates of the clusters) is optional and not essential for the search of substantially matching base call sequences of contiguous subpixels.

In one implementation, first, the origin subpixels (preliminary center coordinates of the clusters) identified by the base caller 114 are used to identify a first set of clusters (by identification of substantially matching base call sequences of contiguous subpixels). Then, subpixels that are not part of the first set of clusters are used to identify a second set of clusters (by identification of substantially matching base call sequences of contiguous subpixels). This allows the technology disclosed to identify additional or extra clusters for which the centers are not identified by the base caller 114. Finally, subpixels that are not part of the first and second sets of clusters are identified as background subpixels.

FIG. 8*b* depicts one example of subpixel base calling. In FIG. 8*b*, each sequencing cycle has an image set with four distinct images (i.e., A, C, T, G images) captured using four different wavelength bands (image/imaging channel) and four different fluorescent dyes (one for each base).

In this example, pixels in images are divided into sixteen subpixels. Subpixels are then separately base called at each sequencing cycle by the base caller 114. To base call a given subpixel at a particular sequencing cycle, the base caller 114 uses intensities of the given subpixel in each of the four A, C, T, G images. For example, intensities in image regions covered by subpixel 1 in each of the four A, C, T, G images of cycle 1 are used to base call subpixel 1 at cycle 1. For subpixel 1, these image regions include top-left one-sixteenth area of the respective top-left pixels in each of the four A, C, T, G images of cycle 1. Similarly, intensities in image regions covered by subpixel m in each of the four A, C, T, G images of cycle n are used to base call subpixel m at cycle n. For subpixel m, these image regions include bottom-right one-sixteenth area of the respective bottom-right pixels in each of the four A, C, T, G images of cycle 1.

This process produces subpixel-wise base call sequences 116 across the plurality of sequencing cycles. Then, the searcher 118 evaluates pairs of contiguous subpixels to determine whether they have a substantially matching base call sequence. If yes, then the pair of subpixels is stored in the cluster map 802 as belonging to a same cluster in a disjointed region. If no, then the pair of subpixels is stored in the cluster map 802 as not belonging to a same disjointed region. The cluster map 802 therefore identifies contiguous sets of sub-pixels for which the base calls for the sub-pixels substantially match across a plurality of cycles. Cluster map 802 therefore uses information from multiple cycles to provide a plurality of clusters with a high confidence that each cluster of the plurality of clusters provides sequence data for a single DNA strand.

Figure 9:
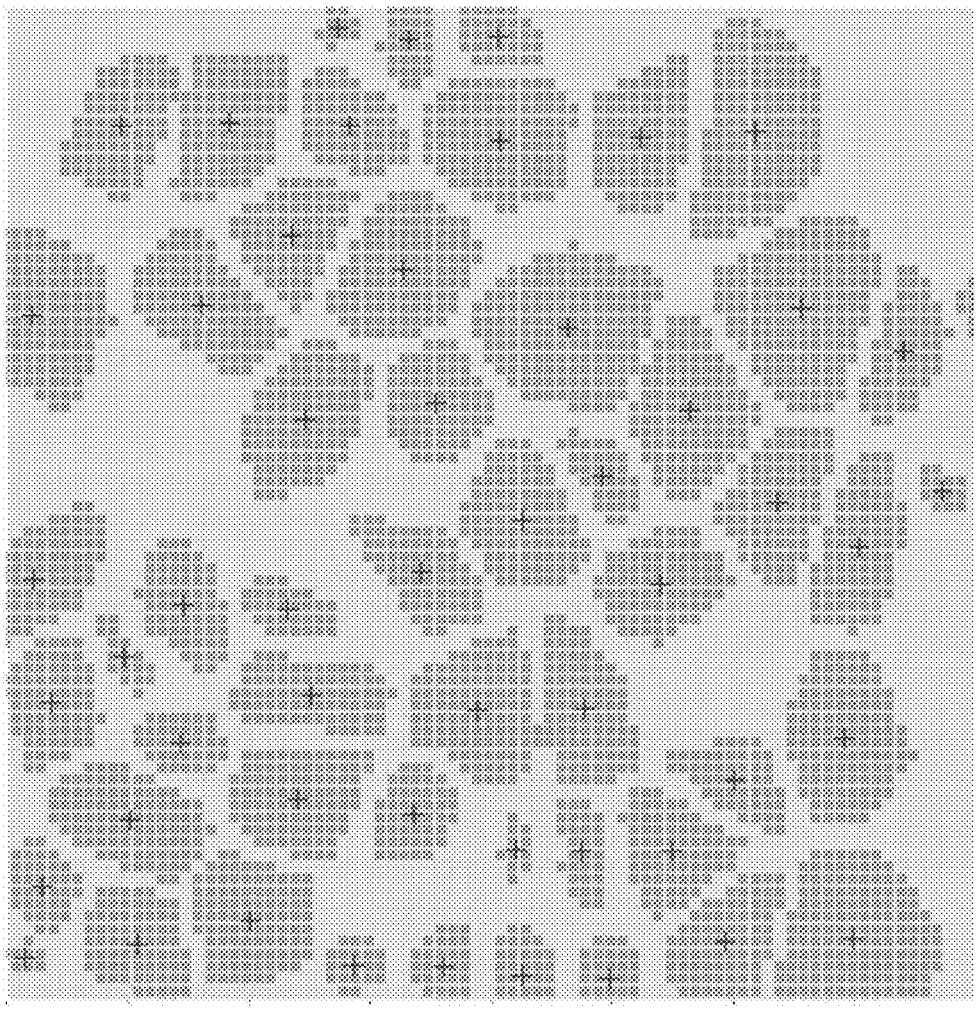
FIG. 9 shows another example of a cluster map that identifies cluster metadata.

A cluster metadata generator 122 then processes the cluster map 802 to determine cluster metadata, including determining spatial distribution of clusters, including their centers (810*a*), shapes, sizes, background, and/or boundaries based on the disjointed regions (FIG. 9).

In some implementations, the cluster metadata generator 122 identifies as background those subpixels in the cluster map 802 that do not belong to any of the disjointed regions and therefore do not contribute to any clusters. Such subpixels are referred to as background subpixels 806*a-c*.

In some implementations, the cluster map 802 identifies cluster boundary portions 808*a-c* between two contiguous subpixels whose base call sequences do not substantially match.

The cluster map is stored in memory (e.g., cluster maps data store 120) for use as ground truth for training a classifier such as the neural network-based template generator 1512 and the neural network-based base caller 1514. The cluster metadata can also be stored in memory (e.g., cluster metadata data store 124).

FIG. 9 shows another example of a cluster map that identifies cluster metadata, including spatial distribution of the clusters, along with cluster centers, cluster shapes, cluster sizes, cluster background, and/or cluster boundaries.

Center of Mass (COM)

Figure 10:
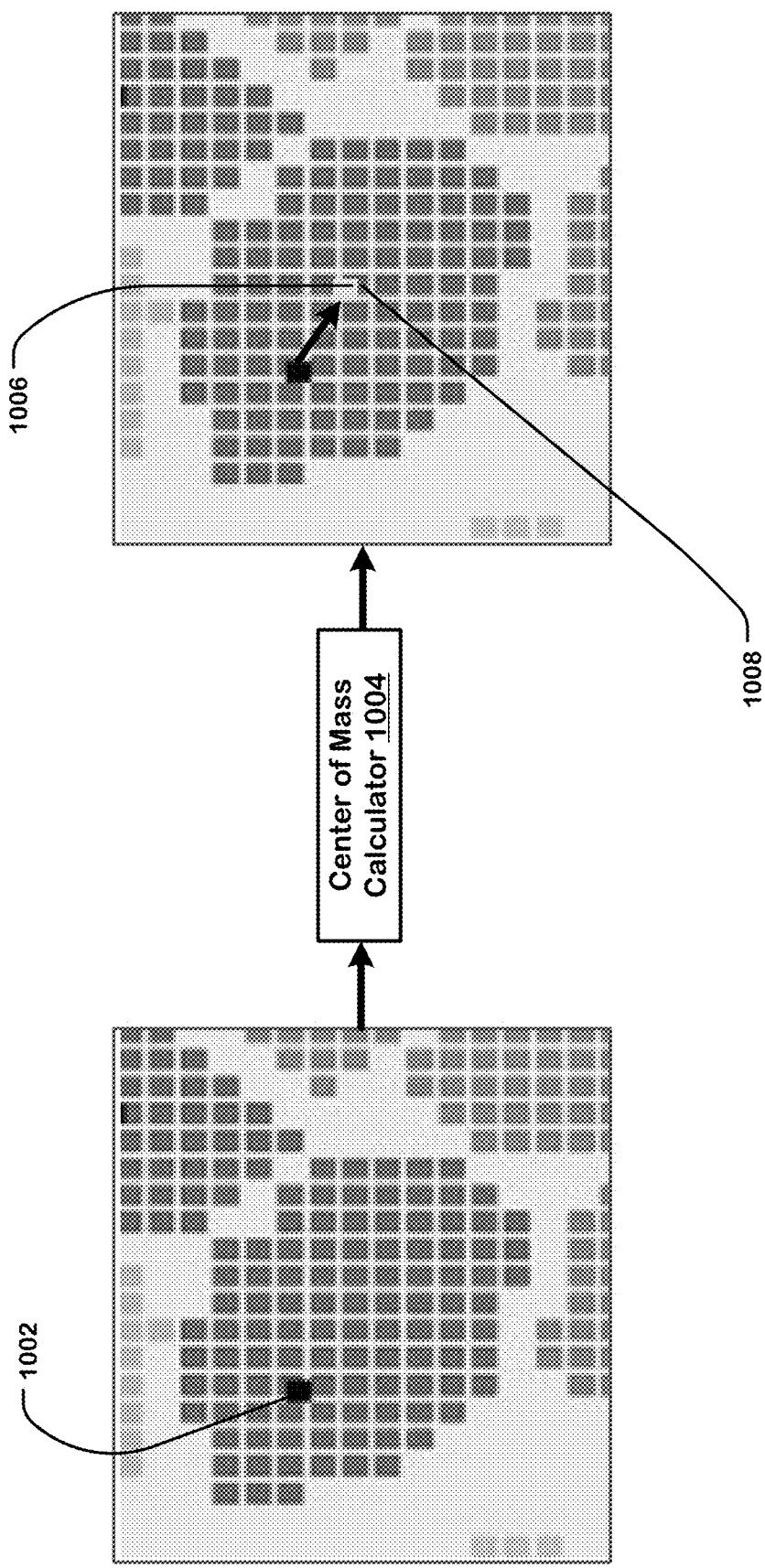
FIG. 10 shows how a center of mass (COM) of a disjointed region in a cluster map is calculated.

FIG. 10 shows how a center of mass (COM) of a disjointed region in a cluster map is calculated. The COM can be used as the "revised" or "improved" center of the corresponding cluster in downstream processing.

In some implementations, a center of mass generator 1004, on a cluster-by-cluster basis, determines hyperlocated center coordinates 1006 of the clusters by calculating centers of mass of the disjointed regions of the cluster map as an average of coordinates of respective contiguous subpixels forming the disjointed regions. It then stores the hyperlocated center coordinates of the clusters in the memory on the cluster-by-cluster basis for use as ground truth for training the classifier.

In some implementations, a subpixel categorizer, on the cluster-by-cluster basis, identifies centers of mass subpixels 1008 in the disjointed regions 804*a-d* of the cluster map 802 at the hyperlocated center coordinates 1006 of the clusters.

In other implementations, the cluster map is upsampled using interpolation. The upsampled cluster map is stored in the memory for use as ground truth for training the classifier.

Decay Factor & Decay Map

Figure 11:
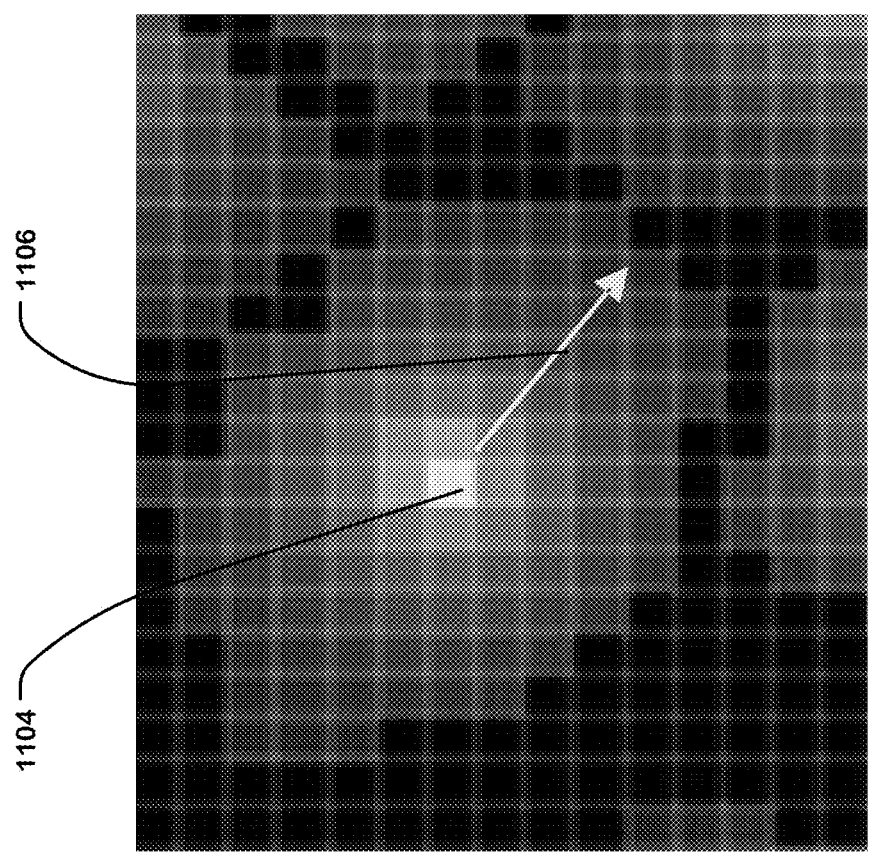
FIG. 11 depicts one implementation of calculation of a weighted decay factor based on the Euclidean distance from a subpixel in a disjointed region to the COM of the disjointed region.

FIG. 11 depicts one implementation of calculation of a weighted decay factor for a subpixel based on the Euclidean distance from the subpixel to the center of mass (COM) of the disjointed region to which the subpixel belongs. In the illustrated implementation, the weighted decay factor gives the highest value to the subpixel containing the COM and decreases for subpixels further away from the COM. The weighted decay factor is used to derive a ground truth decay map 1204 from a cluster map generated from the subpixel base calling discussed above. The ground truth decay map 1204 contains an array of units and assigns at least one output value to each unit in the array. In some implementations, the units are subpixels and each subpixel is assigned an output value based on the weighted decay factor. The ground truth decay map 1204 is then used as ground truth for training the disclosed neural network-based template generator 1512. In some implementations, information from the ground truth decay map 1204 is also used to prepare input for the disclosed neural network-based base caller 1514.

Figure 12:
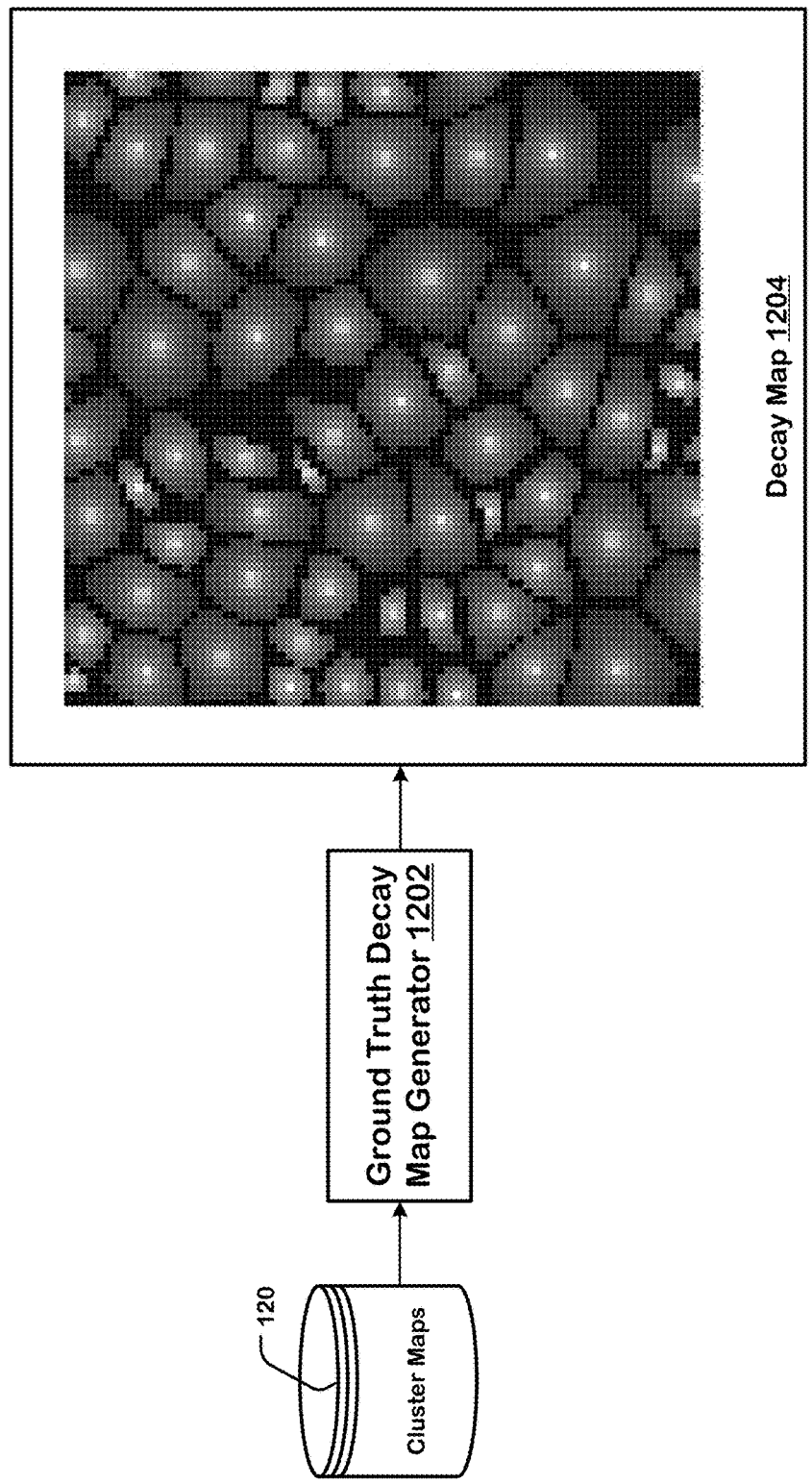
FIG. 12 illustrates one implementation of an example ground truth decay map derived from an example cluster map produced by the subpixel base calling.

FIG. 12 illustrates one implementation of an example ground truth decay map 1204 derived from an example cluster map produced by the subpixel base calling as discussed above. In some implementations, in the upsampled cluster map, on the cluster-by-cluster basis, a value is assigned to each contiguous subpixel in the disjointed regions based on a decay factor 1102 that is proportional to distance 1106 of a contiguous subpixel from a center of mass subpixel 1104 in a disjointed region to which the contiguous subpixel belongs.

FIG. 12 depicts a ground truth decay map 1204. In one implementation, the subpixel value is an intensity value normalized between zero and one. In another implementation, in the upsampled cluster map, a same predetermined value is assigned to all the subpixels identified as the background. In some implementations, the predetermined value is a zero intensity value.

In some implementations, the ground truth decay map 1204 is generated by a ground truth decay map generator 1202 from the upsampled cluster map that expresses the contiguous subpixels in the disjointed regions and the subpixels identified as the background based on their assigned values. The ground truth decay map 1204 is stored in the memory for use as ground truth for training the classifier. In one implementation, each subpixel in the ground truth decay map 1204 has a value normalized between zero and one.

Ternary (Three Class) Map

Figure 13:
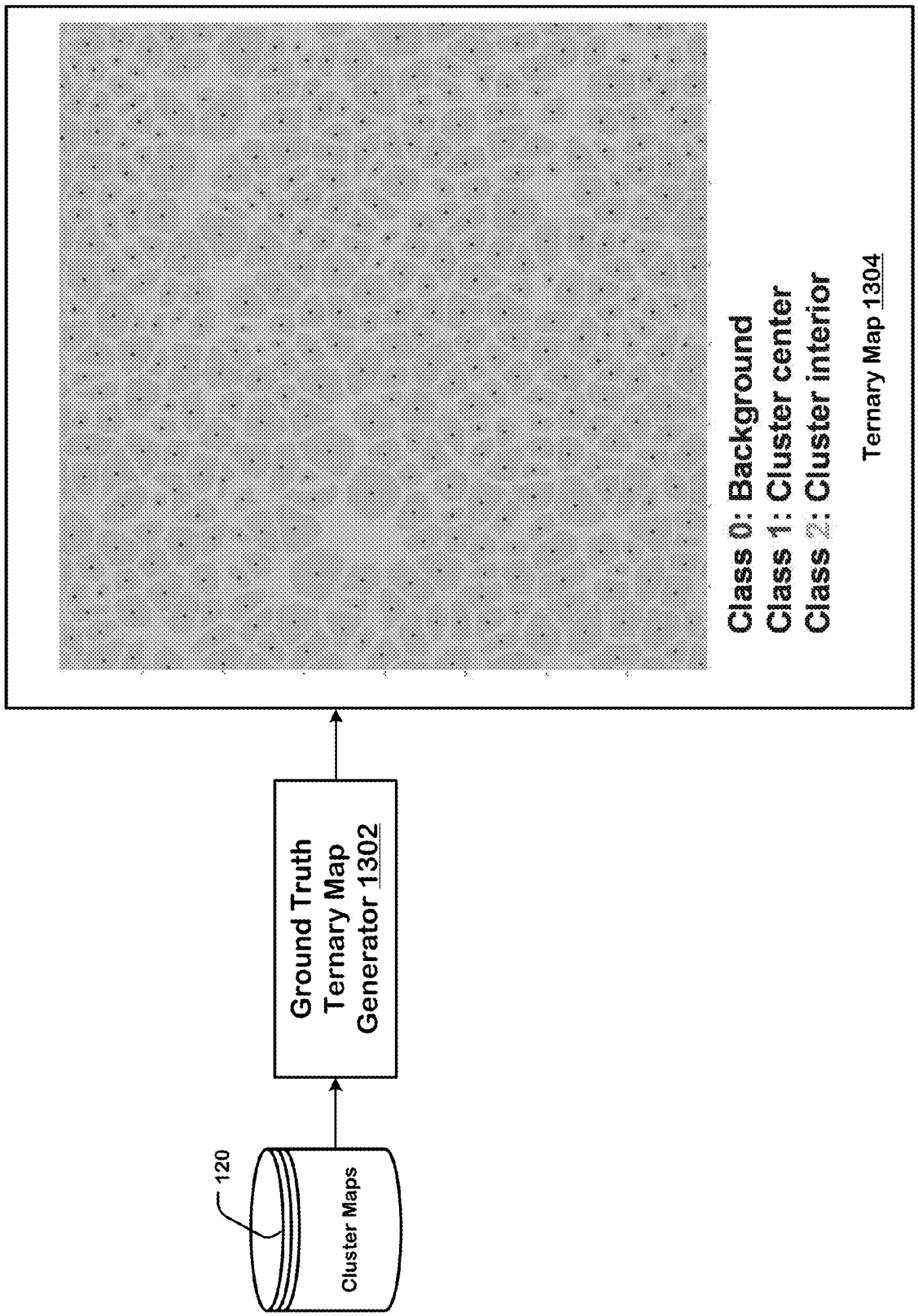
FIG. 13 illustrates one implementation of deriving a ternary map from a cluster map.

FIG. 13 illustrates one implementation of deriving a ground truth ternary map 1304 from a cluster map. The ground truth ternary map 1304 contains an array of units and assigns at least one output value to each unit in the array. By name, ternary map implementations of the ground truth ternary map 1304 assign three output values to each unit in the array, such that, for each unit, a first output value corresponds to a classification label or score for a background class, a second output value corresponds to a classification label or score for a cluster center class, and a third output value corresponds to a classification label or score for a cluster/cluster interior class. The ground truth ternary map 1304 is used as ground truth data for training the neural network-based template generator 1512. In some implementations, information from the ground truth ternary map 1304 is also used to prepare input for the neural network-based base caller 1514.

FIG. 13 depicts an example ground truth ternary map 1304. In another implementation, in the upsampled cluster map, the contiguous subpixels in the disjointed regions are categorized on the cluster-by-cluster basis by a ground truth ternary map generator 1302, as cluster interior subpixels belonging to a same cluster, the centers of mass subpixels as cluster center subpixels, and as background subpixels the subpixels not belonging to any cluster. In some implementations, the categorizations are stored in the ground truth ternary map 1304. These categorizations and the ground truth ternary map 1304 are stored in the memory for use as ground truth for training the classifier.

In other implementations, on the cluster-by-cluster basis, coordinates of the cluster interior subpixels, the cluster center subpixels, and the background subpixels are stored in the memory for use as ground truth for training the classifier. Then, the coordinates are downscaled by a factor used to upsample the cluster map. Then, on the cluster-by-cluster basis, the downscaled coordinates are stored in the memory for use as ground truth for training the classifier.

In yet other implementations, the ground truth ternary map generator 1302 uses the cluster maps to generate the ternary ground truth data 1304 from the upsampled cluster map. The ternary ground truth data 1304 labels the background subpixels as belonging to a background class, the cluster center subpixels as belonging to a cluster center class, and the cluster interior subpixels as belonging to a cluster interior class. In some visualization implementations, color coding can be used to depict and distinguish the different class labels. The ternary ground truth data 1304 is stored in the memory for use as ground truth for training the classifier.

Binary (Two Class) Map

Figure 14:
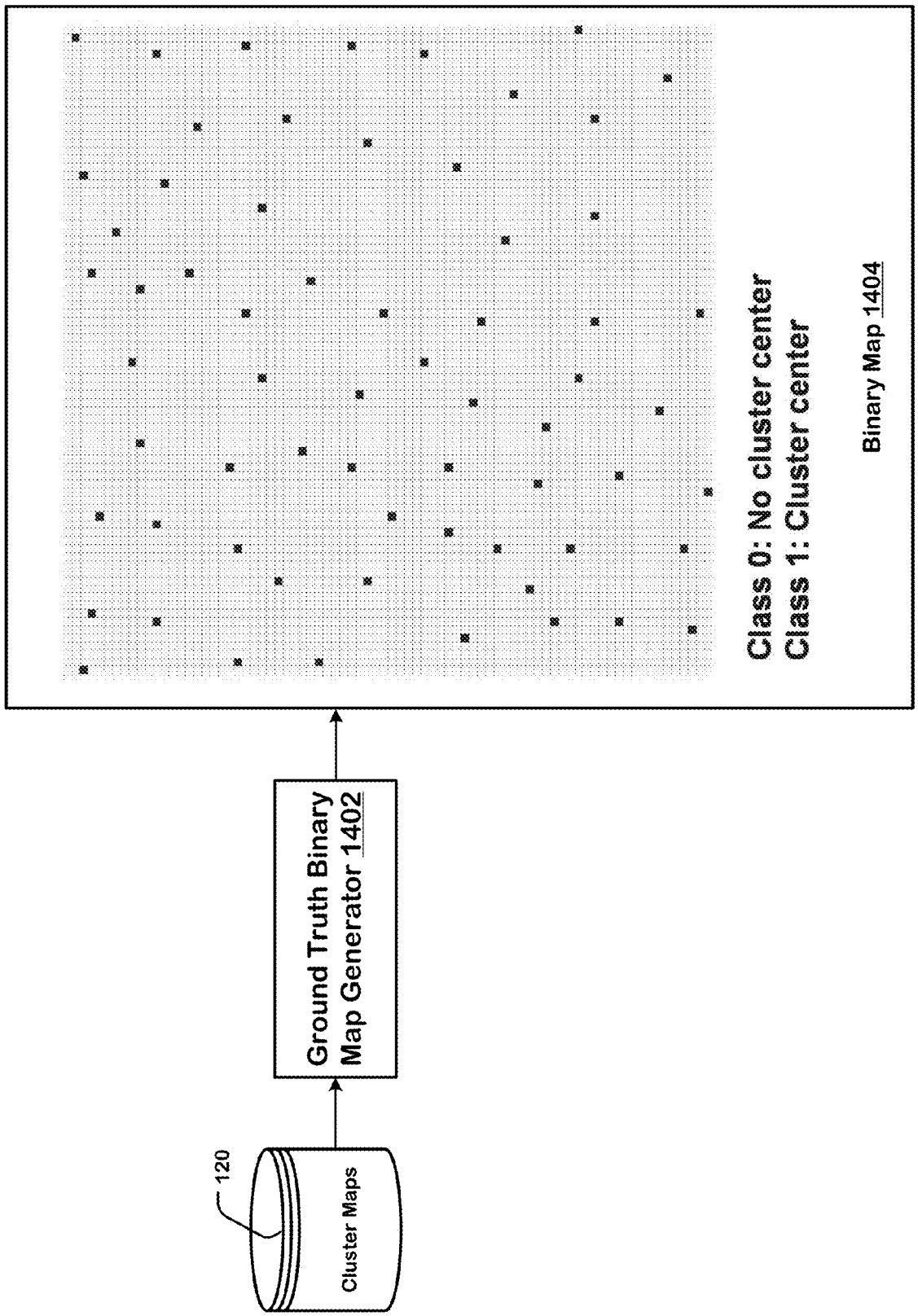
FIG. 14 illustrates one implementation of deriving a binary map from a cluster map.

FIG. 14 illustrates one implementation of deriving a ground truth binary map 1404 from a cluster map. The binary map 1404 contains an array of units and assigns at least one output value to each unit in the array. By name, the binary map assigns two output values to each unit in the array, such that, for each unit, a first output value corresponds to a classification label or score for a cluster center class and a second output value corresponds to a classification label or score for a non-center class. The binary map is used as ground truth data for training the neural network-based template generator 1512. In some implementations, information from the binary map is also used to prepare input for the neural network-based base caller 1514.

FIG. 14 depicts a ground truth binary map 1404. The ground truth binary map generator 1402 uses the cluster maps 120 to generate the binary ground truth data 1404 from the upsampled cluster maps. The binary ground truth data 1404 labels the cluster center subpixels as belonging to a cluster center class and labels all other subpixels as belonging to a non-center class. The binary ground truth data 1404 is stored in the memory for use as ground truth for training the classifier.

In some implementations, the technology disclosed generates cluster maps 120 for a plurality of tiles of the flow cell, stores the cluster maps in memory, and determines spatial distribution of clusters in the tiles based on the cluster maps 120, including their shapes and sizes. Then, the technology disclosed, in the upsampled cluster maps 120 of the clusters in the tiles, categorizes, on a cluster-by-cluster basis, subpixels as cluster interior subpixels belonging to a same cluster, cluster center subpixels, and background subpixels. The technology disclosed then stores the categorizations in the memory for use as ground truth for training the classifier, and stores, on the cluster-by-cluster basis across the tiles, coordinates of the cluster interior subpixels, the cluster center subpixels, and the background subpixels in the memory for use as ground truth for training the classifier. The technology disclosed then downscales the coordinates by the factor used to upsample the cluster map and stores, on the cluster-by-cluster basis across the tiles, the downscaled coordinates in the memory for use as ground truth for training the classifier.

In some implementations, the flow cell has at least one patterned surface with an array of wells that occupy the clusters. In such implementations, based on the determined shapes and sizes of the clusters, the technology disclosed determines: (1) which ones of the wells are substantially occupied by at least one cluster, (2) which ones of the wells are minimally occupied, and (3) which ones of the wells are co-occupied by multiple clusters. This allows for determining respective metadata of multiple clusters that co-occupy a same well, i.e., centers, shapes, and sizes of two or more clusters that share a same well.

In some implementations, the solid support on which samples are amplified into clusters comprises a patterned surface. A "patterned surface" refers to an arrangement of different regions in or on an exposed layer of a solid support. For example, one or more of the regions can be features where one or more amplification primers are present. The features can be separated by interstitial regions where amplification primers are not present. In some implementations, the pattern can be an x-y format of features that are in rows and columns In some implementations, the pattern can be a repeating arrangement of features and/or interstitial regions. In some implementations, the pattern can be a random arrangement of features and/or interstitial regions. Exemplary patterned surfaces that can be used in the methods and compositions set forth herein are described in U.S. Pat. Nos. 8,778,849, 9,079,148, 8,778,848, and US Pub. No. 2014/0243224, each of which is incorporated herein by reference.

In some implementations, the solid support comprises an array of wells or depressions in a surface. This may be fabricated as is generally known in the art using a variety of techniques, including, but not limited to, photolithography, stamping techniques, molding techniques and microetching techniques. As will be appreciated by those in the art, the technique used will depend on the composition and shape of the array substrate.

The features in a patterned surface can be wells in an array of wells (e.g. microwells or nanowells) on glass, silicon, plastic or other suitable solid supports with patterned, covalently-linked gel such as poly(N-(5-azidoacetamidylpentyl) acrylamide-co-acrylamide) (PAZAM, see, for example, US Pub. No. 2013/184796, WO 2016/066586, and WO 2015/002813, each of which is incorporated herein by reference in its entirety). The process creates gel pads used for sequencing that can be stable over sequencing runs with a large number of cycles. The covalent linking of the polymer to the wells is helpful for maintaining the gel in the structured features throughout the lifetime of the structured substrate during a variety of uses. However in many implementations, the gel need not be covalently linked to the wells. For example, in some conditions silane free acrylamide (SFA, see, for example, U.S. Pat. No. 8,563,477, which is incorporated herein by reference in its entirety) which is not covalently attached to any part of the structured substrate, can be used as the gel material.

In particular implementations, a structured substrate can be made by patterning a solid support material with wells (e.g. microwells or nanowells), coating the patterned support with a gel material (e.g. PAZAM, SFA or chemically modified variants thereof, such as the azidolyzed version of SFA (azido-SFA)) and polishing the gel coated support, for example via chemical or mechanical polishing, thereby retaining gel in the wells but removing or inactivating substantially all of the gel from the interstitial regions on the surface of the structured substrate between the wells. Primer nucleic acids can be attached to gel material. A solution of target nucleic acids (e.g. a fragmented human genome) can then be contacted with the polished substrate such that individual target nucleic acids will seed individual wells via interactions with primers attached to the gel material; however, the target nucleic acids will not occupy the interstitial regions due to absence or inactivity of the gel material. Amplification of the target nucleic acids will be confined to the wells since absence or inactivity of gel in the interstitial regions prevents outward migration of the growing nucleic acid colony. The process is conveniently manufacturable, being scalable and utilizing micro- or nano-fabrication methods.

The term "flow cell" as used herein refers to a chamber comprising a solid surface across which one or more fluid reagents can be flowed. Examples of flow cells and related fluidic systems and detection platforms that can be readily used in the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

Throughout this disclosure, the terms "P5" and "P7" are used when referring to amplification primers. It will be understood that any suitable amplification primers can be used in the methods presented herein, and that the use of P5 and P7 are exemplary implementations only. Uses of amplification primers such as P5 and P7 on flow cells is known in the art, as exemplified by the disclosures of WO 2007/010251, WO 2006/064199, WO 2005/065814, WO 2015/106941, WO 1998/044151, and WO 2000/018957, each of which is incorporated by reference in its entirety. For example, any suitable forward amplification primer, whether immobilized or in solution, can be useful in the methods presented herein for hybridization to a complementary sequence and amplification of a sequence. Similarly, any suitable reverse amplification primer, whether immobilized or in solution, can be useful in the methods presented herein for hybridization to a complementary sequence and amplification of a sequence. One of skill in the art will understand how to design and use primer sequences that are suitable for capture, and amplification of nucleic acids as presented herein.

In some implementations, the flow cell has at least one nonpatterned surface and the clusters are unevenly scattered over the nonpatterned surface.

In some implementations, density of the clusters ranges from about 100,000 clusters/mm$^2$ to about 1,000,000 clusters/mm$^2$. In other implementations, density of the clusters ranges from about 1,000,000 clusters/mm$^2$ to about 10,000,000 clusters/mm$^2$.

In one implementation, the preliminary center coordinates of the clusters determined by the base caller are defined in a template image of the tile. In some implementations, a pixel resolution, an image coordinate system, and measurement scales of the image coordinate system are same for the template image and the images.

In another implementation, the technology disclosed relates to determining metadata about clusters on a tile of a flow cell. First, the technology disclosed accesses (1) a set of images of the tile captured during a sequencing run and (2) preliminary center coordinates of the clusters determined by a base caller.

Then, for each image set, the technology disclosed obtains a base call classifying, as one of four bases, (1) origin subpixels that contain the preliminary center coordinates and (2) a predetermined neighborhood of contiguous subpixels that are successively contiguous to respective ones of the origin subpixels. This produces a base call sequence for each of the origin subpixels and for each of the predetermined neighborhood of contiguous subpixels. The predetermined neighborhood of contiguous subpixels can be a m×n subpixel patch centered at subpixels containing the origin subpixels. In one implementation, the subpixel patch is 3×3 subpixels. In other implementations, the image patch can be of any size, such as 5×5, 15×15, 20×20, and so on. In other implementations, the predetermined neighborhood of contiguous subpixels can be a n-connected subpixel neighborhood centered at subpixels containing the origin subpixels.

In one implementation, the technology disclosed identifies as background those subpixels in the cluster map that do not belong to any of the disjointed regions.

Then, the technology disclosed generates a cluster map that identifies the clusters as disjointed regions of contiguous subpixels that: (a) are successively contiguous to at least some of the respective ones of the origin subpixels and (b)

share a substantially matching base call sequence of the one of four bases with the at least some of the respective ones of the origin subpixels.

The technology disclosed then stores the cluster map in memory and determines the shapes and the sizes of the clusters based on the disjointed regions in the cluster map. In other implementations, centers of the clusters are also determined.

Generating Training Data for Template Generator

Figure 15:
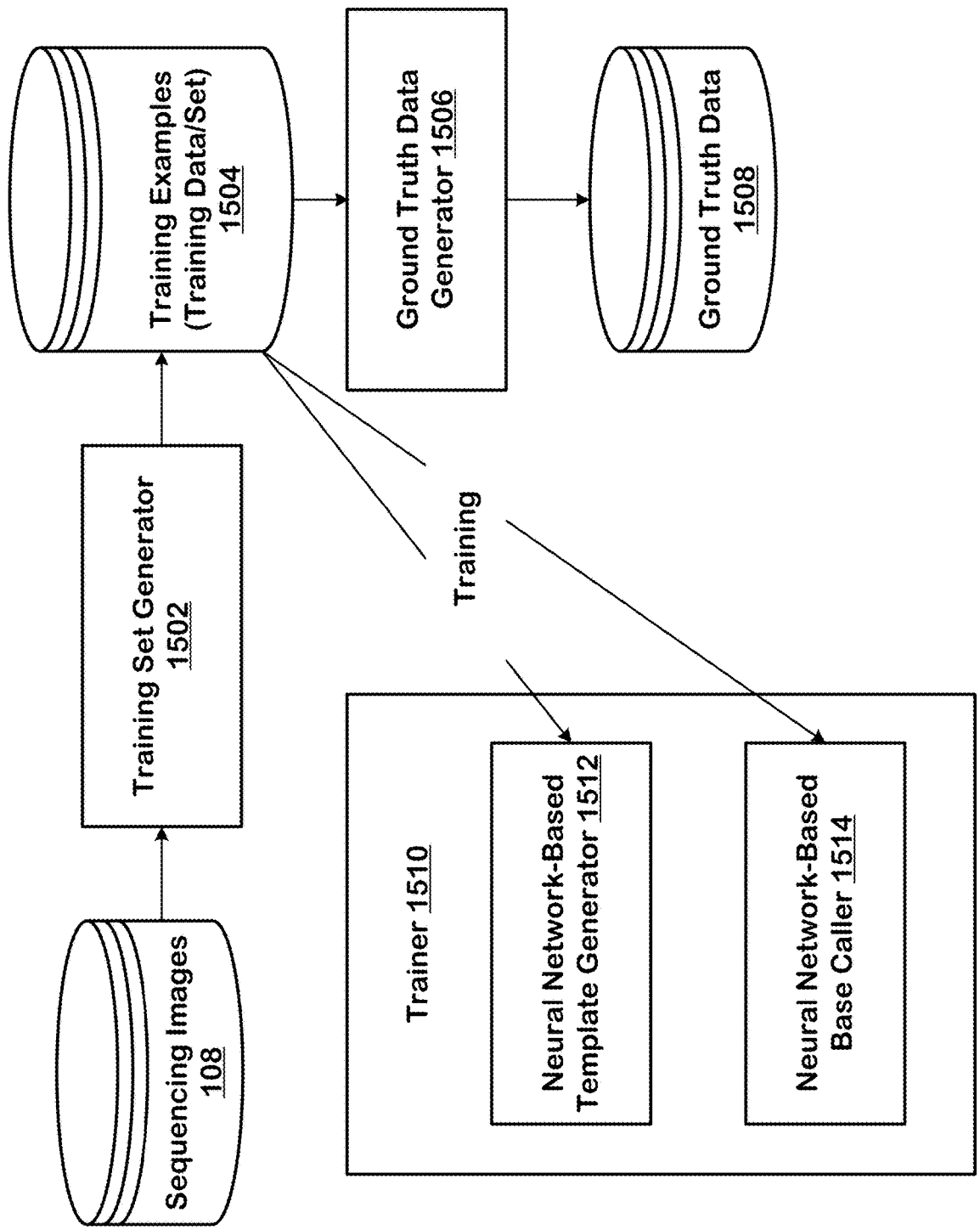
FIG. 15 is a block diagram that shows one implementation of generating training data that is used to train the neural network-based template generator and the neural network-based base caller.

FIG. 15 is a block diagram that shows one implementation of generating training data that is used to train the neural network-based template generator 1512 and the neural network-based base caller 1514.

Figure 16:
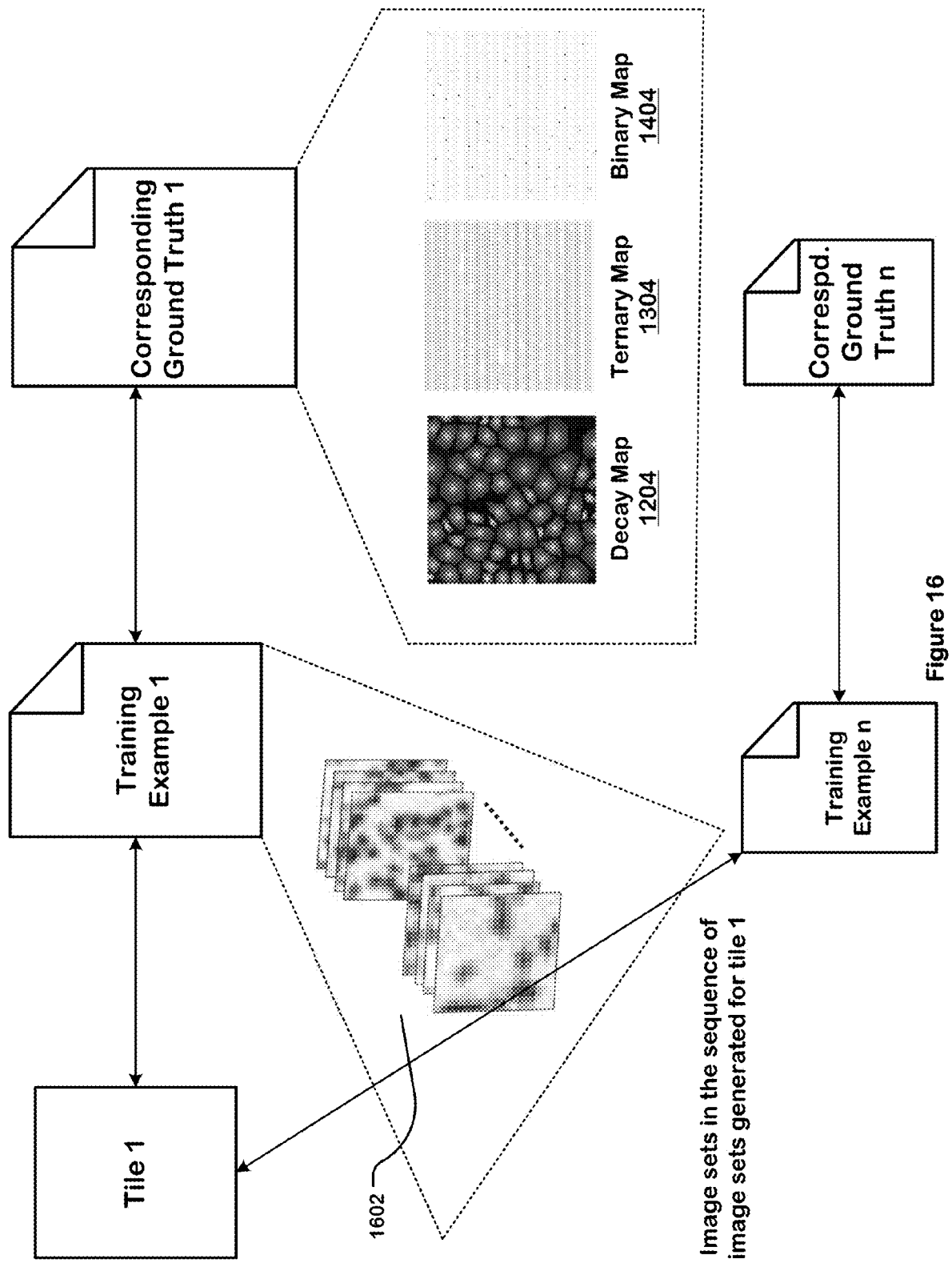
FIG. 16 shows characteristics of the disclosed training examples used to train the neural network-based template generator and the neural network-based base caller.

FIG. 16 shows characteristics of the disclosed training examples used to train the neural network-based template generator 1512 and the neural network-based base caller 1514. Each training example corresponds to a tile and is labelled with a corresponding ground truth data representation. In some implementations, the ground truth data representation is a ground truth mask or a ground truth map that identifies the ground truth cluster metadata in the form of the ground truth decay map 1204, the ground truth ternary map 1304, or the ground truth binary map 1404. In some implementation, multiple training examples correspond to a same tile.

In one implementation, the technology disclosed relates to generating training data 1504 for neural network-based template generation and base calling. First, the technology disclosed accesses a multitude of images 108 of a flow cell 202 captured over a plurality of cycles of a sequencing run. The flow cell 202 has a plurality of tiles. In the multitude of images 108, each of the tiles has a sequence of image sets generated over the plurality of cycles. Each image in the sequence of image sets 108 depicts intensity emissions of clusters 302 and their surrounding background 304 on a particular one of the tiles at a particular one the cycles.

Then, a training set constructor 1502 constructs a training set 1504 that has a plurality of training examples. As shown in FIG. 16, each training example corresponds to a particular one of the tiles and includes image data from at least some image sets in the sequence of image sets 1602 of the particular one of the tiles. In one implementation, the image data includes images in at least some image sets in the sequence of image sets 1602 of the particular one of the tiles. For example, the images can have a resolution of 1800×1800. In other implementations, it can be any resolution such as 100×100, 3000×3000, 10000×10000, and so on. In yet other implementations, the image data includes at least one image patch from each of the images. In one implementation, the image patch covers a portion of the particular one of the tiles. In one example, the image patch can have a resolution of 20×20. In other implementations, the image patch can have any resolution, such as 50×50, 70×70, 90×90, 100×100, 3000×3000, 10000×10000, and so on.

In some implementations, the image data includes an upsampled representation of the image patch. The upsampled representation can have a resolution of 80×80, for example. In other implementations, the upsampled representation can have any resolution, such as 50×50, 70×70, 90×90, 100×100, 3000×3000, 10000×10000, and so on.

In some implementations, multiple training examples correspond to a same particular one of the tiles and respectively include as image data different image patches from each image in each of at least some image sets in a sequence of image sets 1602 of the same particular one of the tiles. In such implementations, at least some of the different image patches overlap with each other.

Then, a ground truth generator 1506 generates at least one ground truth data representation for each of the training examples. The ground truth data representation identifies at least one of spatial distribution of clusters and their surrounding background on the particular one of the tiles whose intensity emissions are depicted by the image data, including at least one of cluster shapes, cluster sizes, and/or cluster boundaries, and/or centers of the clusters.

In one implementation, the ground truth data representation identifies the clusters as disjointed regions of contiguous subpixels, the centers of the clusters as centers of mass subpixels within respective ones of the disjointed regions, and their surrounding background as subpixels that do not belong to any of the disjointed regions.

In one implementation, the ground truth data representation has an upsampled resolution of 80×80. In other implementations, the ground truth data representation can have any resolution, such as 50×50, 70×70, 90×90, 100×100, 3000×3000, 10000×10000, and so on.

In one implementation, the ground truth data representation identifies each subpixel as either being a cluster center or a non-center. In another implementation, the ground truth data representation identifies each subpixel as either being cluster interior, cluster center, or surrounding background.

In some implementations, the technology disclosed stores, in memory, the training examples in the training set 1504 and associated ground truth data 1508 as the training data 1504 for training the neural network-based template generator 1512 and the neural network-based base caller 1514. The training is operationalized by trainer 1510.

In some implementations, the technology disclosed generates the training data for a variety of flow cells, sequencing instruments, sequencing protocols, sequencing chemistries, sequencing reagents, and cluster densities.

Neural Network-Based Template Generator

In an inference or production implementation, the technology disclosed uses peak detection and segmentation to determine cluster metadata. The technology disclosed processes input image data 1702 derived from a series of image sets 1602 through a neural network 1706 to generate an alternative representation 1708 of the input image data 1702. For example, an image set can be for a particular sequencing cycle and include four images, one for each image channel A, C, T, and G. Then, for a sequencing run with fifty sequencing cycles, there will be fifty such image sets, i.e., a total of 200 images. When arranged temporally, fifty image sets with four images-per image set would form the series of image sets 1602. In some implementations, image patches of a certain size are extracted from each image in the fifty image sets, forming fifty image patch sets with four image patches-per image patch set and, in one implementation, this is the input image data 1702. In other implementations, the input image data 1702 comprises image patch sets with four image patches-per image patch set for fewer than the fifty sequencing cycles, i.e., just one, two, three, fifteen, twenty sequencing cycles.

Figure 17:
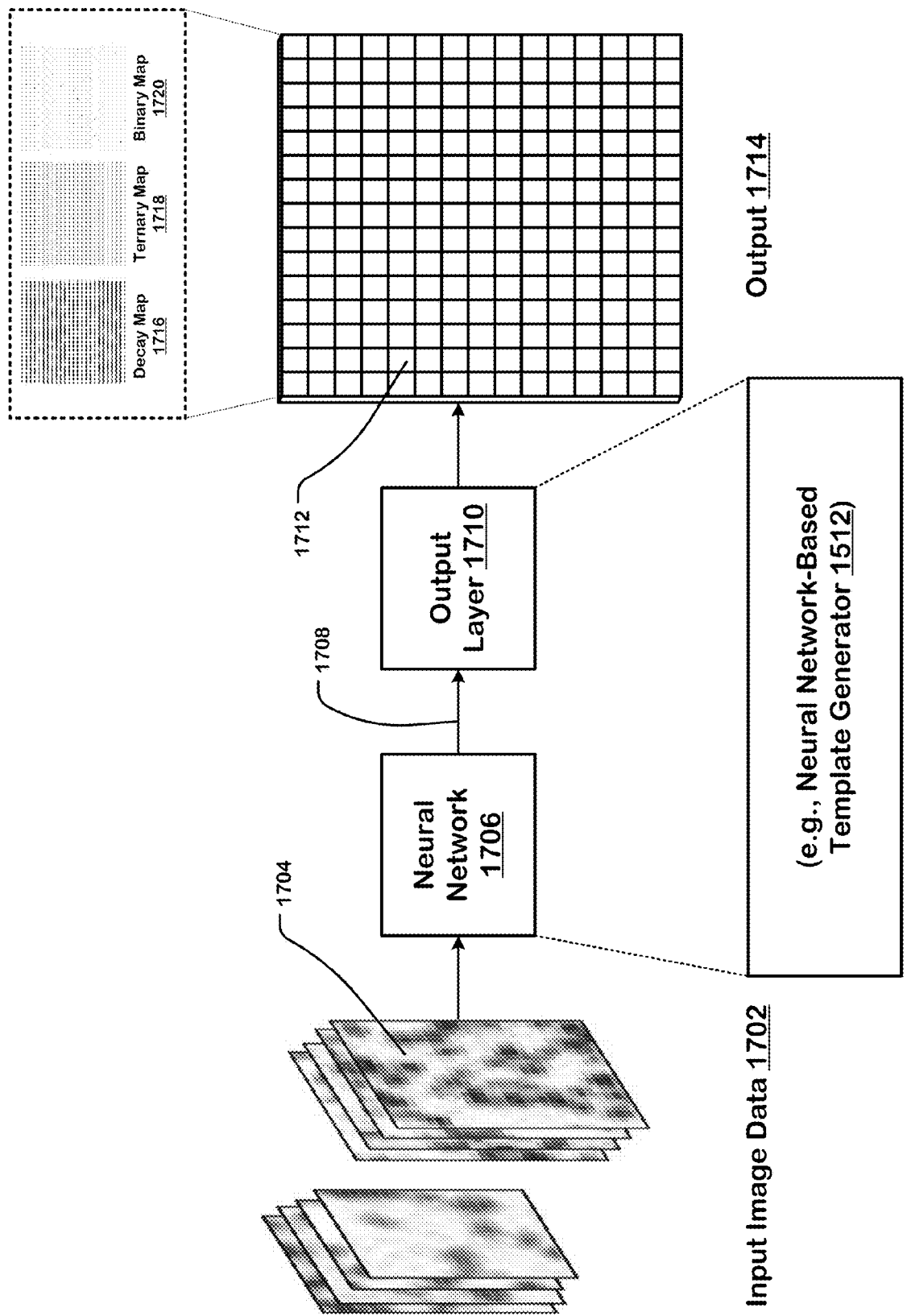
FIG. 17 illustrates one implementation of processing input image data through the disclosed neural network-based template generator and generating an output value for each unit in an array. In one implementation, the array is a decay map. In another implementation, the array is a ternary map. In yet another implementation, the array is a binary map.

FIG. 17 illustrates one implementation of processing input image data 1702 through the neural network-based template generator 1512 and generating an output value for each unit in an array. In one implementation, the array is a decay map 1716. In another implementation, the array is a ternary map 1718. In yet another implementation, the array is a binary map 1720. The array may therefore represent one or more properties of each of a plurality of locations represented in the input image data 1702.

Different than training the template generator using structures in earlier figures, including the ground truth decay map 1204, the ground truth ternary map 1304, and the ground truth binary 1404, the decay map 1716, the ternary map 1718, and/or the binary map 1720 are generated by forward propagation of the trained neural network-based template generator 1512. The forward propagation can be during training or during inference. During the training, due to the backward propagation-based gradient update, the decay map 1716, the ternary map 1718, and the binary map 1720 (i.e., cumulatively the output 1714) progressively match or approach the ground truth decay map 1204, the ground truth ternary map 1304, and the ground truth binary map 1404, respectively.

The size of the image array analyzed during inference depends on the size of the input image data 1702 (e.g., be the same or an upscaled or downscaled version), according to one implementation. Each unit can represent a pixel, a subpixel, or a superpixel. The unit-wise output values of an array can characterize/represent/denote the decay map 1716, the ternary map 1718, or the binary map 1720. In some implementations, the input image data 1702 is also an array of units in the pixel, subpixel, or superpixel resolution. In such an implementation, the neural network-based template generator 1512 uses semantic segmentation techniques to produce an output value for each unit in the input array. Additional details about the input image data 1702 can be found in FIGS. 21b, 22, 23, and 24 and their discussion.

In some implementations, the neural network-based template generator 1512 is a fully convolutional network, such as the one described in J. Long, E. Shelhamer, and T. Darrell, "Fully convolutional networks for semantic segmentation," in CVPR, (2015), which is incorporated herein by reference. In other implementations, the neural network-based template generator 1512 is a U-Net network with skip connections between the decoder and the encoder between the decoder and the encoder, such as the one described in Ronneberger O, Fischer P, Brox T., "U-net: Convolutional networks for biomedical image segmentation," Med. Image Comput. Comput. Assist. Interv. (2015), available at: (http://)link.springer.com/chapter/10.1007/978-3-319-24574-4_28, which is incorporated herein by reference. The U-Net architecture resembles an autoencoder with two main sub-structures: 1) an encoder, which takes an input image and reduces its spatial resolution through multiple convolutional layers to create a representation encoding. 2) A decoder, which takes the representation encoding and increases spatial resolution back to produce a reconstructed image as output. The U-Net introduces two innovations to this architecture: First, the objective function is set to reconstruct a segmentation mask using a loss function; and second, the convolutional layers of the encoder are connected to the corresponding layers of the same resolution in the decoder using skip connections. In yet further implementations, the neural network-based template generator 1512 is a deep fully convolutional segmentation neural network with an encoder subnetwork and a corresponding decoder network. In such an implementation, the encoder subnetwork includes a hierarchy of encoders and the decoder subnetwork includes a hierarchy of decoders that map low resolution encoder feature maps to full input resolution feature maps. Additional details about segmentation networks can be found in Appendix entitled "Segmentation Networks".

In one implementation, the neural network-based template generator 1512 is a convolutional neural network. In another implementation, the neural network-based template generator 1512 is a recurrent neural network. In yet another implementation, the neural network-based template generator 1512 is a residual neural network with residual bocks and residual connections. In a further implementation, the neural network-based template generator 1512 is a combination of a convolutional neural network and a recurrent neural network.

One skilled in the art will appreciate that the neural network-based template generator 1512 (i.e., the neural network 1706 and/or the output layer 1710) can use various padding and striding configurations. It can use different output functions (e.g., classification or regression) and may or may not include one or more fully-connected layers. It can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. It can use one or more loss functions such as logistic regression/log loss, multi-class cross-entropy/softmax loss, binary cross-entropy loss, mean-squared error loss, L1 loss, L2 loss, smooth L1 loss, and Huber loss. It can use any parallelism, efficiency, and compression schemes such TFRecords, compressed encoding (e.g., PNG), sharding, parallel calls for map transformation, batching, prefetching, model parallelism, data parallelism, and synchronous/asynchronous SGD. It can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tan h)), batch normalization layers, regularization layers, dropout, pooling layers (e.g., max or average pooling), global average pooling layers, and attention mechanisms.

In some implementations, each image in the sequence of image sets 1602 covers a tile and depicts intensity emissions of clusters on a tile and their surrounding background captured for a particular imaging channel at a particular one of a plurality of sequencing cycles of a sequencing run performed on a flow cell. In one implementation, the input image data 1702 includes at least one image patch from each of the images in the sequence of image sets 1602. In such an implementation, the image patch covers a portion of the tile. In one example, the image patch has a resolution of 20×20. In other cases, the resolution of the image patch can range from 20×20 to 10000×10000. In another implementation, the input image data 1702 includes an upsampled, subpixel resolution representation of the image patch from each of the images in the sequence of image sets 1602. In one example, the upsampled, subpixel representation has a resolution of 80×80. In other cases, the resolution of the upsampled, subpixel representation can range from 80×80 to 10000×10000.

The input image data 1702 has an array of units 1704 that depicts clusters and their surrounding background. For example, an image set can be for a particular sequencing cycle and include four images, one for each image channel A, C, T, and G. Then, for a sequencing run with fifty sequencing cycles, there will be fifty such image sets, i.e., a total of 200 images. When arranged temporally, fifty image sets with four images-per image set would form the series of image sets 1602. In some implementations, image patches of a certain size are extracted from each image in the fifty image sets, forming fifty image patch sets with four image patches-per image patch set and, in one implementation, this is the input image data 1702. In other implementations, the input image data 1702 comprises image patch sets with four image patches-per image patch set for fewer than the fifty sequencing cycles, i.e., just one, two, three, fifteen, twenty sequencing cycles. The alternative representation is a feature map. The feature map can be a convolved feature or convolved representation when the neural network is a convolutional neural network. The feature map can be a hidden state feature or hidden state representation when the neural network is a recurrent neural network.

Then, the technology disclosed processes the alternative representation 1708 through an output layer 1710 to generate an output 1714 that has an output value 1712 for each unit in the array 1704. The output layer can be a classification layer such as softmax or sigmoid that produces unit-wise output values. In one implementation, the output layer is a ReLU layer or any other activation function layer that produces unit-wise output values.

In one implementation, the units in the input image data 1702 are pixels and therefore pixel-wise output values 1712 are produced in the output 1714. In another implementation, the units in the input image data 1702 are subpixels and therefore subpixel-wise output values 1712 are produced in the output 1714. In yet another implementation, the units in the input image data 1702 are superpixels and therefore superpixel-wise output values 1712 are produced in the output 1714.

Deriving Cluster Metadata from Decay Map, Ternary Map, and/or Binary Map

Figure 18:
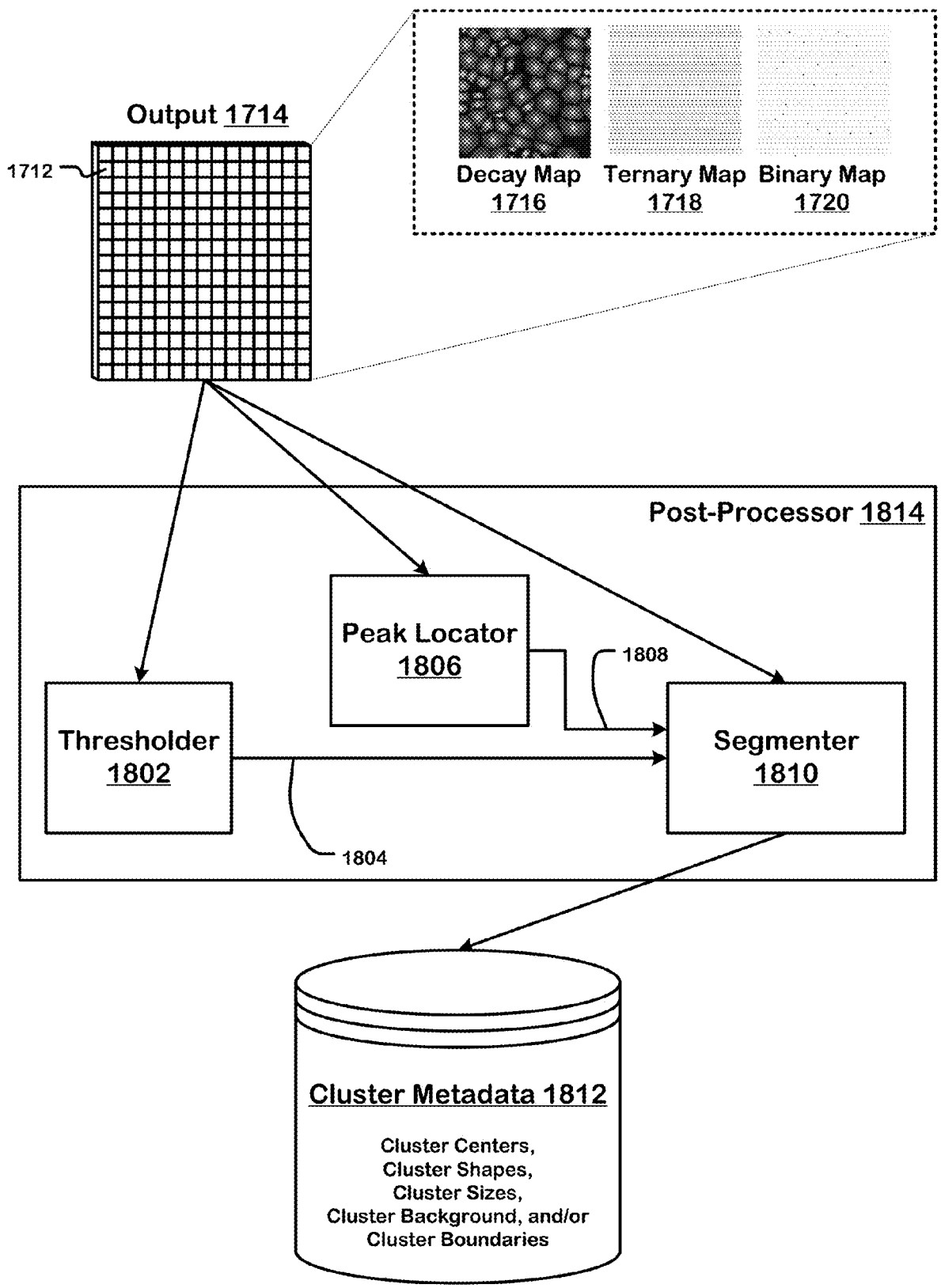
FIG. 18 shows one implementation of post-processing techniques that are applied to the decay map, the ternary map, or the binary map produced by the neural network-based template generator to derive cluster metadata, including cluster centers, cluster shapes, cluster sizes, cluster background, and/or cluster boundaries.

FIG. 18 shows one implementation of post-processing techniques that are applied to the decay map 1716, the ternary map 1718, or the binary map 1720 produced by the neural network-based template generator 1512 to derive cluster metadata, including cluster centers, cluster shapes, cluster sizes, cluster background, and/or cluster boundaries. In some implementations, the post-processing techniques are applied by a post-processor 1814 that further comprises a thresholder 1802, a peak locator 1806, and a segmenter 1810.

The input to the thresholder 1802 is the decay map 1716, the ternary map 1718, or the binary map 1720 produced by template generator 1512, such as the disclosed neural network-based template generator. In one implementation, the thresholder 1802 applies thresholding on the values in the decay map, the ternary map, or the binary map to identify background units 1804 (i.e., subpixels characterizing non-cluster background).) and non-background units. Said differently, once the output 1714 is produced, the thresholder 1802 thresholds output values of the units 1712 and classifies, or can reclassify a first subset of the units 1712 as "background units" 1804 depicting the surrounding background of the clusters and "non-background units" depicting units that potentially belong to clusters. The threshold value applied by the thresholder 1802 can be preset.

The input to the peak locator 1806 is also the decay map 1716, the ternary map 1718, or the binary map 1720 produced by the neural network-based template generator 1512. In one implementation, the peak locator 1806 applies peak detection on the values in the decay map 1716, the ternary map 1718, or the binary map 1720 to identify center units 1808 (i.e., center subpixels characterizing cluster centers). Said differently, the peak locator 1806 processes the output values of the units 1712 in the output 1714 and classifies a second subset of the units 1712 as "center units" 1808 containing centers of the clusters. In some implementations, the centers of the clusters detected by the peak locator 1806 are also the centers of mass of the clusters. The center units 1808 are then provided to the segmenter 1810. Additional details about the peak locator 1806 can be found in the Appendix entitled "Peak Detection".

The thresholding and the peak detection can be done in parallel or one after the other. That is, they are not dependent on each other.

The input to the segmenter 1810 is also the decay map 1716, the ternary map 1718, or the binary map 1720 produced by the neural network-based template generator 1512. Additional supplemental input to the segmenter 1810 comprises the thresholded units (background, non-background) 1804 identified by the thresholder 1802 and the center units 1808 identified by the peak locator 1806. The segmenter 1810 uses the background, non-background 1804 and the center units 1808 to identify disjointed regions 1812 (i.e., non-overlapping groups of contiguous cluster/cluster interior subpixels characterizing clusters). Said differently, the segmenter 1810 processes the output values of the units 1712 in the output 1714 and uses the background, non-background units 1804 and the center units 1808 to determine shapes 1812 of the clusters as non-overlapping regions of contiguous units separated by the background units 1804 and centered at the center units 1808. The output of the segmenter 1810 is cluster metadata 1812. The cluster metadata 1812 identifies cluster centers, cluster shapes, cluster sizes, cluster background, and/or cluster boundaries.

In one implementation, the segmenter 1810 begins with the center units 1808 and determines, for each center unit, a group of successively contiguous units that depict a same cluster whose center of mass is contained in the center unit. In one implementation, the segmenter 1810 uses a so-called "watershed" segmentation technique to subdivide contiguous clusters into multiple adjoining clusters at a valley in intensity. Additional details about the watershed segmentation technique and other segmentation techniques can be found in Appendix entitled "Watershed Segmentation".

In one implementation, the output values of the units 1712 in the output 1714 are continuous values, such as the one encoded in the ground truth decay map 1204. In another implementation, the output values are softmax scores, such as the one encoded in the ground truth ternary map 1304 and the ground truth binary map 1404. In the ground truth decay map 1204, according to one implementation, the contiguous units in the respective ones of the non-overlapping regions have output values weighted according to distance of a contiguous unit from a center unit in a non-overlapping region to which the contiguous unit belongs. In such an implementation, the center units have highest output values within the respective ones of the non-overlapping regions. As discussed above, during the training, due to the backward propagation-based gradient update, the decay map 1716, the ternary map 1718, and the binary map 1720 (i.e., cumulatively the output 1714) progressively match or approach the ground truth decay map 1204, the ground truth ternary map 1304, and the ground truth binary map 1404, respectively.

Pixel Domain—Intensity Extraction from Irregular Cluster Shapes

The discussion now turns to how cluster shapes determined by the technology disclosed can be used to extract intensity of the clusters. Since clusters typically have irregular shapes and contours, the technology disclosed can be used to identify which subpixels contribute to the irregularly shaped disjointed/non-overlapping regions that represent the cluster shapes.

Figure 19:
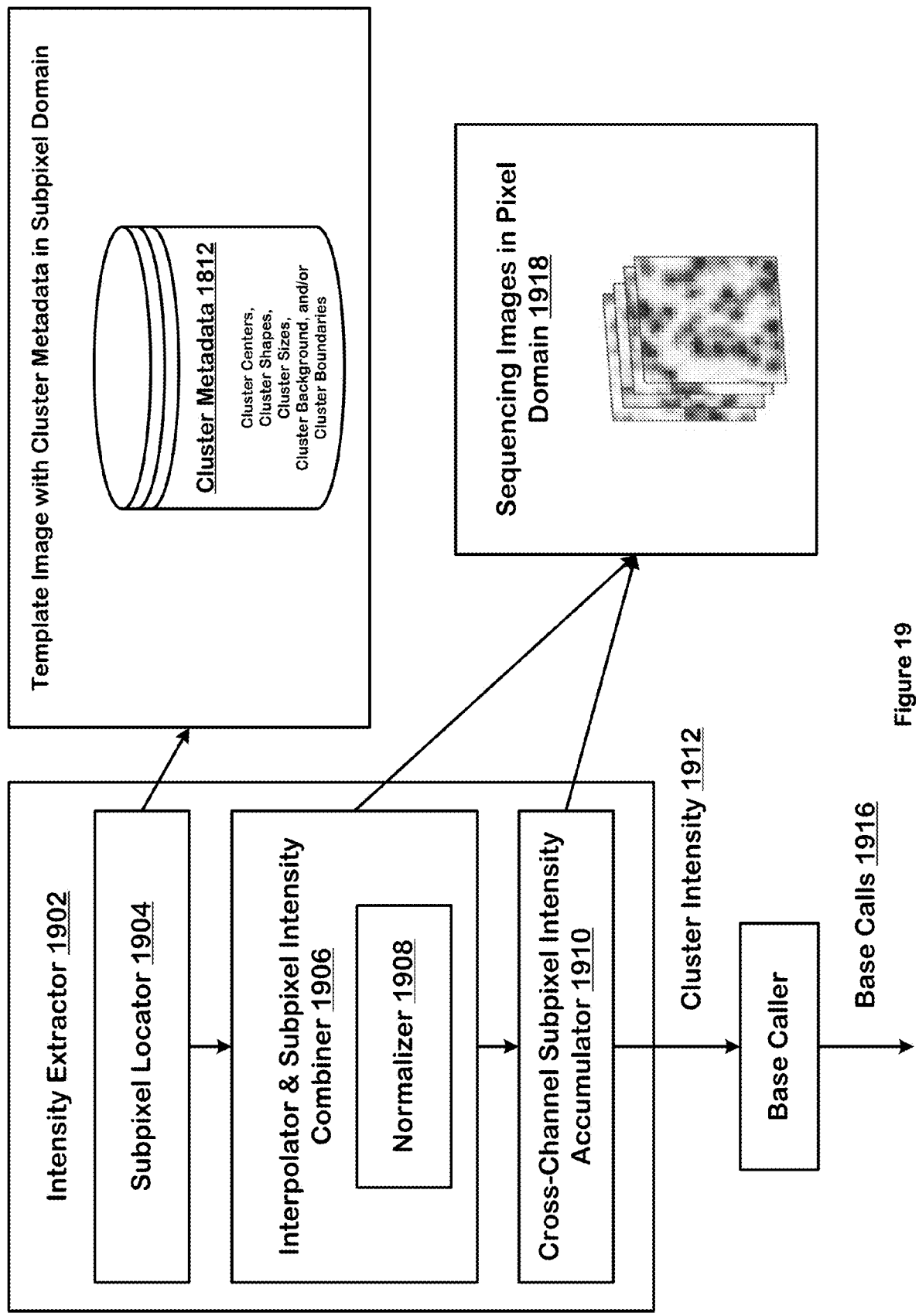
FIG. 19 depicts one implementation of extracting cluster intensity in the pixel domain.

FIG. 19 depicts one implementation of extracting cluster intensity in the pixel domain. "Template image" or "template" can refer to a data structure that contains or identifies the cluster metadata 1812 derived from the decay map 1716, the ternary map 1718, and/or the binary map 1718. The cluster metadata 1812 identifies cluster centers, cluster shapes, cluster sizes, cluster background, and/or cluster boundaries.

In some implementations, the template image is in the upsampled, subpixel domain to distinguish the cluster boundaries at a fine-grained level. However, the sequencing images 108, which contain the cluster and background intensity data, are typically in the pixel domain. Thus, the technology disclosed proposes two approaches to use the cluster shape information encoded in the template image in the upsampled, subpixel resolution to extract intensities of the irregularly shaped clusters from the optical, pixel-resolution sequencing images. In the first approach, depicted in FIG. 19, the non-overlapping groups of contiguous subpixels identified in the template image are located in the pixel resolution sequencing images and their intensities extracted via interpolation. Additional details about this intensity extraction technique can be found in FIG. 33 and its discussion.

In one implementation, when the non-overlapping regions have irregular contours and the units are subpixels, the cluster intensity 1912 of a given cluster is determined by an intensity extractor 1902 as follows.

First, a subpixel locator 1904 identifies subpixels that contribute to the cluster intensity of the given cluster based on a corresponding non-overlapping region of contiguous subpixels that identifies a shape of the given cluster.

Then, the subpixel locator 1904 locates the identified subpixels in one or more optical, pixel-resolution images 1918 generated for one or more imaging channels at a current sequencing cycle. In one implementation, integer or non-integer coordinates (e.g., floating points) are located in the optical, pixel-resolution images, after a downscaling based on a downscaling factor that matches an upsampling factor used to create the subpixel domain.

Then, an interpolator and subpixel intensity combiner 1906, intensities of the identified subpixels in the images processed, combines the interpolated intensities, and normalizes the combined interpolated intensities to produce a per-image cluster intensity for the given cluster in each of the images. The normalization is performed by a normalizer 1908 and is based on a normalization factor. In one implementation, the normalization factor is a number of the identified subpixels. This is done to normalize/account for different cluster sizes and uneven illuminations that clusters receive depending on their location on the flow cell.

Finally, a cross-channel subpixel intensity accumulator 1910 combines the per-image cluster intensity for each of the images to determine the cluster intensity 1912 of the given cluster at the current sequencing cycle.

Then, the given cluster is base called based on the cluster intensity 1912 at the current sequencing cycle by any one of the base callers discussed in this application, yielding base calls 1916.

In some implementations though, when the cluster sizes are large enough, the output of the neural network-based base caller 1514, i.e., the decay map 1716, the ternary map 1718, and the binary map 1720 are in the optical, pixel domain. Accordingly, in such implementations, the template image is also in the optical, pixel domain.

Subpixel Domain—Intensity Extraction from Irregular Cluster Shapes

Figure 20:
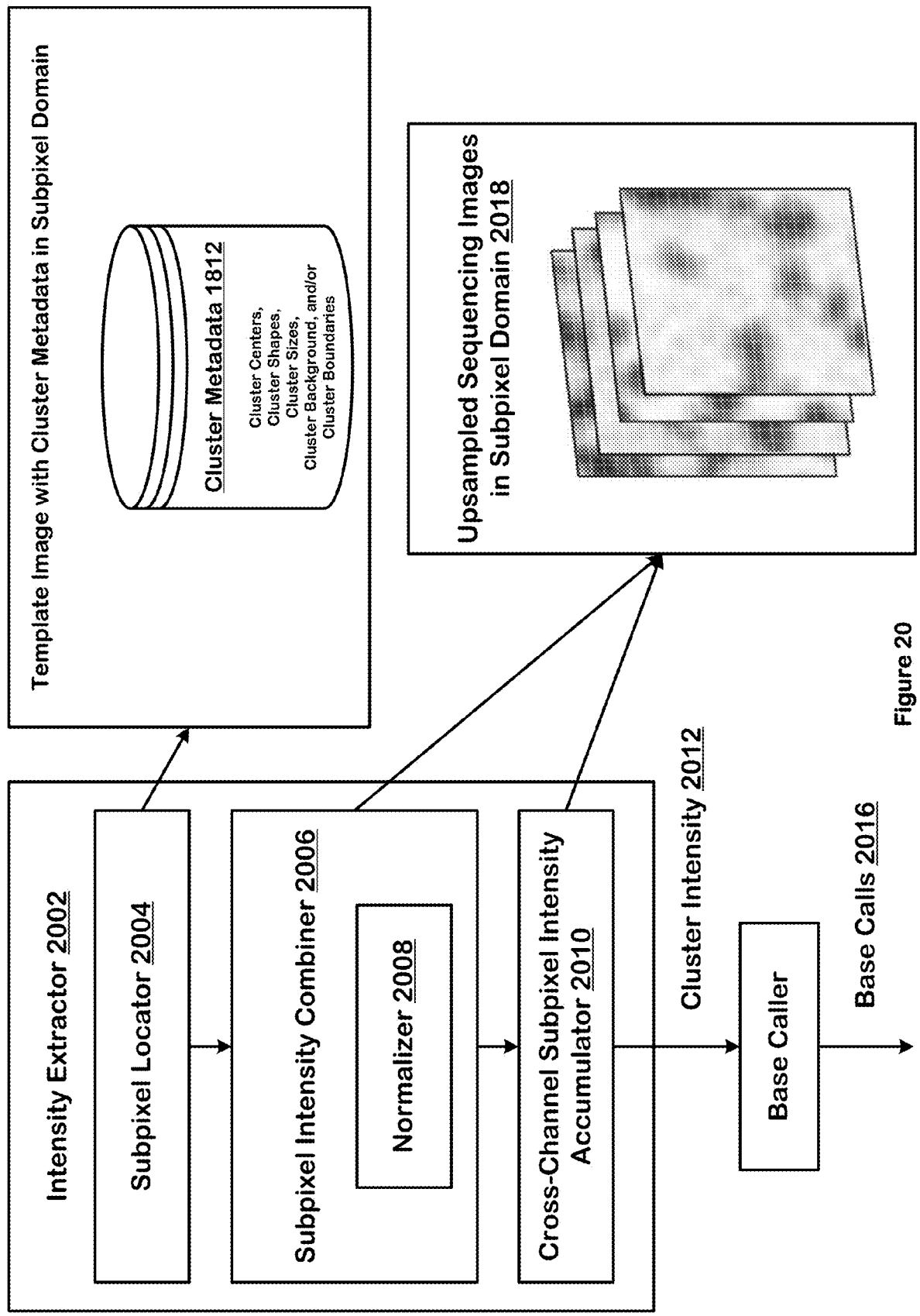
FIG. 20 illustrates one implementation of extracting cluster intensity in the subpixel domain.

FIG. 20 depicts the second approach of extracting cluster intensity in the subpixel domain. In this second approach, the sequencing images in the optical, pixel-resolution are upsampled into the subpixel resolution. This results in correspondence between the "cluster shape depicting subpixels" in the template image and the "cluster intensity depicting subpixels" in the upsampled sequencing images. The cluster intensity is then extracted based on the correspondence. Additional details about this intensity extraction technique can be found in FIG. 33 and its discussion.

In one implementation, when the non-overlapping regions have irregular contours and the units are subpixels, the cluster intensity 2012 of a given cluster is determined by an intensity extractor 2002 as follows.

First, a subpixel locator 2004 identifies subpixels that contribute to the cluster intensity of the given cluster based on a corresponding non-overlapping region of contiguous subpixels that identifies a shape of the given cluster.

Then, the subpixel locator 2004 locates the identified subpixels in one or more subpixel resolution images 2018 upsampled from corresponding optical, pixel-resolution images 1918 generated for one or more imaging channels at a current sequencing cycle. The upsampling can be performed by nearest neighbor intensity extraction, Gaussian based intensity extraction, intensity extraction based on average of 2×2 subpixel area, intensity extraction based on brightest of 2×2 subpixel area, intensity extraction based on average of 3×3 subpixel area, bilinear intensity extraction, bicubic intensity extraction, and/or intensity extraction based on weighted area coverage. These techniques are described in detail in Appendix entitled "Intensity Extraction Methods". The template image can, in some implementations, serve as a mask for intensity extraction.

Then, a subpixel intensity combiner 2006, in each of the upsampled images, combines intensities of the identified subpixels and normalizes the combined intensities to produce a per-image cluster intensity for the given cluster in each of the upsampled images. The normalization is performed by a normalizer 2008 and is based on a normalization factor. In one implementation, the normalization factor is a number of the identified subpixels. This is done to normalize/account for different cluster sizes and uneven illuminations that clusters receive depending on their location on the flow cell.

Finally, a cross-channel, subpixel-intensity accumulator 2010 combines the per-image cluster intensity for each of the upsampled images to determine the cluster intensity 2012 of the given cluster at the current sequencing cycle.

Then, the given cluster is base called based on the cluster intensity 2012 at the current sequencing cycle by any one of the base callers discussed in this application, yielding base calls 2016.

Types of Neural Network-Based Template Generators

Figure 21A:
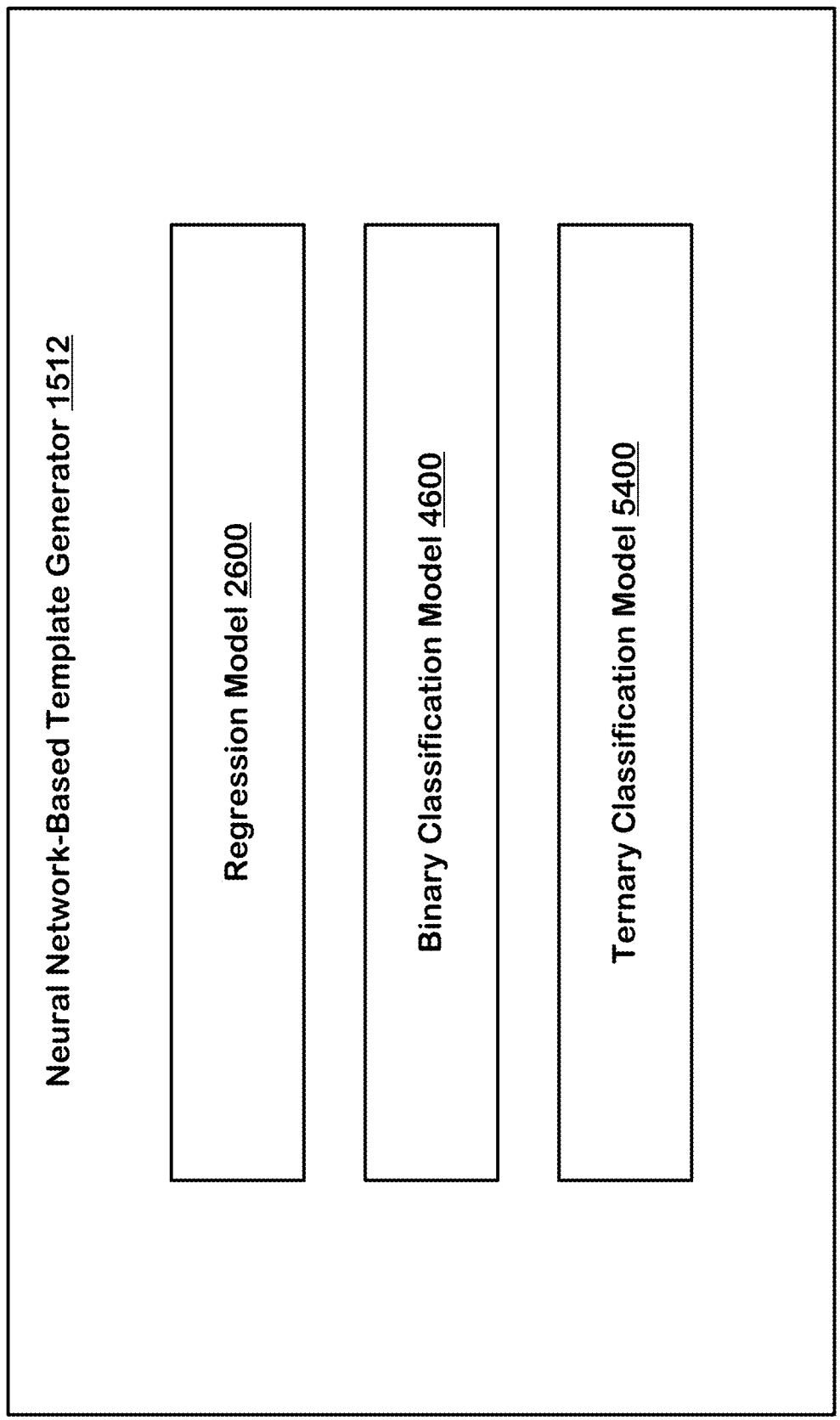
FIG. 21a shows three different implementations of the neural network-based template generator.

The discussion now turns to details of three different implementations of the neural network-based template generator 1512. There are shown in FIG. 21a and include: (1) the decay map-based template generator 2600 (also called the regression model), (2) the binary map-based template generator 4600 (also called the binary classification model), and (3) the ternary map-based template generator 5400 (also called the ternary classification model).

In one implementation, the regression model 2600 is a fully convolutional network. In another implementation, the regression model 2600 is a U-Net network with skip connections between the decoder and the encoder. In one implementation, the binary classification model 4600 is a fully convolutional network. In another implementation, the binary classification model 4600 is a U-Net network with skip connections between the decoder and the encoder. In one implementation, the ternary classification model 5400 is a fully convolutional network. In another implementation, the ternary classification model 5400 is a U-Net network with skip connections between the decoder and the encoder.

Input Image Data

Figure 21B:
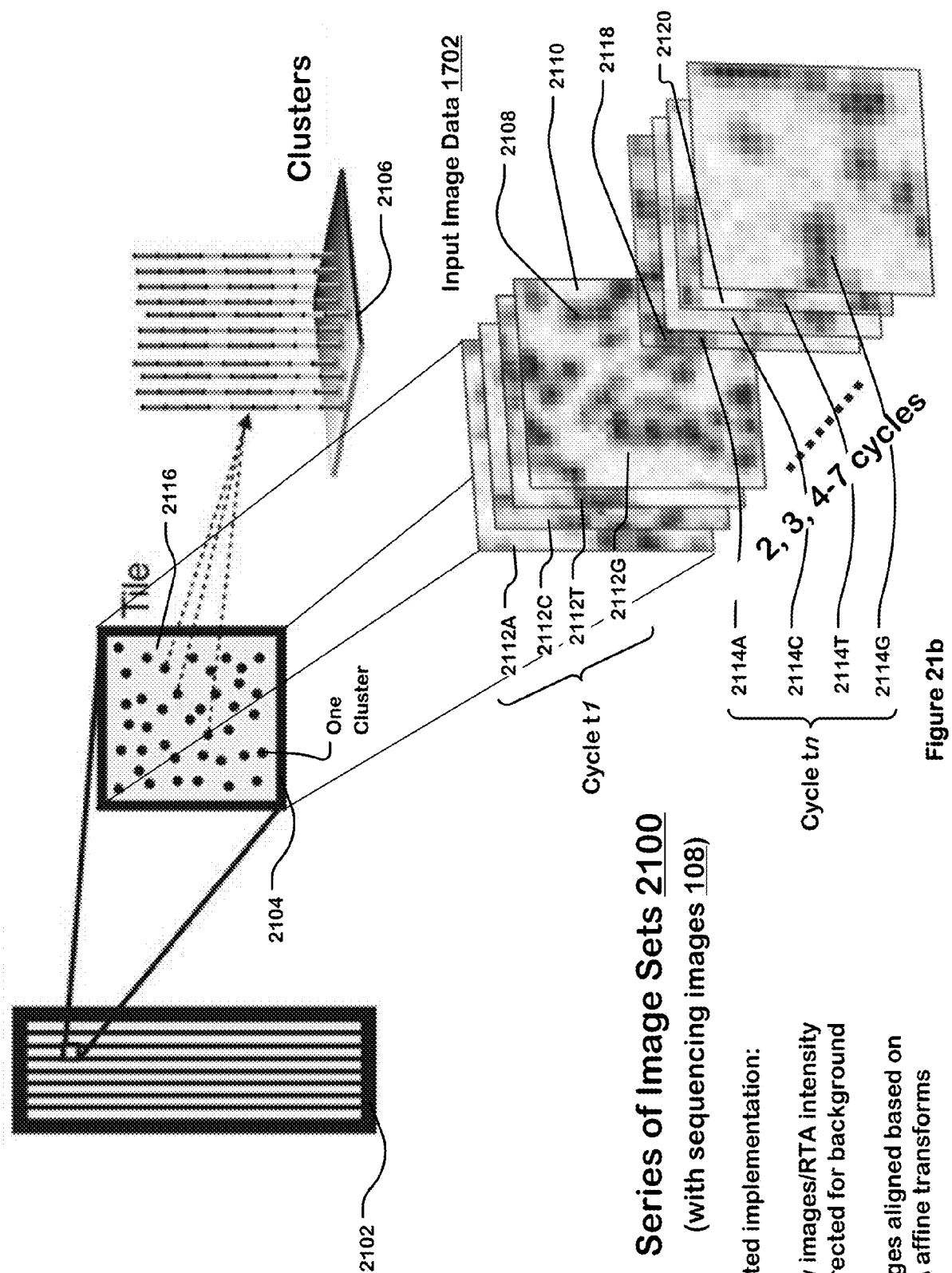
FIG. 21b depicts one implementation of the input image data that is fed as input to the neural network-based template generator 1512. The input image data comprises a series of image sets with sequencing images that are generated during a certain number of initial sequences cycles of a sequencing arm.

FIG. 21*b* depicts one implementation of the input image data 1702 that is fed as input to the neural network-based template generator 1512. The input image data 1702 comprises a series of image sets 2100 with the sequencing images 108 that are generated during a certain number of initial sequences cycles of a sequencing run (e.g., the first 2 to 7 sequencing cycles).

In some implementations, intensities of the sequencing images 108 are corrected for background and/or aligned with each other using affine transformation. In one implementation, the sequencing run utilizes four-channel chemistry and each image set has four images. In another implementation, the sequencing run utilizes two-channel chemistry and each image set has two images. In yet another implementation, the sequencing run utilizes one-channel chemistry and each image set has two images. In yet other implementations, each image set has only one image. These and other different implementations are described in Appendices 6 and 9.

Each image 2116 in the series of image sets 2100 covers a tile 2104 of a flow cell 2102 and depicts intensity emissions of clusters 2106 on the tile 2104 and their surrounding background captured for a particular image channel at a particular one of a plurality of sequencing cycles of the sequencing run. In one example, for cycle t1, the image set includes four images 2112A, 2112C, 2112T, and 2112G: one image for each base A, C, T, and G labeled with a corresponding fluorescent dye and imaged in a corresponding wavelength band (image/imaging channel).

For illustration purposes, in image 2112G, FIG. 21*b* depicts cluster intensity emissions as 2108 and background intensity emissions as 2110. In another example, for cycle hi, the image set also includes four images 2114A, 2114C, 2114T, and 2114G: one image for each base A, C, T, and G labeled with a corresponding fluorescent dye and imaged in a corresponding wavelength band (image/imaging channel) Also for illustration purposes, in image 2114A, FIG. 21*b* depicts cluster intensity emissions as 2118 and, in image 2114T, depicts background intensity emissions as 2120.

The input image data 1702 is encoded using intensity channels (also called imaged channels). For each of the c images obtained from the sequencer for a particular sequencing cycle, a separate imaged channel is used to encode its intensity signal data. Consider, for example, that the sequencing run uses the 2-channel chemistry which produces a red image and a green image at each sequencing cycle. In such a case, the input data 2632 comprises (i) a first red imaged channel with w×h pixels that depict intensity emissions of the one or more clusters and their surrounding background captured in the red image and (ii) a second green imaged channel with w×h pixels that depict intensity emissions of the one or more clusters and their surrounding background captured in the green image.

Non-Image Data

In another implementation, the input data to the neural network-based template generator 1512 and the neural network-based base caller 1514 is based on pH changes induced by the release of hydrogen ions during molecule extension. The pH changes are detected and converted to a voltage change that is proportional to the number of bases incorporated (e.g., in the case of Ion Torrent).

In yet another implementation, the input data is constructed from nanopore sensing that uses biosensors to measure the disruption in current as an analyte passes through a nanopore or near its aperture while determining the identity of the base. For example, the Oxford Nanopore Technologies (ONT) sequencing is based on the following concept: pass a single strand of DNA (or RNA) through a membrane via a nanopore and apply a voltage difference across the membrane. The nucleotides present in the pore will affect the pore's electrical resistance, so current measurements over time can indicate the sequence of DNA bases passing through the pore. This electrical current signal (the 'squiggle' due to its appearance when plotted) is the raw data gathered by an ONT sequencer. These measurements are stored as 16-bit integer data acquisition (DAC) values, taken at 4 kHz frequency (for example). With a DNA strand velocity of −450 base pairs per second, this gives approximately nine raw observations per base on average. This signal is then processed to identify breaks in the open pore signal corresponding to individual reads. These stretches of raw signal are base called—the process of converting DAC values into a sequence of DNA bases. In some implementations, the input data comprises normalized or scaled DAC values.

In another implementation, image data is not used as input to the neural network-based template generator 1512 or the neural network-based base caller 1514. Instead, the input to the neural network-based template generator 1512 and the neural network-based base caller 1514 is based on pH changes induced by the release of hydrogen ions during molecule extension. The pH changes are detected and converted to a voltage change that is proportional to the number of bases incorporated (e.g., in the case of Ion Torrent).

In yet another implementation, the input to the neural network-based template generator 1512 and the neural network-based base caller 1514 is constructed from nanopore sensing that uses biosensors to measure the disruption in current as an analyte passes through a nanopore or near its aperture while determining the identity of the base. For example, the Oxford Nanopore Technologies (ONT) sequencing is based on the following concept: pass a single strand of DNA (or RNA) through a membrane via a nanopore and apply a voltage difference across the membrane. The nucleotides present in the pore will affect the pore's electrical resistance, so current measurements over time can indicate the sequence of DNA bases passing through the pore. This electrical current signal (the 'squiggle' due to its appearance when plotted) is the raw data gathered by an ONT sequencer. These measurements are stored as 16-bit integer data acquisition (DAC) values, taken at 4 kHz frequency (for example). With a DNA strand velocity of −450 base pairs per second, this gives approximately nine raw observations per base on average. This signal is then processed to identify breaks in the open pore signal corresponding to individual reads. These stretches of raw signal are base called—the process of converting DAC values into a sequence of DNA bases. In some implementations, the input data 2632 comprises normalized or scaled DAC values.

Patch Extraction

Figure 22:
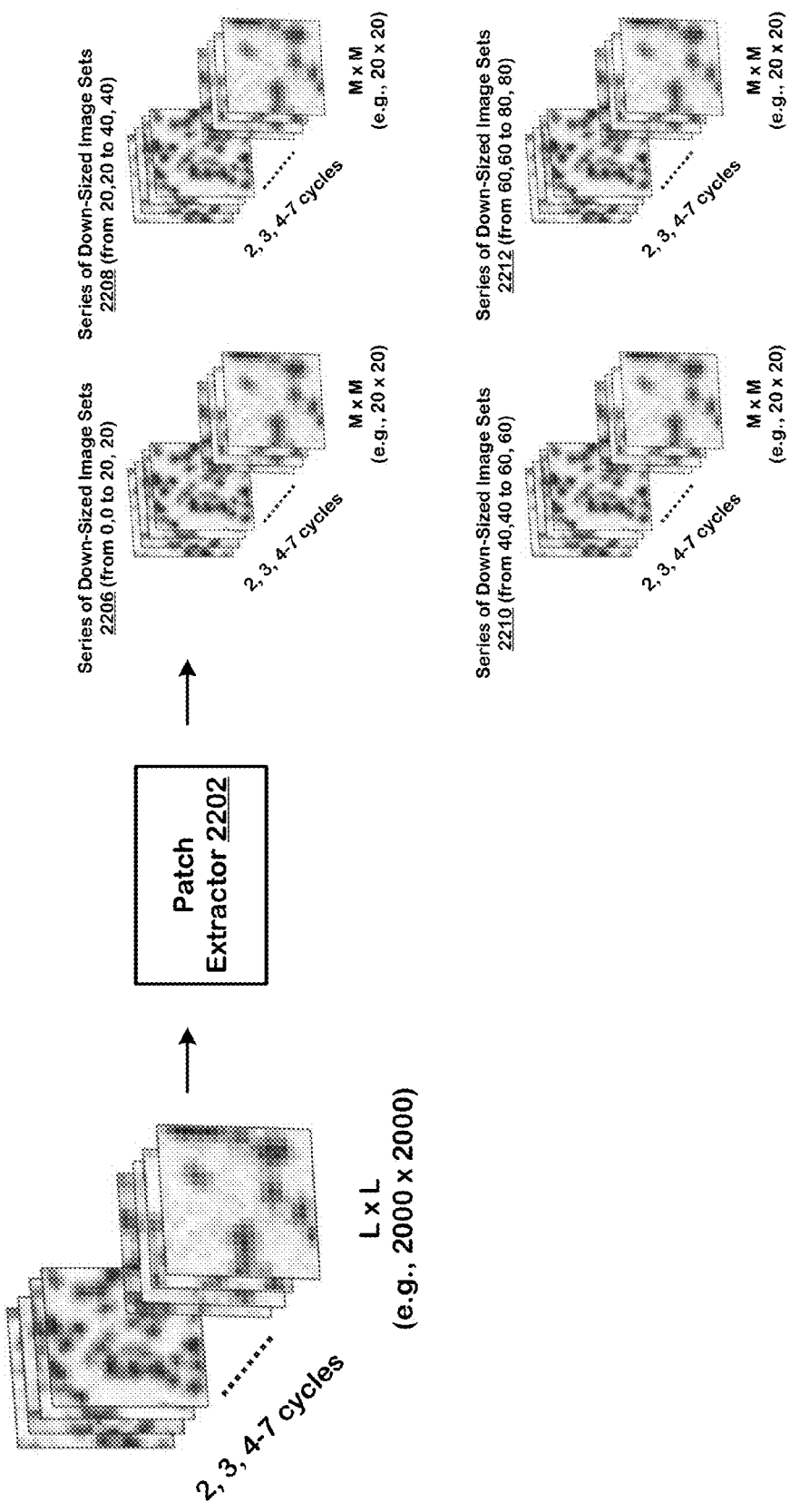
FIG. 22 shows one implementation of extracting patches from the series of image sets in FIG. 21b to produce a series of "down-sized" image sets that form the input image data.

FIG. 22 shows one implementation of extracting patches from the series of image sets 2100 in FIG. 21*b* to produce a series of "down-sized" image sets that form the input image data 1702. In the illustrated implementation, the sequencing images 108 in the series of image sets 2100 are of size L×L (e.g., 2000×2000). In other implementations, L is any number ranging from 1 and 10,000.

In one implementation, a patch extractor 2202 extracts patches from the sequencing images 108 in the series of image sets 2100 and produces a series of down-sized image sets 2206, 2208, 2210, and 2212. Each image in the series of down-sized image sets is a patch of size M×M (e.g., 20×20) that is extracted from a corresponding sequencing image in the series of image sets 2100. The size of the patches can be preset. In other implementations, M is any number ranging from 1 and 1000.

In FIG. 22, four example series of down-sized image sets are shown. The first example series of down-sized image sets 2206 is extracted from coordinates 0,0 to 20,20 in the sequencing images 108 in the series of image sets 2100. The second example series of down-sized image sets 2208 is extracted from coordinates 20,20 to 40,40 in the sequencing images 108 in the series of image sets 2100. The third example series of down-sized image sets 2210 is extracted from coordinates 40,40 to 60,60 in the sequencing images 108 in the series of image sets 2100. The fourth example series of down-sized image sets 2212 is extracted from coordinates 60,60 to 80,80 in the sequencing images 108 in the series of image sets 2100.

In some implementations, the series of down-sized image sets form the input image data 1702 that is fed as input to the neural network-based template generator 1512. Multiple series of down-sized image sets can be simultaneously fed as an input batch and a separate output can be produced for each series in the input batch.

Upsampling

Figure 23:
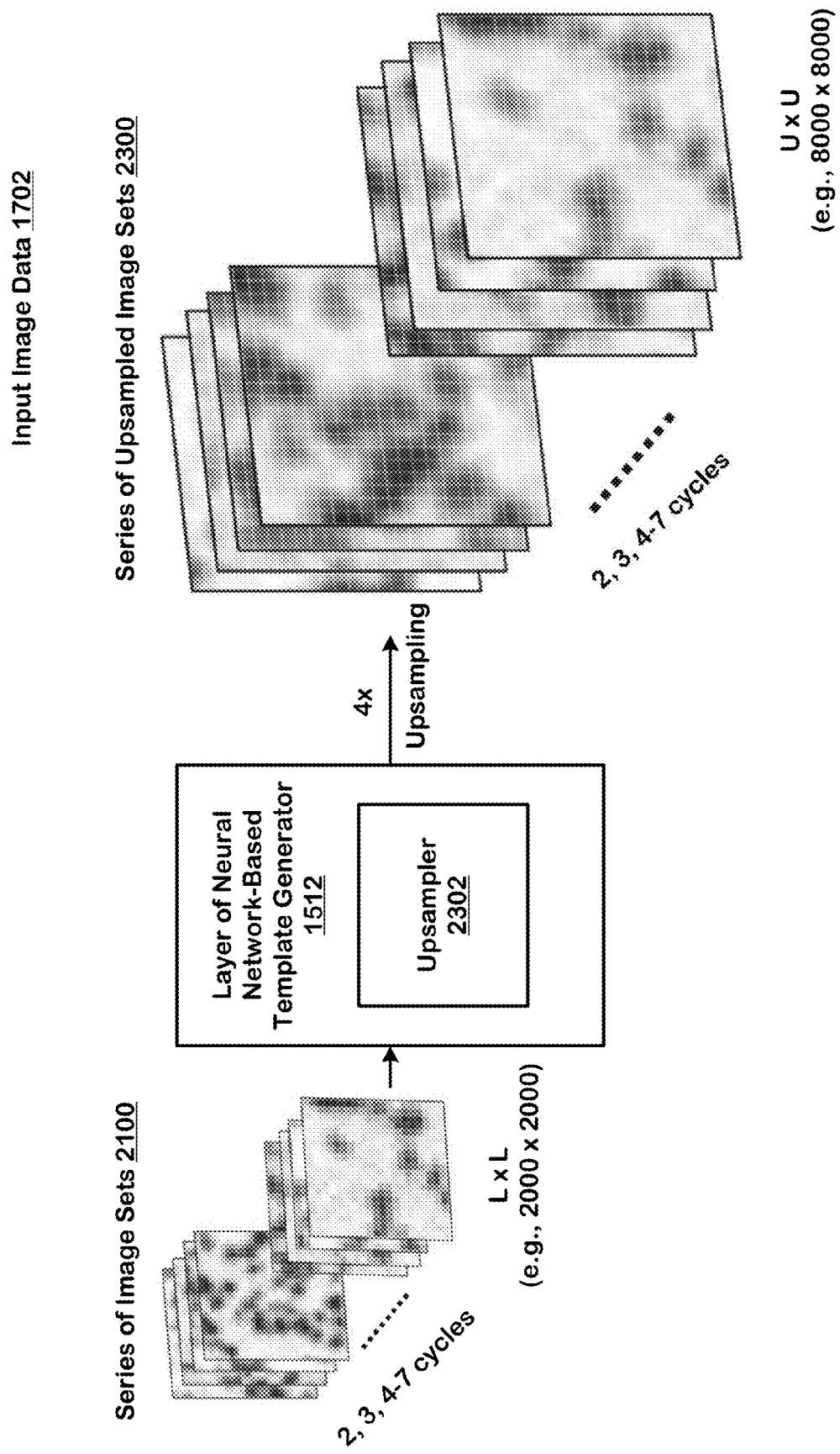
FIG. 23 depicts one implementation of upsampling the series of image sets in FIG. 21b to produce a series of "upsampled" image sets that forms the input image data.

FIG. 23 depicts one implementation of upsampling the series of image sets 2100 in FIG. 21b to produce a series of "upsampled" image sets 2300 that forms the input image data 1702.

In one implementation, an upsampler 2302 uses interpolation (e.g., bicubic interpolation) to upsample the sequencing images 108 in the series of image sets 2100 by an upsampling factor (e.g., 4×) and the series of upsampled image sets 2300.

In the illustrated implementation, the sequencing images 108 in the series of image sets 2100 are of size L×L (e.g., 2000×2000) and are upsampled by an upsampling factor of four to produce upsampled images of size U×U (e.g., 8000×8000) in the series of upsampled image sets 2300.

In one implementation, the sequencing images 108 in the series of image sets 2100 are fed directly to the neural network-based template generator 1512 and the upsampling is performed by an initial layer of the neural network-based template generator 1512. That is, the upsampler 2302 is part of the neural network-based template generator 1512 and operates as its first layer that upsamples the sequencing images 108 in the series of image sets 2100 and produces the series of upsampled image sets 2300.

In some implementations, the series of upsampled image sets 2300 forms the input image data 1702 that is fed as input to the neural network-based template generator 1512.

Figure 24:
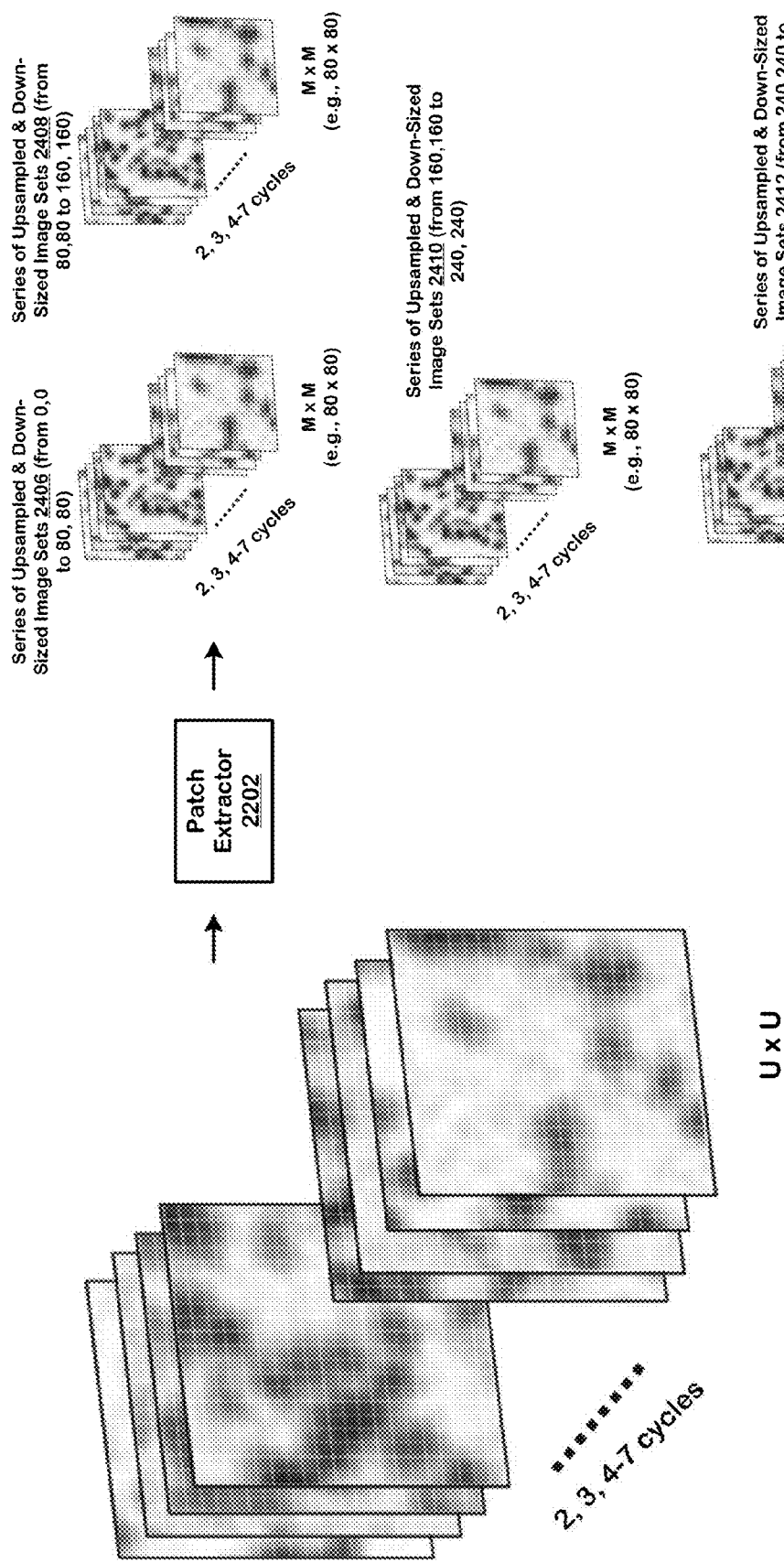
FIG. 24 shows one implementation of extracting patches from the series of upsampled image sets in FIG. 23 to produce a series of "upsampled and down-sized" image sets that form the input image data.

FIG. 24 shows one implementation of extracting patches from the series of upsampled image sets 2300 in FIG. 23 to produce a series of "upsampled and down-sized" image sets 2406, 2408, 2410, and 2412 that form the input image data 1702.

In one implementation, the patch extractor 2202 extracts patches from the upsampled images in the series of upsampled image sets 2300 and produces series of upsampled and down-sized image sets 2406, 2408, 2410, and 2412. Each upsampled image in the series of upsampled and down-sized image sets is a patch of size M×M (e.g., 80×80) that is extracted from a corresponding upsampled image in the series of upsampled image sets 2300. The size of the patches can be preset. In other implementations, M is any number ranging from 1 and 1000.

In FIG. 24, four example series of upsampled and down-sized image sets are shown. The first example series of upsampled and down-sized image sets 2406 is extracted from coordinates 0,0 to 80,80 in the upsampled images in the series of upsampled image sets 2300. The second example series of upsampled and down-sized image sets 2408 is extracted from coordinates 80,80 to 160,160 in the upsampled images in the series of upsampled image sets 2300. The third example series of upsampled and down-sized image sets 2410 is extracted from coordinates 160,160 to 240,240 in the upsampled images in the series of upsampled image sets 2300. The fourth example series of upsampled and down-sized image sets 2412 is extracted from coordinates 240,240 to 320,320 in the upsampled images in the series of upsampled image sets 2300.

In some implementations, the series of upsampled and down-sized image sets form the input image data 1702 that is fed as input to the neural network-based template generator 1512. Multiple series of upsampled and down-sized image sets can be simultaneously fed as an input batch and a separate output can be produced for each series in the input batch.

Output

The three models are trained to produce different outputs. This is achieved by using different types of ground truth data representations as training labels. The regression model 2600 is trained to produce output that characterizes/represents/denotes a so-called "decay map" 1716. The binary classification model 4600 is trained to produce output that characterizes/represents/denotes a so-called "binary map" 1720. The ternary classification model 5400 is trained to produce output that characterizes/represents/denotes a so-called "ternary map" 1718.

The output 1714 of each type of model comprises an array of units 1712. The units 1712 can be pixels, subpixels, or superpixels. The output of each type of model includes unit-wise output values, such that the output values of an array of units together characterize/represent/denote the decay map 1716 in the case of the regression model 2600, the binary map 1720 in the case of the binary classification model 4600, and the ternary map 1718 in the case of the ternary classification model 5400. More details follow.

Ground Truth Data Generation

Figure 25:
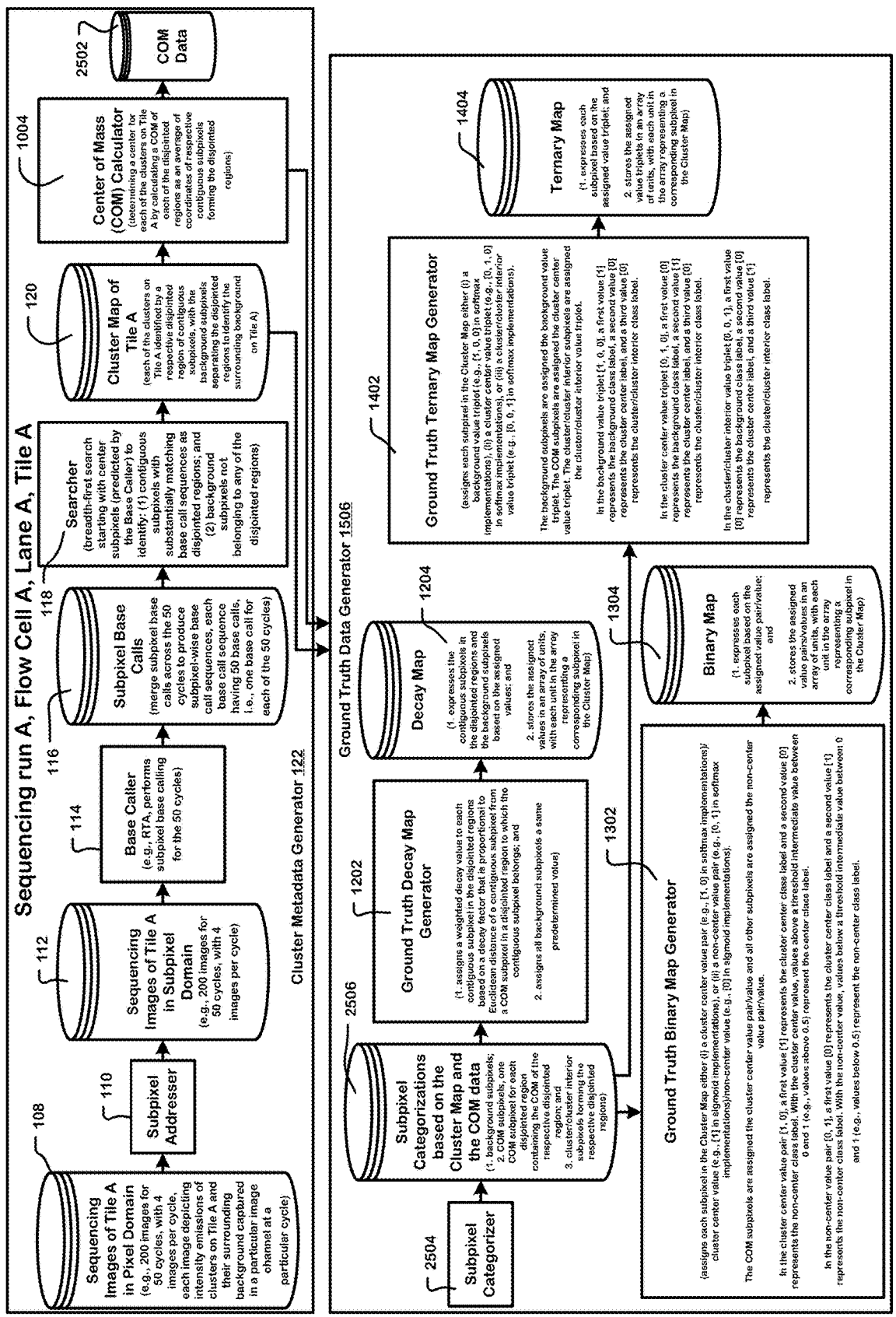
FIG. 25 illustrates one implementation of an overall example process of generating ground truth data for training the neural network-based template generator.

FIG. 25 illustrates one implementation of an overall example process of generating ground truth data for training the neural network-based template generator 1512. For the regression model 2600, the ground truth data can be the decay map 1204. For the binary classification model 4600, the ground truth data can be the binary map 1404. For the ternary classification model 5400, the ground truth data can be the ternary map 1304. The ground truth data is generated from the cluster metadata. The cluster metadata is generated by the cluster metadata generator 122. The ground truth data is generated by the ground truth data generator 1506.

In the illustrated implementation, the ground truth data is generated for tile A that is on lane A of flow cell A. The ground truth data is generated from the sequencing images 108 of tile A captured during sequencing run A. The sequencing images 108 of tile A are in the pixel domain. In one example involving 4-channel chemistry that generates four sequencing images per sequencing cycle, two hundred sequencing images 108 for fifty sequencing cycles are accessed. Each of the two hundred sequencing images 108 depicts intensity emissions of clusters on tile A and their surrounding background captured in a particular image channel at a particular sequencing cycle.

The subpixel addresser 110 converts the sequencing images 108 into the subpixel domain (e.g., by dividing each pixel into a plurality of subpixels) and produces sequencing images 112 in the subpixel domain.

The base caller 114 (e.g., RTA) then processes the sequencing images 112 in the subpixel domain and produces a base call for each subpixel and for each of the fifty sequencing cycles. This is referred to herein as "subpixel base calling".

The subpixel base calls 116 are then merged to produce, for each subpixel, a base call sequence across the fifty sequencing cycles. Each subpixel's base call sequence has fifty base calls, i.e., one base call for each of the fifty sequencing cycles.

The searcher 118 evaluates base call sequences of contiguous subpixels on a pair-wise basis. The search involves evaluating each subpixel to determine with which of its contiguous subpixels it shares a substantially matching base call sequence. Base call sequences of contiguous subpixels are "substantially matching" when a predetermined portion of base calls match on an ordinal position-wise basis (e.g., >=41 matches in 45 cycles, <=4 mismatches in 45 cycles, <=4 mismatches in 50 cycles, or <=2 mismatches in 34 cycles).

In some implementations, the base caller 114 also identifies preliminary center coordinates of the clusters. Subpixels that contain the preliminary center coordinates are referred to as center or origin subpixels. Some example preliminary center coordinates (604a-c) identified by the base caller 114 and corresponding origin subpixels (606a-c) are shown in FIG. 6. However, identification of the origin subpixels (preliminary center coordinates of the clusters) is not needed, as explained below. In some implementations, the searcher 118 uses a breadth-first search for identifying substantially matching base call sequences of the subpixels by beginning with the origin subpixels 606a-c and continuing with successively contiguous non-origin subpixels 702a-c. This again is optional, as explained below.

The search for substantially matching base call sequences of the subpixels does not need identification of the origin subpixels (preliminary center coordinates of the clusters) because the search can be done for all the subpixels and the search does not have to start from the origin subpixels and instead can start from any subpixel (e.g., 0,0 subpixel or any random subpixel). Thus, since each subpixel is evaluated to determine whether it shares a substantially matching base call sequence with another contiguous subpixel, the search does not have to utilize the origin subpixels and can start with any subpixel.

Irrespective of whether origin subpixels are used or not, certain clusters are identified that do not contain the origin subpixels (preliminary center coordinates of the clusters) predicted by the base caller 114. Some examples of clusters identified by the merging of the subpixel base calls and not containing an origin subpixel are clusters 812a, 812b, 812c, 812d, and 812e in FIG. 8a. Therefore, use of the base caller 114 for identification of origin subpixels (preliminary center coordinates of the clusters) is optional and not essential for the search of substantially matching base call sequences of the subpixels.

The searcher 118: (1) identifies contiguous subpixels with substantially matching base call sequences as so-called "disjointed regions", (2) further evaluates base call sequences of those subpixels that do not belong to any of the disjointed regions already identified at (1) to yield additional disjointed regions, and (3) then identifies background subpixels as those subpixels that do not belong to any of the disjointed regions already identified at (1) and (2). Action (2) allows the technology disclosed to identify additional or extra clusters for which the centers are not identified by the base caller 114.

The results of the searcher 118 are encoded in a so-called "cluster map" of tile A and stored in the cluster map data store 120. In the cluster map, each of the clusters on tile A are identified by a respective disjointed region of contiguous subpixels, with background subpixels separating the disjointed regions to identify the surrounding background on tile A.

The center of mass (COM) calculator 1004 determines a center for each of the clusters on tile A by calculating a COM of each of the disjointed regions as an average of coordinates of respective contiguous subpixels forming the disjointed regions. The centers of mass of the clusters are stored as COM data 2502.

A subpixel categorizer 2504 uses the cluster map and the COM data 2502 to produce subpixel categorizations 2506. The subpixel categorizations 2506 classify subpixels in the cluster map as (1) backgrounds subpixels, (2) COM subpixels (one COM subpixel for each disjointed region containing the COM of the respective disjointed region), and (3) cluster/cluster interior subpixels forming the respective disjointed regions. That is, each subpixel in the cluster map is assigned one of the three categories.

Based on the subpixel categorizations 2506, in some implementations, (i) the ground truth decay map 1204 is produced by the ground truth decay map generator 1202, (ii) the ground truth binary map 1304 is produced by the ground truth binary map generator 1302, and (iii) the ground truth ternary map 1404 is produced by the ground truth ternary map generator 1402.

1. Regression Model

Figure 26:
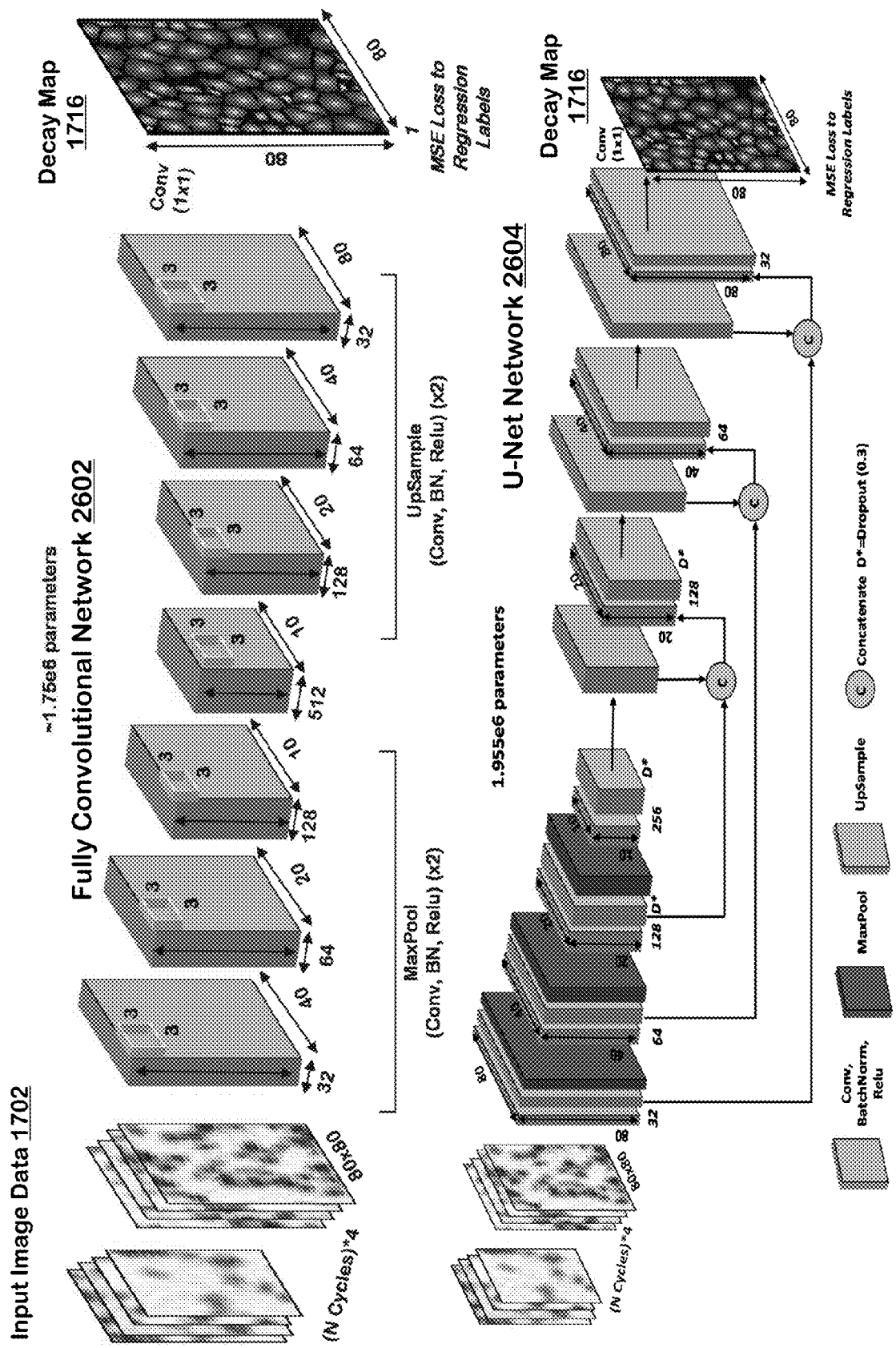
FIG. 26 illustrates one implementation of the regression model.

FIG. 26 illustrates one implementation of the regression model 2600. In the illustrated implementation, the regression model 2600 is a fully convolutional network 2602 that processes the input image data 1702 through an encoder subnetwork and a corresponding decoder subnetwork. The encoder subnetwork includes a hierarchy of encoders. The decoder subnetwork includes a hierarchy of decoders that map low resolution encoder feature maps to a full input resolution decay map 1716. In another implementation, the regression model 2600 is a U-Net network 2604 with skip connections between the decoder and the encoder. Additional details about the segmentation networks can be found in the Appendix entitled "Segmentation Networks".

Decay Map

Figure 27:
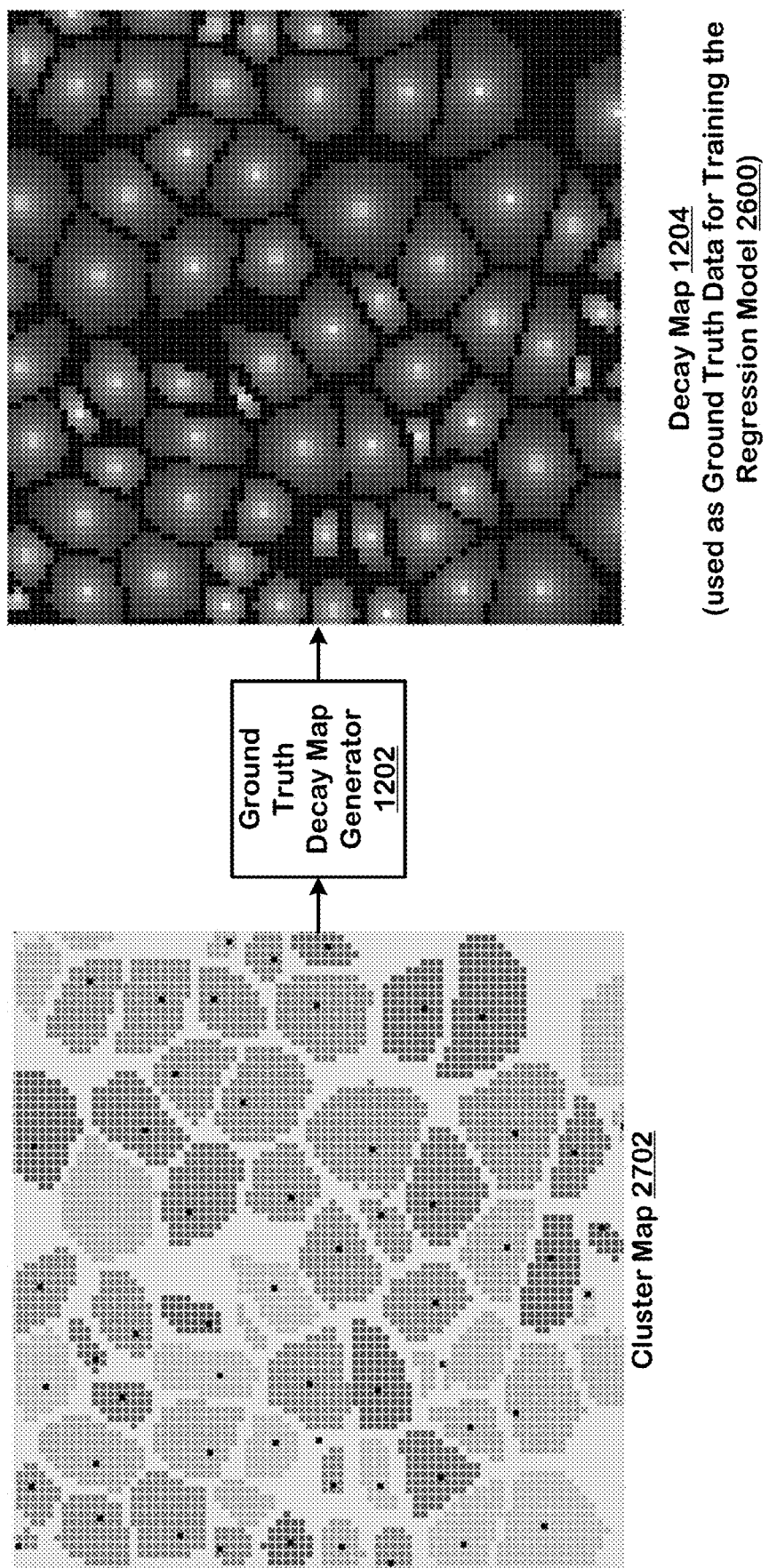
FIG. 27 depicts one implementation of generating a ground truth decay map from a cluster map. The ground truth decay map is used as ground truth data for training the regression model.

FIG. 27 depicts one implementation of generating a ground truth decay map 1204 from a cluster map 2702. The ground truth decay map 1204 is used as ground truth data for training the regression model 2600. In the ground truth decay map 1204, the ground truth decay map generator 1202 assigns a weighted decay value to each contiguous subpixel in the disjointed regions based on a weighted decay factor. The weighted decay value is proportional to Euclidean distance of a contiguous subpixel from a center of mass (COM) subpixel in a disjointed region to which the contiguous subpixel belongs, such that the weighted decay value is highest (e.g., 1 or 100) for the COM subpixel and decreases for subpixels further away from the COM subpixel. In some implementations, the weighted decay value is multiplied by a preset factor, such as 100.

Further, the ground truth decay map generator 1202 assigns all background subpixels a same predetermine value (e.g., a minimalist background value).

The ground truth decay map 1204 expresses the contiguous subpixels in the disjointed regions and the background subpixels based on the assigned values. The ground truth decay map 1204 also stores the assigned values in an array of units, with each unit in the array representing a corresponding subpixel in the input.

Training

Figure 28:
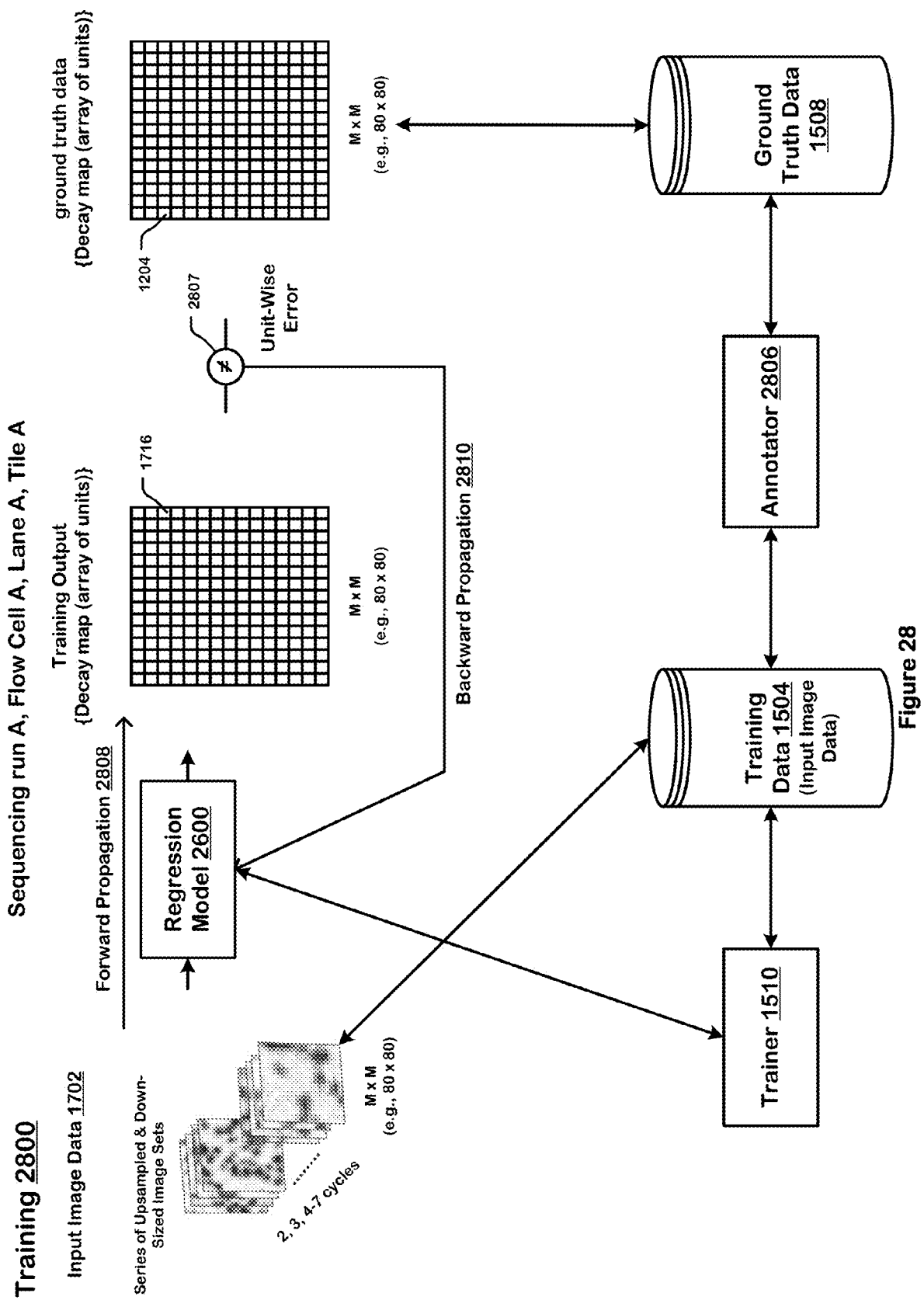
FIG. 28 is one implementation of training the regression model using a backpropagation-based gradient update technique.

FIG. 28 is one implementation of training 2800 the regression model 2600 using a backpropagation-based gradient update technique that modifies parameters of the regression model 2600 until the decay map 1716 produced by the regression model 2600 as training output during the training 2800 progressively approaches or matches the ground truth decay map 1204.

The training 2800 includes iteratively optimizing a loss function that minimizes error 2807 between the decay map 1716 and the ground truth decay map 1204, and updating parameters of the regression model 2600 based on the error 2807. In one implementation, the loss function is mean squared error and the error is minimized on a subpixel-by-subpixel basis between weighted decay values of corresponding subpixels in the decay map 1716 and the ground truth decay map 1204.

The training 2800 includes hundreds, thousands, and/or millions of iterations of forward propagation 2808 and backward propagation 2810, including parallelization techniques such as batching. The training data 1504 includes, as the input image data 1702, a series of upsampled and down-sized image sets. The training data 1504 is annotated with ground truth labels by an annotator 2806. The training 2800 is operationalized by the trainer 1510 using a stochastic gradient update algorithm such as ADAM.

Inference

Figure 29:
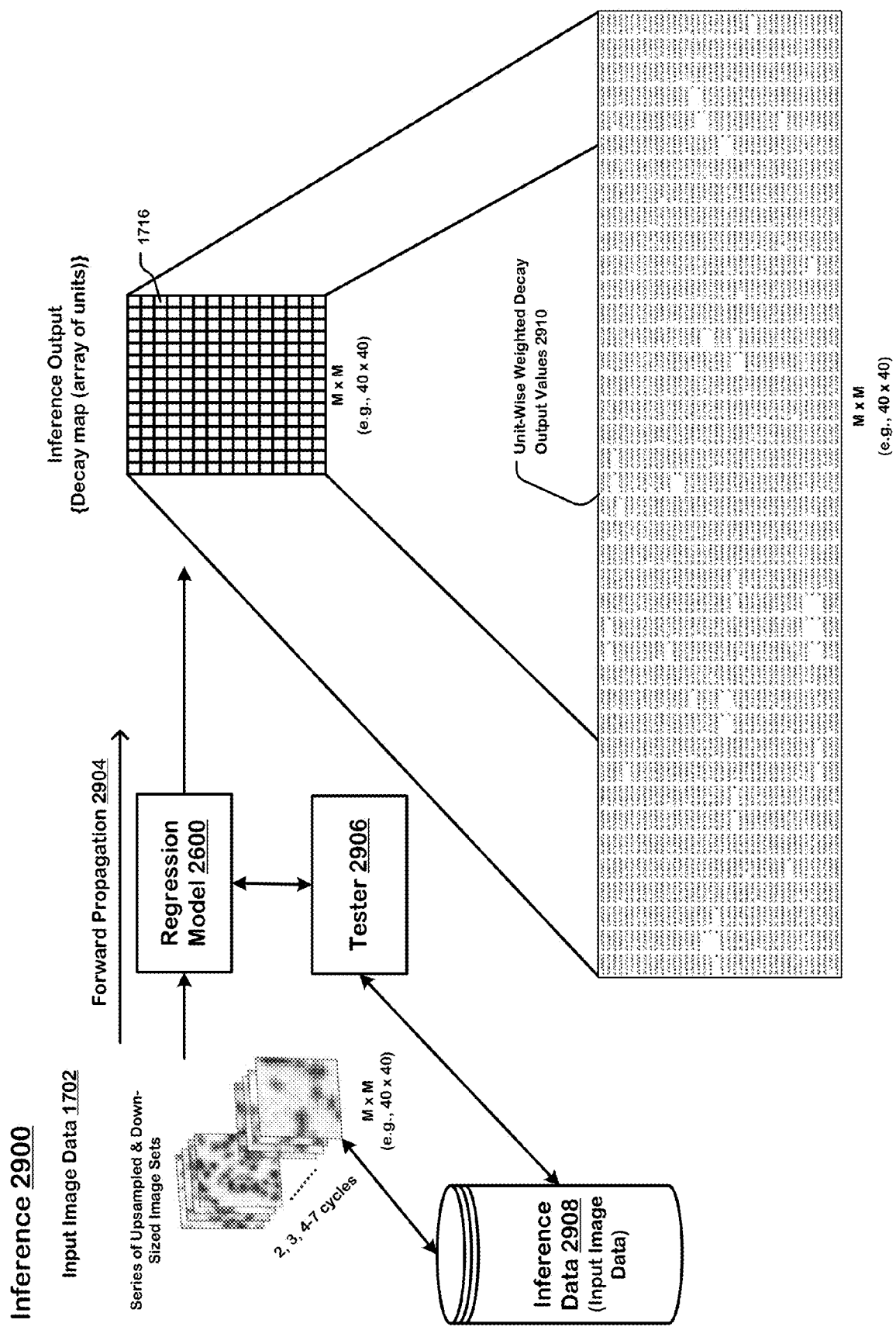
FIG. 29 is one implementation of template generation by the regression model during inference.

FIG. 29 is one implementation of template generation by the regression model 2600 during inference 2900 in which the decay map 1716 is produced by the regression model 2600 as the inference output during the inference 2900. One example of the decay map 1716 is disclosed in the Appendix titled "Regression_Model_Sample_Ouput". The Appendix includes unit-wise weighted decay output values 2910 that together represent the decay map 1716.

The inference 2900 includes hundreds, thousands, and/or millions of iterations of forward propagation 2904, including parallelization techniques such as batching. The inference 2900 is performed on inference data 2908 that includes, as the input image data 1702, a series of upsampled and down-sized image sets. The inference 2900 is operationalized by a tester 2906.

Watershed Segmentation

Figure 30:
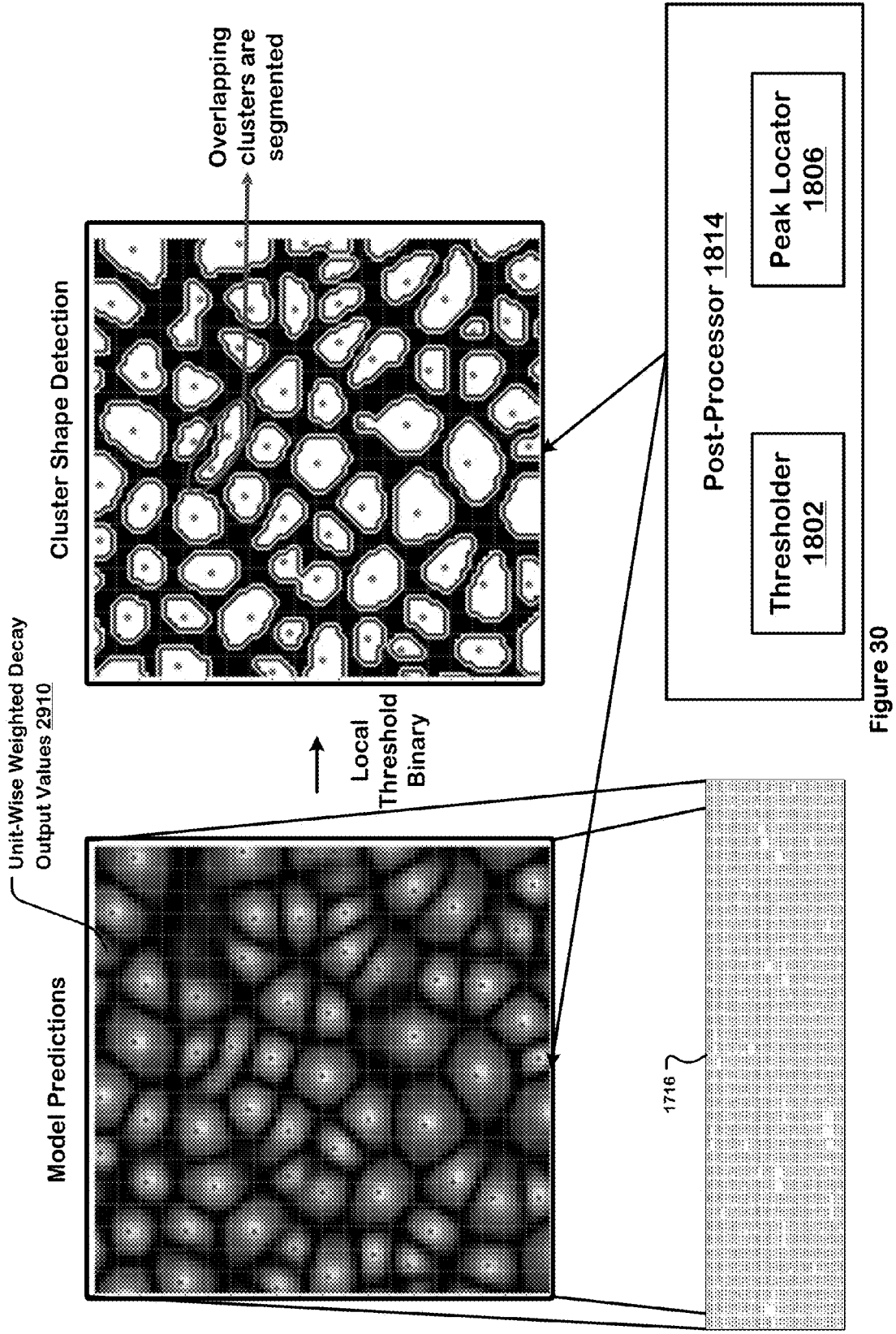
FIG. 30 illustrates one implementation of subjecting the decay map to post-processing to identify cluster metadata.

FIG. 30 illustrates one implementation of subjecting the decay map 1716 to (i) thresholding to identify background subpixels characterizing cluster background and to (ii) peak detection to identify center subpixels characterizing cluster centers. The thresholding is performed by the thresholder 1802 that uses a local threshold binary to produce binarized output. The peak detection is performed by the peak locator 1806 to identify the cluster centers. Additional details about the peak locator can be found in the Appendix entitled "Peak Detection".

Figure 31:
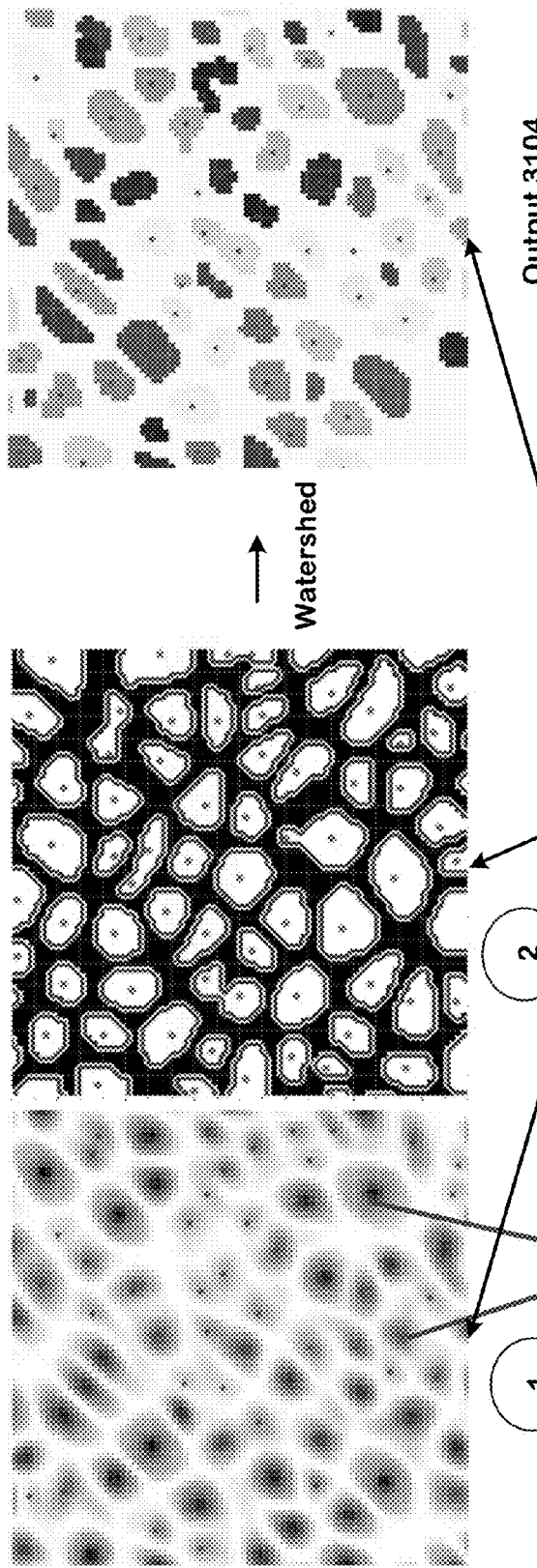
FIG. 31 depicts one implementation of a watershed segmentation technique identifying non-overlapping groups of contiguous cluster/cluster interior subpixels that characterize the clusters.

FIG. 31 depicts one implementation of a watershed segmentation technique that takes as input the background subpixels and the center subpixels respectively identified by the thresholder 1802 and the peak locator 1806, finds valleys in intensity between adjoining clusters, and outputs non-overlapping groups of contiguous cluster/cluster interior subpixels characterizing the clusters. Additional details about the watershed segmentation technique can be found in the Appendix entitled "Watershed Segmentation".

In one implementation, a watershed segmenter 3102 takes as input (1) negativized output values 2910 in the decay map 1716, (2) binarized output of the thresholder 1802, and (3) cluster centers identified by the peak locator 1806. Then, based on the input, the watershed segmenter 3102 produces output 3104. In the output 3104, each cluster center is identified as a unique set/group of subpixels that belong to the cluster center (as long as the subpixels are "1" in the binary output, i.e., not background subpixels). Further, the clusters are filtered based on containing at least four subpixels. The watershed segmenter 3102 can be part of the segmenter 1810, which in turn is part of the post-processor 1814.

Network Architecture

FIG. 32 is a table that shows an example U-Net architecture of the regression model 2600, along with details of the layers of the regression model 2600, dimensionality of the output of the layers, magnitude of the model parameters, and interconnections between the layers. Similar details are disclosed in the file titled "Regression_Model_Example_Architecture", which is submitted as an appendix to this application.

Cluster Intensity Extraction

FIG. 33 illustrates different approaches of extracting cluster intensity using cluster shape information identified in a template image. As discussed above, the template image identifies the cluster shape information in the upsampled, subpixel resolution. However, the cluster intensity information is in the sequencing images 108, which are typically in the optical, pixel-resolution.

According to a first approach, coordinates of the subpixels are located in the sequencing images 108 and their respective intensities extracted using bilinear interpolation and normalized based on a count of the subpixels that contribute to a cluster.

The second approach uses a weighted area coverage technique to modulate the intensity of a pixel according to a number of subpixels that contribute to the pixel. Here too, the modulated pixel intensity is normalized by a subpixel count parameter.

The third approach upsamples the sequencing images into the subpixel domain using bicubic interpolation, sums the intensity of the upsampled pixels belonging to a cluster, and normalizes the summed intensity based on a count of the upsampled pixels that belong to the cluster.

Experimental Results and Observations

Figure 34:
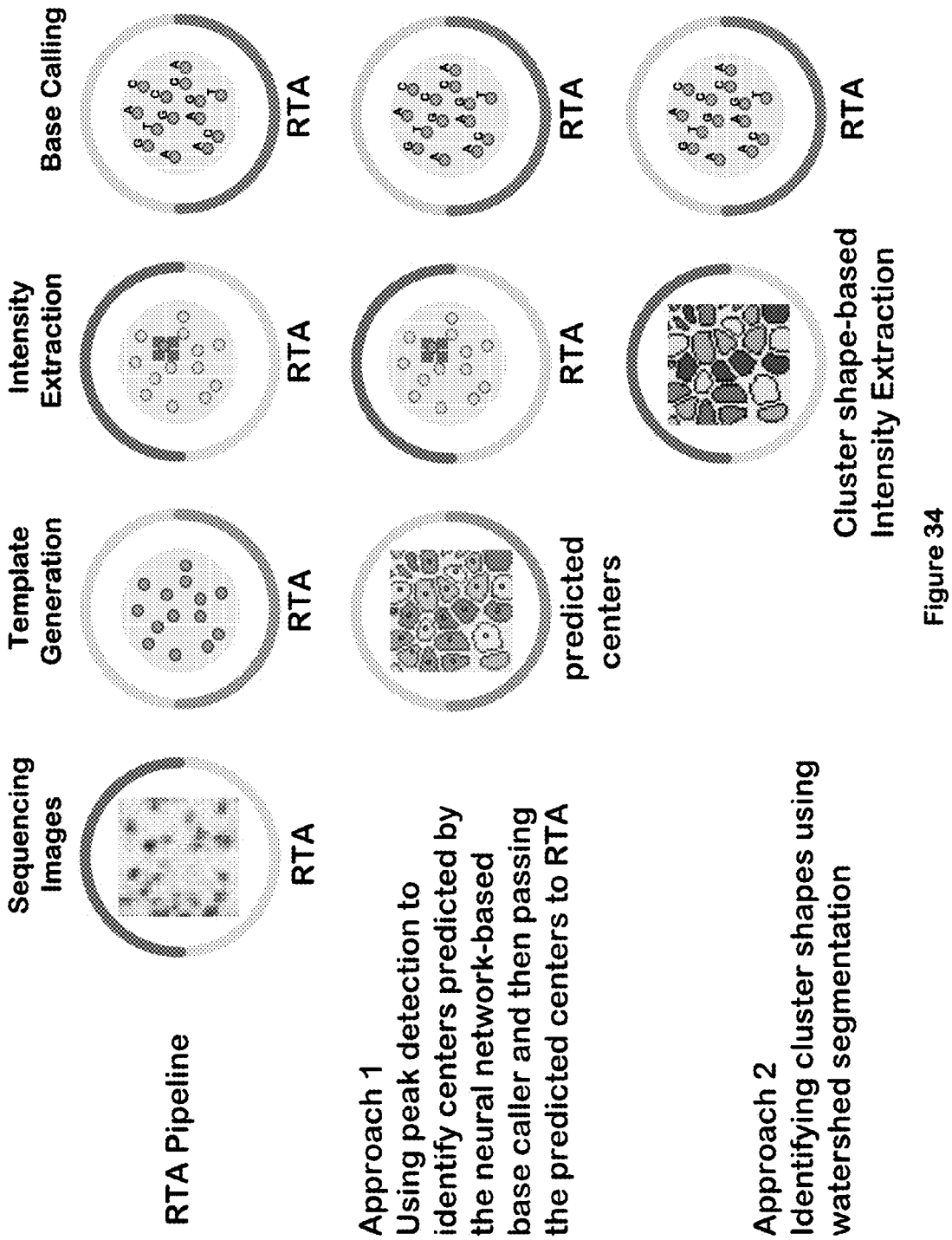
FIG. 34 shows different approaches of base calling using the outputs of the regression model.

FIG. 34 shows different approaches of base calling using the outputs of the regression model 2600. In the first approach, the cluster centers identified from the output of the neural network-based template generator 1512 in the template image are fed to a base caller (e.g., Illumina's Real-Time Analysis software, referred to herein as "RTA base caller") for base calling.

In the second approach, instead of the cluster centers, the cluster intensities extracted from the sequencing images based on the cluster shape information in the template image are fed to the RTA base caller for base calling.

FIG. 35 illustrates the difference in base calling performance when the RTA base caller uses ground truth center of mass (COM) location as the cluster center, as opposed to using a non-COM location as the cluster center. The results show that using COM improves base calling.

Example Model Outputs

FIG. 36 shows, on the left, an example decay map 1716 produced by the regression model 2600. On the right, FIG. 36 also shows an example ground truth decay map 1204 that the regression model 2600 approximates during the training.

Both the decay map 1716 and the ground truth decay map 1204 depict clusters as disjointed regions of contiguous subpixels, the centers of the clusters as center subpixels at centers of mass of the respective ones of the disjointed regions, and their surrounding background as background subpixels not belonging to any of the disjointed regions.

Also, the contiguous subpixels in the respective ones of the disjointed regions have values weighted according to distance of a contiguous subpixel from a center subpixel in a disjointed region to which the contiguous subpixel belongs. In one implementation, the center subpixels have the highest values within the respective ones of the disjointed regions. In one implementation, the background subpixels all have a same minimalist background value within a decay map.

Figure 37:
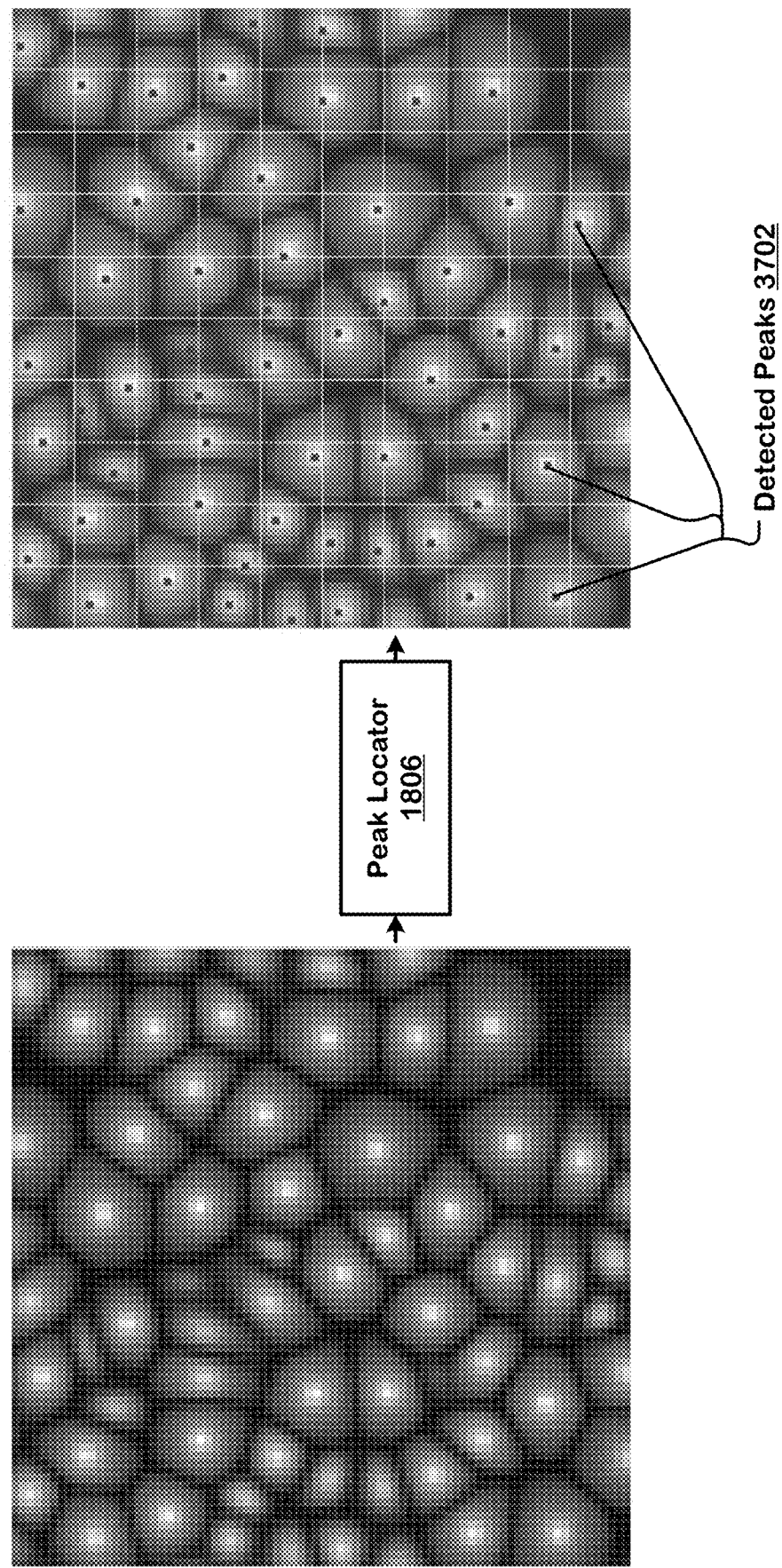
FIG. 37 portrays one implementation of the peak locator identifying cluster centers in the decay map by detecting peaks.

FIG. 37 portrays one implementation of the peak locator 1806 identifying cluster centers in a decay map by detecting peaks 3702. Additional details about the peak locator can be found in the Appendix entitled "Peak Detection".

FIG. 38 compares peaks detected by the peak locator 1806 in the decay map 1716 produced by the regression model 2600 with peaks in a corresponding ground truth decay map 1204. The red markers are peaks predicted by the regression model 2600 as cluster centers and the green markers are the ground truth centers of mass of the clusters.

More Experimental Results and Observations

Figure 39:
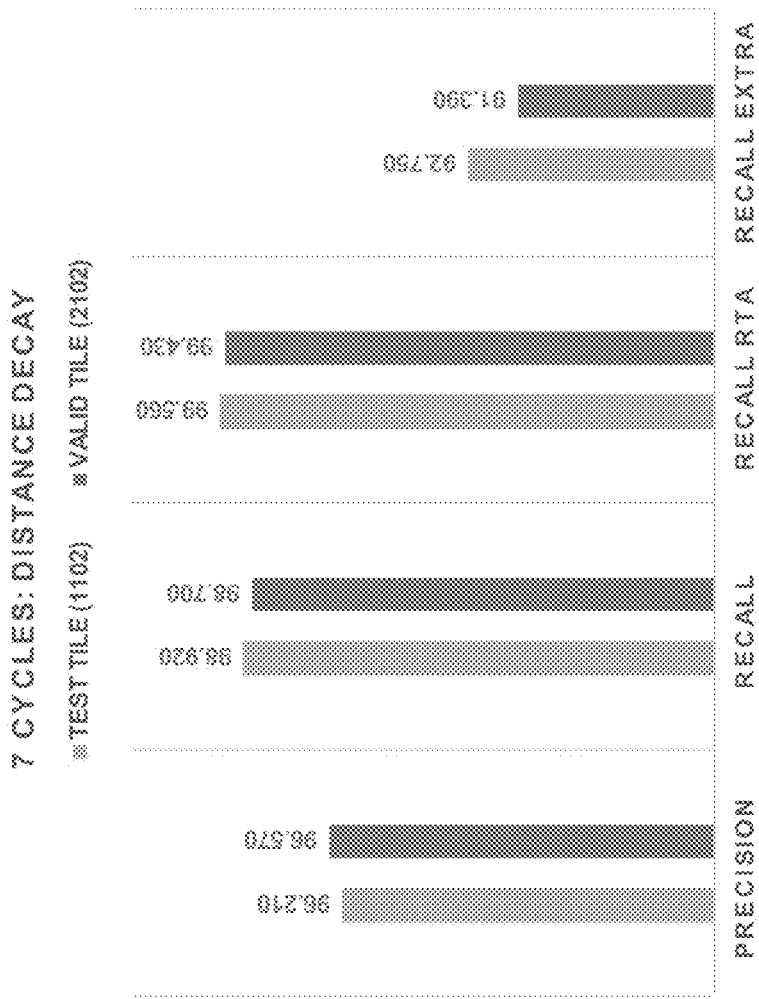
FIG. 39 illustrates performance of the regression model using precision and recall statistics.

FIG. 39 illustrates performance of the regression model 2600 using precision and recall statistics. The precision and recall statistics demonstrate that the regression model 2600 is good at recovering all identified cluster centers.

FIG. 40 compares performance of the regression model 2600 with the RTA base caller for 20 pM library concentration (normal run). Outperforming the RTA base caller, the regression model 2600 identifies 34, 323 (4.46%) more clusters in a higher cluster density environment (i.e., 988, 884 clusters).

FIG. 40 also shows results for other sequencing metrics such as number of clusters that pass the chastity filter ("% PF" (pass-filter)), number of aligned reads ("% Aligned"), number of duplicate reads ("% Duplicate"), number of reads mismatching the reference sequence for all reads aligned to the reference sequence ("% Mismatch"), bases called with quality score 30 and above ("% Q30 bases"), and so on.

FIG. 41 compares performance of the regression model 2600 with the RTA base caller for 30 pM library concentration (dense run). Outperforming the RTA base caller, the regression model 2600 identifies 34, 323 (6.27%) more clusters in a much higher cluster density environment (i.e., 1,351,588 clusters).

FIG. 41 also shows results for other sequencing metrics such as number of clusters that pass the chastity filter ("% PF" (pass-filter)), number of aligned reads ("% Aligned"), number of duplicate reads ("% Duplicate"), number of reads mismatching the reference sequence for all reads aligned to the reference sequence ("% Mismatch"), bases called with quality score 30 and above ("% Q30 bases"), and so on.

Figure 42:
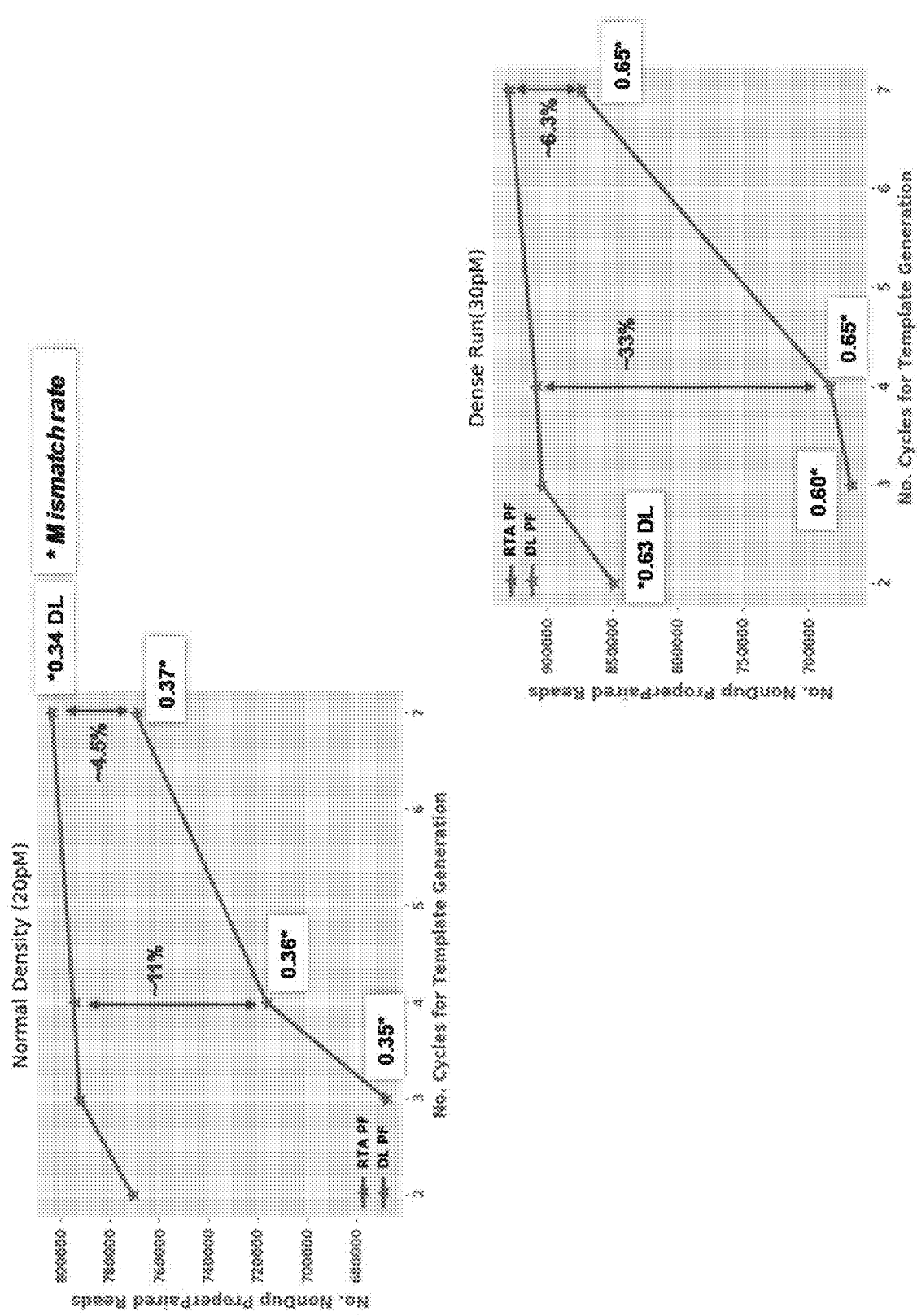
FIG. 42 compares number of non-duplicate proper read pairs, i.e., the number of paired reads that do not have both reads aligned inwards within a reasonable distance detected by the regression model versus the same detected by the RTA base caller.

FIG. 42 compares number of non-duplicate (unique or deduplicated) proper read pairs, i.e., the number of paired reads that have both reads aligned inwards within a reasonable distance detected by the regression model 2600 versus the same detected by the RTA base caller. The comparison is made both for the 20 pM normal run and the 30 pM dense run.

More importantly, FIG. 42 shows that the disclosed neural network-based template generators are able to detect more clusters in fewer sequencing cycles of input to template generation than the RTA base caller. In just four sequencing cycles, the regression model 2600 identifies 11% more non-duplicate proper read pairs than the RTA base caller during the 20 pM normal run and 33% more non-duplicate proper read pairs than the RTA base caller during the 30 pM dense run. In just seven sequencing cycles, the regression model 2600 identifies 4.5% more non-duplicate proper read pairs than the RTA base caller during the 20 pM normal run and 6.3% more non-duplicate proper read pairs than the RTA base caller during the 30 pM dense run.

FIG. 43 shows, on the right, a first decay map produced by the regression model 2600. The first decay map identifies clusters and their surrounding background imaged during the 20 pM normal run, along with their spatial distribution depicting cluster shapes, cluster sizes, and cluster centers.

On the left, FIG. 43 shows a second decay map produced by the regression model 2600. The second decay map identifies clusters and their surrounding background imaged during the 30 pM dense run, along with their spatial distribution depicting cluster shapes, cluster sizes, and cluster centers.

FIG. 44 compares performance of the regression model 2600 with the RTA base caller for 40 pM library concentration (highly dense run). The regression model 2600 produced 89,441,688 more aligned bases than the RTA base caller in a much higher cluster density environment (i.e., 1,509,395 clusters).

FIG. 44 also shows results for other sequencing metrics such as number of clusters that pass the chastity filter ("% PF" (pass-filter)), number of aligned reads ("% Aligned"), number of duplicate reads ("% Duplicate"), number of reads mismatching the reference sequence for all reads aligned to the reference sequence ("% Mismatch"), bases called with a quality score 30 and above ("% Q30 bases"), and so on.

More Example Model Outputs

Figure 45:
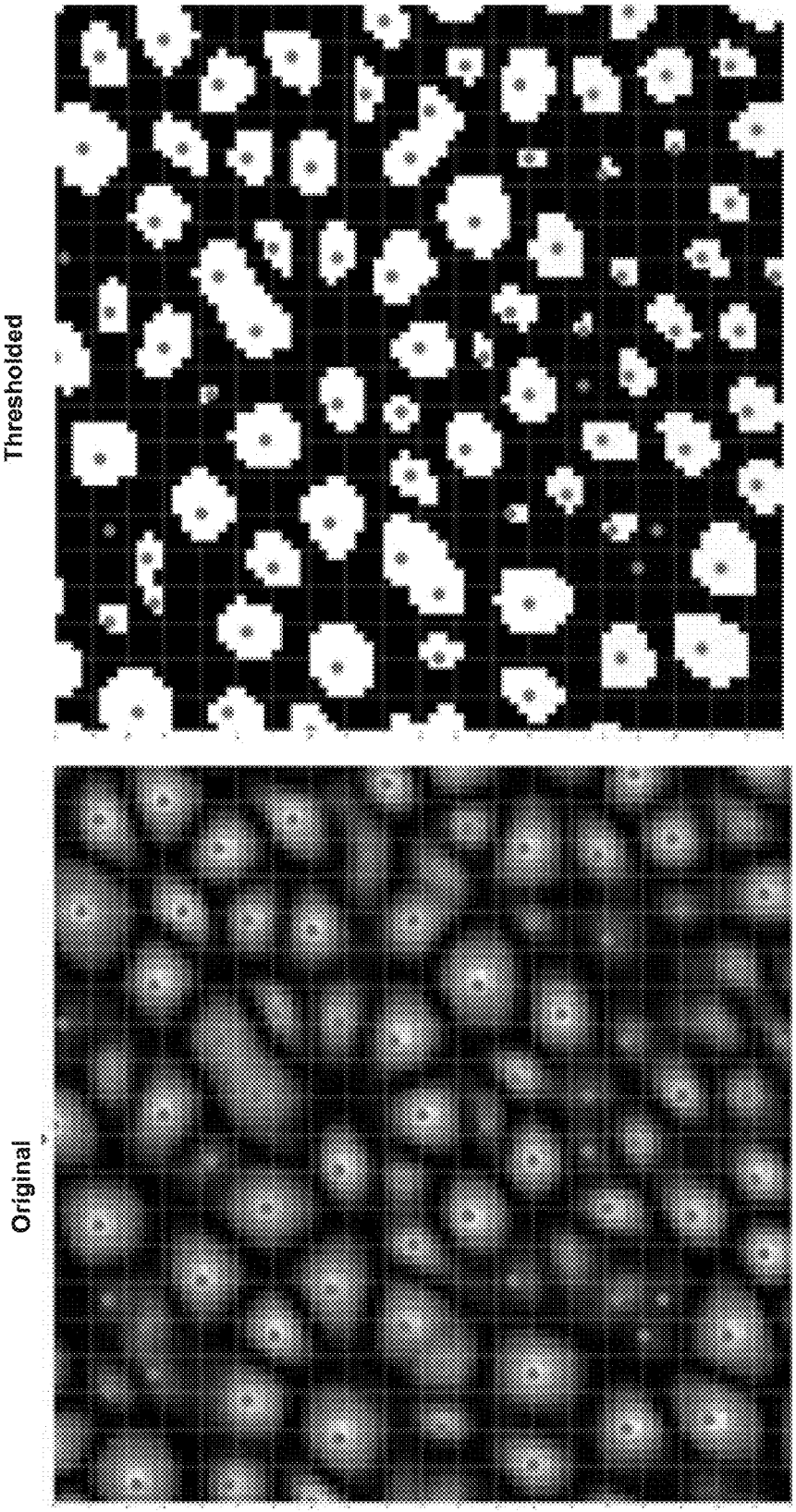
FIG. 45 shows, on the left, a first decay map produced by the regression model. On the right.

FIG. 45 shows, on the left, a first decay map produced by the regression model 2600. The first decay map identifies clusters and their surrounding background imaged during the 40 pM normal run, along with their spatial distribution depicting cluster shapes, cluster sizes, and cluster centers.

On the right, FIG. 45 shows the results of the thresholding and the peak locating applied to the first decay map to distinguish the respective clusters from each other and from the background and to identify their respective cluster centers. In some implementations, intensities of the respective clusters are identified and a chastity filter (or passing filter) applied to reduce the mismatch rate.

2. Binary Classification Model

Figure 46:
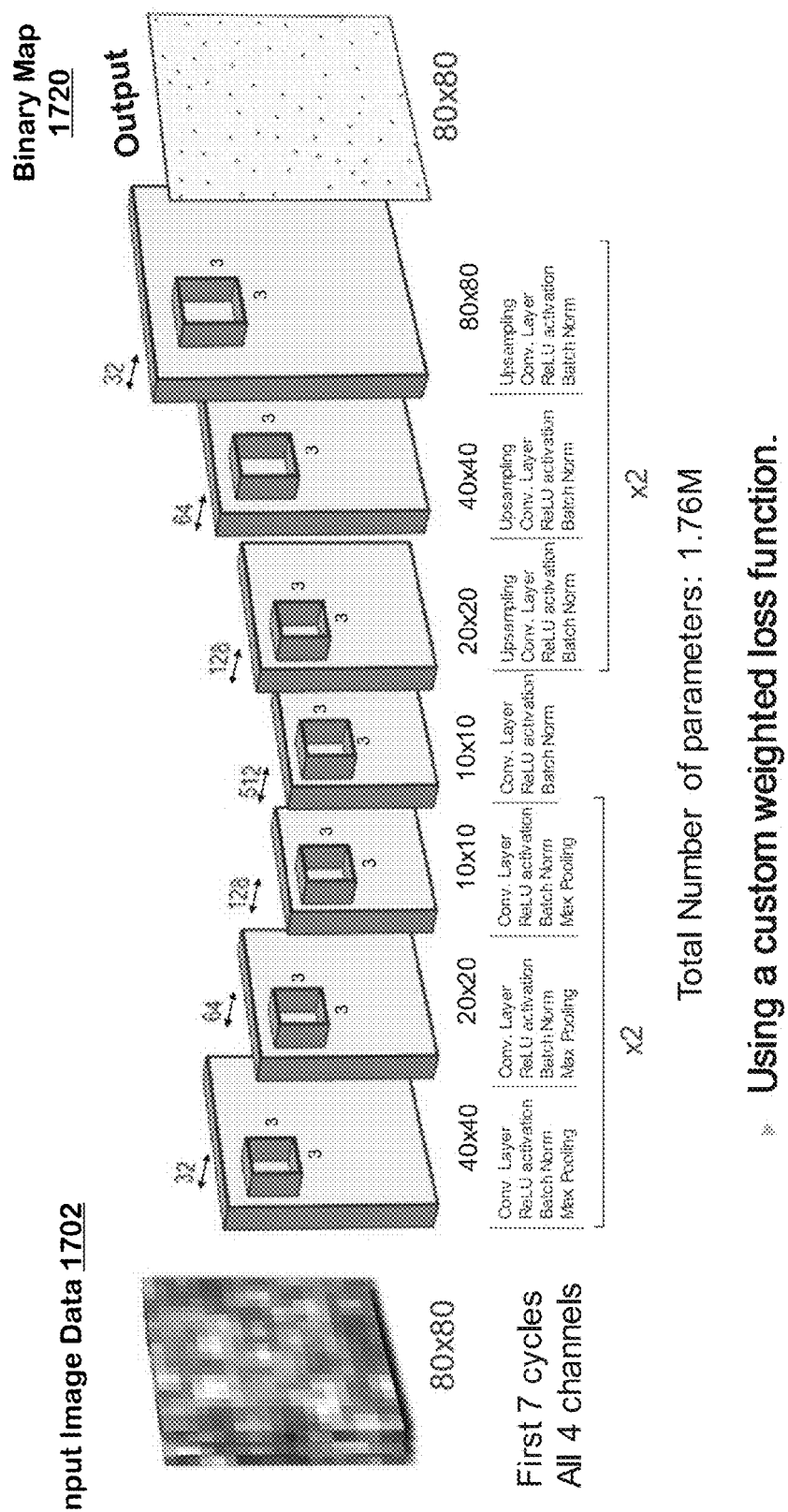
FIG. 46 illustrates one implementation of the binary classification model.

FIG. 46 illustrates one implementation of the binary classification model 4600. In the illustrated implementation, the binary classification model 4600 is a deep fully convolutional segmentation neural network that processes the input image data 1702 through an encoder subnetwork and a corresponding decoder subnetwork. The encoder subnetwork includes a hierarchy of encoders. The decoder subnetwork includes a hierarchy of decoders that map low resolution encoder feature maps to a full input resolution binary map 1720. In another implementation, the binary classification model 4600 is a U-Net network with skip connections between the decoder and the encoder. Additional details about the segmentation networks can be found in the Appendix entitled "Segmentation Networks".

Binary Map

The final output layer of the binary classification model 4600 is a unit-wise classification layer that produces a classification label for each unit in an output array. In some implementations, the unit-wise classification layer is a subpixel-wise classification layer that produces a softmax classification score distribution for each subpixel in the binary map 1720 across two classes, namely, a cluster center class and a non-cluster class, and the classification label for a given subpixel is determined from the corresponding softmax classification score distribution.

In other implementations, the unit-wise classification layer is a subpixel-wise classification layer that produces a sigmoid classification score for each subpixel in the binary map 1720, such that the activation of a unit is interpreted as the probability that the unit belongs to the first class and, conversely, one minus the activation gives the probability that it belongs to the second class.

The binary map 1720 expresses each subpixel based on the predicted classification scores. The binary map 1720 also stores the predicted value classification scores in an array of units, with each unit in the array representing a corresponding subpixel in the input.

Training

Figure 47:
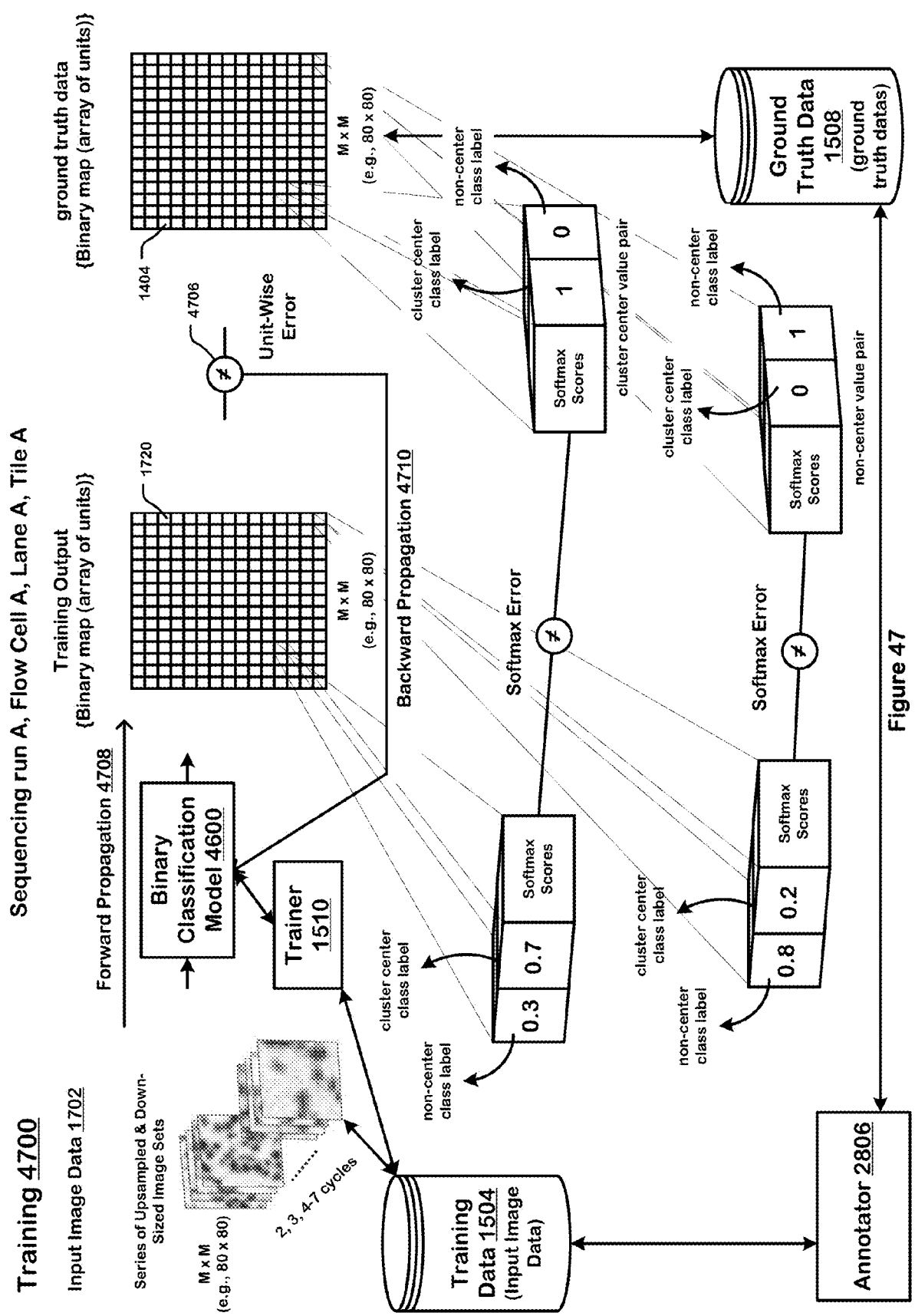
FIG. 47 is one implementation of training the binary classification model using a backpropagation-based gradient update technique that involves softmax scores.

FIG. 47 is one implementation of training 4700 the binary classification model 4600 using a backpropagation-based gradient update technique that modifies parameters of the binary classification model 4600 until the binary map 1720 of the binary classification model 4600 progressively approaches or matches the ground truth binary map 1404.

In the illustrated implementation, the final output layer of the binary classification model 4600 is a softmax-based subpixel-wise classification layer. In softmax implementations, the ground truth binary map generator 1402 assigns each ground truth subpixel either (i) a cluster center value pair (e.g., [1, 0]) or (ii) a non-center value pair (e.g., [0, 1]).

In the cluster center value pair [1, 0], a first value [1] represents the cluster center class label and a second value [0] represents the non-center class label. In the non-center value pair [0, 1], a first value [0] represents the cluster center class label and a second value [1] represents the non-center class label.

The ground truth binary map 1404 expresses each subpixel based on the assigned value pair/value. The ground truth binary map 1404 also stores the assigned value pairs/values in an array of units, with each unit in the array representing a corresponding subpixel in the input.

The training includes iteratively optimizing a loss function that minimizes error 4706 (e.g., softmax error) between the binary map 1720 and the ground truth binary map 1404, and updating parameters of the binary classification model 4600 based on the error 4706.

In one implementation, the loss function is a custom-weighted binary cross-entropy loss and the error 4706 is minimized on a subpixel-by-subpixel basis between predicted classification scores (e.g., softmax scores) and labelled class scores (e.g., softmax scores) of corresponding subpixels in the binary map 1720 and the ground truth binary map 1404, as shown in FIG. 47.

The custom-weighted loss function gives more weight to the COM subpixels, such that the cross-entropy loss is multiplied by a corresponding reward (or penalty) weight specified in a reward (or penalty) matrix whenever a COM subpixel is misclassified. Additional details about the custom-weighted loss function can be found in the Appendix entitled "Custom-Weighted Loss Function".

The training 4700 includes hundreds, thousands, and/or millions of iterations of forward propagation 4708 and backward propagation 4710, including parallelization techniques such as batching. The training data 1504 includes, as the input image data 1702, a series of upsampled and down-sized image sets. The training data 1504 is annotated with ground truth labels by the annotator 2806. The training 2800 is operationalized by the trainer 1510 using a stochastic gradient update algorithm such as ADAM.

Figure 48:
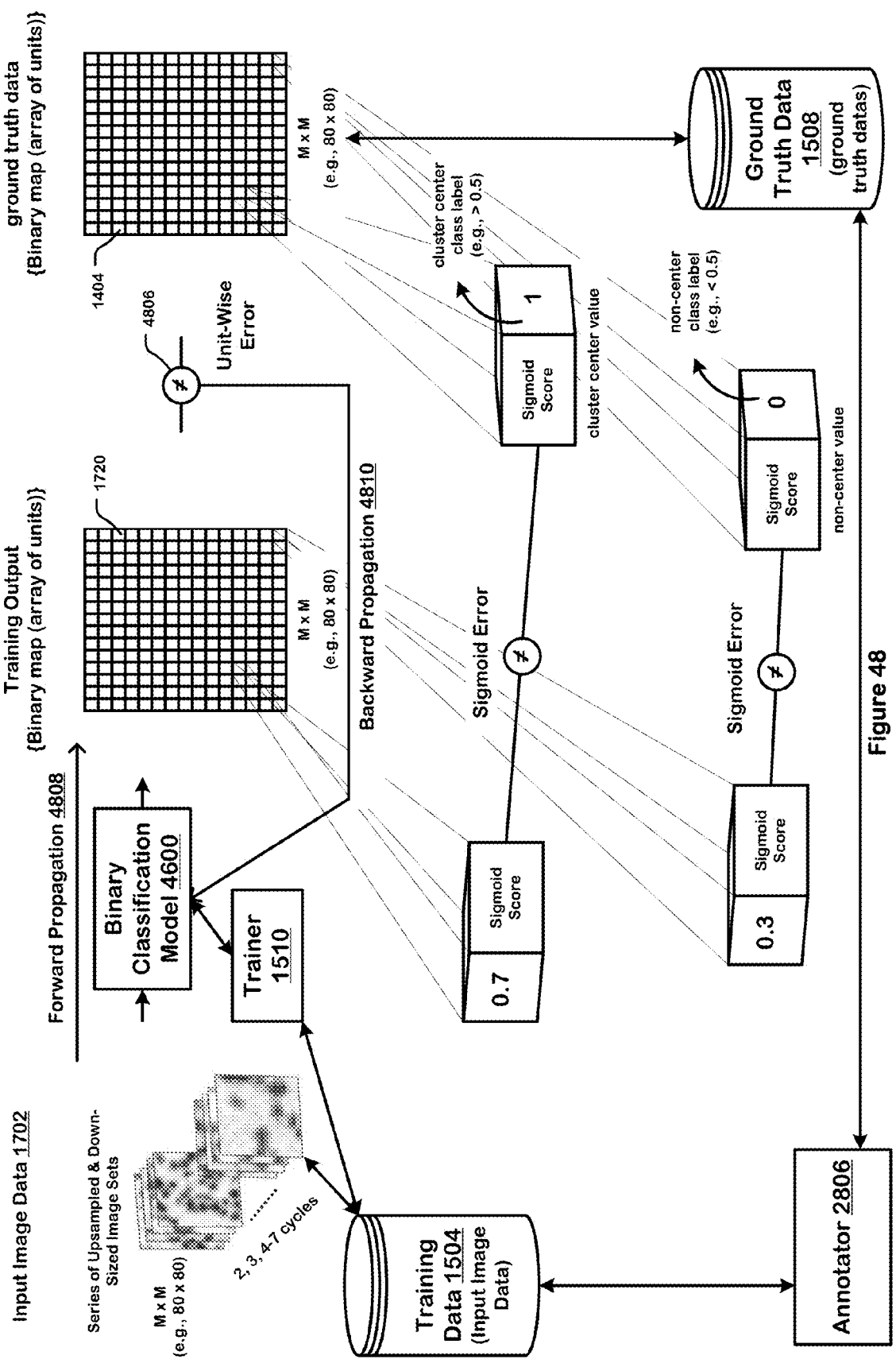
FIG. 48 is another implementation of training the binary classification model using a backpropagation-based gradient update technique that involves sigmoid scores.

FIG. 48 is another implementation of training 4800 the binary classification model 4600, in which the final output layer of the binary classification model 4600 is a sigmoid-based subpixel-wise classification layer.

In sigmoid implementations, the ground truth binary map generator 1302 assigns each ground truth subpixel either (i) a cluster center value (e.g., [1]) or (ii) a non-center value (e.g., [0]). The COM subpixels are assigned the cluster center value pair/value and all other subpixels are assigned the non-center value pair/value.

With the cluster center value, values above a threshold intermediate value between 0 and 1 (e.g., values above 0.5) represent the center class label. With the non-center value, values below a threshold intermediate value between 0 and 1 (e.g., values below 0.5) represent the non-center class label.

The ground truth binary map 1404 expresses each subpixel based on the assigned value pair/value. The ground truth binary map 1404 also stores the assigned value pairs/values in an array of units, with each unit in the array representing a corresponding subpixel in the input.

The training includes iteratively optimizing a loss function that minimizes error 4806 (e.g., sigmoid error) between the binary map 1720 and the ground truth binary map 1404, and updating parameters of the binary classification model 4600 based on the error 4806.

In one implementation, the loss function is a custom-weighted binary cross-entropy loss and the error 4806 is minimized on a subpixel-by-subpixel basis between predicted scores (e.g., sigmoid scores) and labelled scores (e.g., sigmoid scores) of corresponding subpixels in the binary map 1720 and the ground truth binary map 1404, as shown in FIG. 48.

The custom-weighted loss function gives more weight to the COM subpixels, such that the cross-entropy loss is multiplied by a corresponding reward (or penalty) weight specified in a reward (or penalty) matrix whenever a COM subpixel is misclassified. Additional details about the custom-weighted loss function can be found in the Appendix entitled "Custom-Weighted Loss Function".

The training 4800 includes hundreds, thousands, and/or millions of iterations of forward propagation 4808 and backward propagation 4810, including parallelization techniques such as batching. The training data 1504 includes, as the input image data 1702, a series of upsampled and down-sized image sets. The training data 1504 is annotated with ground truth labels by the annotator 2806. The training 2800 is operationalized by the trainer 1510 using a stochastic gradient update algorithm such as ADAM.

Figure 49:
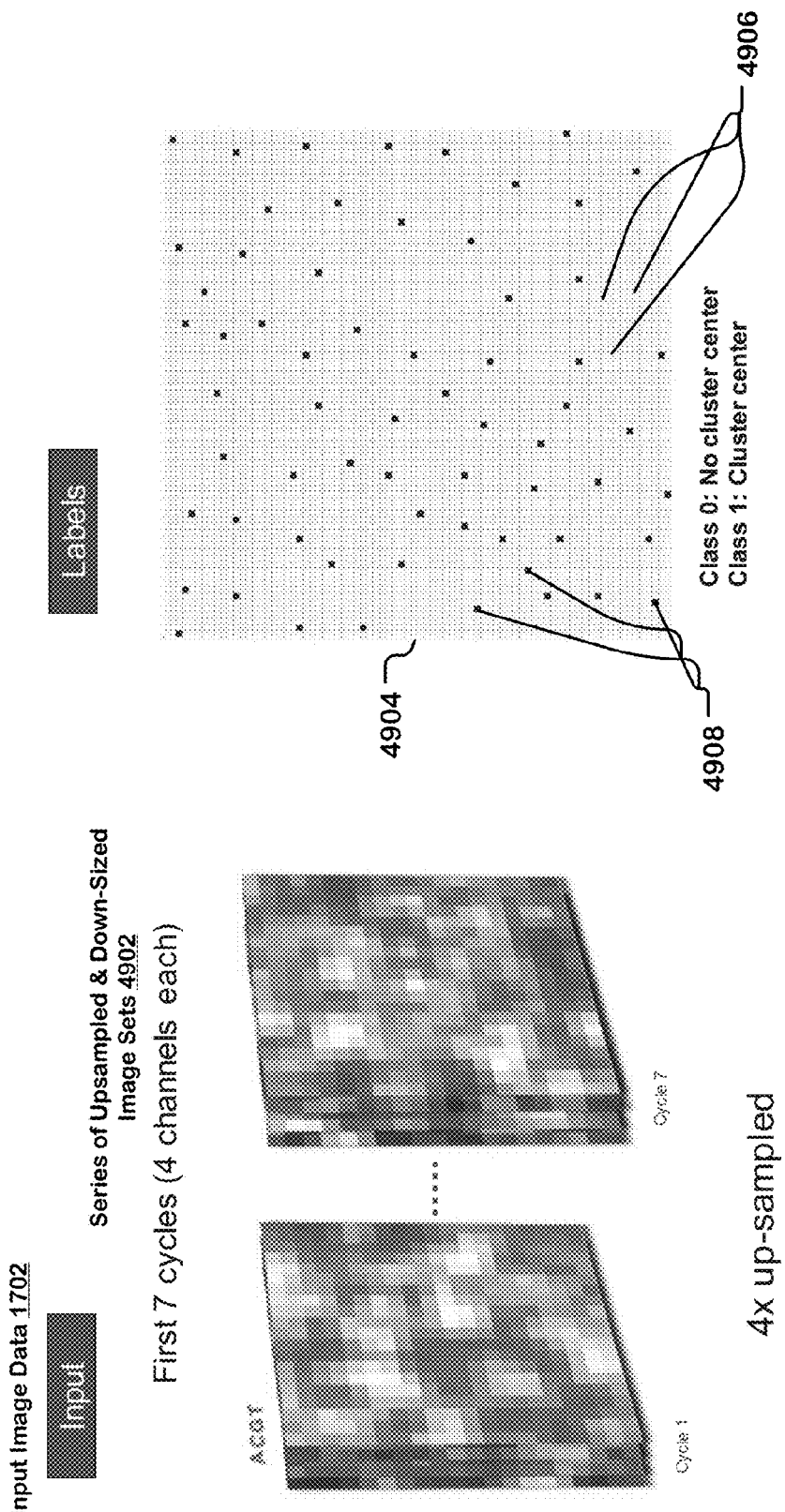
FIG. 49 illustrates another implementation of the input image data fed to the binary classification model and the corresponding class labels used to train the binary classification model.

FIG. 49 illustrates another implementation of the input image data 1702 fed to the binary classification model 4600 and the corresponding class labels 4904 used to train the binary classification model 4600.

In the illustrated implementation, the input image data 1702 comprises a series of upsampled and down-sized image sets 4902. The class labels 4904 comprise two classes: (1) "no cluster center" and (2) "cluster center", which are distinguished using different output values. That is, (1) the light green units/subpixels 4906 represent subpixels that are predicted by the binary classification model 4600 to not contain the cluster centers and (2) the dark green subpixels 4908 represent units/subpixels that are predicted by the binary classification model 4600 to contain the cluster centers.

Inference

Figure 50:
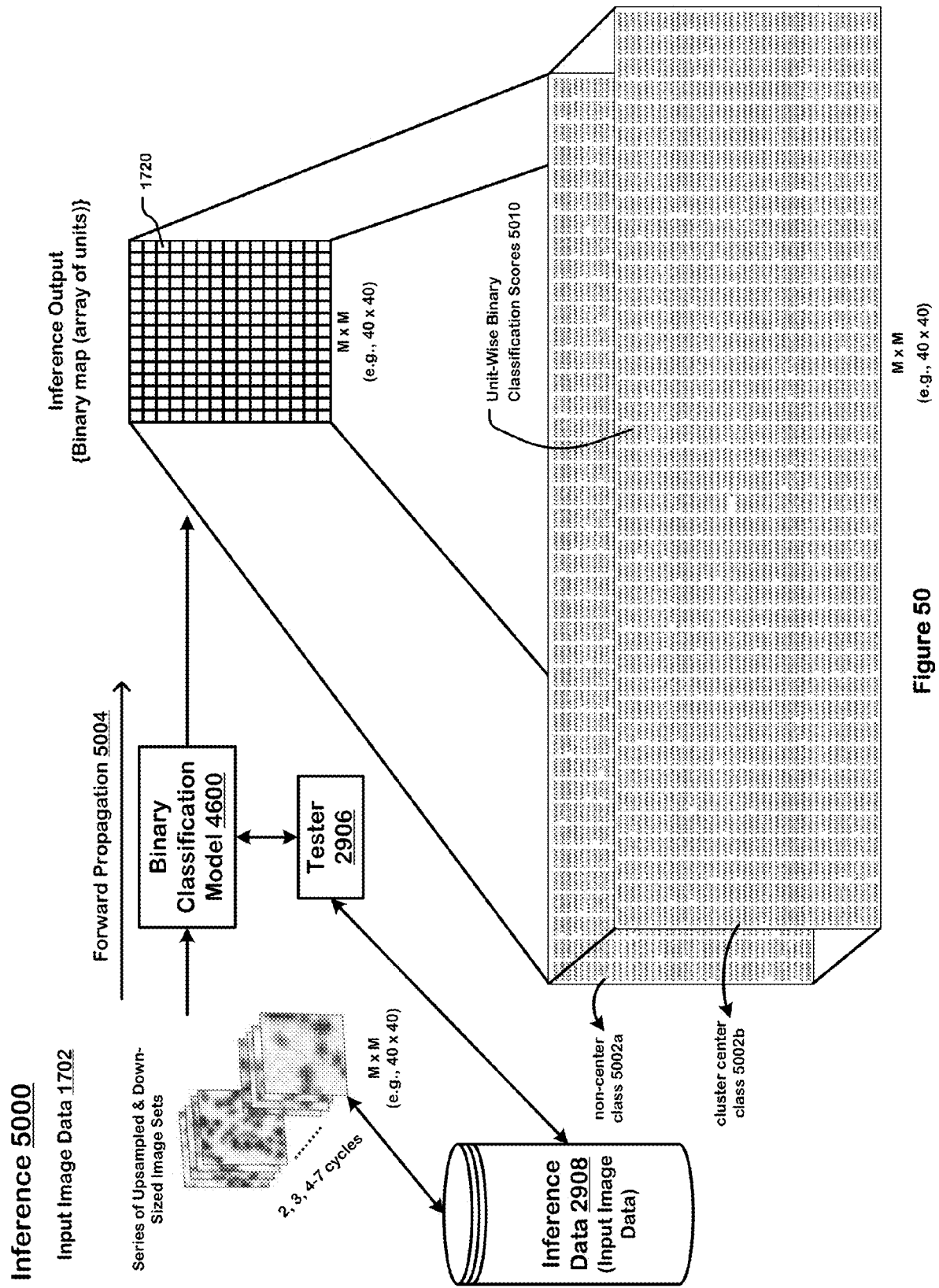
FIG. 50 is one implementation of template generation by the binary classification model during inference.

FIG. 50 is one implementation of template generation by the binary classification model 4600 during inference 5000 in which the binary map 1720 is produced by the binary classification model 4600 as the inference output during the inference 5000. One example of the binary map 1720 includes unit-wise binary classification scores 5010 that together represent the binary map 1720. In the softmax applications, the binary map 1720 has a first array 5002*a* of unit-wise classification scores for the non-center class and a second array 5002*b* of unit-wise classification scores for the cluster center class.

The inference 5000 includes hundreds, thousands, and/or millions of iterations of forward propagation 5004, including parallelization techniques such as batching. The inference 5000 is performed on inference data 2908 that includes, as the input image data 1702, a series of upsampled and down-sized image sets. The inference 5000 is operationalized by the tester 2906.

In some implementations, the binary map 1720 is subjected to post-processing techniques discussed above, such as thresholding, peak detection, and/or watershed segmentation to generate cluster metadata.

Peak Detection

Figure 51:
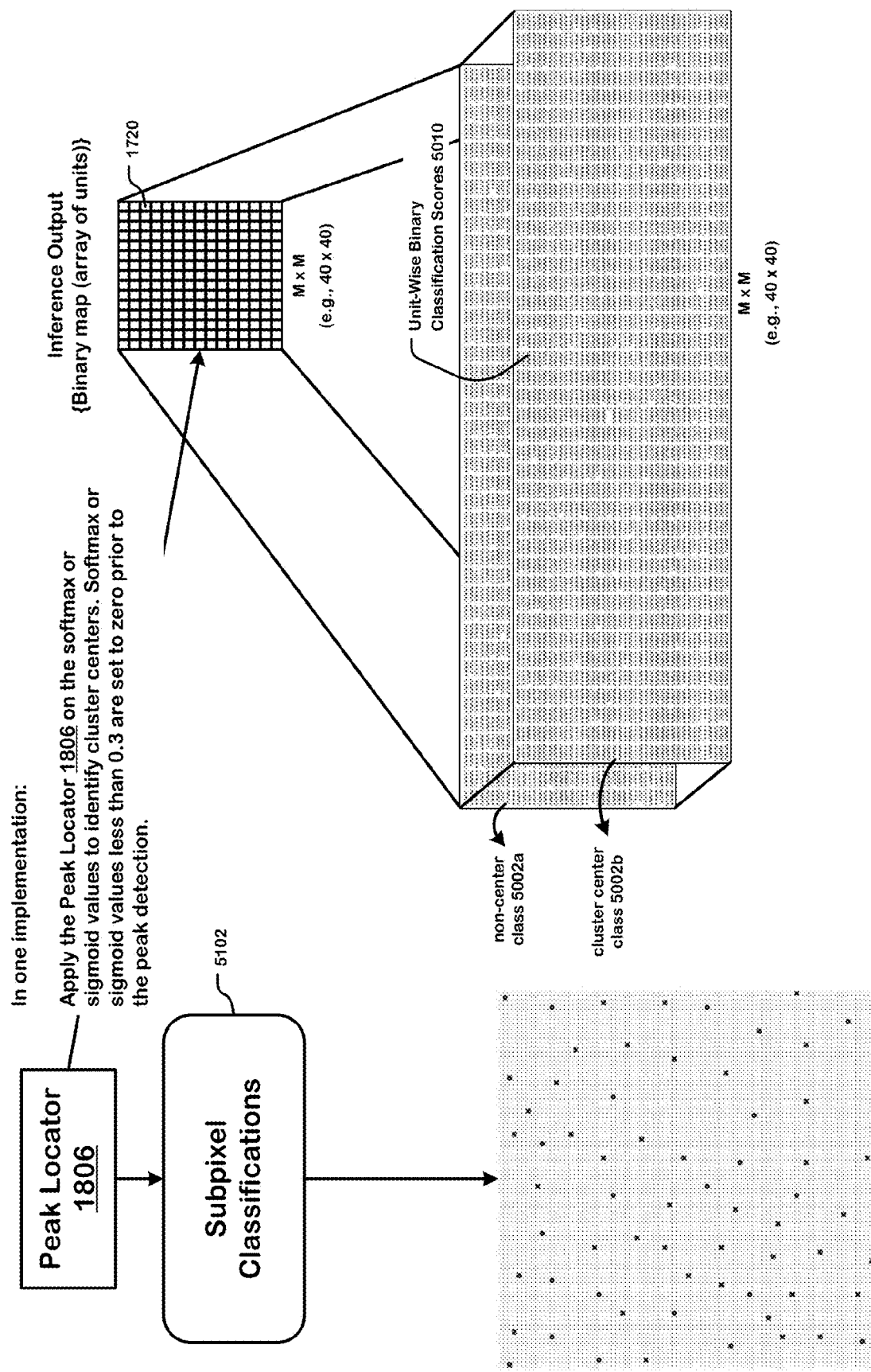
FIG. 51 illustrates one implementation of subjecting the binary map to peak detection to identify cluster centers.

FIG. 51 depicts one implementation of subjecting the binary map 1720 to peak detection to identify cluster centers. As discussed above, the binary map 1720 is an array of units that classifies each subpixel based on the predicted classification scores, with each unit in the array representing a corresponding subpixel in the input. The classification scores can be softmax scores or sigmoid scores.

In the softmax applications, the binary map 1720 includes two arrays: (1) a first array 5002*a* of unit-wise classification scores for the non-center class and (2) a second array 5002*b* of unit-wise classification scores for the cluster center class. In both the arrays, each unit represents a corresponding subpixel in the input.

To determine which subpixels in the input contain the cluster centers and which do not contain the cluster centers, the peak locator 1806 applies peak detection on the units in the binary map 1720. The peak detection identifies those units that have classification scores (e.g., softmax/sigmoid scores) above a preset threshold. The identified units are inferred as the cluster centers and their corresponding subpixels in the input are determined to contain the cluster centers and stored as cluster center subpixels in a subpixel classifications data store 5102. Additional details about the peak locator 1806 can be found in the Appendix entitled "Peak Detection".

The remaining units and their corresponding subpixels in the input are determined to not contain the cluster centers and stored as non-center subpixels in the subpixel classifications data store 5102.

In some implementations, prior to applying the peak detection, those units that have classification scores below a certain background threshold (e.g., 0.3) are set to zero. In some implementations, such units and their corresponding subpixels in the input are inferred to denote the background surrounding the clusters and stored as background subpixels in the subpixel classifications data store 5102. In other implementations, such units can be considered noise and ignored.

Example Model Outputs

Figure 52A:
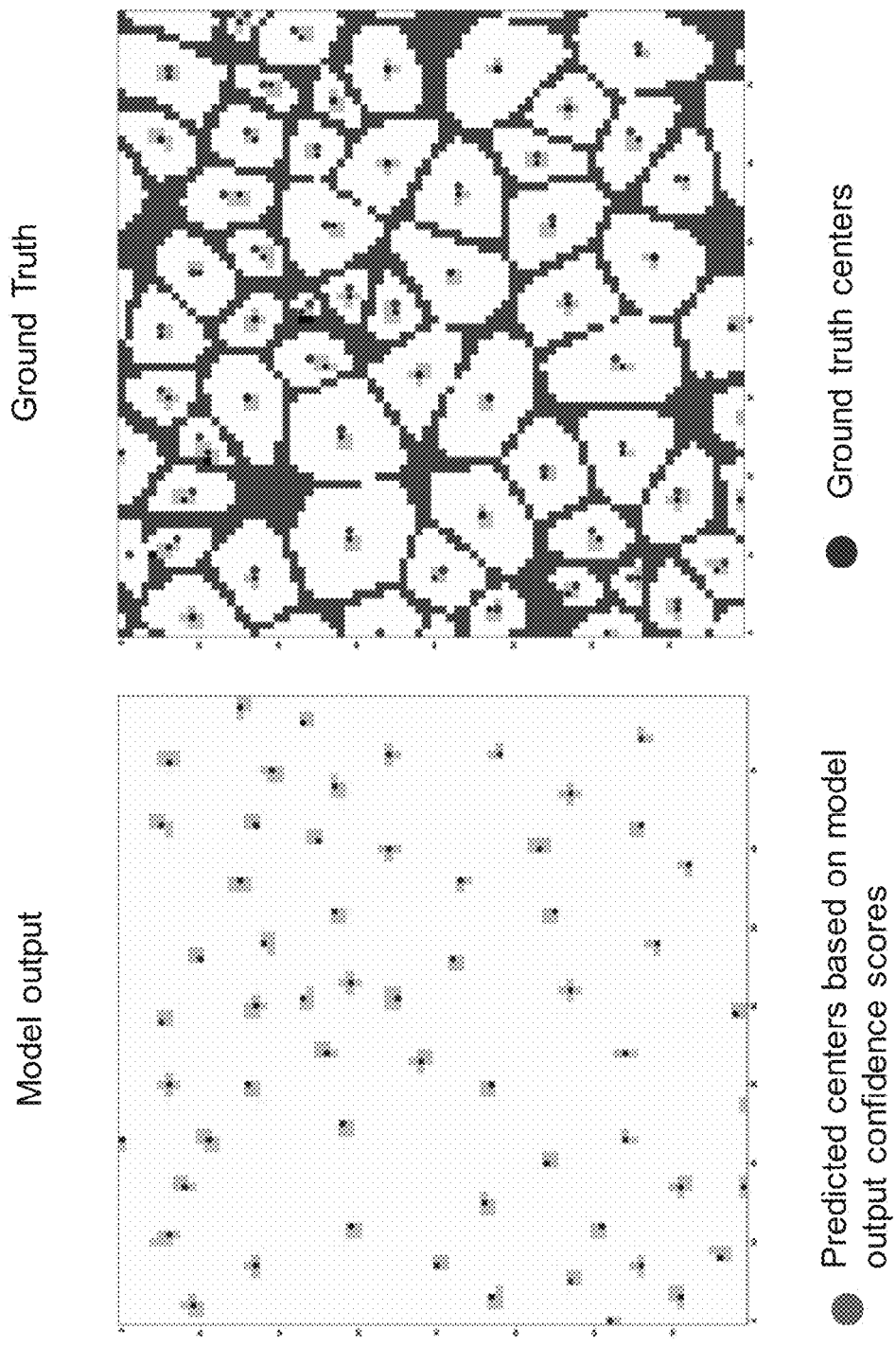
FIG. 52a shows, on the left, an example binary map produced by the binary classification model. On the right, FIG. 52a also shows an example ground truth binary map that the binary classification model approximates during the training.

FIG. 52*a* shows, on the left, an example binary map produced by the binary classification model 4600. On the right, FIG. 52*a* also shows an example ground truth binary map that the binary classification model 4600 approximates during the training. The binary map has a plurality of subpixels and classifies each subpixel as either a cluster center or a non-center. Similarly, the ground truth binary map has a plurality of subpixels and classifies each subpixel as either a cluster center or a non-center.

Experimental Results and Observations

FIG. 52*b* illustrates performance of the binary classification model 4600 using recall and precision statistics. Applying these statistics, the binary classification model 4600 outperforms the RTA base caller.

Network Architecture

FIG. 53 is a table that shows an example architecture of the binary classification model 4600, along with details of the layers of the binary classification model 4600, dimensionality of the output of the layers, magnitude of the model parameters, and interconnections between the layers. Similar details are disclosed in the Appendix titled "Binary_Classification_Model_Example_Architecture".

3. Ternary (Three Class) Classification Model

Figure 54:
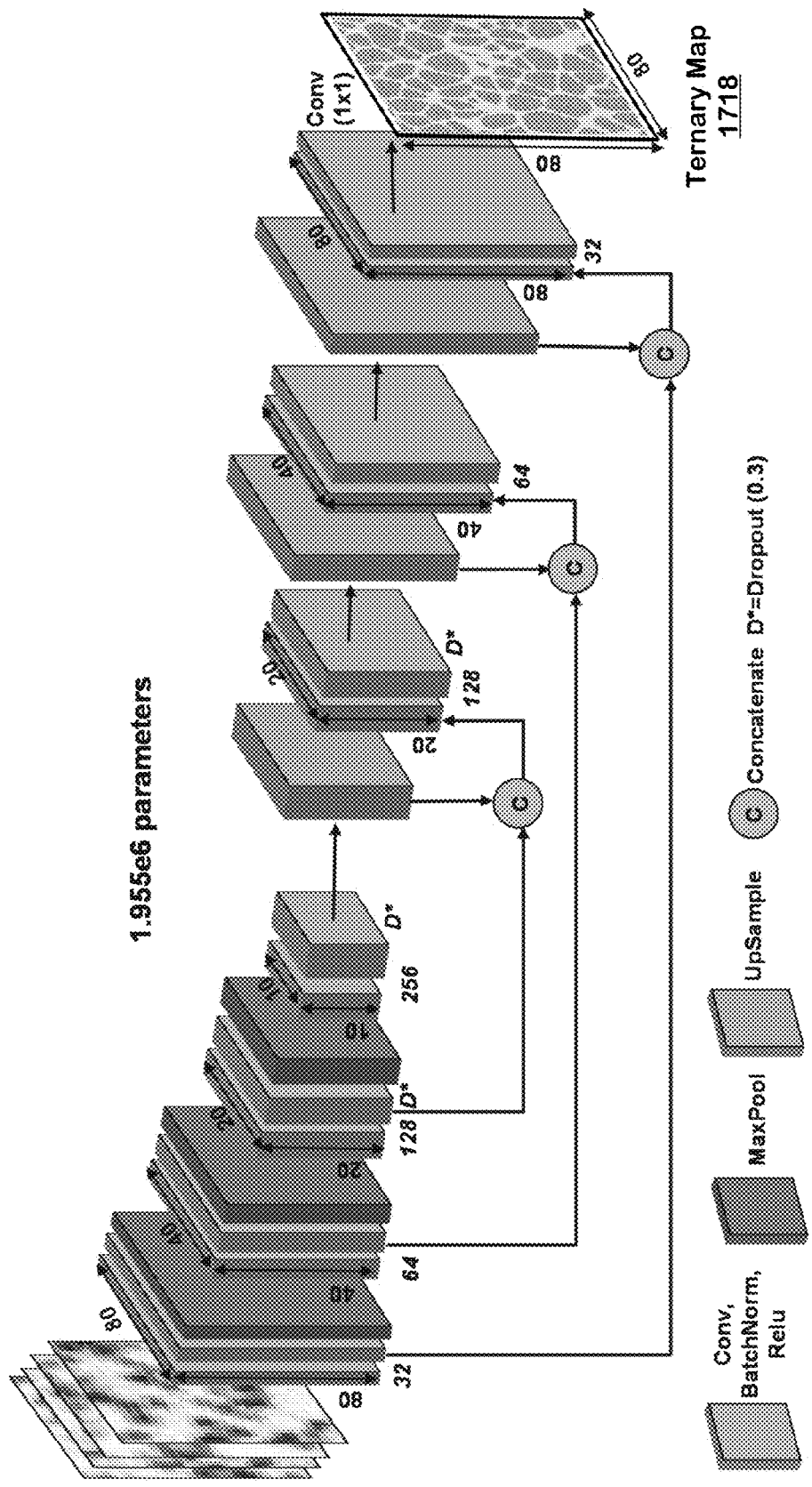
FIG. 54 illustrates one implementation of the ternary classification model.

FIG. 54 illustrates one implementation of the ternary classification model 5400. In the illustrated implementation, the ternary classification model 5400 is a deep fully convolutional segmentation neural network that processes the input image data 1702 through an encoder subnetwork and a corresponding decoder subnetwork. The encoder subnetwork includes a hierarchy of encoders. The decoder subnetwork includes a hierarchy of decoders that map low resolution encoder feature maps to a full input resolution ternary map 1718. In another implementation, the ternary classification model 5400 is a U-Net network with skip connections between the decoder and the encoder. Additional details about the segmentation networks can be found in the Appendix entitled "Segmentation Networks".

Ternary Map

The final output layer of the ternary classification model 5400 is a unit-wise classification layer that produces a classification label for each unit in an output array. In some implementations, the unit-wise classification layer is a subpixel-wise classification layer that produces a softmax classification score distribution for each subpixel in the ternary map 1718 across three classes, namely, a background class, a cluster center class, and a cluster/cluster interior class, and the classification label for a given subpixel is determined from the corresponding softmax classification score distribution.

The ternary map 1718 expresses each subpixel based on the predicted classification scores. The ternary map 1718 also stores the predicted value classification scores in an array of units, with each unit in the array representing a corresponding subpixel in the input.

Training

Figure 55:
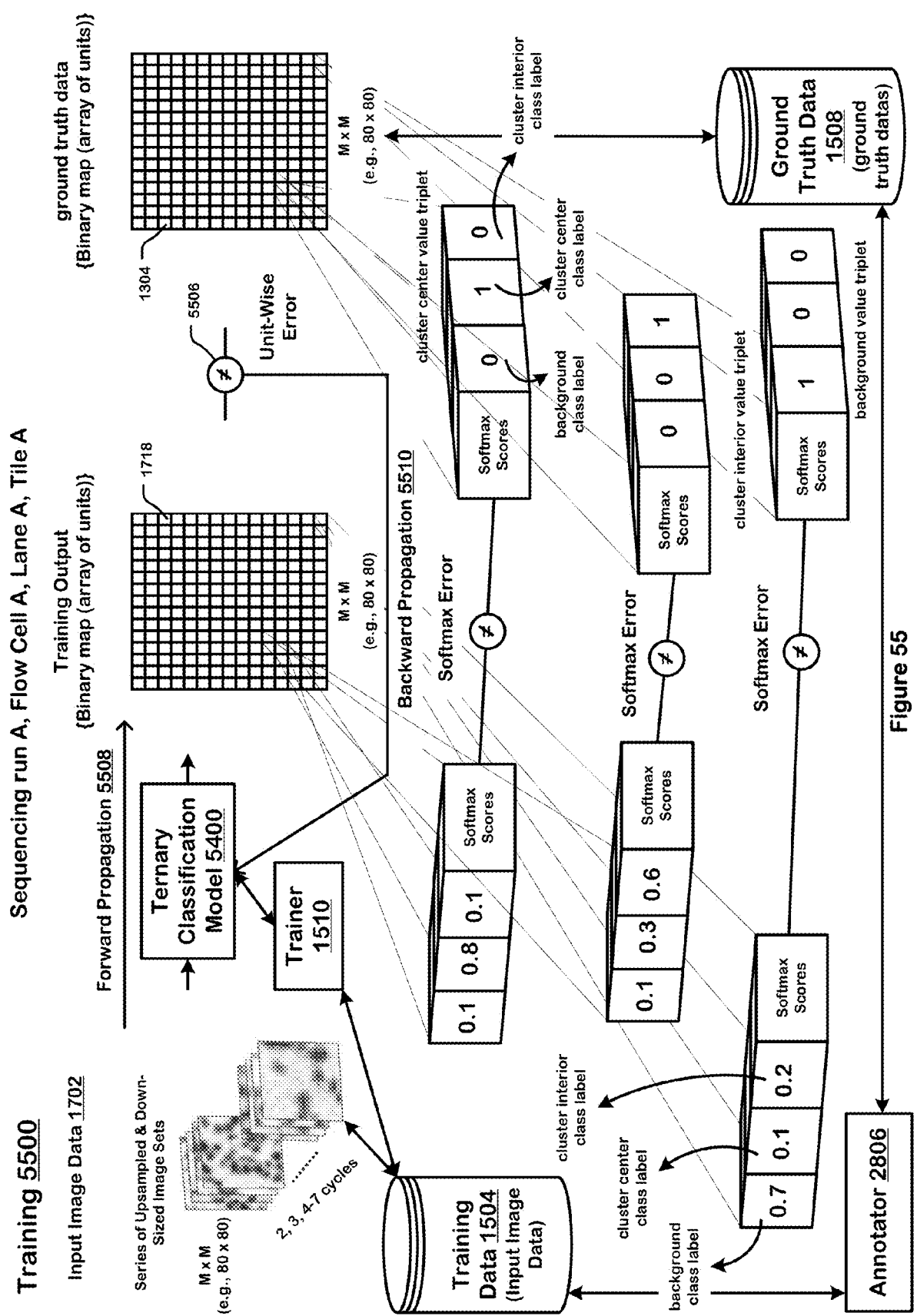
FIG. 55 is one implementation of training the ternary classification model using a backpropagation-based gradient update technique.

FIG. 55 is one implementation of training 5500 the ternary classification model 5400 using a backpropagation-based gradient update technique that modifies parameters of the ternary classification model 5400 until the ternary map 1718 of the ternary classification model 5400 progressively approaches or matches training ground truth ternary maps 1304.

In the illustrated implementation, the final output layer of the ternary classification model 5400 is a softmax-based subpixel-wise classification layer. In softmax implementations, the ground truth ternary map generator 1402 assigns each ground truth subpixel either (i) a background value triplet (e.g., [1, 0, 0]), (ii) a cluster center value triplet (e.g., [0, 1, 0]), or (iii) a cluster/cluster interior value triplet (e.g., [0, 0, 1]).

The background subpixels are assigned the background value triplet. The center of mass (COM) subpixels are assigned the cluster center value triplet. The cluster/cluster interior subpixels are assigned the cluster/cluster interior value triplet.

In the background value triplet [1, 0, 0], a first value [1] represents the background class label, a second value [0] represents the cluster center label, and a third value [0] represents the cluster/cluster interior class label.

In the cluster center value triplet [0, 1, 0], a first value [0] represents the background class label, a second value [1] represents the cluster center label, and a third value [0] represents the cluster/cluster interior class label.

In the cluster/cluster interior value triplet [0, 0, 1], a first value [0] represents the background class label, a second value [0] represents the cluster center label, and a third value [1] represents the cluster/cluster interior class label.

The ground truth ternary map 1304 expresses each subpixel based on the assigned value triplet. The ground truth ternary map 1304 also stores the assigned triplets in an array of units, with each unit in the array representing a corresponding subpixel in the input.

The training includes iteratively optimizing a loss function that minimizes error 5506 (e.g., softmax error) between the ternary map 1718 and the ground truth ternary map 1304, and updating parameters of the ternary classification model 5400 based on the error 5506.

In one implementation, the loss function is a custom-weighted categorical cross-entropy loss and the error 5506 is minimized on a subpixel-by-subpixel basis between predicted classification scores (e.g., softmax scores) and labelled class scores (e.g., softmax scores) of corresponding subpixels in the ternary map 1718 and the ground truth ternary map 1304, as shown in FIG. 54.

The custom-weighted loss function gives more weight to the COM subpixels, such that the cross-entropy loss is multiplied by a corresponding reward (or penalty) weight specified in a reward (or penalty) matrix whenever a COM subpixel is misclassified. Additional details about the custom-weighted loss function can be found in the Appendix entitled "Custom-Weighted Loss Function".

The training 5500 includes hundreds, thousands, and/or millions of iterations of forward propagation 5508 and backward propagation 5510, including parallelization techniques such as batching. The training data 1504 includes, as the input image data 1702, a series of upsampled and down-sized image sets. The training data 1504 is annotated with ground truth labels by the annotator 2806. The training 5500 is operationalized by the trainer 1510 using a stochastic gradient update algorithm such as ADAM.

Figure 56:
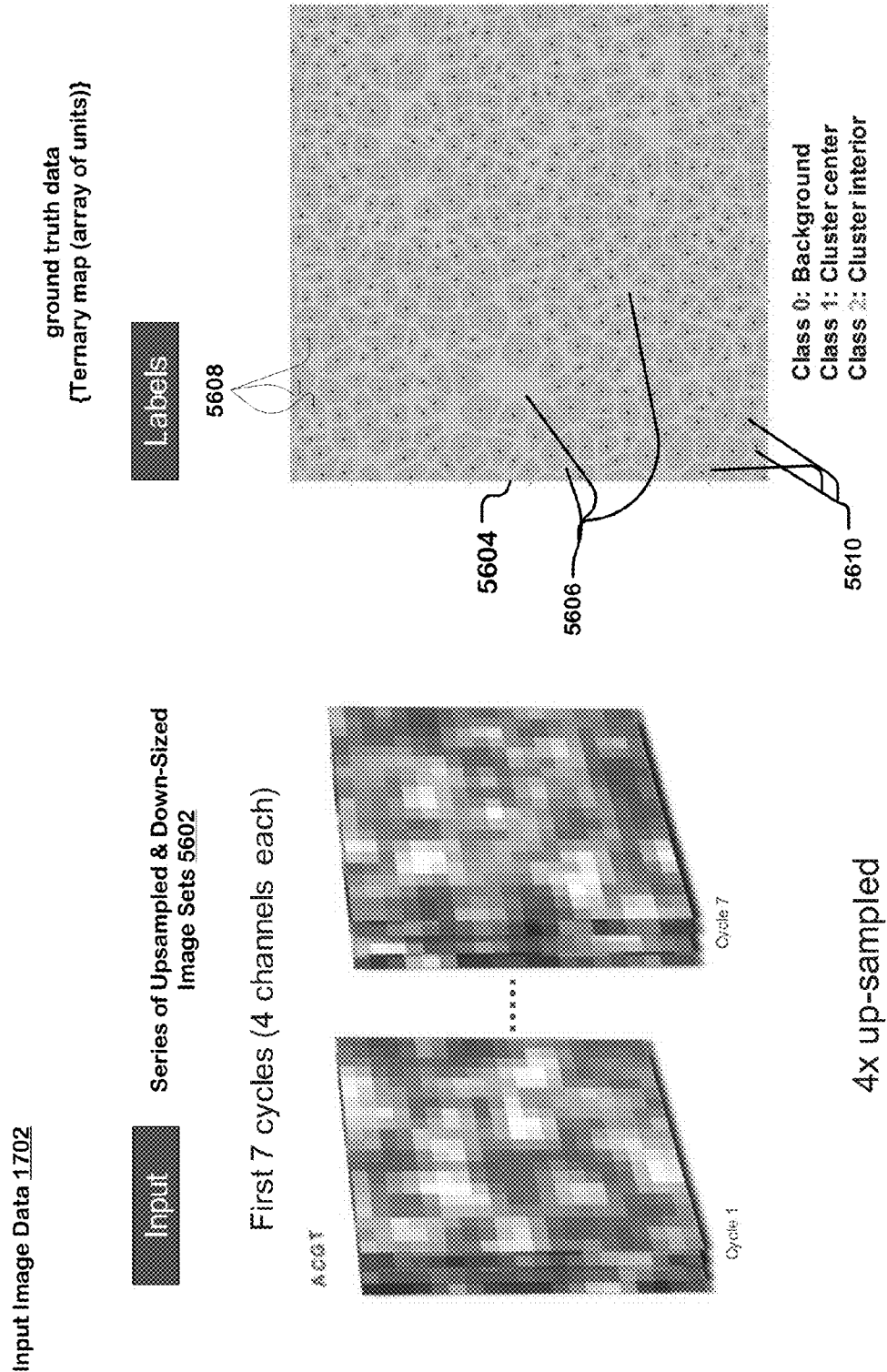
FIG. 56 illustrates another implementation of the input image data fed to the ternary classification model and the corresponding class labels used to train the ternary classification model.

FIG. 56 illustrates one implementation of input image data 1702 fed to the ternary classification model 5400 and the corresponding class labels used to train the ternary classification model 5400.

In the illustrated implementation, the input image data 1702 comprises a series of upsampled and down-sized image sets 5602. The class labels 5604 comprise three classes: (1) "background class", (2) "cluster center class", and (3) "cluster interior class", which are distinguished using different output values. For example, some of these different output values can be visually represented as follows: (1) the grey units/subpixels 5606 represent subpixels that are predicted by the ternary classification model 5400 to be the background, (2) the dark green units/subpixels 5608 represent subpixels that are predicted by the ternary classification model 5400 to contain the cluster centers, and (3) the light green subpixels 5610 represent subpixels that are predicted by the ternary classification model 5400 to contain the interior of the clusters.

Network Architecture

FIG. 57 is a table that shows an example architecture of the ternary classification model 5400, along with details of the layers of the ternary classification model 5400, dimensionality of the output of the layers, magnitude of the model parameters, and interconnections between the layers. Similar details are disclosed in the Appendix titled "Ternary_Classification_Model_Example_Architecture".

Inference

Figure 58:
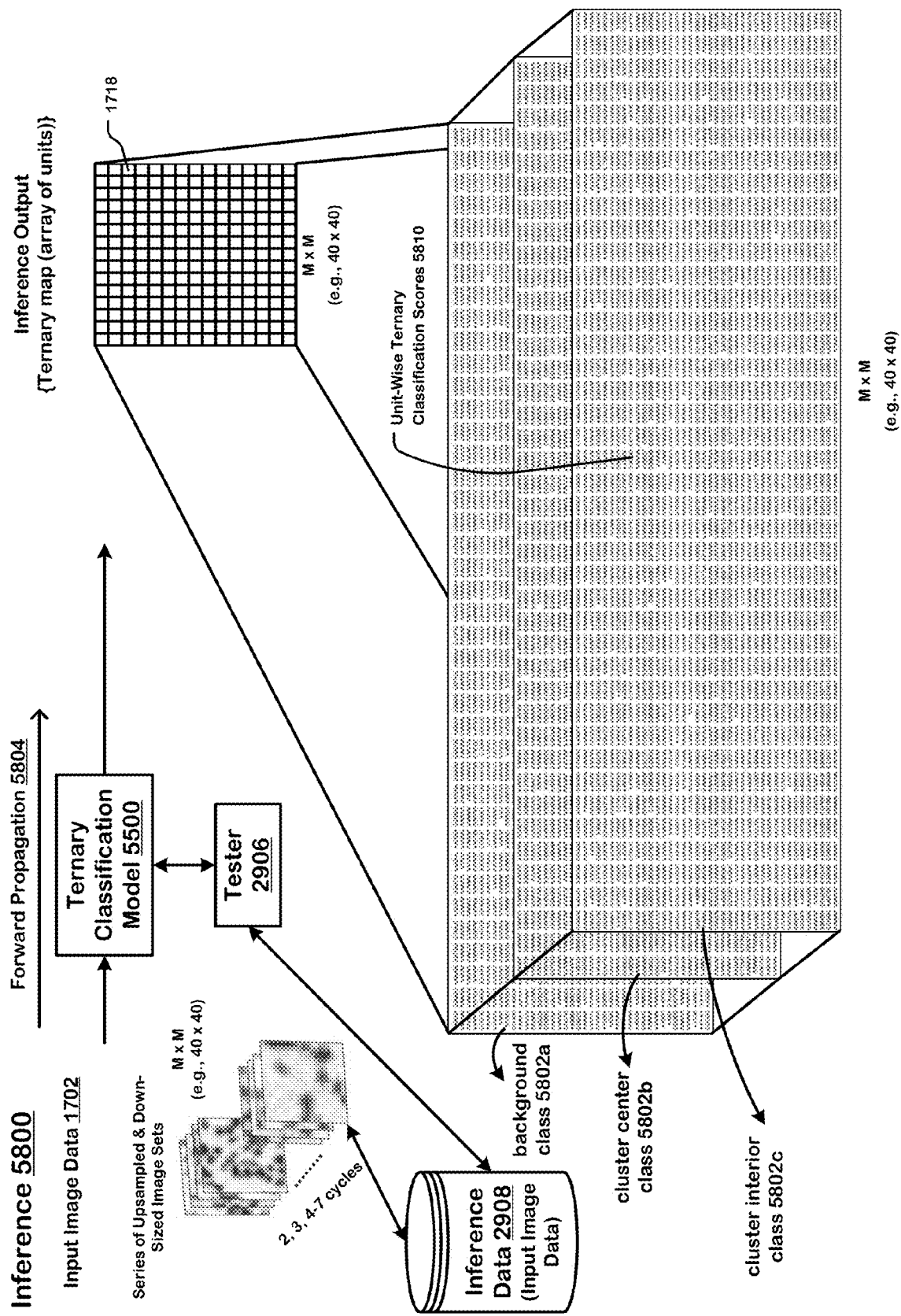
FIG. 58 is one implementation of template generation by the ternary classification model during inference.

FIG. 58 is one implementation of template generation by the ternary classification model 5400 during inference 5800 in which the ternary map 1718 is produced by the ternary classification model 5400 as the inference output during the inference 5800. One example of the ternary map 1718 is disclosed in the Appendix titled "Ternary_Classification_Model_Sample_Ouput". The Appendix includes unit-wise binary classification scores 5810 that together represent the ternary map 1718. In the softmax applications, the Appendix has a first array 5802a of unit-wise classification scores for the background class, a second array 5802b of unit-wise classification scores for the cluster center class, and a third array 5802c of unit-wise classification scores for the cluster/cluster interior class.

The inference 5800 includes hundreds, thousands, and/or millions of iterations of forward propagation 5804, including parallelization techniques such as batching. The inference 5800 is performed on inference data 2908 that includes, as the input image data 1702, a series of upsampled and down-sized image sets. The inference 5000 is operationalized by the tester 2906.

In some implementations, the ternary map 1718 is produced by the ternary classification model 5400 using post-processing techniques discussed above, such as thresholding, peak detection, and/or watershed segmentation.

Figure 59:
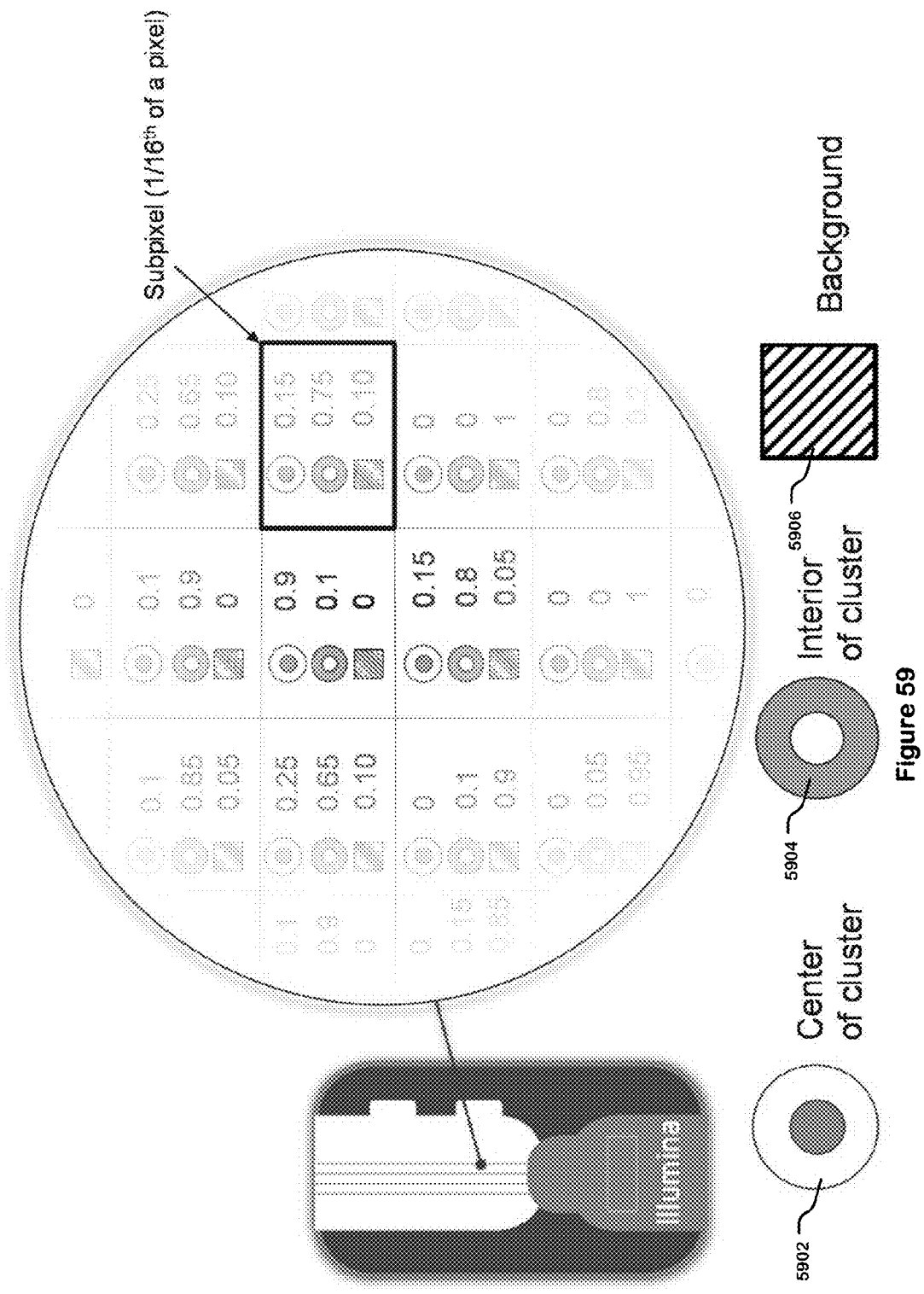
FIG. 59 shows a ternary map produced by the ternary classification model.

FIG. 59 graphically portrays the ternary map 1718 produced by the ternary classification model 5400 in which each subpixel has a three-way softmax classification score distribution for the three corresponding classes, namely, the background class 5906, the cluster center class 5902, and the cluster/cluster interior class 5904.

Figure 60:
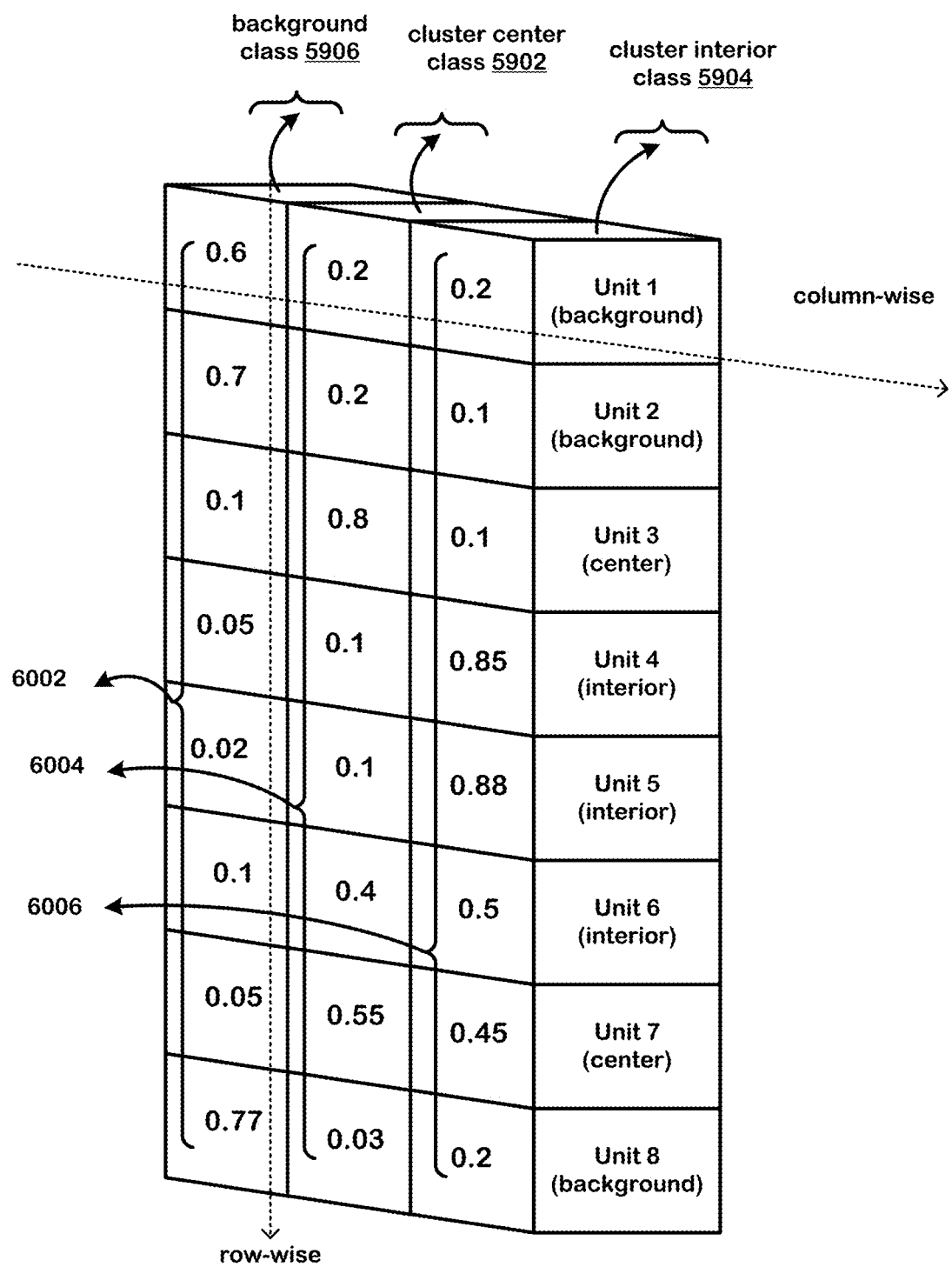
FIG. 60 depicts an array of units produced by the ternary classification model 5400, along with the unit-wise output values.

FIG. 60 depicts an array of units produced by the ternary classification model 5400, along with the unit-wise output values. As depicted, each unit has three output values for the three corresponding classes, namely, the background class 5906, the cluster center class 5902, and the cluster/cluster interior class 5904. For each classification (column-wise), each unit is assigned the class that has the highest output value, as indicated by the class in parenthesis under each unit. In some implementations, the output values 6002, 6004, and 6006 are analyzed for each of the respective classes 5906, 5902, and 5904 (row-wise).

Peak Detection & Watershed Segmentation

Figure 61:
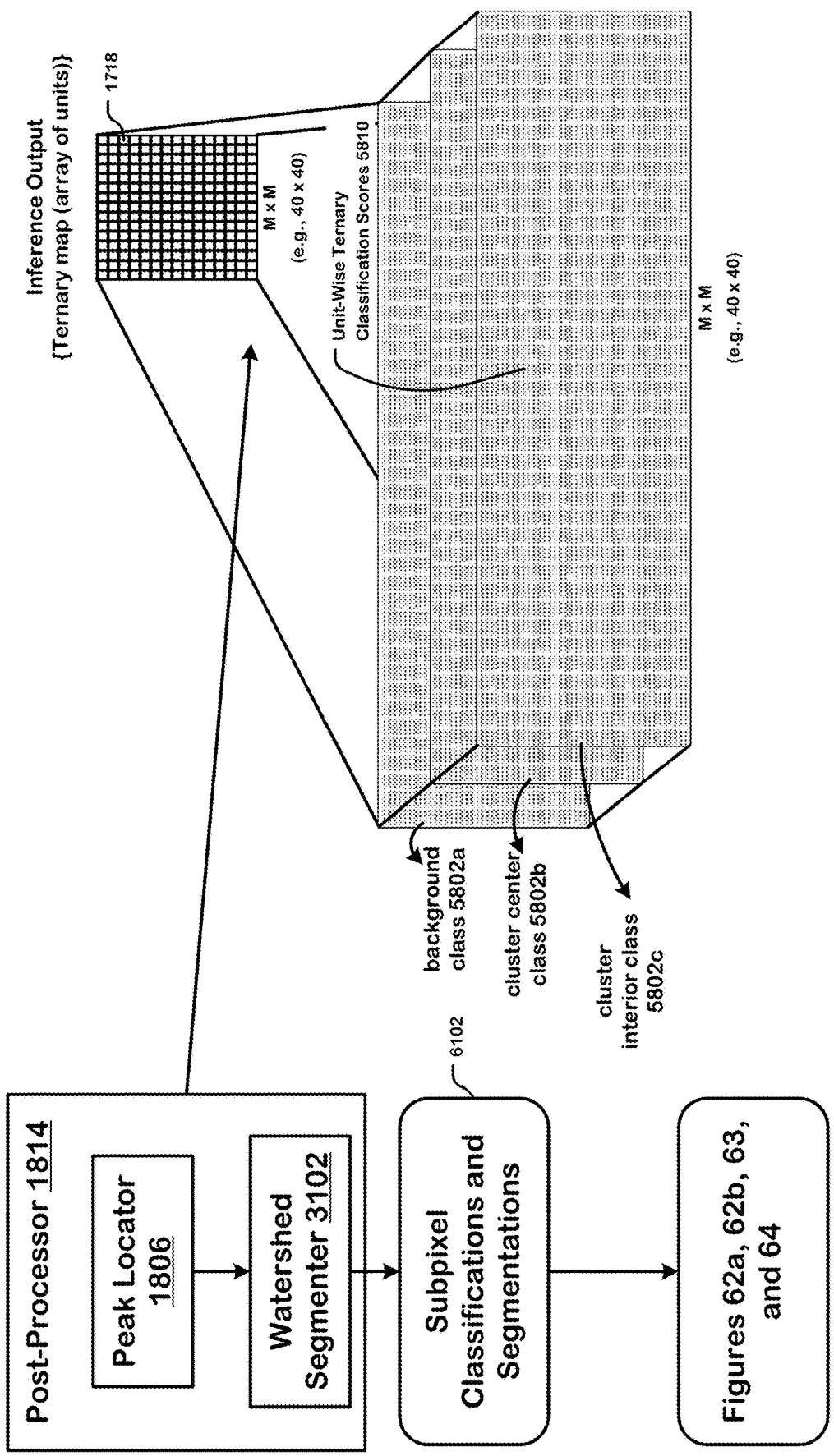
FIG. 61 shows one implementation of subjecting the ternary map to post-processing to identify cluster centers, cluster background, and cluster interior.

FIG. 61 shows one implementation of subjecting the ternary map 1718 to post-processing to identify cluster centers, cluster background, and cluster interior. As discussed above, the ternary map 1718 is an array of units that classifies each subpixel based on the predicted classification scores, with each unit in the array representing a corresponding subpixel in the input. The classification scores can be softmax scores.

In the softmax applications, the ternary map 1718 includes three arrays: (1) a first array 5802a of unit-wise classification scores for the background class, (2) a second array 5802b of unit-wise classification scores for the cluster center class, and (3) a third array 5802c of unit-wise classification scores for the cluster interior class. In all three arrays, each unit represents a corresponding subpixel in the input.

To determine which subpixels in the input contain the cluster centers, which contain the interior of the clusters, and which contain the background, the peak locator 1806 applies peak detection on softmax values in the ternary map 1718 for the cluster center class 5802b. The peak detection identifies those units that have classification scores (e.g., softmax scores) above a preset threshold. The identified units are inferred as the cluster centers and their corresponding subpixels in the input are determined to contain the cluster centers and stored as cluster center subpixels in a subpixel classifications and segmentations data store 6102. Additional details about the peak locator 1806 can be found in the Appendix entitled "Peak Detection".

In some implementations, prior to applying the peak detection, those units that have classification scores below a certain noise threshold (e.g., 0.3) are set to zero. Such units can be considered noise and ignored.

Also, units that have classification scores for the background class 5802a above a certain background threshold (e.g., equal to or greater than 0.5) and their corresponding subpixels in the input are inferred to denote the background surrounding the clusters and stored as background subpixels in the subpixel classifications and segmentations data store 6102.

Then, the watershed segmentation algorithm, operationalized by the watershed segmenter 3102, is used to determine the shapes of the clusters. In some implementations, the background units/subpixels are used as a mask by the watershed segmentation algorithm. Classification scores of the unit/subpixels inferred as the cluster centers and the cluster interior are summed to produce so-called "cluster labels". The cluster centers are used as watershed markers, for separation by intensity valleys by the watershed segmentation algorithm.

In one implementation, negativized cluster labels are provided as an input image to the watershed segmenter 3102 that performs segmentation and produces the cluster shapes as disjointed regions of contiguous cluster interior subpixels separated by the background subpixels. Furthermore, each disjointed region includes a corresponding cluster center subpixel. In some implementations, the corresponding cluster center subpixel is the center of the disjointed region to which it belongs. In other implementations, centers of mass (COM) of the disjointed regions are calculated based on the underlying location coordinates and stored as new centers of the clusters.

The outputs of the watershed segmenter 3102 are stored in the subpixel classifications and segmentations data store 6102. Additional details about the watershed segmentation algorithm and other segmentation algorithms can be found in Appendix entitled "Watershed Segmentation".

Example outputs of the peak locator 1806 and the watershed segmenter 3102 are shown in FIGS. 62a, 62b, 63, and 64.

Example Model Outputs

Figure 62A:
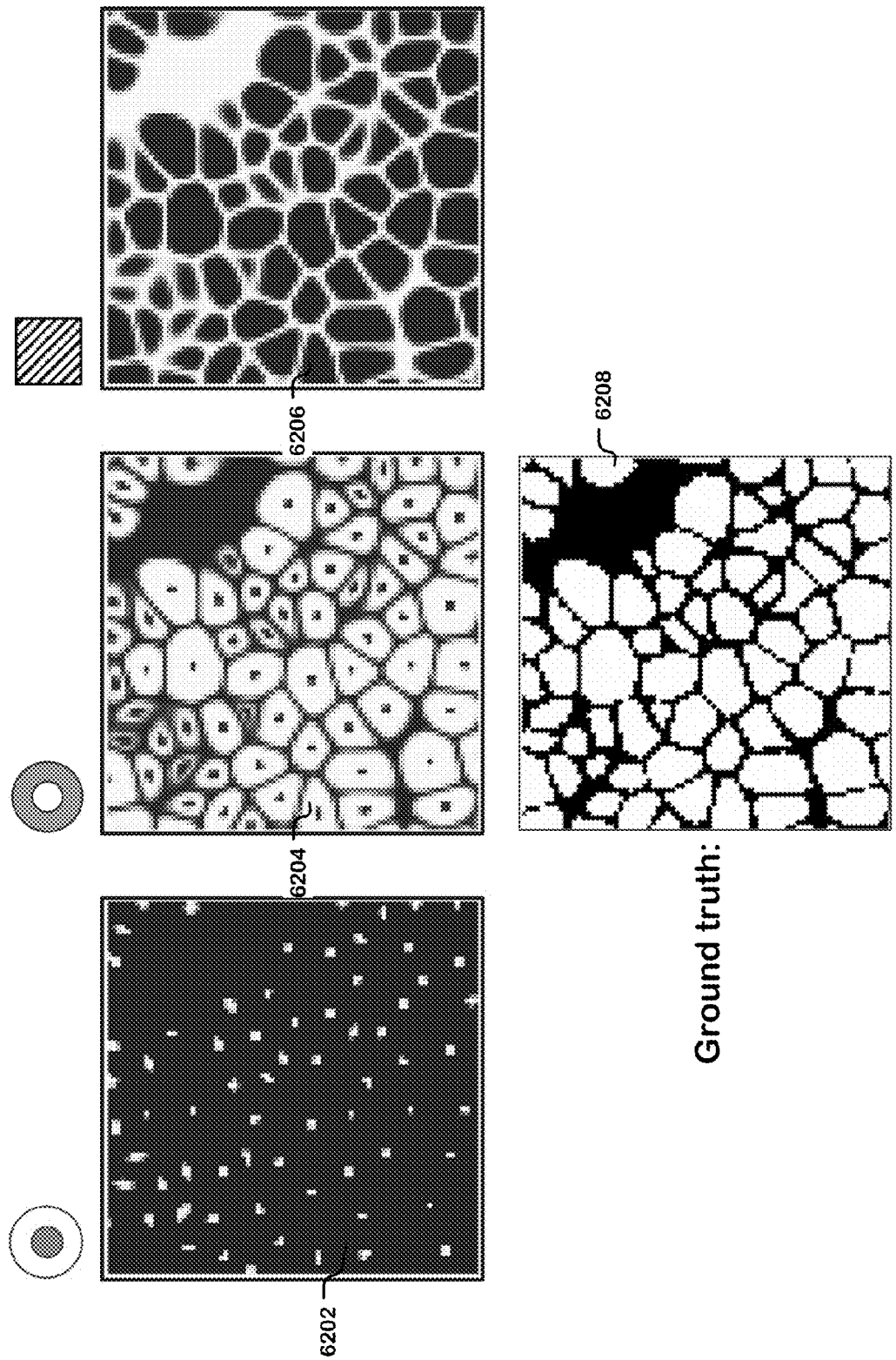
FIG. 62a shows example predictions of the ternary classification model.

FIG. 62a shows example predictions of the ternary classification model 5400. FIG. 62a shows four maps and each map has an array of units. The first map 6202 (left most) shows each unit's output values for the cluster center class 5802b. The second map 6204 shows each unit's output values for the cluster/cluster interior class 5802c. The third map 6206 (right most) shows each unit's output values for the background class 5802a. The fourth map 6208 (bottom) is a binary mask of ground truth ternary map 6008 that assigns each unit the class label that has the highest output value.

Figure 62B:
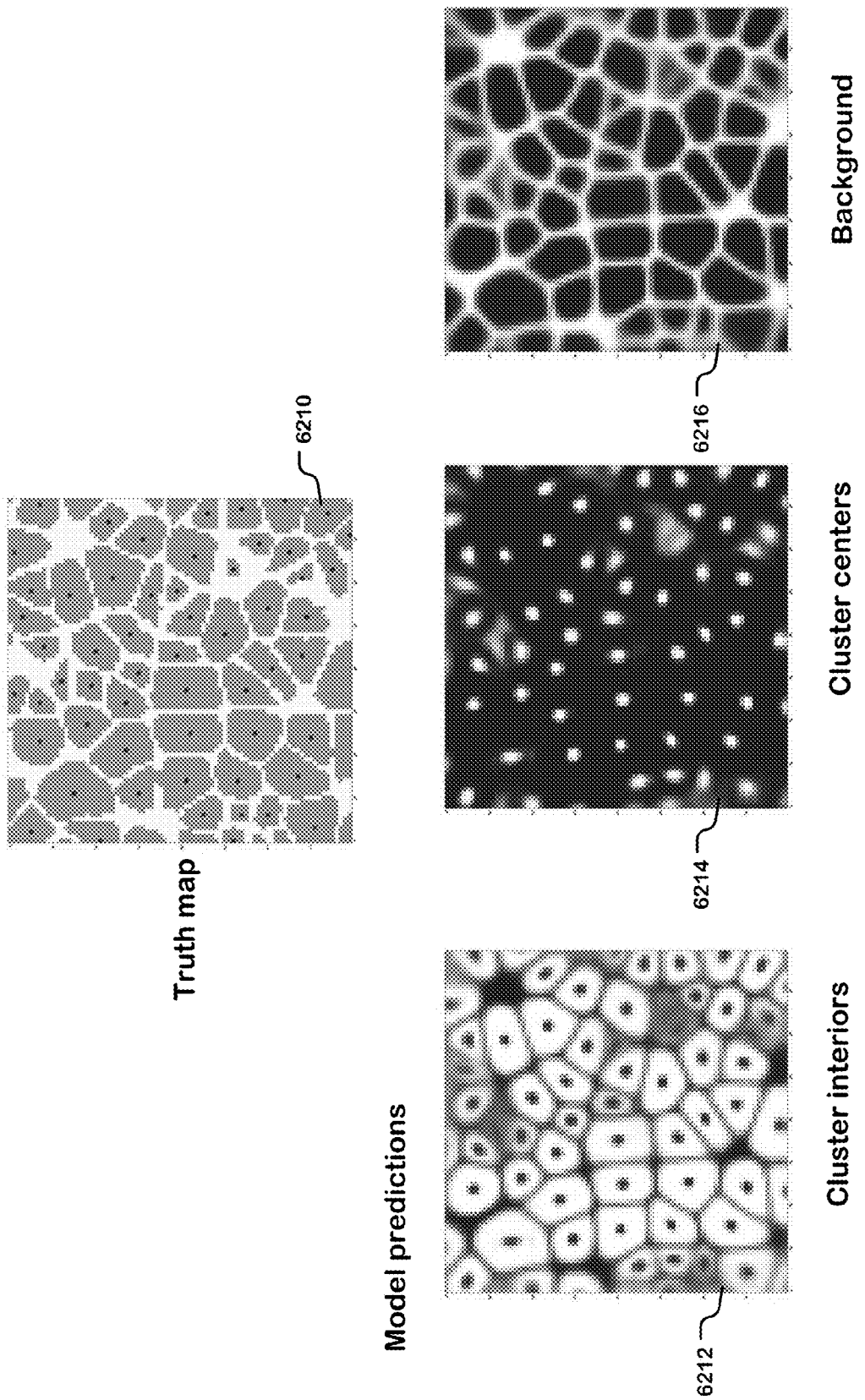
FIG. 62b illustrates other example predictions of the ternary classification model.

FIG. 62b illustrates other example predictions of the ternary classification model 5400. FIG. 62b shows four maps and each map has an array of units. The first map 6212 (bottom left most) shows each unit's output values for the cluster/cluster interior class. The second map 6214 shows each unit's output values for the cluster center class. The third map 6216 (bottom right most) shows each unit's output values for the background class. The fourth map (top) 6210 is the ground truth ternary map that assigns each unit the class label that has the highest output value.

FIG. 62c shows yet other example predictions of the ternary classification model 5400. FIG. 64 shows four maps and each map has an array of units. The first map 6220 (bottom left most) shows each unit's output values for the cluster/cluster interior class. The second map 6222 shows each unit's output values for the cluster center class. The third map 6224 (bottom right most) shows each unit's output values for the background class. The fourth map 6218 (top) is the ground truth ternary map that assigns each unit the class label that has the highest output value.

Figure 63:
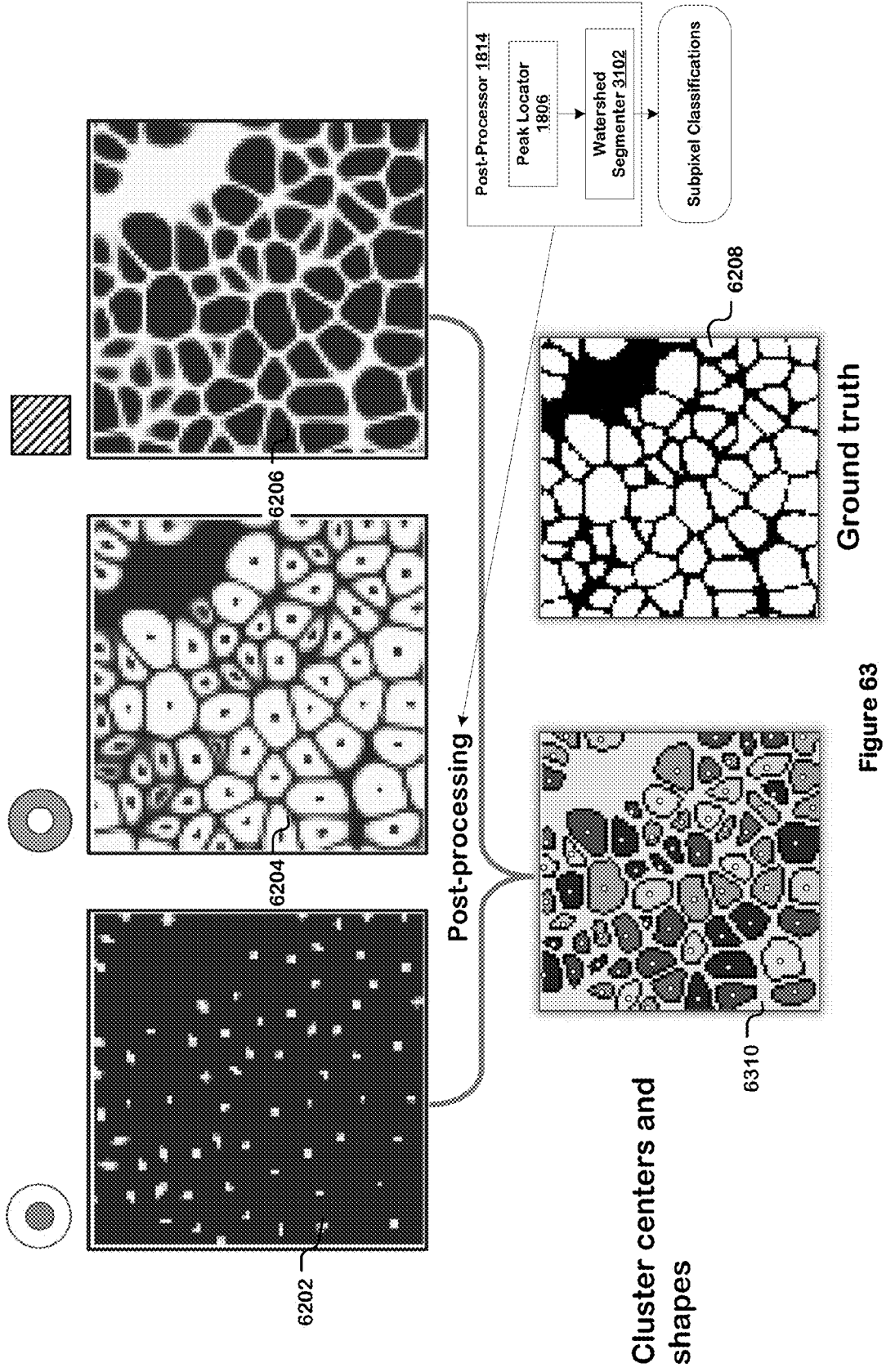

FIG. 63 depicts one implementation of deriving the cluster centers and cluster shapes from the output of the ternary classification model 5400 in FIG. 62a by subjecting the output to post-processing. The post-processing (e.g., peak locating, watershed segmentation) generates cluster shape data and other metadata, which is identified in the cluster map 6310.

Experimental Results and Observations

FIG. 64 compares performance of the binary classification model 4600, the regression model 2600, and the RTA base caller. The performance is evaluated using a variety of sequencing metrics. One metric is the total number of clusters detected ("# clusters"), which can be measured by the number of unique cluster centers that are detected. Another metric is the number of detected clusters that pass the chastity filter ("% PF" (pass-filter)). During cycles 1-25 of a sequencing run, the chastity filter removes the least reliable clusters from the image extraction results. Clusters "pass filter" if no more than one base call has a chastity value below 0.6 in the first 25 cycles. Chastity is defined as the ratio of the brightest base intensity divided by the sum of the brightest and the second brightest base intensities. This metric goes beyond the quantity of the detected clusters and also conveys their quality, i.e., how many of the detected clusters can be used for accurate base calling and downstream secondary and ternary analysis such as variant calling and variant pathogenicity annotation.

Other metrics that measure how good the detected clusters are for downstream analysis include the number of aligned reads produced from the detected clusters ("% Aligned"), the number of duplicate reads produced from the detected clusters ("% Duplicate"), the number of reads produced from the detected clusters mismatching the reference sequence for all reads aligned to the reference sequence ("% Mismatch"), the number of reads produced from the detected clusters whose portions do not match well to the reference sequence on either side and thus are ignored for the alignment ("% soft clipped"), the number of bases called for the detected clusters with quality score 30 and above ("% Q30 bases"), the number of paired reads produced from the detected clusters that have both reads aligned inwards within a reasonable distance ("total proper read pairs"), and the number of unique or deduplicated proper read pairs produced from the detected clusters ("non-duplicate proper read pairs").

As shown in FIG. 64, both the binary classification model 4600 and the regression model 2600 outperform the RTA base caller at template generation on most of the metrics.

Figure 65:
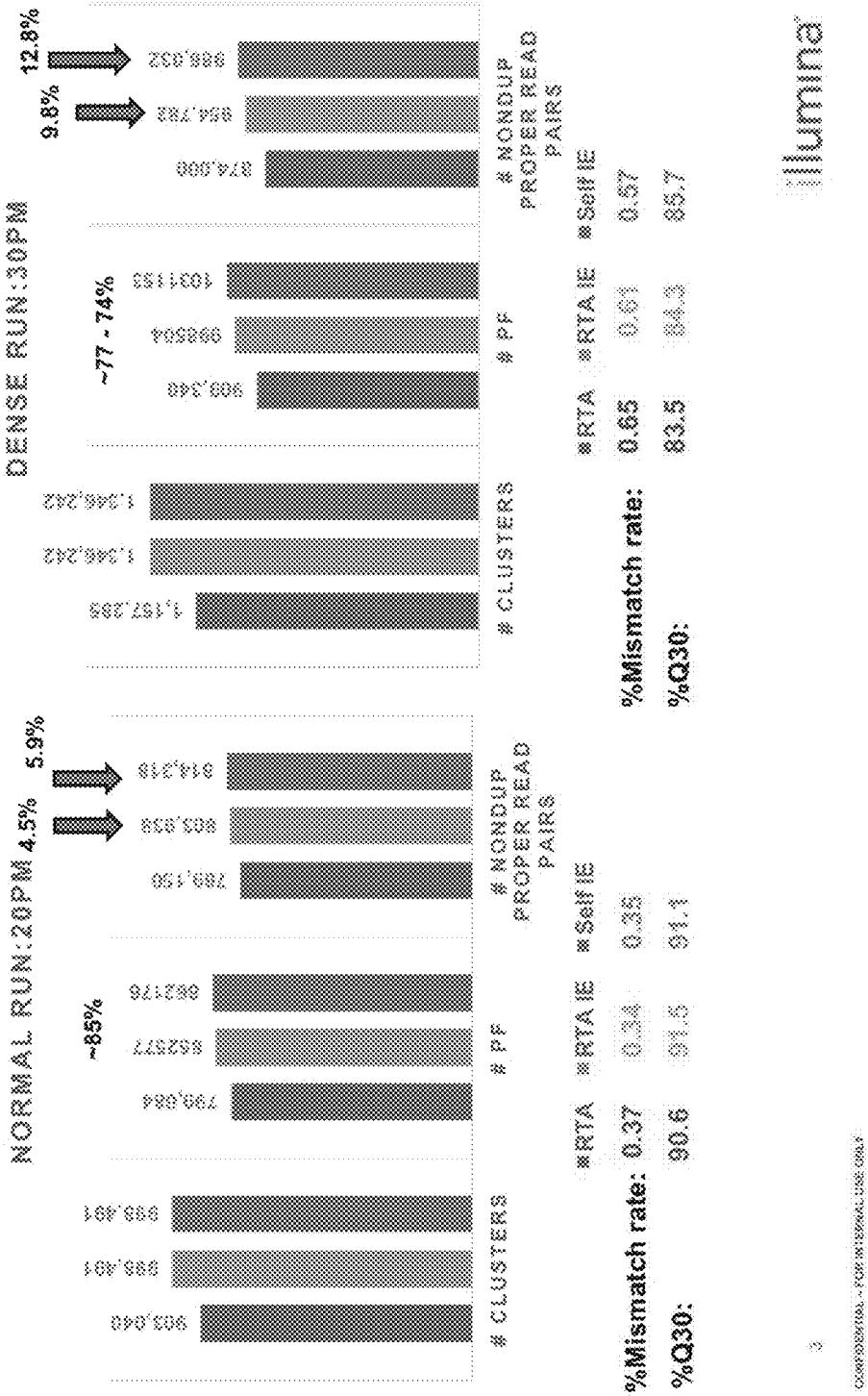
FIG. 65 compares the performance of the ternary classification model with that of the RTA base caller under three contexts, five sequencing metrics, and two run densities.

FIG. 65 compares the performance of the ternary classification model 5400 with that of the RTA base caller under three contexts, five sequencing metrics, and two run densities.

In the first context called "RTA", the cluster centers are detected by the RTA base caller, the intensity extraction from the clusters is done by the RTA base caller, and the clusters are also base called using the RTA base caller. In the second context called "RTA IE", the cluster centers are detected by the ternary classification model 5400; however, the intensity extraction from the clusters is done by the RTA base caller and the clusters are also base called using the RTA base caller. In the third context called "Self IE", the cluster centers are detected by the ternary classification model 5400 and the intensity extraction from the clusters is done using the cluster shape-based intensity extraction techniques disclosed herein (note that the cluster shape information is generated by the ternary classification model 5400); but the clusters are base called using the RTA base caller.

The performance is compared between the ternary classification model 5400 and the RTA base caller along five metrics: (1) the total number of clusters detected ("# clusters"), (2) the number of detected clusters that pass the chastity filter ("# PF"), (3) the number of unique or deduplicated proper read pairs produced from the detected clusters ("# nondup proper read pairs"), (4) the rate of mismatches between a sequence read produced from the detected clusters and a reference sequence after alignment ("% Mismatch rate"), and (5) bases called for the detected clusters with quality score 30 and above ("% Q30").

The performance is compared between the ternary classification model 5400 and the RTA base caller under the three contexts and the five metrics for two types of sequencing runs: (1) a normal run with 20 pM library concentration and (2) a dense run with 30 pM library concentration.

As shown in FIG. 65, the ternary classification model 5400 outperforms the RTA base caller on all the metrics.

Figure 66:
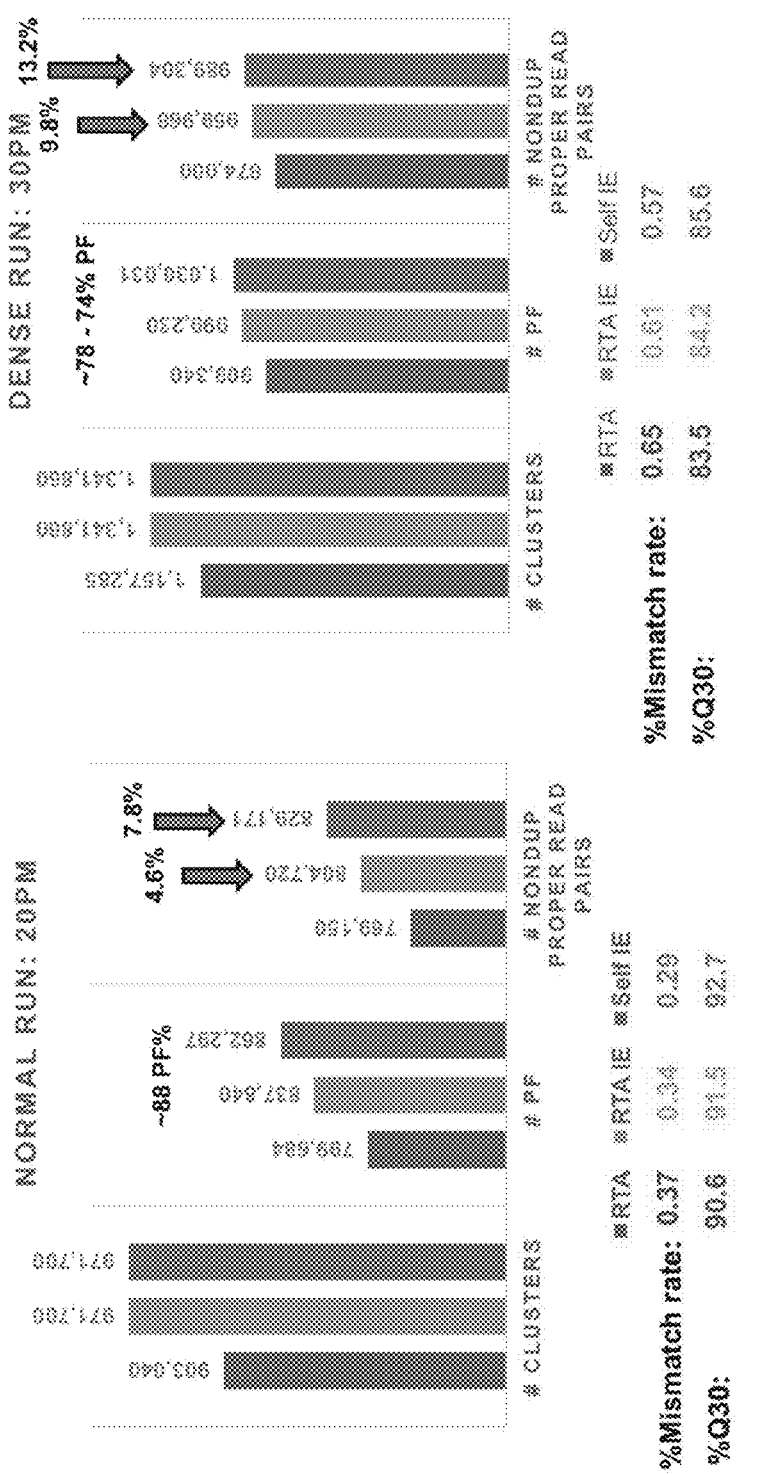
FIG. 66 compares the performance of the regression model with that of the RTA base caller under the three contexts, the five sequencing metrics, and the two run densities discussed in FIG. 65.

Under the same three contexts, five metrics, and two run densities, FIG. 66 shows that the regression model 2600 outperforms the RTA base caller on all the metrics.

Figure 67:
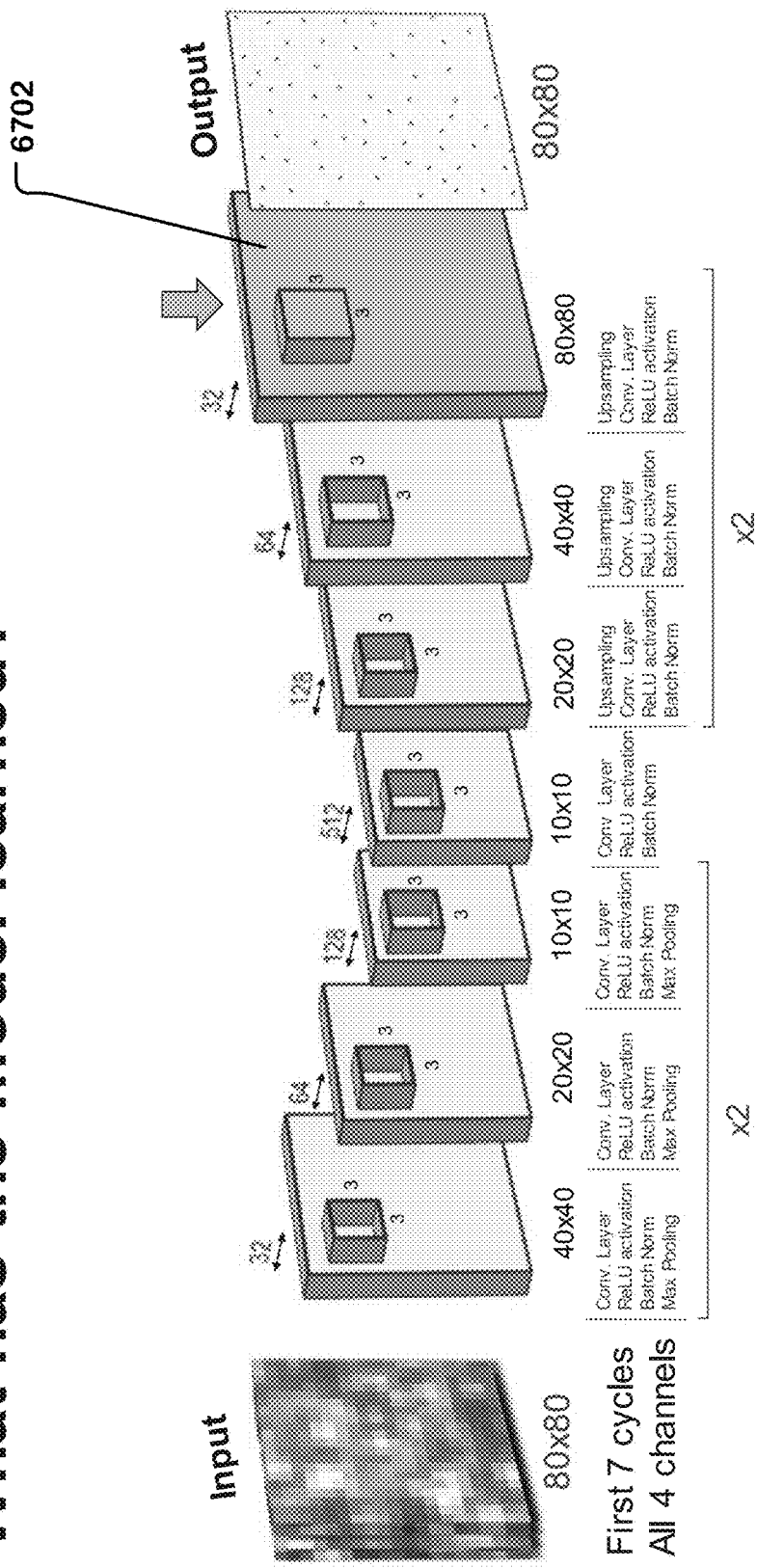
FIG. 67 focuses on the penultimate layer of the neural network-based template generator.

FIG. 67 focuses on the penultimate layer 6702 of the neural network-based template generator 1512.

Figure 68:
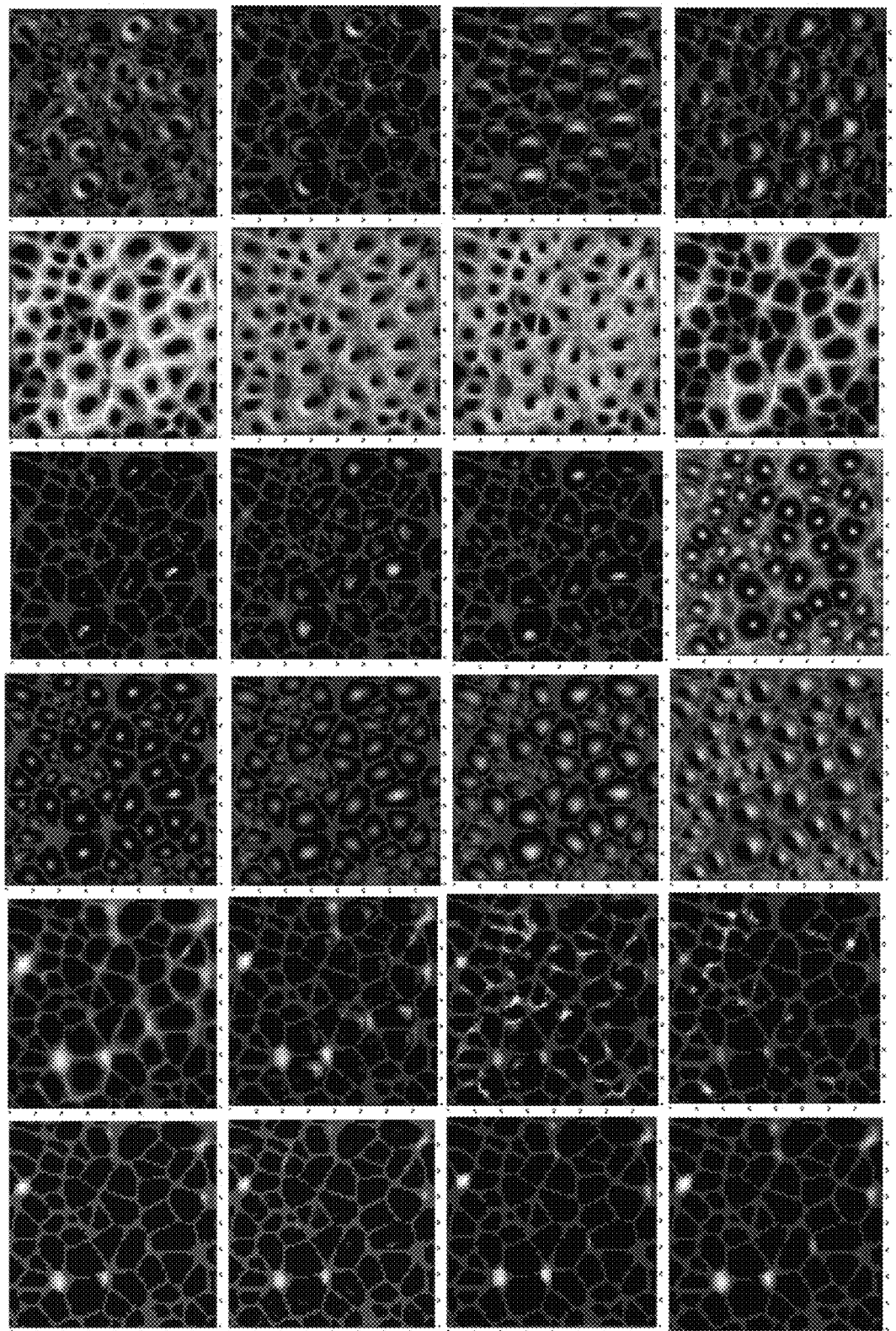
FIG. 68 visualizes what the penultimate layer of the neural network-based template generator has learned as a result of the backpropagation-based gradient update training. The illustrated implementation visualizes twenty-four out of the thirty-two trained convolution filters of the penultimate layer depicted in FIG. 67.

FIG. 68 visualizes what the penultimate layer 6702 of the neural network-based template generator 1512 has learned as a result of the backpropagation-based gradient update training. The illustrated implementation visualizes twenty-four out of the thirty-two convolution filters of the penultimate layer 6702 overlaid on the ground truth cluster shapes. As shown in FIG. 68, the penultimate layer 6702 has learned the cluster metadata, including spatial distribution of the clusters such as cluster centers, cluster shapes, cluster sizes, cluster background, and cluster boundaries.

Figure 69:
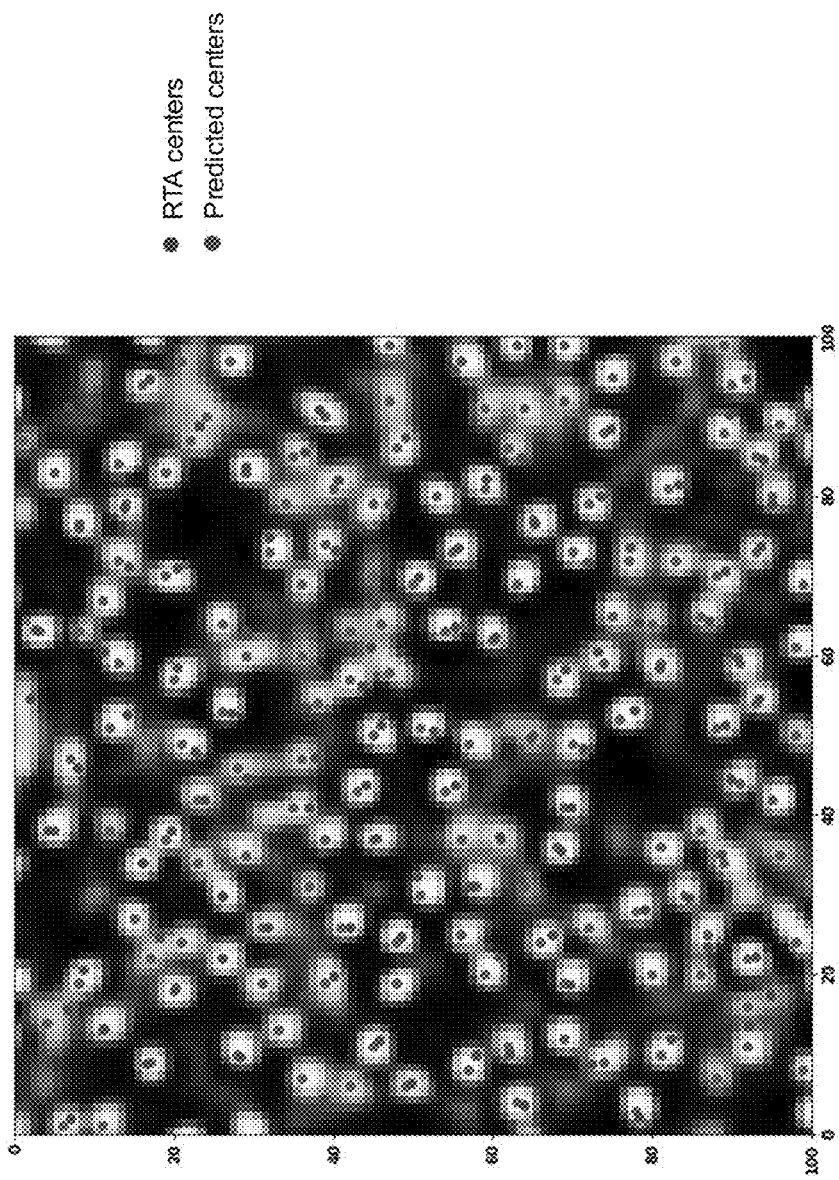
FIG. 69 overlays cluster center predictions of the binary classification model (in blue) onto those of the RTA base caller (in pink).

FIG. 69 overlays cluster center predictions of the binary classification model 4600 (in blue) onto those of the RTA base caller (in pink). The predictions are made on sequencing image data from the Illumina NextSeq sequencer.

FIG. 70 overlays cluster center predictions made by the RTA base caller (in pink) onto visualization of the trained convolution filters of the penultimate layer of the binary classification model 4600. These convolution filters are learned as a result of training on sequencing image data from the Illumina NextSeq sequencer.

FIG. 71 illustrates one implementation of training data used to train the neural network-based template generator 1512. In this implementation, the training data is obtained from dense flow cells that produce data with storm probe images. In another implementation, the training data is obtained from dense flow cells that produce data with fewer bridge amplification cycles.

Figure 72:
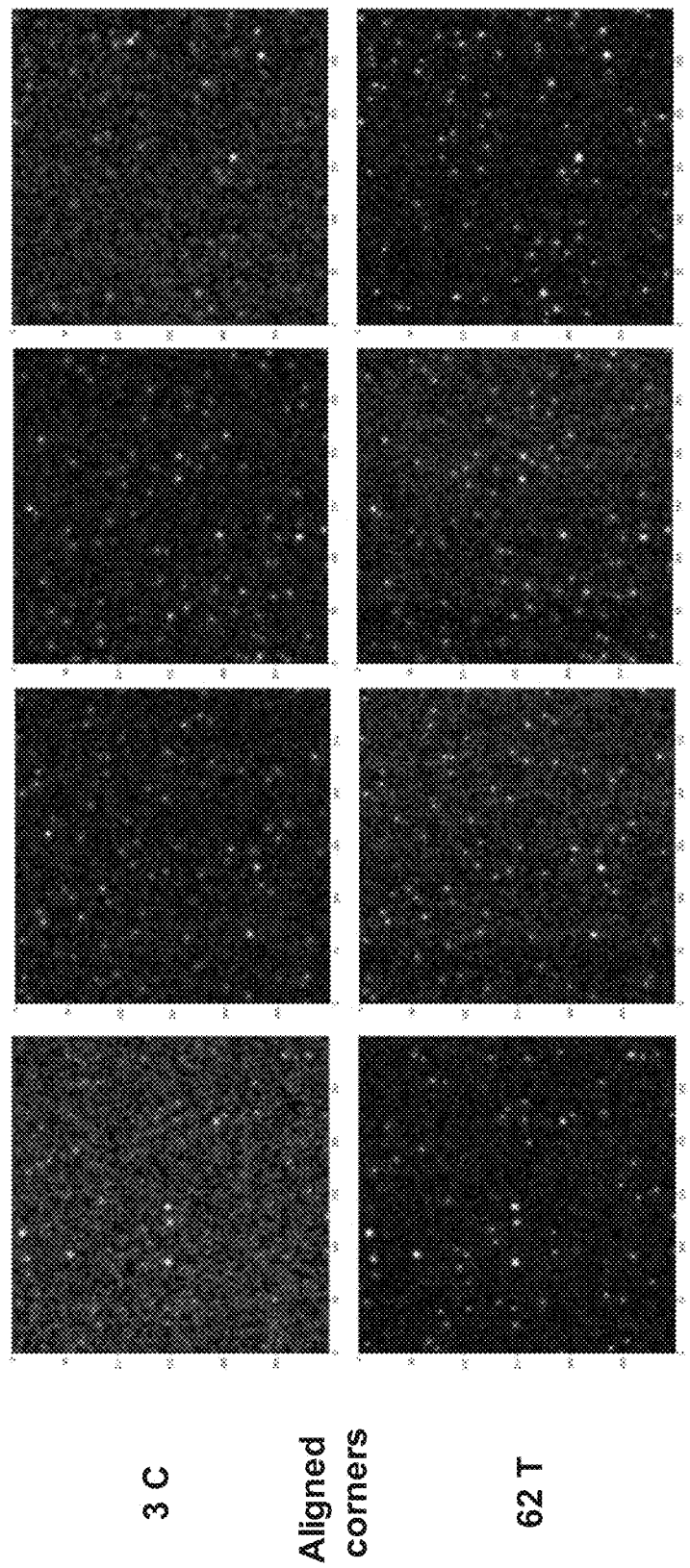
FIG. 72 is one implementation of using beads for image registration based on cluster center predictions of the neural network-based template generator.

FIG. 72 is one implementation of using beads for image registration based on cluster center predictions of the neural network-based template generator 1512.

Figure 73:
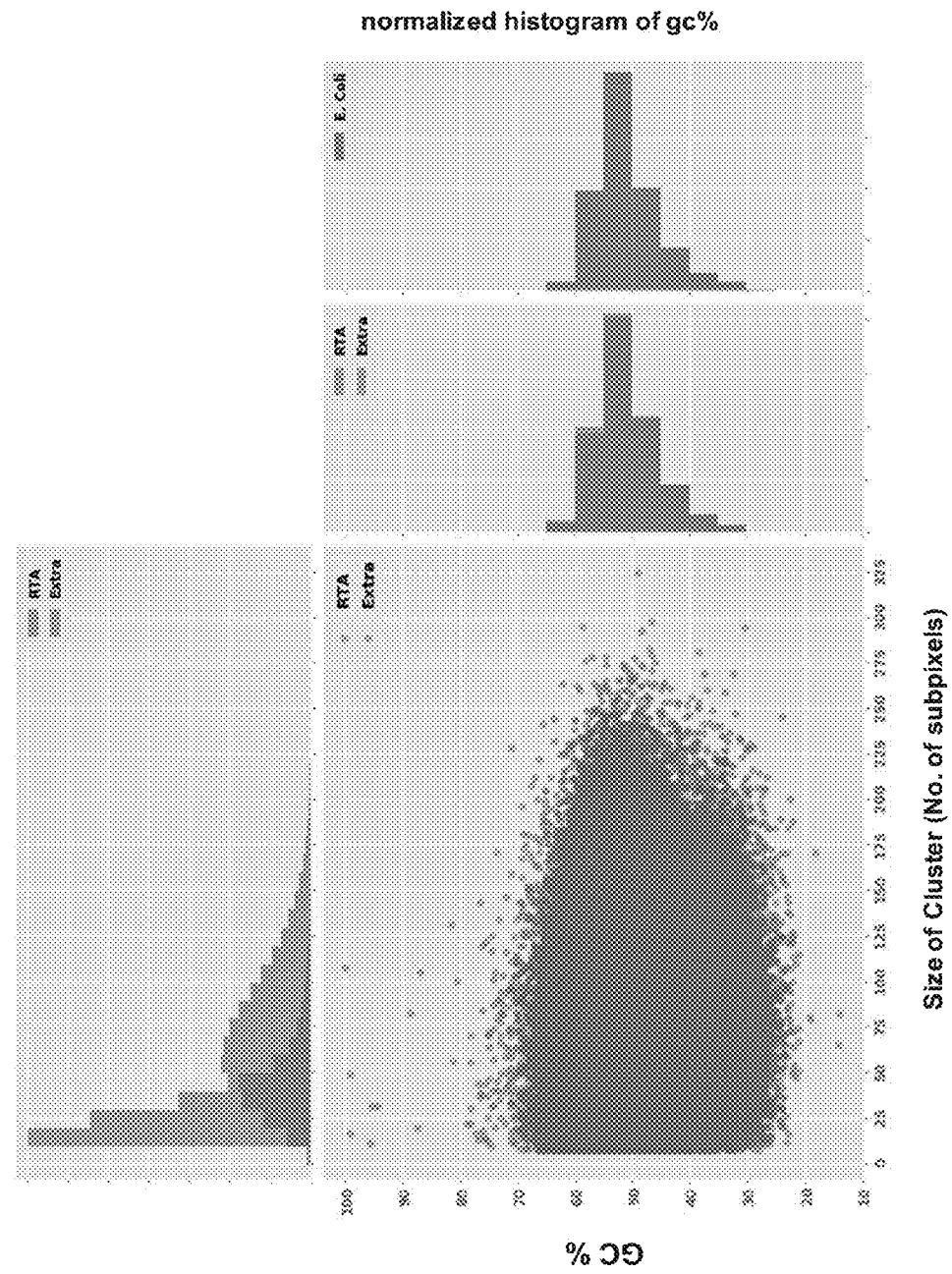
FIG. 73 illustrates one implementation of cluster statistics of clusters identified by the neural network-based template generator.

FIG. 73 illustrates one implementation of cluster statistics of clusters identified by the neural network-based template generator 1512. The cluster statistics include cluster size based on number of contributive subpixels and GC-content.

FIG. 74 shows how the neural network-based template generator 1512's ability to distinguish between adjacent clusters improves when the number of initial sequencing cycles for which the input image data 1702 is used increases from five to seven. For five sequencing cycles, a single cluster is identified by a single disjointed region of contiguous subpixels. For seven sequencing cycles, the single cluster is segmented into two adjacent clusters, each having their own disjointed regions of contiguous subpixels.

FIG. 75 illustrates the difference in base calling performance when a RTA base caller uses ground truth center of mass (COM) location as the cluster center, as opposed to when a non-COM location is used as the cluster center.

FIG. 76 portrays the performance of the neural network-based template generator 1512 on extra detected clusters.

FIG. 77 shows different datasets used for training the neural network-based template generator 1512.

Sequencing System

Figure 78A:
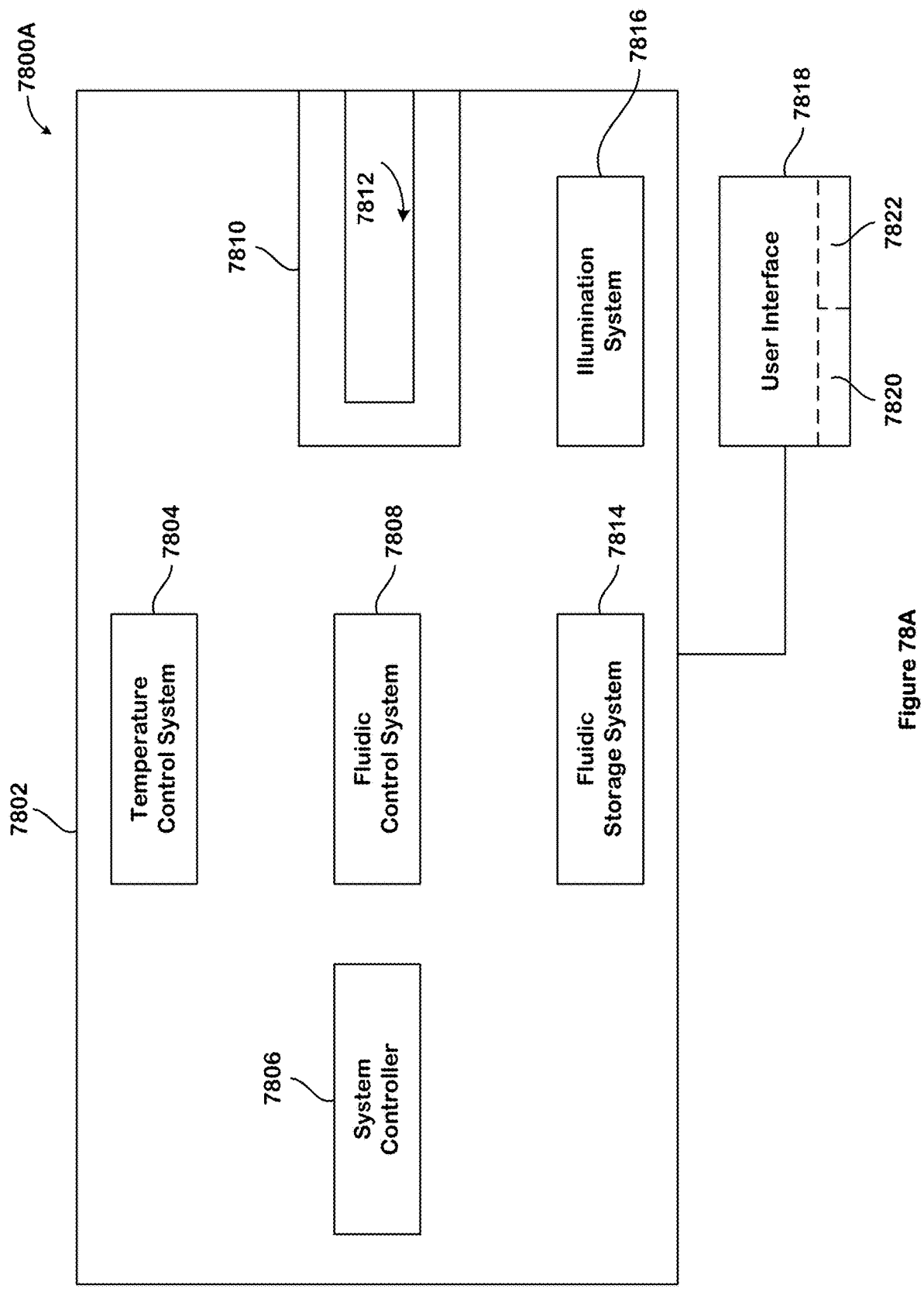
FIGS. 78A and 78B depict one implementation of a sequencing system. The sequencing system comprises a configurable processor.
Figure 78B:
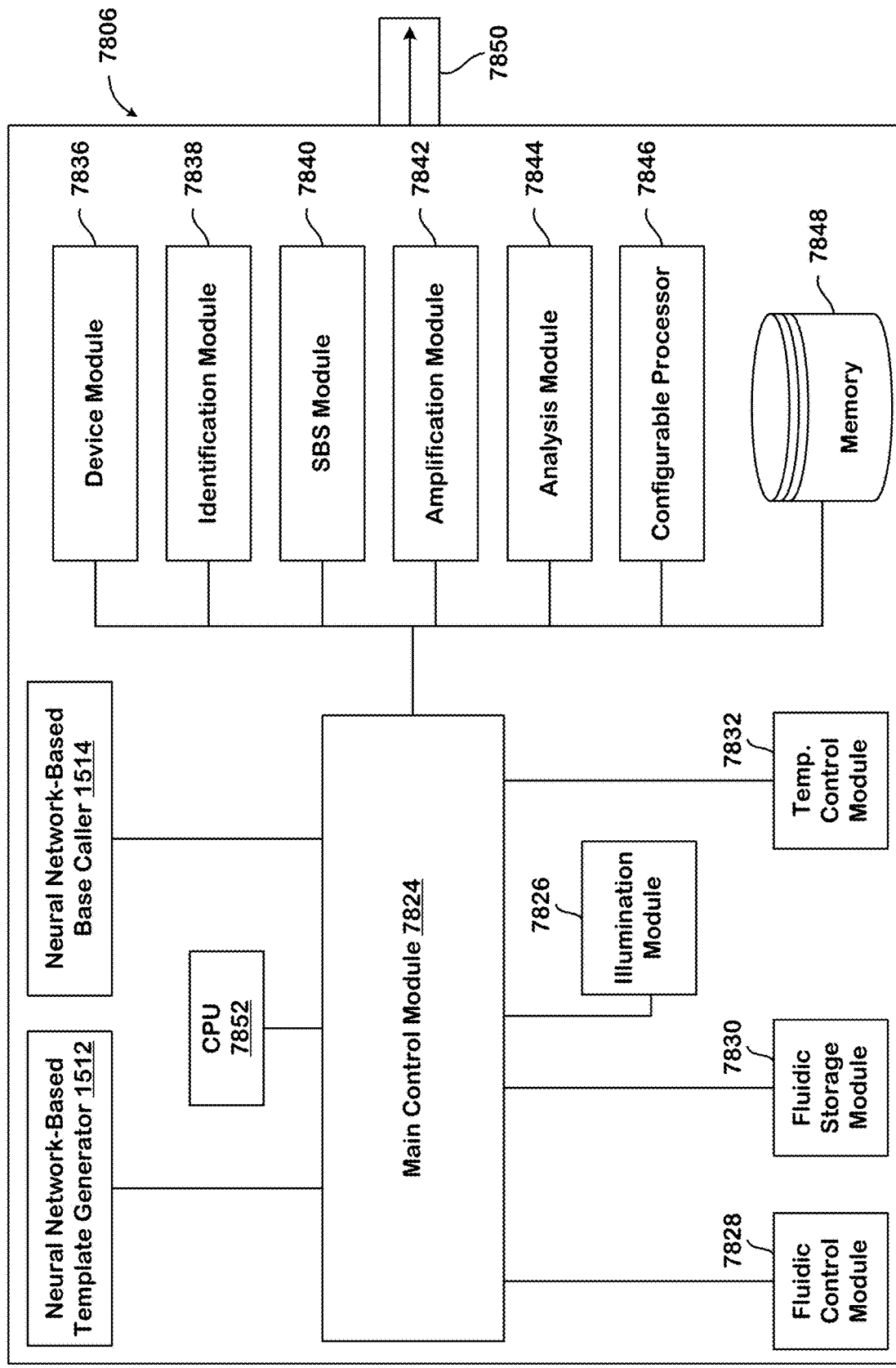

FIGS. 78A and 78B depict one implementation of a sequencing system 7800A. The sequencing system 7800A comprises a configurable processor 7846. The configurable processor 7846 implements the base calling techniques disclosed herein. The sequencing system is also referred to as a "sequencer."

The sequencing system 7800A can operate to obtain any information or data that relates to at least one of a biological or chemical substance. In some implementations, the sequencing system 7800A is a workstation that may be similar to a bench-top device or desktop computer. For example, a majority (or all) of the systems and components for conducting the desired reactions can be within a common housing 7802.

In particular implementations, the sequencing system 7800A is a nucleic acid sequencing system configured for various applications, including but not limited to de novo sequencing, resequencing of whole genomes or target genomic regions, and metagenomics. The sequencer may also be used for DNA or RNA analysis. In some implementations, the sequencing system 7800A may also be configured to generate reaction sites in a biosensor. For example, the sequencing system 7800A may be configured to receive a sample and generate surface attached clusters of clonally amplified nucleic acids derived from the sample. Each cluster may constitute or be part of a reaction site in the biosensor.

The exemplary sequencing system 7800A may include a system receptacle or interface 7810 that is configured to interact with a biosensor 7812 to perform desired reactions within the biosensor 7812. In the following description with respect to FIG. 78A, the biosensor 7812 is loaded into the system receptacle 7810. However, it is understood that a cartridge that includes the biosensor 7812 may be inserted into the system receptacle 7810 and in some states the cartridge can be removed temporarily or permanently. As described above, the cartridge may include, among other things, fluidic control and fluidic storage components.

In particular implementations, the sequencing system 7800A is configured to perform a large number of parallel reactions within the biosensor 7812. The biosensor 7812 includes one or more reaction sites where desired reactions can occur. The reaction sites may be, for example, immobilized to a solid surface of the biosensor or immobilized to beads (or other movable substrates) that are located within corresponding reaction chambers of the biosensor. The reaction sites can include, for example, clusters of clonally amplified nucleic acids. The biosensor 7812 may include a solid-state imaging device (e.g., CCD or CMOS imager) and a flow cell mounted thereto. The flow cell may include one or more flow channels that receive a solution from the sequencing system 7800A and direct the solution toward the reaction sites. Optionally, the biosensor 7812 can be configured to engage a thermal element for transferring thermal energy into or out of the flow channel.

The sequencing system 7800A may include various components, assemblies, and systems (or sub-systems) that interact with each other to perform a predetermined method or assay protocol for biological or chemical analysis. For example, the sequencing system 7800A includes a system controller 7806 that may communicate with the various components, assemblies, and sub-systems of the sequencing system 7800A and also the biosensor 7812. For example, in addition to the system receptacle 7810, the sequencing system 7800A may also include a fluidic control system 7808 to control the flow of fluid throughout a fluid network of the sequencing system 7800A and the biosensor 7812; a fluid storage system 7814 that is configured to hold all fluids (e.g., gas or liquids) that may be used by the bioassay system; a temperature control system 7804 that may regulate the temperature of the fluid in the fluid network, the fluid storage system 7814, and/or the biosensor 7812; and an illumination system 7816 that is configured to illuminate the biosensor 7812. As described above, if a cartridge having the biosensor 7812 is loaded into the system receptacle 7810, the cartridge may also include fluidic control and fluidic storage components.

Also shown, the sequencing system 7800A may include a user interface 7818 that interacts with the user. For example, the user interface 7818 may include a display 7820 to display or request information from a user and a user input device 7822 to receive user inputs. In some implementations, the display 7820 and the user input device 7822 are the same device. For example, the user interface 7818 may include a touch-sensitive display configured to detect the presence of an individual's touch and also identify a location of the touch on the display. However, other user input devices 7822 may be used, such as a mouse, touchpad, keyboard, keypad, handheld scanner, voice-recognition system, motion-recognition system, and the like. As will be discussed in greater detail below, the sequencing system 7800A may communicate with various components, including the biosensor 7812 (e.g., in the form of a cartridge), to perform the desired reactions. The sequencing system 7800A may also be configured to analyze data obtained from the biosensor to provide a user with desired information.

The system controller 7806 may include any processor-based or microprocessor-based system, including systems using microcontrollers, reduced instruction set computers (RISC), application specific integrated circuits (ASICs), field programmable gate array (FPGAs), coarse-grained reconfigurable architectures (CGRAs), logic circuits, and any other circuit or processor capable of executing functions described herein. The above examples are exemplary only, and are thus not intended to limit in any way the definition and/or meaning of the term system controller. In the exemplary implementation, the system controller 7806 executes a set of instructions that are stored in one or more storage elements, memories, or modules in order to at least one of obtain and analyze detection data. Detection data can include a plurality of sequences of pixel signals, such that a sequence of pixel signals from each of the millions of sensors (or pixels) can be detected over many base calling cycles. Storage elements may be in the form of information sources or physical memory elements within the sequencing system 7800A.

The set of instructions may include various commands that instruct the sequencing system 7800A or biosensor 7812 to perform specific operations such as the methods and processes of the various implementations described herein. The set of instructions may be in the form of a software program, which may form part of a tangible, non-transitory computer readable medium or media. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the sequencing system 7800A, processed in response to user inputs, or processed in response to a request made by another processing machine (e.g., a remote request through a communication link). In the illustrated implementation, the system controller 7806 includes an analysis module 7844. In other implementations, system controller 7806 does not include the analysis module 7844 and instead has access to the analysis module 7844 (e.g., the analysis module 7844 may be separately hosted on cloud).

The system controller 7806 may be connected to the biosensor 7812 and the other components of the sequencing system 7800A via communication links. The system controller 7806 may also be communicatively connected to off-site systems or servers. The communication links may be hardwired, corded, or wireless. The system controller 7806 may receive user inputs or commands, from the user interface 7818 and the user input device 7822.

The fluidic control system 7808 includes a fluid network and is configured to direct and regulate the flow of one or more fluids through the fluid network. The fluid network may be in fluid communication with the biosensor 7812 and the fluid storage system 7814. For example, select fluids may be drawn from the fluid storage system 7814 and directed to the biosensor 7812 in a controlled manner, or the fluids may be drawn from the biosensor 7812 and directed toward, for example, a waste reservoir in the fluid storage system 7814. Although not shown, the fluidic control system 7808 may include flow sensors that detect a flow rate or pressure of the fluids within the fluid network. The sensors may communicate with the system controller 7806.

The temperature control system 7804 is configured to regulate the temperature of fluids at different regions of the fluid network, the fluid storage system 7814, and/or the biosensor 7812. For example, the temperature control system 7804 may include a thermocycler that interfaces with the biosensor 7812 and controls the temperature of the fluid that flows along the reaction sites in the biosensor 7812. The temperature control system 7804 may also regulate the temperature of solid elements or components of the sequencing system 7800A or the biosensor 7812. Although not shown, the temperature control system 7804 may include sensors to detect the temperature of the fluid or other components. The sensors may communicate with the system controller 7806.

The fluid storage system 7814 is in fluid communication with the biosensor 7812 and may store various reaction components or reactants that are used to conduct the desired reactions therein. The fluid storage system 7814 may also store fluids for washing or cleaning the fluid network and biosensor 7812 and for diluting the reactants. For example, the fluid storage system 7814 may include various reservoirs to store samples, reagents, enzymes, other biomolecules, buffer solutions, aqueous, and non-polar solutions, and the like. Furthermore, the fluid storage system 7814 may also include waste reservoirs for receiving waste products from the biosensor 7812. In implementations that include a cartridge, the cartridge may include one or more of a fluid storage system, fluidic control system or temperature control system. Accordingly, one or more of the components set forth herein as relating to those systems can be contained within a cartridge housing. For example, a cartridge can have various reservoirs to store samples, reagents, enzymes, other biomolecules, buffer solutions, aqueous, and non-polar solutions, waste, and the like. As such, one or more of a fluid storage system, fluidic control system or temperature control system can be removably engaged with a bioassay system via a cartridge or other biosensor.

The illumination system 7816 may include a light source (e.g., one or more LEDs) and a plurality of optical components to illuminate the biosensor. Examples of light sources may include lasers, arc lamps, LEDs, or laser diodes. The optical components may be, for example, reflectors, dichroics, beam splitters, collimators, lenses, filters, wedges, prisms, mirrors, detectors, and the like. In implementations that use an illumination system, the illumination system 7816 may be configured to direct an excitation light to reaction sites. As one example, fluorophores may be excited by green wavelengths of light, as such the wavelength of the excitation light may be approximately 532 nm. In one implementation, the illumination system 7816 is configured to produce illumination that is parallel to a surface normal of a surface of the biosensor 7812. In another implementation, the illumination system 7816 is configured to produce illumination that is off-angle relative to the surface normal of the surface of the biosensor 7812. In yet another implementation, the illumination system 7816 is configured to produce illumination that has plural angles, including some parallel illumination and some off-angle illumination.

The system receptacle or interface 7810 is configured to engage the biosensor 7812 in at least one of a mechanical, electrical, and fluidic manner. The system receptacle 7810 may hold the biosensor 7812 in a desired orientation to facilitate the flow of fluid through the biosensor 7812. The system receptacle 7810 may also include electrical contacts that are configured to engage the biosensor 7812 so that the sequencing system 7800A may communicate with the biosensor 7812 and/or provide power to the biosensor 7812. Furthermore, the system receptacle 7810 may include fluidic ports (e.g., nozzles) that are configured to engage the biosensor 7812. In some implementations, the biosensor 7812 is removably coupled to the system receptacle 7810 in a mechanical manner, in an electrical manner, and also in a fluidic manner.

In addition, the sequencing system 7800A may communicate remotely with other systems or networks or with other bioassay systems 7800A. Detection data obtained by the bioassay system(s) 7800A may be stored in a remote database.

FIG. 78B is a block diagram of a system controller 7806 that can be used in the system of FIG. 78A. In one implementation, the system controller 7806 includes one or more processors or modules that can communicate with one another. Each of the processors or modules may include an algorithm (e.g., instructions stored on a tangible and/or non-transitory computer readable storage medium) or sub-algorithms to perform particular processes. The system controller 7806 is illustrated conceptually as a collection of modules, but may be implemented utilizing any combination of dedicated hardware boards, DSPs, processors, etc. Alternatively, the system controller 7806 may be implemented utilizing an off-the-shelf PC with a single processor or multiple processors, with the functional operations distributed between the processors. As a further option, the modules described below may be implemented utilizing a hybrid configuration in which certain modular functions are performed utilizing dedicated hardware, while the remaining modular functions are performed utilizing an off-the-shelf PC and the like. The modules also may be implemented as software modules within a processing unit.

During operation, a communication port 7850 may transmit information (e.g., commands) to or receive information (e.g., data) from the biosensor 7812 (FIG. 78A) and/or the sub-systems 7808, 7814, 7804 (FIG. 78A). In implementations, the communication port 7850 may output a plurality of sequences of pixel signals. A communication link 7834 may receive user input from the user interface 7818 (FIG. 78A) and transmit data or information to the user interface 7818. Data from the biosensor 7812 or sub-systems 7808, 7814, 7804 may be processed by the system controller 7806 in real-time during a bioassay session. Additionally or alternatively, data may be stored temporarily in a system memory during a bioassay session and processed in slower than real-time or off-line operation.

As shown in FIG. 78B, the system controller 7806 may include a plurality of modules 7826-7848 that communicate with a main control module 7824, along with a central processing unit (CPU) 7852. The main control module 7824 may communicate with the user interface 7818 (FIG. 78A). Although the modules 7826-7848 are shown as communicating directly with the main control module 7824, the modules 7826-7848 may also communicate directly with each other, the user interface 7818, and the biosensor 7812. Also, the modules 7826-7848 may communicate with the main control module 7824 through the other modules.

The plurality of modules 7826-7848 include system modules 7828-7832, 7826 that communicate with the sub-systems 7808, 7814, 7804, and 7816, respectively. The fluidic control module 7828 may communicate with the fluidic control system 7808 to control the valves and flow sensors of the fluid network for controlling the flow of one or more fluids through the fluid network. The fluid storage module 7830 may notify the user when fluids are low or when the waste reservoir is at or near capacity. The fluid storage module 7830 may also communicate with the temperature control module 7832 so that the fluids may be stored at a desired temperature. The illumination module 7826 may communicate with the illumination system 7816 to illuminate the reaction sites at designated times during a protocol, such as after the desired reactions (e.g., binding events) have occurred. In some implementations, the illumination module 7826 may communicate with the illumination system 7816 to illuminate the reaction sites at designated angles.

The plurality of modules 7826-7848 may also include a device module 7836 that communicates with the biosensor 7812 and an identification module 7838 that determines identification information relating to the biosensor 7812. The device module 7836 may, for example, communicate with the system receptacle 7810 to confirm that the biosensor has established an electrical and fluidic connection with the sequencing system 7800A. The identification module 7838 may receive signals that identify the biosensor 7812. The identification module 7838 may use the identity of the biosensor 7812 to provide other information to the user. For example, the identification module 7838 may determine and then display a lot number, a date of manufacture, or a protocol that is recommended to be run with the biosensor 7812.

The plurality of modules 7826-7848 also includes an analysis module 7844 (also called signal processing module or signal processor) that receives and analyzes the signal data (e.g., image data) from the biosensor 7812. Analysis module 7844 includes memory (e.g., RAM or Flash) to store detection/image data. Detection data can include a plurality of sequences of pixel signals, such that a sequence of pixel signals from each of the millions of sensors (or pixels) can be detected over many base calling cycles. The signal data may be stored for subsequent analysis or may be transmitted to the user interface 7818 to display desired information to the user. In some implementations, the signal data may be processed by the solid-state imager (e.g., CMOS image sensor) before the analysis module 7844 receives the signal data.

The analysis module 7844 is configured to obtain image data from the light detectors at each of a plurality of sequencing cycles. The image data is derived from the emission signals detected by the light detectors and process the image data for each of the plurality of sequencing cycles through the neural network-based template generator 1512 and/or the neural network-based base caller 1514 and produce a base call for at least some of the analytes at each of the plurality of sequencing cycle. The light detectors can be part of one or more over-head cameras (e.g., Illumina's GAIIx's CCD camera taking images of the clusters on the biosensor 7812 from the top), or can be part of the biosensor 7812 itself (e.g., Illumina's iSeq's CMOS image sensors underlying the clusters on the biosensor 7812 and taking images of the clusters from the bottom).

The output of the light detectors is the sequencing images, each depicting intensity emissions of the clusters and their surrounding background. The sequencing images depict intensity emissions generated as a result of nucleotide incorporation in the sequences during the sequencing. The intensity emissions are from associated analytes and their surrounding background. The sequencing images are stored in memory 7848.

Protocol modules 7840 and 7842 communicate with the main control module 7824 to control the operation of the sub-systems 7808, 7814, and 7804 when conducting predetermined assay protocols. The protocol modules 7840 and 7842 may include sets of instructions for instructing the sequencing system 7800A to perform specific operations pursuant to predetermined protocols. As shown, the protocol module may be a sequencing-by-synthesis (SBS) module 7840 that is configured to issue various commands for performing sequencing-by-synthesis processes. In SBS, extension of a nucleic acid primer along a nucleic acid template is monitored to determine the sequence of nucleotides in the template. The underlying chemical process can be polymerization (e.g., as catalyzed by a polymerase enzyme) or ligation (e.g., catalyzed by a ligase enzyme). In a particular polymerase-based SBS implementation, fluorescently labeled nucleotides are added to a primer (thereby extending the primer) in a template dependent fashion such that detection of the order and type of nucleotides added to the primer can be used to determine the sequence of the template. For example, to initiate a first SBS cycle, commands can be given to deliver one or more labeled nucleotides, DNA polymerase, etc., into/through a flow cell that houses an array of nucleic acid templates. The nucleic acid templates may be located at corresponding reaction sites. Those reaction sites where primer extension causes a labeled nucleotide to be incorporated can be detected through an imaging event. During an imaging event, the illumination system 7816 may provide an excitation light to the reaction sites. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for implementations that use reversible termination a command can be given to deliver a deblocking reagent to the flow cell (before or after detection occurs). One or more commands can be given to effect wash(es) between the various delivery steps. The cycle can then be repeated n times to extend the primer by n nucleotides, thereby detecting a sequence of length n. Exemplary sequencing techniques are described, for example, in Bentley et al., Nature 456:53-59 (20078); WO 04/0178497; U.S. Pat. No. 7,057,026; WO 91/066778; WO 07/123744; U.S. Pat. Nos. 7,329,492; 7,211,414; 7,315,019; 7,405,2781, and US 20078/01470780782, each of which is incorporated herein by reference.

For the nucleotide delivery step of an SBS cycle, either a single type of nucleotide can be delivered at a time, or multiple different nucleotide types (e.g., A, C, T and G together) can be delivered. For a nucleotide delivery configuration where only a single type of nucleotide is present at a time, the different nucleotides need not have distinct labels since they can be distinguished based on temporal separation inherent in the individualized delivery. Accordingly, a sequencing method or apparatus can use single color detection. For example, an excitation source need only provide excitation at a single wavelength or in a single range of wavelengths. For a nucleotide delivery configuration where delivery results in multiple different nucleotides being present in the flow cell at one time, sites that incorporate different nucleotide types can be distinguished based on different fluorescent labels that are attached to respective nucleotide types in the mixture. For example, four different nucleotides can be used, each having one of four different fluorophores. In one implementation, the four different fluorophores can be distinguished using excitation in four different regions of the spectrum. For example, four different excitation radiation sources can be used. Alternatively, fewer than four different excitation sources can be used, but optical filtration of the excitation radiation from a single source can be used to produce different ranges of excitation radiation at the flow cell.

In some implementations, fewer than four different colors can be detected in a mixture having four different nucleotides. For example, pairs of nucleotides can be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. Exemplary apparatus and methods for distinguishing four different nucleotides using detection of fewer than four colors are described for example in US Pat. App. Ser. Nos. 61/5378,294 and 61/619,78778, which are incorporated herein by reference in their entireties. U.S. application Ser. No. 13/624,200, which was filed on Sep. 21, 2012, is also incorporated by reference in its entirety.

The plurality of protocol modules may also include a sample-preparation (or generation) module 7842 that is configured to issue commands to the fluidic control system 7808 and the temperature control system 7804 for amplifying a product within the biosensor 7812. For example, the biosensor 7812 may be engaged to the sequencing system 7800A. The amplification module 7842 may issue instructions to the fluidic control system 7808 to deliver necessary amplification components to reaction chambers within the biosensor 7812. In other implementations, the reaction sites may already contain some components for amplification, such as the template DNA and/or primers. After delivering the amplification components to the reaction chambers, the amplification module 7842 may instruct the temperature control system 7804 to cycle through different temperature stages according to known amplification protocols. In some implementations, the amplification and/or nucleotide incorporation is performed isothermally.

The SBS module 7840 may issue commands to perform bridge PCR where clusters of clonal amplicons are formed on localized areas within a channel of a flow cell. After generating the amplicons through bridge PCR, the amplicons may be "linearized" to make single stranded template DNA, or sstDNA, and a sequencing primer may be hybridized to a universal sequence that flanks a region of interest. For example, a reversible terminator-based sequencing by synthesis method can be used as set forth above or as follows.

Each base calling or sequencing cycle can extend an sstDNA by a single base which can be accomplished for example by using a modified DNA polymerase and a mixture of four types of nucleotides. The different types of nucleotides can have unique fluorescent labels, and each nucleotide can further have a reversible terminator that allows only a single-base incorporation to occur in each cycle. After a single base is added to the sstDNA, excitation light may be incident upon the reaction sites and fluorescent emissions may be detected. After detection, the fluorescent label and the terminator may be chemically cleaved from the sstDNA. Another similar base calling or sequencing cycle may follow. In such a sequencing protocol, the SBS module 7840 may instruct the fluidic control system 7808 to direct a flow of reagent and enzyme solutions through the biosensor 7812. Exemplary reversible terminator-based SBS methods which can be utilized with the apparatus and methods set forth herein are described in US Patent Application Publication No. 2007/0166705 A1, US Patent Application Publication No. 2006/017878901 A1, U.S. Pat. No. 7,057,026, US Patent Application Publication No. 2006/0240439 A1, US Patent Application Publication No. 2006/027814714709 A1, PCT Publication No. WO 05/0657814, US Patent Application Publication No. 2005/014700900 A1, PCT Publication No. WO 06/078B199 and PCT Publication No. WO 07/01470251, each of which is incorporated herein by reference in its entirety. Exemplary reagents for reversible terminator-based SBS are described in U.S. Pat. Nos. 7,541,444; 7,057,026; 7,414,14716; U.S. Pat. Nos. 7,427,673; 7,566,537; 7,592,435 and WO 07/1478353678, each of which is incorporated herein by reference in its entirety.

In some implementations, the amplification and SBS modules may operate in a single assay protocol where, for example, template nucleic acid is amplified and subsequently sequenced within the same cartridge.

The sequencing system 7800A may also allow the user to reconfigure an assay protocol. For example, the sequencing system 7800A may offer options to the user through the user interface 7818 for modifying the determined protocol. For example, if it is determined that the biosensor 7812 is to be used for amplification, the sequencing system 7800A may request a temperature for the annealing cycle. Furthermore, the sequencing system 7800A may issue warnings to a user if a user has provided user inputs that are generally not acceptable for the selected assay protocol.

In implementations, the biosensor 7812 includes millions of sensors (or pixels), each of which generates a plurality of sequences of pixel signals over successive base calling cycles. The analysis module 7844 detects the plurality of sequences of pixel signals and attributes them to corresponding sensors (or pixels) in accordance to the row-wise and/or column-wise location of the sensors on an array of sensors.

Figure 79:
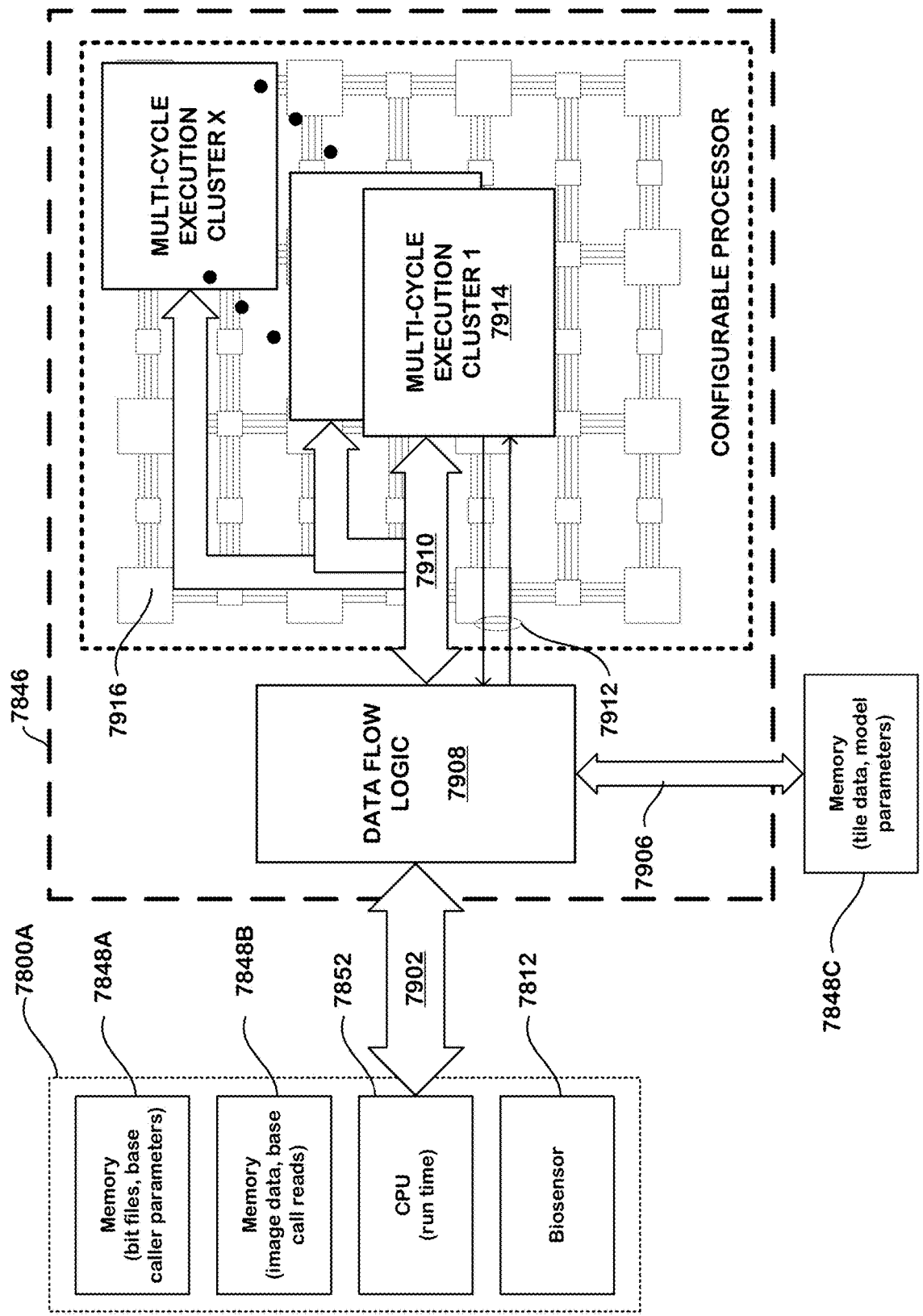
FIG. 79 is a simplified block diagram of a system for analysis of sensor data from the sequencing system, such as base call sensor outputs.

FIG. 79 is a simplified block diagram of a system for analysis of sensor data from the sequencing system 7800A, such as base call sensor outputs. In the example of FIG. 79, the system includes the configurable processor 7846. The configurable processor 7846 can execute a base caller (e.g., the neural network-based template generator 1512 and/or the neural network-based base caller 1514) in coordination with a runtime program executed by the central processing unit (CPU) 7852 (i.e., a host processor). The sequencing system 7800A comprises the biosensor 7812 and flow cells. The flow cells can comprise one or more tiles in which clusters of genetic material are exposed to a sequence of analyte flows used to cause reactions in the clusters to identify the bases in the genetic material. The sensors sense the reactions for each cycle of the sequence in each tile of the flow cell to provide tile data. Genetic sequencing is a data intensive operation, which translates base call sensor data into sequences of base calls for each cluster of genetic material sensed in during a base call operation.

The system in this example includes the CPU 7852, which executes a runtime program to coordinate the base call operations, memory 7848B to store sequences of arrays of tile data, base call reads produced by the base calling operation, and other information used in the base call operations. Also, in this illustration the system includes memory 7848A to store a configuration file (or files), such as FPGA bit files, and model parameters for the neural networks used to configure and reconfigure the configurable processor 7846, and execute the neural networks. The sequencing system 7800A can include a program for configuring a configurable processor and in some embodiments a reconfigurable processor to execute the neural networks.

The sequencing system 7800A is coupled by a bus 7902 to the configurable processor 7846. The bus 7902 can be implemented using a high throughput technology, such as in one example bus technology compatible with the PCIe standards (Peripheral Component Interconnect Express) currently maintained and developed by the PCI-SIG (PCI Special Interest Group). Also in this example, a memory 7848A is coupled to the configurable processor 7846 by bus 7906. The memory 7848A can be on-board memory, disposed on a circuit board with the configurable processor 7846. The memory 7848A is used for high speed access by the configurable processor 7846 of working data used in the base call operation. The bus 7906 can also be implemented using a high throughput technology, such as bus technology compatible with the PCIe standards.

Configurable processors, including field programmable gate arrays FPGAs, coarse grained reconfigurable arrays CGRAs, and other configurable and reconfigurable devices, can be configured to implement a variety of functions more efficiently or faster than might be achieved using a general purpose processor executing a computer program. Configuration of configurable processors involves compiling a functional description to produce a configuration file, referred to sometimes as a bitstream or bit file, and distributing the configuration file to the configurable elements on the processor. The configuration file defines the logic functions to be executed by the configurable processor, by configuring the circuit to set data flow patterns, use of distributed memory and other on-chip memory resources, lookup table contents, operations of configurable logic blocks and configurable execution units like multiply-and-accumulate units, configurable interconnects and other elements of the configurable array. A configurable processor is reconfigurable if the configuration file may be changed in the field, by changing the loaded configuration file. For example, the configuration file may be stored in volatile SRAM elements, in non-volatile read-write memory elements, and in combinations of the same, distributed among the array of configurable elements on the configurable or reconfigurable processor. A variety of commercially available configurable processors are suitable for use in a base calling operation as described herein. Examples include Google's Tensor Processing Unit (TPU)™, rackmount solutions like GX4 Rackmount Series™, GX9 Rackmount Series™, NVIDIA DGX-1™, Microsoft™ Stratix V FPGA™, Graphcore's Intelligent Processor Unit (IPU)™, Qualcomm's Zeroth Platform™ with Snapdragon Processors™, NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, Lambda GPU Server with Testa V100s™, Xilinx Alveo™ U200, Xilinx Alveo™ U250, Xilinx Alveo™ U280, Intel/Altera Stratix™ GX2800, Intel/Altera Stratix™ GX2800, and Intel Stratix™ GX10M. In some examples, a host CPU can be implemented on the same integrated circuit as the configurable processor.

Embodiments described herein implement the neural network-based template generator 1512 and/or the neural network-based base caller 1514 using the configurable processor 7846. The configuration file for the configurable processor 7846 can be implemented by specifying the logic functions to be executed using a high level description language HDL or a register transfer level RTL language specification. The specification can be compiled using the resources designed for the selected configurable processor to generate the configuration file. The same or similar specification can be compiled for the purposes of generating a design for an application-specific integrated circuit which may not be a configurable processor.

Alternatives for the configurable processor configurable processor 7846, in all embodiments described herein, therefore include a configured processor comprising an application specific ASIC or special purpose integrated circuit or set of integrated circuits, or a system-on-a-chip SOC device, or a graphics processing unit (GPU) processor or a coarse-grained reconfigurable architecture (CGRA) processor, configured to execute a neural network based base call operation as described herein.

In general, configurable processors and configured processors described herein, as configured to execute runs of a neural network, are referred to herein as neural network processors.

The configurable processor 7846 is configured in this example by a configuration file loaded using a program executed by the CPU 7852, or by other sources, which configures the array of configurable elements 7916 (e.g., configuration logic blocks (CLB) such as look up tables (LUTs), flip-flops, compute processing units (PMUs), and compute memory units (CMUs), configurable I/O blocks, programmable interconnects), on the configurable processor to execute the base call function. In this example, the configuration includes data flow logic 7908 which is coupled to the buses 7902 and 7906 and executes functions for distributing data and control parameters among the elements used in the base call operation.

Also, the configurable processor 7846 is configured with base call execution logic 7908 to execute the neural network-based template generator 1512 and/or the neural network-based base caller 1514. The logic 7908 comprises multi-cycle execution clusters (e.g., 7914) which, in this example, includes execution cluster 1 through execution cluster X. The number of multi-cycle execution clusters can be selected according to a trade-off involving the desired throughput of the operation, and the available resources on the configurable processor 7846.

The multi-cycle execution clusters are coupled to the data flow logic 7908 by data flow paths 7910 implemented using configurable interconnect and memory resources on the configurable processor 7846. Also, the multi-cycle execution clusters are coupled to the data flow logic 7908 by control paths 7912 implemented using configurable interconnect and memory resources for example on the configurable processor 7846, which provide control signals indicating available execution clusters, readiness to provide input units for execution of a run of the neural network-based template generator 1512 and/or the neural network-based base caller 1514 to the available execution clusters, readiness to provide trained parameters for the neural network-based template generator 1512 and/or the neural network-based base caller 1514, readiness to provide output patches of base call classification data, and other control data used for execution of the neural network-based template generator 1512 and/or the neural network-based base caller 1514.

The configurable processor 7846 is configured to execute runs of the neural network-based template generator 1512 and/or the neural network-based base caller 1514 using trained parameters to produce classification data for the sensing cycles of the base calling operation. A run of the neural network-based template generator 1512 and/or the neural network-based base caller 1514 is executed to produce classification data for a subject sensing cycle of the base calling operation. A run of the neural network-based template generator 1512 and/or the neural network-based base caller 1514 operates on a sequence including a number N of arrays of tile data from respective sensing cycles of N sensing cycles, where the N sensing cycles provide sensor data for different base call operations for one base position per operation in time sequence in the examples described herein. Optionally, some of the N sensing cycles can be out of sequence if needed according to a particular neural network model being executed. The number N can be any number greater than one. In some examples described herein, sensing cycles of the N sensing cycles represent a set of sensing cycles for at least one sensing cycle preceding the subject sensing cycle and at least one sensing cycle following the subject cycle in time sequence. Examples are described herein in which the number N is an integer equal to or greater than five.

The data flow logic 7908 is configured to move tile data and at least some trained parameters of the model parameters from the memory 7848A to the configurable processor 7846 for runs of the neural network-based template generator 1512 and/or the neural network-based base caller 1514, using input units for a given run including tile data for spatially aligned patches of the N arrays. The input units can be moved by direct memory access operations in one DMA operation, or in smaller units moved during available time slots in coordination with the execution of the neural network deployed.

Tile data for a sensing cycle as described herein can comprise an array of sensor data having one or more features. For example, the sensor data can comprise two images which are analyzed to identify one of four bases at a base position in a genetic sequence of DNA, RNA, or other genetic material. The tile data can also include metadata about the images and the sensors. For example, in embodiments of the base calling operation, the tile data can comprise information about alignment of the images with the clusters such as distance from center information indicating the distance of each pixel in the array of sensor data from the center of a cluster of genetic material on the tile.

During execution of the neural network-based template generator 1512 and/or the neural network-based base caller 1514 as described below, tile data can also include data produced during execution of the neural network-based template generator 1512 and/or the neural network-based base caller 1514, referred to as intermediate data, which can be reused rather than recomputed during a run of the neural network-based template generator 1512 and/or the neural network-based base caller 1514. For example, during execution of the neural network-based template generator 1512 and/or the neural network-based base caller 1514, the data flow logic 7908 can write intermediate data to the memory 7848A in place of the sensor data for a given patch of an array of tile data. Embodiments like this are described in more detail below.

As illustrated, a system is described for analysis of base call sensor output, comprising memory (e.g., 7848A) accessible by the runtime program storing tile data including sensor data for a tile from sensing cycles of a base calling operation. Also, the system includes a neural network processor, such as configurable processor 7846 having access to the memory. The neural network processor is configured to execute runs of a neural network using trained parameters to produce classification data for sensing cycles. As described herein, a run of the neural network is operating on a sequence of N arrays of tile data from respective sensing cycles of N sensing cycles, including a subject cycle, to produce the classification data for the subject cycle. The data flow logic 908 is provided to move tile data and the trained parameters from the memory to the neural network processor for runs of the neural network using input units including data for spatially aligned patches of the N arrays from respective sensing cycles of N sensing cycles.

Also, a system is described in which the neural network processor has access to the memory, and includes a plurality of execution clusters, the execution clusters in the plurality of execution clusters configured to execute a neural network. The data flow logic 7908 has access to the memory and to execution clusters in the plurality of execution clusters, to provide input units of tile data to available execution clusters in the plurality of execution clusters, the input units including a number N of spatially aligned patches of arrays of tile data from respective sensing cycles, including a subject sensing cycle, and to cause the execution clusters to apply the N spatially aligned patches to the neural network to produce output patches of classification data for the spatially aligned patch of the subject sensing cycle, where N is greater than 1.

Figure 80:
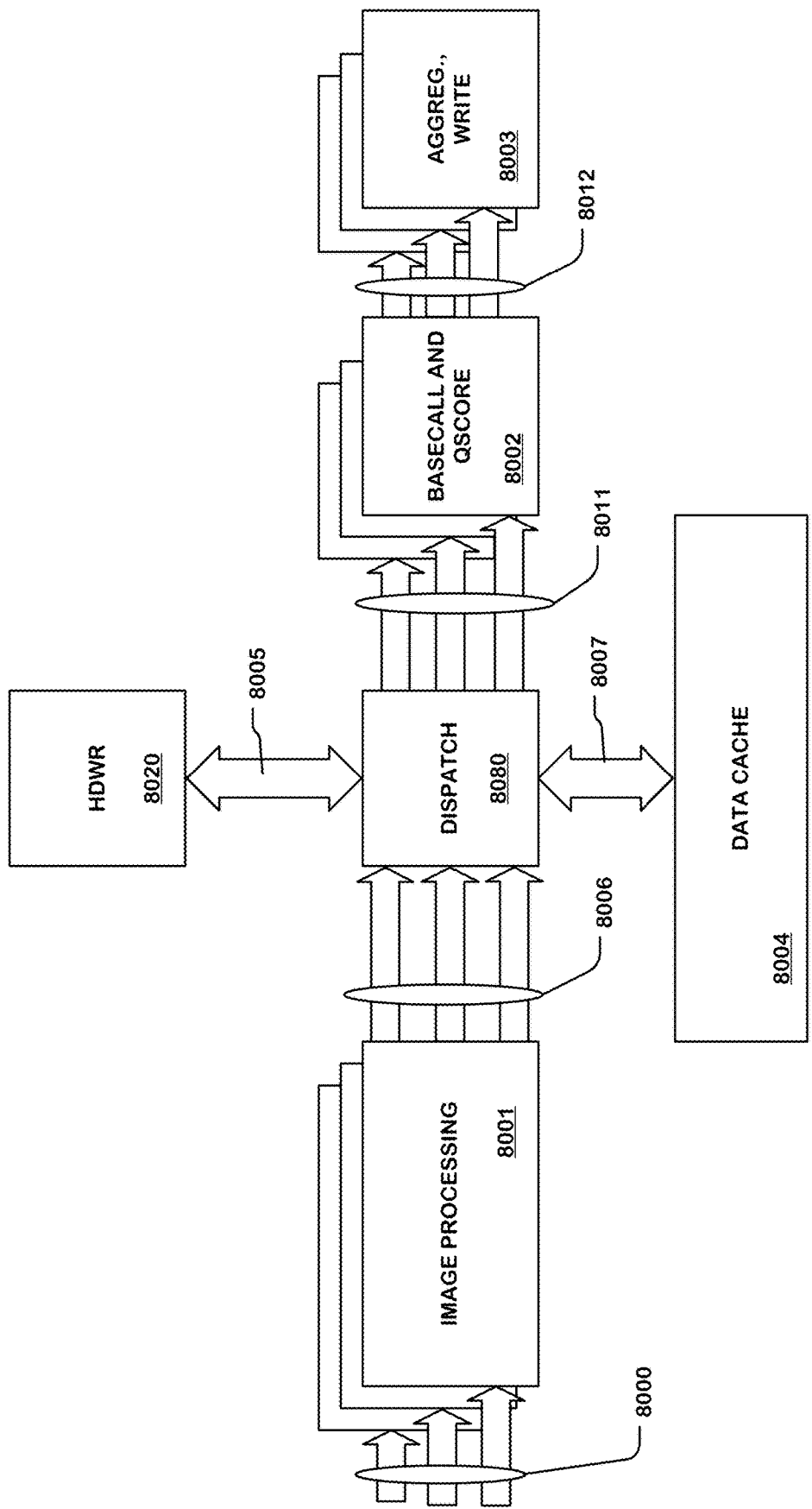
FIG. 80 is a simplified diagram showing aspects of the base calling operation, including functions of a runtime program executed by a host processor.

FIG. 80 is a simplified diagram showing aspects of the base calling operation, including functions of a runtime program executed by a host processor. In this diagram, the output of image sensors from a flow cell are provided on lines 8000 to image processing threads 8001, which can perform processes on images such as alignment and arrangement in an array of sensor data for the individual tiles and resampling of images, and can be used by processes which calculate a tile cluster mask for each tile in the flow cell, which identifies pixels in the array of sensor data that correspond to clusters of genetic material on the corresponding tile of the flow cell. The outputs of the image processing threads 8001 are provided on lines 8006 to a dispatch logic 8010 in the CPU which routes the arrays of tile data to a data cache 8004 (e.g., SSD storage) on a high-speed bus 8007, or on high-speed bus 8005 to the neural network processor hardware 8020, such as the configurable processor 7846 of FIG. 79, according to the state of the base calling operation. The processed and transformed images can be stored on the data cache 8004 for sensing cycles that were previously used. The hardware 8020 returns classification data output by the neural network to the dispatch logic 8080, which passes the information to the data cache 8004, or on lines 8011 to threads 8002 that perform base call and quality score computations using the classification data, and can arrange the data in standard formats for base call reads. The outputs of the threads 8002 that perform base calling and quality score computations are provided on lines 8012 to threads 8003 that aggregate the base call reads, perform other operations such as data compression, and write the resulting base call outputs to specified destinations for utilization by the customers.

In some embodiments, the host can include threads (not shown) that perform final processing of the output of the hardware 8020 in support of the neural network. For example, the hardware 8020 can provide outputs of classification data from a final layer of the multi-cluster neural network. The host processor can execute an output activation function, such as a softmax function, over the classification data to configure the data for use by the base call and quality score threads 8002. Also, the host processor can execute input operations (not shown), such as batch normalization of the tile data prior to input to the hardware 8020.

Figure 81:
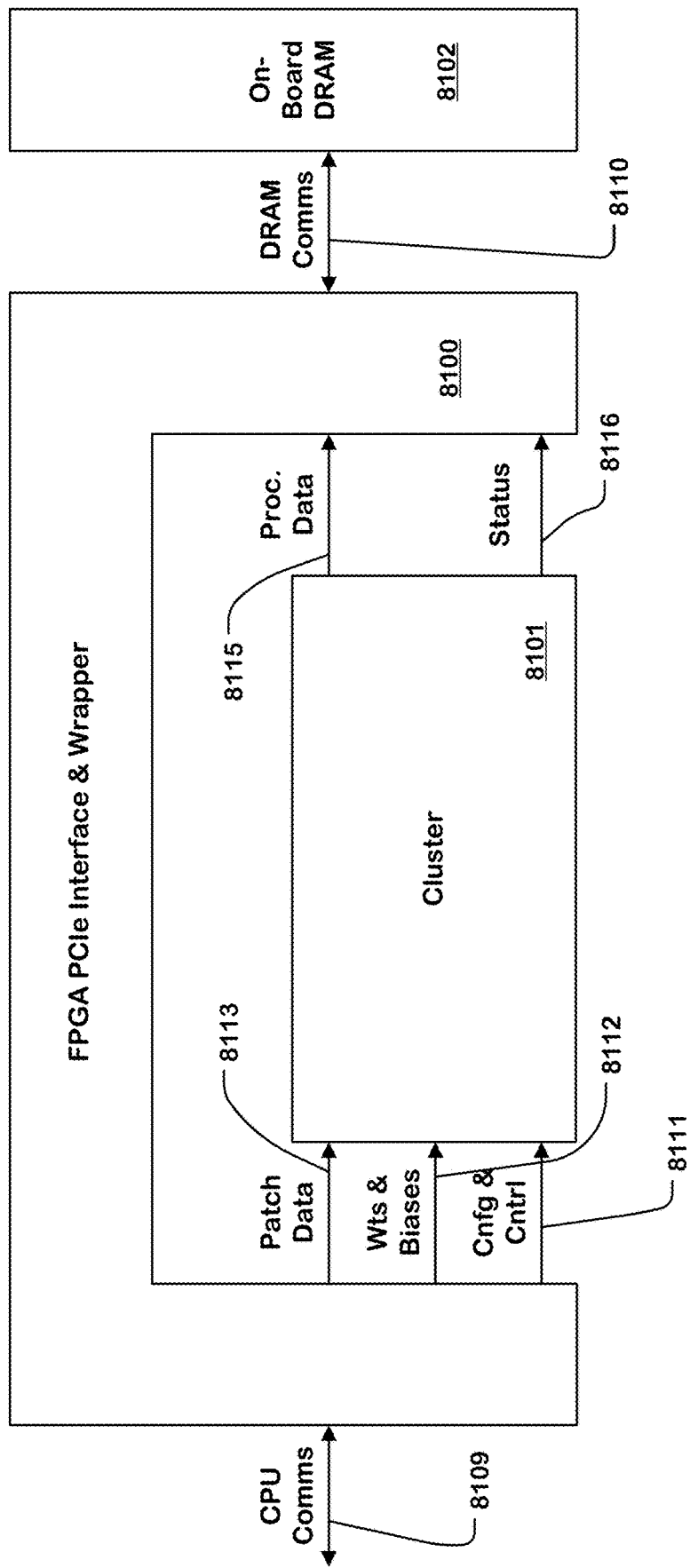
FIG. 81 is a simplified diagram of a configuration of a configurable processor such as the one depicted in FIG. 79.

FIG. 81 is a simplified diagram of a configuration of a configurable processor 7846 such as that of FIG. 79. In FIG. 81, the configurable processor 7846 comprises an FPGA with a plurality of high speed PCIe interfaces. The FPGA is configured with a wrapper 8100 which comprises the data flow logic 7908 described with reference to FIG. 79. The wrapper 8100 manages the interface and coordination with a runtime program in the CPU across the CPU communication link 8109 and manages communication with the on-board DRAM 8102 (e.g., memory 7848A) via DRAM communication link 8110. The data flow logic 7908 in the wrapper 8100 provides patch data retrieved by traversing the arrays of tile data on the on-board DRAM 8102 for the number N cycles to a cluster 8101, and retrieves process data 8115 from the cluster 8101 for delivery back to the on-board DRAM 8102. The wrapper 8100 also manages transfer of data between the on-board DRAM 8102 and host memory, for both the input arrays of tile data, and for the output patches of classification data. The wrapper transfers patch data on line 8113 to the allocated cluster 8101. The wrapper provides trained parameters, such as weights and biases on line 8112 to the cluster 8101 retrieved from the on-board DRAM 8102. The wrapper provides configuration and control data on line 8111 to the cluster 8101 provided from, or generated in response to, the runtime program on the host via the CPU communication link 8109. The cluster can also provide status signals on line 8116 to the wrapper 8100, which are used in cooperation with control signals from the host to manage traversal of the arrays of tile data to provide spatially aligned patch data, and to execute the multi-cycle neural network over the patch data using the resources of the cluster 8101.

As mentioned above, there can be multiple clusters on a single configurable processor managed by the wrapper 8100 configured for executing on corresponding ones of multiple patches of the tile data. Each cluster can be configured to provide classification data for base calls in a subject sensing cycle using the tile data of multiple sensing cycles described herein.

In examples of the system, model data, including kernel data like filter weights and biases can be sent from the host CPU to the configurable processor, so that the model can be updated as a function of cycle number. A base calling operation can comprise, for a representative example, on the order of hundreds of sensing cycles. Base calling operation can include paired end reads in some embodiments. For example, the model trained parameters may be updated once every 20 cycles (or other number of cycles), or according to update patterns implemented for particular systems and neural network models. In some embodiments including paired end reads in which a sequence for a given string in a genetic cluster on a tile includes a first part extending from a first end down (or up) the string, and a second part extending from a second end up (or down) the string, the trained parameters can be updated on the transition from the first part to the second part.

In some examples, image data for multiple cycles of sensing data for a tile can be sent from the CPU to the wrapper 8100. The wrapper 8100 can optionally do some pre-processing and transformation of the sensing data and write the information to the on-board DRAM 8102. The input tile data for each sensing cycle can include arrays of sensor data including on the order of 4000×3000 pixels per sensing cycle per tile or more, with two features representing colors of two images of the tile, and one or two bytes per feature per pixel. For an embodiment in which the number N is three sensing cycles to be used in each run of the multi-cycle neural network, the array of tile data for each run of the multi-cycle neural network can consume on the order of hundreds of megabytes per tile. In some embodiments of the system, the tile data also includes an array of DFC data, stored once per tile, or other type of metadata about the sensor data and the tiles.

In operation, when a multi-cycle cluster is available, the wrapper allocates a patch to the cluster. The wrapper fetches a next patch of tile data in the traversal of the tile and sends it to the allocated cluster along with appropriate control and configuration information. The cluster can be configured with enough memory on the configurable processor to hold a patch of data including patches from multiple cycles in some systems, that is being worked on in place, and a patch of data that is to be worked on when the current patch of processing is finished using a ping-pong buffer technique or raster scanning technique in various embodiments.

When an allocated cluster completes its run of the neural network for the current patch and produces an output patch, it will signal the wrapper. The wrapper will read the output patch from the allocated cluster, or alternatively the allocated cluster will push the data out to the wrapper. Then the wrapper will assemble output patches for the processed tile in the DRAM 8102. When the processing of the entire tile has been completed, and the output patches of data transferred to the DRAM, the wrapper sends the processed output array for the tile back to the host/CPU in a specified format. In some embodiments, the on-board DRAM 8102 is managed by memory management logic in the wrapper 8100. The runtime program can control the sequencing operations to complete analysis of all the arrays of tile data for all the cycles in the run in a continuous flow to provide real time analysis.

Technical Improvements and Terminology

Base calling includes incorporation or attachment of a fluorescently-labeled tag with an analyte. The analyte can be a nucleotide or an oligonucleotide, and the tag can be for a particular nucleotide type (A, C, T, or G). Excitation light is directed toward the analyte having the tag, and the tag emits a detectable fluorescent signal or intensity emission. The intensity emission is indicative of photons emitted by the excited tag that is chemically attached to the analyte.

Throughout this application, including the claims, when phrases such as or similar to "images, image data, or image regions depicting intensity emissions of analytes and their surrounding background" are used, they refer to the intensity emissions of the tags attached to the analytes. A person skilled in the art will appreciate that the intensity emissions of the attached tags are representative of or equivalent to the intensity emissions of the analytes to which the tags are attached, and are therefore used interchangeably. Similarly, properties of the analytes refer to properties of the tags attached to the analytes or of the intensity emissions from the attached tags. For example, a center of an analyte refers to the center of the intensity emissions emitted by a tag attached to the analyte. In another example, the surrounding background of an analyte refers to the surrounding background of the intensity emissions emitted by a tag attached to the analyte.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The technology disclosed uses neural networks to improve the quality and quantity of nucleic acid sequence information that can be obtained from a nucleic acid sample such as a nucleic acid template or its complement, for instance, a DNA or RNA polynucleotide or other nucleic acid sample. Accordingly, certain implementations of the technology disclosed provide higher throughput polynucleotide sequencing, for instance, higher rates of collection of DNA or RNA sequence data, greater efficiency in sequence data collection, and/or lower costs of obtaining such sequence data, relative to previously available methodologies.

The technology disclosed uses neural networks to identify the center of a solid-phase nucleic acid cluster and to analyze optical signals that are generated during sequencing of such clusters, to discriminate unambiguously between adjacent, abutting or overlapping clusters in order to assign a sequencing signal to a single, discrete source cluster. These and related implementations thus permit retrieval of meaningful information, such as sequence data, from regions of high-density cluster arrays where useful information could not previously be obtained from such regions due to confounding effects of overlapping or very closely spaced adjacent clusters, including the effects of overlapping signals (e.g., as used in nucleic acid sequencing) emanating therefrom.

As described in greater detail below, in certain implementations there is provided a composition that comprises a solid support having immobilized thereto one or a plurality of nucleic acid clusters as provided herein. Each cluster comprises a plurality of immobilized nucleic acids of the same sequence and has an identifiable center having a detectable center label as provided herein, by which the identifiable center is distinguishable from immobilized nucleic acids in a surrounding region in the cluster. Also described herein are methods for making and using such clusters that have identifiable centers.

The presently disclosed implementations will find uses in numerous situations where advantages are obtained from the ability to identify, determine, annotate, record or otherwise assign the position of a substantially central location within a cluster, such as high-throughput nucleic acid sequencing, development of image analysis algorithms for assigning optical or other signals to discrete source clusters, and other applications where recognition of the center of an immobilized nucleic acid cluster is desirable and beneficial.

In certain implementations, the present invention contemplates methods that relate to high-throughput nucleic acid analysis such as nucleic acid sequence determination (e.g., "sequencing"). Exemplary high-throughput nucleic acid analyses include without limitation de novo sequencing, re-sequencing, whole genome sequencing, gene expression analysis, gene expression monitoring, epigenetic analysis, genome methylation analysis, allele specific primer extension (APSE), genetic diversity profiling, whole genome polymorphism discovery and analysis, single nucleotide polymorphism analysis, hybridization based sequence determination methods, and the like. One skilled in the art will appreciate that a variety of different nucleic acids can be analyzed using the methods and compositions of the present invention.

Although the implementations of the present invention are described in relation to nucleic acid sequencing, they are applicable in any field where image data acquired at different time points, spatial locations or other temporal or physical perspectives is analyzed. For example, the methods and systems described herein are useful in the fields of molecular and cell biology where image data from microarrays, biological specimens, cells, organisms and the like is acquired and at different time points or perspectives and analyzed. Images can be obtained using any number of techniques known in the art including, but not limited to, fluorescence microscopy, light microscopy, confocal microscopy, optical imaging, magnetic resonance imaging, tomography scanning or the like. As another example, the methods and systems described herein can be applied where image data obtained by surveillance, aerial or satellite imaging technologies and the like is acquired at different time points or perspectives and analyzed. The methods and systems are particularly useful for analyzing images obtained for a field of view in which the analytes being viewed remain in the same locations relative to each other in the field of view. The analytes may however have characteristics that differ in separate images, for example, the analytes may appear different in separate images of the field of view. For example, the analytes may appear different with regard to the color of a given analyte detected in different images, a change in the intensity of signal detected for a given analyte in different images, or even the appearance of a signal for a given analyte in one image and disappearance of the signal for the analyte in another image.

Examples described herein may be used in various biological or chemical processes and systems for academic or commercial analysis. More specifically, examples described herein may be used in various processes and systems where it is desired to detect an event, property, quality, or characteristic that is indicative of a designated reaction. For example, examples described herein include light detection devices, biosensors, and their components, as well as bioassay systems that operate with biosensors. In some examples, the devices, biosensors and systems may include a flow cell and one or more light sensors that are coupled together (removably or fixedly) in a substantially unitary structure.

The devices, biosensors and bioassay systems may be configured to perform a plurality of designated reactions that may be detected individually or collectively. The devices, biosensors and bioassay systems may be configured to perform numerous cycles in which the plurality of designated reactions occurs in parallel. For example, the devices, biosensors and bioassay systems may be used to sequence a dense array of DNA features through iterative cycles of enzymatic manipulation and light or image detection/acquisition. As such, the devices, biosensors and bioassay systems (e.g., via one or more cartridges) may include one or more microfluidic channel that delivers reagents or other reaction components in a reaction solution to a reaction site of the devices, biosensors and bioassay systems. In some examples, the reaction solution may be substantially acidic, such as comprising a pH of less than or equal to about 5, or less than or equal to about 4, or less than or equal to about 3. In some other examples, the reaction solution may be substantially alkaline/basic, such as comprising a pH of greater than or equal to about 8, or greater than or equal to about 9, or greater than or equal to about 10. As used herein, the term "acidity" and grammatical variants thereof refer to a pH value of less than about 7, and the terms "basicity," "alkalinity" and grammatical variants thereof refer to a pH value of greater than about 7.

In some examples, the reaction sites are provided or spaced apart in a predetermined manner, such as in a uniform or repeating pattern. In some other examples, the reaction sites are randomly distributed. Each of the reaction sites may be associated with one or more light guides and one or more light sensors that detect light from the associated reaction site. In some examples, the reaction sites are located in reaction recesses or chambers, which may at least partially compartmentalize the designated reactions therein.

As used herein, a "designated reaction" includes a change in at least one of a chemical, electrical, physical, or optical property (or quality) of a chemical or biological substance of interest, such as an analyte-of-interest. In particular examples, a designated reaction is a positive binding event, such as incorporation of a fluorescently labeled biomolecule with an analyte-of-interest, for example. More generally, a designated reaction may be a chemical transformation, chemical change, or chemical interaction. A designated reaction may also be a change in electrical properties. In particular examples, a designated reaction includes the incorporation of a fluorescently-labeled molecule with an analyte. The analyte may be an oligonucleotide and the fluorescently-labeled molecule may be a nucleotide. A designated reaction may be detected when an excitation light is directed toward the oligonucleotide having the labeled nucleotide, and the fluorophore emits a detectable fluorescent signal. In alternative examples, the detected fluorescence is a result of chemiluminescence or bioluminescence. A designated reaction may also increase fluorescence (or Förster) resonance energy transfer (FRET), for example, by bringing a donor fluorophore in proximity to an acceptor fluorophore, decrease FRET by separating donor and acceptor fluorophores, increase fluorescence by separating a quencher from a fluorophore, or decrease fluorescence by co-locating a quencher and fluorophore.

As used herein, a "reaction solution," "reaction component" or "reactant" includes any substance that may be used to obtain at least one designated reaction. For example, potential reaction components include reagents, enzymes, samples, other biomolecules, and buffer solutions, for example. The reaction components may be delivered to a reaction site in a solution and/or immobilized at a reaction site. The reaction components may interact directly or indirectly with another substance, such as an analyte-of-interest immobilized at a reaction site. As noted above, the reaction solution may be substantially acidic (i.e., include a relatively high acidity) (e.g., comprising a pH of less than or equal to about 5, a pH less than or equal to about 4, or a pH less than or equal to about 3) or substantially alkaline/basic (i.e., include a relatively high alkalinity/basicity) (e.g., comprising a pH of greater than or equal to about 8, a pH of greater than or equal to about 9, or a pH of greater than or equal to about 10).

As used herein, the term "reaction site" is a localized region where at least one designated reaction may occur. A reaction site may include support surfaces of a reaction structure or substrate where a substance may be immobilized thereon. For example, a reaction site may include a surface of a reaction structure (which may be positioned in a channel of a flow cell) that has a reaction component thereon, such as a colony of nucleic acids thereon. In some such examples, the nucleic acids in the colony have the same sequence, being for example, clonal copies of a single stranded or double stranded template. However, in some examples a reaction site may contain only a single nucleic acid molecule, for example, in a single stranded or double stranded form.

A plurality of reaction sites may be randomly distributed along the reaction structure or arranged in a predetermined manner (e.g., side-by-side in a matrix, such as in microarrays). A reaction site can also include a reaction chamber or recess that at least partially defines a spatial region or volume configured to compartmentalize the designated reaction. As used herein, the term "reaction chamber" or "reaction recess" includes a defined spatial region of the support structure (which is often in fluid communication with a flow channel) A reaction recess may be at least partially separated from the surrounding environment other or spatial regions. For example, a plurality of reaction recesses may be separated from each other by shared walls, such as a detection surface. As a more specific example, the reaction recesses may be nanowells comprising an indent, pit, well, groove, cavity or depression defined by interior surfaces of a detection surface and have an opening or aperture (i.e., be open-sided) so that the nanowells can be in fluid communication with a flow channel.

In some examples, the reaction recesses of the reaction structure are sized and shaped relative to solids (including semi-solids) so that the solids may be inserted, fully or partially, therein. For example, the reaction recesses may be sized and shaped to accommodate a capture bead. The capture bead may have clonally amplified DNA or other substances thereon. Alternatively, the reaction recesses may be sized and shaped to receive an approximate number of beads or solid substrates. As another example, the reaction recesses may be filled with a porous gel or substance that is configured to control diffusion or filter fluids or solutions that may flow into the reaction recesses.

In some examples, light sensors (e.g., photodiodes) are associated with corresponding reaction sites. A light sensor that is associated with a reaction site is configured to detect light emissions from the associated reaction site via at least one light guide when a designated reaction has occurred at the associated reaction site. In some cases, a plurality of light sensors (e.g. several pixels of a light detection or camera device) may be associated with a single reaction site. In other cases, a single light sensor (e.g. a single pixel) may be associated with a single reaction site or with a group of reaction sites. The light sensor, the reaction site, and other features of the biosensor may be configured so that at least some of the light is directly detected by the light sensor without being reflected.

As used herein, a "biological or chemical substance" includes biomolecules, samples-of-interest, analytes-of-interest, and other chemical compound(s). A biological or chemical substance may be used to detect, identify, or analyze other chemical compound(s), or function as intermediaries to study or analyze other chemical compound(s). In particular examples, the biological or chemical substances include a biomolecule. As used herein, a "biomolecule" includes at least one of a biopolymer, nucleoside, nucleic acid, polynucleotide, oligonucleotide, protein, enzyme, polypeptide, antibody, antigen, ligand, receptor, polysaccharide, carbohydrate, polyphosphate, cell, tissue, organism, or fragment thereof or any other biologically active chemical compound(s) such as analogs or mimetics of the aforementioned species. In a further example, a biological or chemical substance or a biomolecule includes an enzyme or reagent used in a coupled reaction to detect the product of another reaction such as an enzyme or reagent, such as an enzyme or reagent used to detect pyrophosphate in a pyrosequencing reaction. Enzymes and reagents useful for pyrophosphate detection are described, for example, in U.S. Patent Publication No. 2005/0244870 A1, which is incorporated by reference in its entirety.

Biomolecules, samples, and biological or chemical substances may be naturally occurring or synthetic and may be suspended in a solution or mixture within a reaction recess or region. Biomolecules, samples, and biological or chemical substances may also be bound to a solid phase or gel material. Biomolecules, samples, and biological or chemical substances may also include a pharmaceutical composition. In some cases, biomolecules, samples, and biological or chemical substances of interest may be referred to as targets, probes, or analytes.

As used herein, a "biosensor" includes a device that includes a reaction structure with a plurality of reaction sites that is configured to detect designated reactions that occur at or proximate to the reaction sites. A biosensor may include a solid-state light detection or "imaging" device (e.g., CCD or CMOS light detection device) and, optionally, a flow cell mounted thereto. The flow cell may include at least one flow channel that is in fluid communication with the reaction sites. As one specific example, the biosensor is configured to fluidically and electrically couple to a bioassay system. The bioassay system may deliver a reaction solution to the reaction sites according to a predetermined protocol (e.g., sequencing-by-synthesis) and perform a plurality of imaging events. For example, the bioassay system may direct reaction solutions to flow along the reaction sites. At least one of the reaction solutions may include four types of nucleotides having the same or different fluorescent labels. The nucleotides may bind to the reaction sites, such as to corresponding oligonucleotides at the reaction sites. The bioassay system may then illuminate the reaction sites using an excitation light source (e.g., solid-state light sources, such as light-emitting diodes (LEDs)). The excitation light may have a predetermined wavelength or wavelengths, including a range of wavelengths. The fluorescent labels excited by the incident excitation light may provide emission signals (e.g., light of a wavelength or wavelengths that differ from the excitation light and, potentially, each other) that may be detected by the light sensors.

As used herein, the term "immobilized," when used with respect to a biomolecule or biological or chemical substance, includes substantially attaching the biomolecule or biological or chemical substance at a molecular level to a surface, such as to a detection surface of a light detection device or reaction structure. For example, a biomolecule or biological or chemical substance may be immobilized to a surface of the reaction structure using adsorption techniques including non-covalent interactions (e.g., electrostatic forces, van der Waals, and dehydration of hydrophobic interfaces) and covalent binding techniques where functional groups or linkers facilitate attaching the biomolecules to the surface Immobilizing biomolecules or biological or chemical substances to the surface may be based upon the properties of the surface, the liquid medium carrying the biomolecule or biological or chemical substance, and the properties of the biomolecules or biological or chemical substances themselves. In some cases, the surface may be functionalized (e.g., chemically or physically modified) to facilitate immobilizing the biomolecules (or biological or chemical substances) to the surface.

In some examples, nucleic acids can be immobilized to the reaction structure, such as to surfaces of reaction recesses thereof. In particular examples, the devices, biosensors, bioassay systems and methods described herein may include the use of natural nucleotides and also enzymes that are configured to interact with the natural nucleotides. Natural nucleotides include, for example, ribonucleotides or deoxyribonucleotides. Natural nucleotides can be in the mono-, di-, or tri-phosphate form and can have a base selected from adenine (A), Thymine (T), uracil (U), guanine (G) or cytosine (C). It will be understood, however, that non-natural nucleotides, modified nucleotides or analogs of the aforementioned nucleotides can be used.

As noted above, a biomolecule or biological or chemical substance may be immobilized at a reaction site in a reaction recess of a reaction structure. Such a biomolecule or biological substance may be physically held or immobilized within the reaction recesses through an interference fit, adhesion, covalent bond, or entrapment. Examples of items or solids that may be disposed within the reaction recesses include polymer beads, pellets, agarose gel, powders, quantum dots, or other solids that may be compressed and/or held within the reaction chamber. In certain implementations, the reaction recesses may be coated or filled with a hydrogel layer capable of covalently binding DNA oligonucleotides. In particular examples, a nucleic acid superstructure, such as a DNA ball, can be disposed in or at a reaction recess, for example, by attachment to an interior surface of the reaction recess or by residence in a liquid within the reaction recess. A DNA ball or other nucleic acid superstructure can be performed and then disposed in or at a reaction recess. Alternatively, a DNA ball can be synthesized in situ at a reaction recess. A substance that is immobilized in a reaction recess can be in a solid, liquid, or gaseous state.

As used herein, the term "analyte" is intended to mean a point or area in a pattern that can be distinguished from other points or areas according to relative location. An individual analyte can include one or more molecules of a particular type. For example, an analyte can include a single target nucleic acid molecule having a particular sequence or an analyte can include several nucleic acid molecules having the same sequence (and/or complementary sequence, thereof). Different molecules that are at different analytes of a pattern can be differentiated from each other according to the locations of the analytes in the pattern. Example analytes include without limitation, wells in a substrate, beads (or other particles) in or on a substrate, projections from a substrate, ridges on a substrate, pads of gel material on a substrate, or channels in a substrate.

Any of a variety of target analytes that are to be detected, characterized, or identified can be used in an apparatus, system or method set forth herein. Exemplary analytes include, but are not limited to, nucleic acids (e.g., DNA, RNA or analogs thereof), proteins, polysaccharides, cells, antibodies, epitopes, receptors, ligands, enzymes (e.g. kinases, phosphatases or polymerases), small molecule drug candidates, cells, viruses, organisms, or the like.

The terms "analyte", "nucleic acid", "nucleic acid molecule", and "polynucleotide" are used interchangeably herein. In various implementations, nucleic acids may be used as templates as provided herein (e.g., a nucleic acid template, or a nucleic acid complement that is complementary to a nucleic acid nucleic acid template) for particular types of nucleic acid analysis, including but not limited to nucleic acid amplification, nucleic acid expression analysis, and/or nucleic acid sequence determination or suitable combinations thereof. Nucleic acids in certain implementations include, for instance, linear polymers of deoxyribonucleotides in 3'-5' phosphodiester or other linkages, such as deoxyribonucleic acids (DNA), for example, single- and double-stranded DNA, genomic DNA, copy DNA or complementary DNA (cDNA), recombinant DNA, or any form of synthetic or modified DNA. In other implementations, nucleic acids include for instance, linear polymers of ribonucleotides in 3'-5' phosphodiester or other linkages such as ribonucleic acids (RNA), for example, single- and double-stranded RNA, messenger (mRNA), copy RNA or complementary RNA (cRNA), alternatively spliced mRNA, ribosomal RNA, small nucleolar RNA (snoRNA), microRNAs (miRNA), small interfering RNAs (sRNA), piwi RNAs (piRNA), or any form of synthetic or modified RNA. Nucleic acids used in the compositions and methods of the present invention may vary in length and may be intact or full-length molecules or fragments or smaller parts of larger nucleic acid molecules. In particular implementations, a nucleic acid may have one or more detectable labels, as described elsewhere herein.

The terms "analyte", "cluster", "nucleic acid cluster", "nucleic acid colony", and "DNA cluster" are used interchangeably and refer to a plurality of copies of a nucleic acid template and/or complements thereof attached to a solid support. Typically and in certain preferred implementations, the nucleic acid cluster comprises a plurality of copies of template nucleic acid and/or complements thereof, attached via their 5' termini to the solid support. The copies of nucleic acid strands making up the nucleic acid clusters may be in a single or double stranded form. Copies of a nucleic acid template that are present in a cluster can have nucleotides at corresponding positions that differ from each other, for example, due to presence of a label moiety. The corresponding positions can also contain analog structures having different chemical structure but similar Watson-Crick base-pairing properties, such as is the case for uracil and thymine.

Colonies of nucleic acids can also be referred to as "nucleic acid clusters". Nucleic acid colonies can optionally be created by cluster amplification or bridge amplification techniques as set forth in further detail elsewhere herein. Multiple repeats of a target sequence can be present in a single nucleic acid molecule, such as a concatamer created using a rolling circle amplification procedure.

The nucleic acid clusters of the invention can have different shapes, sizes and densities depending on the conditions used. For example, clusters can have a shape that is substantially round, multi-sided, donut-shaped or ring-shaped. The diameter of a nucleic acid cluster can be designed to be from about 0.2 μm to about 6 μm, about 0.3 μm to about 4 μm, about 0.4 μm to about 3 μm, about 0.5 μm to about 2 μm, about 0.75 μm to about 1.5 μm, or any intervening diameter. In a particular implementation, the diameter of a nucleic acid cluster is about 0.5 μm, about 1 μm, about 1.5 μm, about 2 μm, about 2.5 μm, about 3 μm, about 4 μm, about 5 μm, or about 6 μm. The diameter of a nucleic acid cluster may be influenced by a number of parameters, including, but not limited to the number of amplification cycles performed in producing the cluster, the length of the nucleic acid template or the density of primers attached to the surface upon which clusters are formed. The density of nucleic acid clusters can be designed to typically be in the range of $0.1/mm^2$, $1/mm^2$, $10/mm^2$, $100/mm^2$, $1,000/mm^2$, $10,000/mm^2$ to $100,000/mm^2$. The present invention further contemplates, in part, higher density nucleic acid clusters, for example, $100,000/mm^2$ to $1,000,000/mm^2$ and $1,000,000/mm^2$ to $10,000,000/mm^2$.

As used herein, an "analyte" is an area of interest within a specimen or field of view. When used in connection with microarray devices or other molecular analytical devices, an analyte refers to the area occupied by similar or identical molecules. For example, an analyte can be an amplified oligonucleotide or any other group of a polynucleotide or polypeptide with a same or similar sequence. In other implementations, an analyte can be any element or group of elements that occupy a physical area on a specimen. For example, an analyte could be a parcel of land, a body of water or the like. When an analyte is imaged, each analyte will have some area. Thus, in many implementations, an analyte is not merely one pixel.

The distances between analytes can be described in any number of ways. In some implementations, the distances between analytes can be described from the center of one analyte to the center of another analyte. In other implementations, the distances can be described from the edge of one analyte to the edge of another analyte, or between the outer-most identifiable points of each analyte. The edge of an analyte can be described as the theoretical or actual physical boundary on a chip, or some point inside the boundary of the analyte. In other implementations, the distances can be described in relation to a fixed point on the specimen or in the image of the specimen.

Generally several implementations will be described herein with respect to a method of analysis. It will be understood that systems are also provided for carrying out the methods in an automated or semi-automated way. Accordingly, this disclosure provides neural network-based template generation and base calling systems, wherein the systems can include a processor; a storage device; and a program for image analysis, the program including instructions for carrying out one or more of the methods set forth herein. Accordingly, the methods set forth herein can be carried out on a computer, for example, having components set forth herein or otherwise known in the art.

The methods and systems set forth herein are useful for analyzing any of a variety of objects. Particularly useful objects are solid supports or solid-phase surfaces with attached analytes. The methods and systems set forth herein provide advantages when used with objects having a repeating pattern of analytes in an xy plane. An example is a microarray having an attached collection of cells, viruses, nucleic acids, proteins, antibodies, carbohydrates, small molecules (such as drug candidates), biologically active molecules or other analytes of interest.

An increasing number of applications have been developed for arrays with analytes having biological molecules such as nucleic acids and polypeptides. Such microarrays typically include deoxyribonucleic acid (DNA) or ribonucleic acid (RNA) probes. These are specific for nucleotide sequences present in humans and other organisms. In certain applications, for example, individual DNA or RNA probes can be attached at individual analytes of an array. A test sample, such as from a known person or organism, can be exposed to the array, such that target nucleic acids (e.g., gene fragments, mRNA, or amplicons thereof) hybridize to complementary probes at respective analytes in the array. The probes can be labeled in a target specific process (e.g., due to labels present on the target nucleic acids or due to enzymatic labeling of the probes or targets that are present in hybridized form at the analytes). The array can then be examined by scanning specific frequencies of light over the analytes to identify which target nucleic acids are present in the sample.

Biological microarrays may be used for genetic sequencing and similar applications. In general, genetic sequencing comprises determining the order of nucleotides in a length of target nucleic acid, such as a fragment of DNA or RNA. Relatively short sequences are typically sequenced at each analyte, and the resulting sequence information may be used in various bioinformatics methods to logically fit the sequence fragments together so as to reliably determine the sequence of much more extensive lengths of genetic material from which the fragments were derived. Automated, computer-based algorithms for characteristic fragments have been developed, and have been used more recently in genome mapping, identification of genes and their function, and so forth. Microarrays are particularly useful for characterizing genomic content because a large number of variants are present and this supplants the alternative of performing many experiments on individual probes and targets. The microarray is an ideal format for performing such investigations in a practical manner.

Any of a variety of analyte arrays (also referred to as "microarrays") known in the art can be used in a method or system set forth herein. A typical array contains analytes, each having an individual probe or a population of probes. In the latter case, the population of probes at each analyte is typically homogenous having a single species of probe. For example, in the case of a nucleic acid array, each analyte can have multiple nucleic acid molecules each having a common sequence. However, in some implementations the populations at each analyte of an array can be heterogeneous. Similarly, protein arrays can have analytes with a single protein or a population of proteins typically, but not always, having the same amino acid sequence. The probes can be attached to the surface of an array for example, via covalent linkage of the probes to the surface or via non-covalent interaction(s) of the probes with the surface. In some implementations, probes, such as nucleic acid molecules, can be attached to a surface via a gel layer as described, for example, in U.S. patent application Ser. No. 13/784,368 and US Pat. App. Pub. No. 2011/0059865 A1, each of which is incorporated herein by reference.

Example arrays include, without limitation, a BeadChip Array available from Illumina, Inc. (San Diego, Calif.) or others such as those where probes are attached to beads that are present on a surface (e.g. beads in wells on a surface) such as those described in U.S. Pat. Nos. 6,266,459; 6,355,431; 6,770,441; 6,859,570; or 7,622,294; or PCT Publication No. WO 00/63437, each of which is incorporated herein by reference. Further examples of commercially available microarrays that can be used include, for example, an Affymetrix® GeneChip® microarray or other microarray synthesized in accordance with techniques sometimes referred to as VLSIPS™ (Very Large Scale Immobilized Polymer Synthesis) technologies. A spotted microarray can also be used in a method or system according to some implementations of the present disclosure. An example spotted microarray is a CodeLink™ Array available from Amersham Biosciences. Another microarray that is useful is one that is manufactured using inkjet printing methods such as SurePrint™ Technology available from Agilent Technologies.

Other useful arrays include those that are used in nucleic acid sequencing applications. For example, arrays having amplicons of genomic fragments (often referred to as clusters) are particularly useful such as those described in Bentley et al., Nature 456:53-59 (2008), WO 04/018497; WO 91/06678; WO 07/123744; U.S. Pat. Nos. 7,329,492; 7,211,414; 7,315,019; 7,405,281, or 7,057,026; or US Pat. App. Pub. No. 2008/0108082 A1, each of which is incorporated herein by reference. Another type of array that is useful for nucleic acid sequencing is an array of particles produced from an emulsion PCR technique. Examples are described in Dressman et al., Proc. Natl. Acad. Sci. USA 100:8817-8822 (2003), WO 05/010145, US Pat. App. Pub. No. 2005/0130173 or US Pat. App. Pub. No. 2005/0064460, each of which is incorporated herein by reference in its entirety.

Arrays used for nucleic acid sequencing often have random spatial patterns of nucleic acid analytes. For example, HiSeq or MiSeq sequencing platforms available from Illumina Inc. (San Diego, Calif.) utilize flow cells upon which nucleic acid arrays are formed by random seeding followed by bridge amplification. However, patterned arrays can also be used for nucleic acid sequencing or other analytical applications. Example patterned arrays, methods for their manufacture and methods for their use are set forth in U.S. Ser. No. 13/787,396; U.S. Ser. No. 13/783,043; U.S. Ser. No. 13/784,368; US Pat. App. Pub. No. 2013/0116153 A1; and US Pat. App. Pub. No. 2012/0316086 A1, each of which is incorporated herein by reference. The analytes of such patterned arrays can be used to capture a single nucleic acid template molecule to seed subsequent formation of a homogenous colony, for example, via bridge amplification. Such patterned arrays are particularly useful for nucleic acid sequencing applications.

The size of an analyte on an array (or other object used in a method or system herein) can be selected to suit a particular application. For example, in some implementations, an analyte of an array can have a size that accommodates only a single nucleic acid molecule. A surface having a plurality of analytes in this size range is useful for constructing an array of molecules for detection at single molecule resolution. Analytes in this size range are also useful for use in arrays having analytes that each contain a colony of nucleic acid molecules. Thus, the analytes of an array can each have an area that is no larger than about 1 $mm^2$, no larger than about 500 $\mu m^2$, no larger than about 100 $\mu m^2$, no larger than about 10 $\mu m^2$, no larger than about 1 $\mu m^2$, no larger than about 500 $nm^2$, or no larger than about 100 $nm^2$, no larger than about 10 $nm^2$, no larger than about 5 $nm^2$, or no larger than about 1 $nm^2$. Alternatively or additionally, the analytes of an array will be no smaller than about 1 $mm^2$, no smaller than about 500 $\mu m^2$, no smaller than about 100 $\mu m^2$, no smaller than about 10 $\mu m^2$, no smaller than about 1 $\mu m^2$, no smaller than about 500 $nm^2$, no smaller than about 100 $nm^2$, no smaller than about 10 $nm^2$, no smaller than about 5 $nm^2$, or no smaller than about 1 $nm^2$. Indeed, an analyte can have a size that is in a range between an upper and lower limit selected from those exemplified above. Although several size ranges for analytes of a surface have been exemplified with respect to nucleic acids and on the scale of nucleic acids, it will be understood that analytes in these size ranges can be used for applications that do not include nucleic acids. It will be further understood that the size of the analytes need not necessarily be confined to a scale used for nucleic acid applications.

For implementations that include an object having a plurality of analytes, such as an array of analytes, the analytes can be discrete, being separated with spaces between each other. An array useful in the invention can have analytes that are separated by edge to edge distance of at most 100 µm, 50 µm, 10 µm, 5 µm, 1 µm, 0.5 µm, or less. Alternatively or additionally, an array can have analytes that are separated by an edge to edge distance of at least 0.5 µm, 1 µm, 5 µm, 10 µm, 50 µm, 100 µm, or more. These ranges can apply to the average edge to edge spacing for analytes as well as to the minimum or maximum spacing.

In some implementations the analytes of an array need not be discrete and instead neighboring analytes can abut each other. Whether or not the analytes are discrete, the size of the analytes and/or pitch of the analytes can vary such that arrays can have a desired density. For example, the average analyte pitch in a regular pattern can be at most 100 µm, 50 µm, 10 µm, 5 µm, 1 µm, 0.5 µm, or less. Alternatively or additionally, the average analyte pitch in a regular pattern can be at least 0.5 µm, 1 µm, 5 µm, 10 µm, 50 µm, 100 µm, or more. These ranges can apply to the maximum or minimum pitch for a regular pattern as well. For example, the maximum analyte pitch for a regular pattern can be at most 100 µm, 50 µm, 10 µm, 5 µm, 1 µm, 0.5 µm, or less; and/or the minimum analyte pitch in a regular pattern can be at least 0.5 µm, 1 µm, 5 µm, 10 µm, 50 µm, 100 µm, or more.

The density of analytes in an array can also be understood in terms of the number of analytes present per unit area. For example, the average density of analytes for an array can be at least about $1 \times 10^3$ analytes/mm$^2$, $1 \times 10^4$ analytes/mm$^2$, $1 \times 10^5$ analytes/mm$^2$, $1 \times 10^6$ analytes/mm$^2$, $1 \times 10^7$ analytes/mm$^2$, $1 \times 10^8$ analytes/mm$^2$, or $1 \times 10^9$ analytes/mm$^2$, or higher. Alternatively or additionally the average density of analytes for an array can be at most about $1 \times 10^9$ analytes/mm$^2$, $1 \times 10^8$ analytes/mm$^2$, $1 \times 10^7$ analytes/mm$^2$, $1 \times 10^6$ analytes/mm$^2$, $1 \times 10^5$ analytes/mm$^2$, $1 \times 10^4$ analytes/mm$^2$, or $1 \times 10^3$ analytes/mm$^2$, or less.

The above ranges can apply to all or part of a regular pattern including, for example, all or part of an array of analytes.

The analytes in a pattern can have any of a variety of shapes. For example, when observed in a two dimensional plane, such as on the surface of an array, the analytes can appear rounded, circular, oval, rectangular, square, symmetric, asymmetric, triangular, polygonal, or the like. The analytes can be arranged in a regular repeating pattern including, for example, a hexagonal or rectilinear pattern. A pattern can be selected to achieve a desired level of packing. For example, round analytes are optimally packed in a hexagonal arrangement. Of course other packing arrangements can also be used for round analytes and vice versa.

A pattern can be characterized in terms of the number of analytes that are present in a subset that forms the smallest geometric unit of the pattern. The subset can include, for example, at least about 2, 3, 4, 5, 6, 10 or more analytes. Depending upon the size and density of the analytes the geometric unit can occupy an area of less than 1 mm$^2$, 500 µm$^2$, 100 µm$^2$, 50 µm$^2$, 10 µm$^2$, 1 µm$^2$, 500 nm$^2$, 100 nm$^2$, 50 nm$^2$, 10 nm$^2$, or less. Alternatively or additionally, the geometric unit can occupy an area of greater than 10 nm$^2$, 50 nm$^2$, 100 nm$^2$, 500 nm$^2$, 1 µm$^2$, 10 µm$^2$, 50 µm$^2$, 100 µm$^2$, 500 µm$^2$, 1 mm$^2$, or more. Characteristics of the analytes in a geometric unit, such as shape, size, pitch and the like, can be selected from those set forth herein more generally with regard to analytes in an array or pattern.

An array having a regular pattern of analytes can be ordered with respect to the relative locations of the analytes but random with respect to one or more other characteristic of each analyte. For example, in the case of a nucleic acid array, the nuclei acid analytes can be ordered with respect to their relative locations but random with respect to one's knowledge of the sequence for the nucleic acid species present at any particular analyte. As a more specific example, nucleic acid arrays formed by seeding a repeating pattern of analytes with template nucleic acids and amplifying the template at each analyte to form copies of the template at the analyte (e.g., via cluster amplification or bridge amplification) will have a regular pattern of nucleic acid analytes but will be random with regard to the distribution of sequences of the nucleic acids across the array. Thus, detection of the presence of nucleic acid material generally on the array can yield a repeating pattern of analytes, whereas sequence specific detection can yield non-repeating distribution of signals across the array.

It will be understood that the description herein of patterns, order, randomness and the like pertain not only to analytes on objects, such as analytes on arrays, but also to analytes in images. As such, patterns, order, randomness and the like can be present in any of a variety of formats that are used to store, manipulate or communicate image data including, but not limited to, a computer readable medium or computer component such as a graphical user interface or other output device.

As used herein, the term "image" is intended to mean a representation of all or part of an object. The representation can be an optically detected reproduction. For example, an image can be obtained from fluorescent, luminescent, scatter, or absorption signals. The part of the object that is present in an image can be the surface or other xy plane of the object. Typically, an image is a 2 dimensional representation, but in some cases information in the image can be derived from 3 or more dimensions. An image need not include optically detected signals. Non-optical signals can be present instead. An image can be provided in a computer readable format or medium such as one or more of those set forth elsewhere herein.

As used herein, "image" refers to a reproduction or representation of at least a portion of a specimen or other object. In some implementations, the reproduction is an optical reproduction, for example, produced by a camera or other optical detector. The reproduction can be a non-optical reproduction, for example, a representation of electrical signals obtained from an array of nanopore analytes or a representation of electrical signals obtained from an ion-sensitive CMOS detector. In particular implementations non-optical reproductions can be excluded from a method or apparatus set forth herein. An image can have a resolution capable of distinguishing analytes of a specimen that are present at any of a variety of spacings including, for example, those that are separated by less than 100 µm, 50 µm, 10 µm, 5 µm, 1 µm or 0.5 µm.

As used herein, "acquiring", "acquisition" and like terms refer to any part of the process of obtaining an image file. In some implementations, data acquisition can include generating an image of a specimen, looking for a signal in a specimen, instructing a detection device to look for or generate an image of a signal, giving instructions for further analysis or transformation of an image file, and any number of transformations or manipulations of an image file.

As used herein, the term "template" refers to a representation of the location or relation between signals or analytes. Thus, in some implementations, a template is a physical grid with a representation of signals corresponding to analytes in a specimen. In some implementations, a template can be a chart, table, text file or other computer file indicative of locations corresponding to analytes. In implementations presented herein, a template is generated in order to track the location of analytes of a specimen across a set of images of the specimen captured at different reference points. For example, a template could be a set of x,y coordinates or a set of values that describe the direction and/or distance of one analyte with respect to another analyte.

As used herein, the term "specimen" can refer to an object or area of an object of which an image is captured. For example, in implementations where images are taken of the surface of the earth, a parcel of land can be a specimen. In other implementations where the analysis of biological molecules is performed in a flow cell, the flow cell may be divided into any number of subdivisions, each of which may be a specimen. For example, a flow cell may be divided into various flow channels or lanes, and each lane can be further divided into 2, 3, 4, 5, 6, 7, 8, 9, 10, 20, 30, 40, 50, 60 70, 80, 90, 100, 110, 120, 140, 160, 180, 200, 400, 600, 800, 1000 or more separate regions that are imaged. One example of a flow cell has 8 lanes, with each lane divided into 120 specimens or tiles. In another implementation, a specimen may be made up of a plurality of tiles or even an entire flow cell. Thus, the image of each specimen can represent a region of a larger surface that is imaged.

It will be appreciated that references to ranges and sequential number lists described herein include not only the enumerated number but all real numbers between the enumerated numbers.

As used herein, a "reference point" refers to any temporal or physical distinction between images. In a preferred implementation, a reference point is a time point. In a more preferred implementation, a reference point is a time point or cycle during a sequencing reaction. However, the term "reference point" can include other aspects that distinguish or separate images, such as angle, rotational, temporal, or other aspects that can distinguish or separate images.

As used herein, a "subset of images" refers to a group of images within a set. For example, a subset may contain 1, 2, 3, 4, 6, 8, 10, 12, 14, 16, 18, 20, 30, 40, 50, 60 or any number of images selected from a set of images. In particular implementations, a subset may contain no more than 1, 2, 3, 4, 6, 8, 10, 12, 14, 16, 18, 20, 30, 40, 50, 60 or any number of images selected from a set of images. In a preferred implementation, images are obtained from one or more sequencing cycles with four images correlated to each cycle. Thus, for example, a subset could be a group of 16 images obtained through four cycles.

A base refers to a nucleotide base or nucleotide, A (adenine), C (cytosine), T (thymine), or G (guanine). This application uses "base(s)" and "nucleotide(s)" interchangeably.

The term "chromosome" refers to the heredity-bearing gene carrier of a living cell, which is derived from chromatin strands comprising DNA and protein components (especially histones). The conventional internationally recognized individual human genome chromosome numbering system is employed herein.

The term "site" refers to a unique position (e.g., chromosome ID, chromosome position and orientation) on a reference genome. In some implementations, a site may be a residue, a sequence tag, or a segment's position on a sequence. The term "locus" may be used to refer to the specific location of a nucleic acid sequence or polymorphism on a reference chromosome.

The term "sample" herein refers to a sample, typically derived from a biological fluid, cell, tissue, organ, or organism containing a nucleic acid or a mixture of nucleic acids containing at least one nucleic acid sequence that is to be sequenced and/or phased. Such samples include, but are not limited to sputum/oral fluid, amniotic fluid, blood, a blood fraction, fine needle biopsy samples (e.g., surgical biopsy, fine needle biopsy, etc.), urine, peritoneal fluid, pleural fluid, tissue explant, organ culture and any other tissue or cell preparation, or fraction or derivative thereof or isolated therefrom. Although the sample is often taken from a human subject (e.g., patient), samples can be taken from any organism having chromosomes, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc.

The term "sequence" includes or represents a strand of nucleotides coupled to each other. The nucleotides may be based on DNA or RNA. It should be understood that one sequence may include multiple sub-sequences. For example, a single sequence (e.g., of a PCR amplicon) may have 350 nucleotides. The sample read may include multiple sub-sequences within these 350 nucleotides. For instance, the sample read may include first and second flanking subsequences having, for example, 20-50 nucleotides. The first and second flanking sub-sequences may be located on either side of a repetitive segment having a corresponding sub-sequence (e.g., 40-100 nucleotides). Each of the flanking sub-sequences may include (or include portions of) a primer sub-sequence (e.g., 10-30 nucleotides). For ease of reading, the term "sub-sequence" will be referred to as "sequence," but it is understood that two sequences are not necessarily separate from each other on a common strand. To differentiate the various sequences described herein, the sequences may be given different labels (e.g., target sequence, primer sequence, flanking sequence, reference sequence, and the like). Other terms, such as "allele," may be given different labels to differentiate between like objects. The application uses "read(s)" and "sequence read(s)" interchangeably.

The term "paired-end sequencing" refers to sequencing methods that sequence both ends of a target fragment. Paired-end sequencing may facilitate detection of genomic rearrangements and repetitive segments, as well as gene fusions and novel transcripts. Methodology for paired-end sequencing are described in PCT publication WO07010252, PCT application Serial No. PCTGB2007/003798 and US patent application publication US 2009/0088327, each of which is incorporated by reference herein. In one example, a series of operations may be performed as follows; (a) generate clusters of nucleic acids; (b) linearize the nucleic acids; (c) hybridize a first sequencing primer and carry out repeated cycles of extension, scanning and deblocking, as set forth above; (d) "invert" the target nucleic acids on the flow cell surface by synthesizing a complimentary copy; (e) linearize the resynthesized strand; and (f) hybridize a second sequencing primer and carry out repeated cycles of extension, scanning and deblocking, as set forth above. The inversion operation can be carried out be delivering reagents as set forth above for a single cycle of bridge amplification.

The term "reference genome" or "reference sequence" refers to any particular known genome sequence, whether partial or complete, of any organism which may be used to reference identified sequences from a subject. For example, a reference genome used for human subjects as well as many other organisms is found at the National Center for Biotechnology Information at ncbi.nlm nih gov. A "genome" refers to the complete genetic information of an organism or virus, expressed in nucleic acid sequences. A genome includes both the genes and the noncoding sequences of the DNA. The reference sequence may be larger than the reads that are aligned to it. For example, it may be at least about 100 times larger, or at least about 1000 times larger, or at least about 10,000 times larger, or at least about 105 times larger, or at least about 106 times larger, or at least about 107 times larger. In one example, the reference genome sequence is that of a full length human genome. In another example, the reference genome sequence is limited to a specific human chromosome such as chromosome 13. In some implementations, a reference chromosome is a chromosome sequence from human genome version hg19. Such sequences may be referred to as chromosome reference sequences, although the term reference genome is intended to cover such sequences. Other examples of reference sequences include genomes of other species, as well as chromosomes, sub-chromosomal regions (such as strands), etc., of any species. In various implementations, the reference genome is a consensus sequence or other combination derived from multiple individuals. However, in certain applications, the reference sequence may be taken from a particular individual. In other implementations, the "genome" also covers so-called "graph genomes", which use a particular storage format and representation of the genome sequence. In one implementation, graph genomes store data in a linear file. In another implementation, the graph genomes refer to a representation where alternative sequences (e.g., different copies of a chromosome with small differences) are stored as different paths in a graph. Additional information regarding graph genome implementations can be found in (https://) www.biorxiv.org/content/biorxiv/early/2018/03/20/ 194530.full.pdf, the content of which is hereby incorporated herein by reference in its entirety.

The term "read" refer to a collection of sequence data that describes a fragment of a nucleotide sample or reference. The term "read" may refer to a sample read and/or a reference read. Typically, though not necessarily, a read represents a short sequence of contiguous base pairs in the sample or reference. The read may be represented symbolically by the base pair sequence (in ATCG) of the sample or reference fragment. It may be stored in a memory device and processed as appropriate to determine whether the read matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

Next-generation sequencing methods include, for example, sequencing by synthesis technology (Illumina), pyrosequencing (454), ion semiconductor technology (Ion Torrent sequencing), single-molecule real-time sequencing (Pacific Biosciences) and sequencing by ligation (SOLiD sequencing). Depending on the sequencing methods, the length of each read may vary from about 30 bp to more than 10,000 bp. For example, the DNA sequencing method using SOLiD sequencer generates nucleic acid reads of about 50 bp. For another example, Ion Torrent Sequencing generates nucleic acid reads of up to 400 bp and 454 pyrosequencing generates nucleic acid reads of about 700 bp. For yet another example, single-molecule real-time sequencing methods may generate reads of 10,000 bp to 15,000 bp. Therefore, in certain implementations, the nucleic acid sequence reads have a length of 30-100 bp, 50-200 bp, or 50-400 bp.

The terms "sample read", "sample sequence" or "sample fragment" refer to sequence data for a genomic sequence of interest from a sample. For example, the sample read comprises sequence data from a PCR amplicon having a forward and reverse primer sequence. The sequence data can be obtained from any select sequence methodology. The sample read can be, for example, from a sequencing-by-synthesis (SBS) reaction, a sequencing-by-ligation reaction, or any other suitable sequencing methodology for which it is desired to determine the length and/or identity of a repetitive element. The sample read can be a consensus (e.g., averaged or weighted) sequence derived from multiple sample reads. In certain implementations, providing a reference sequence comprises identifying a locus-of-interest based upon the primer sequence of the PCR amplicon.

The term "raw fragment" refers to sequence data for a portion of a genomic sequence of interest that at least partially overlaps a designated position or secondary position of interest within a sample read or sample fragment. Non-limiting examples of raw fragments include a duplex stitched fragment, a simplex stitched fragment, a duplex un-stitched fragment and a simplex un-stitched fragment. The term "raw" is used to indicate that the raw fragment includes sequence data having some relation to the sequence data in a sample read, regardless of whether the raw fragment exhibits a supporting variant that corresponds to and authenticates or confirms a potential variant in a sample read. The term "raw fragment" does not indicate that the fragment necessarily includes a supporting variant that validates a variant call in a sample read. For example, when a sample read is determined by a variant call application to exhibit a first variant, the variant call application may determine that one or more raw fragments lack a corresponding type of "supporting" variant that may otherwise be expected to occur given the variant in the sample read.

The terms "mapping", "aligned," "alignment," or "aligning" refer to the process of comparing a read or tag to a reference sequence and thereby determining whether the reference sequence contains the read sequence. If the reference sequence contains the read, the read may be mapped to the reference sequence or, in certain implementations, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

The term "indel" refers to the insertion and/or the deletion of bases in the DNA of an organism. A micro-indel represents an indel that results in a net change of 1 to 50 nucleotides. In coding regions of the genome, unless the length of an indel is a multiple of 3, it will produce a frameshift mutation. Indels can be contrasted with point mutations. An indel inserts and deletes nucleotides from a sequence, while a point mutation is a form of substitution that replaces one of the nucleotides without changing the overall number in the DNA. Indels can also be contrasted with a Tandem Base Mutation (TBM), which may be defined as substitution at adjacent nucleotides (primarily substitutions at two adjacent nucleotides, but substitutions at three adjacent nucleotides have been observed.

The term "variant" refers to a nucleic acid sequence that is different from a nucleic acid reference. Typical nucleic acid sequence variant includes without limitation single nucleotide polymorphism (SNP), short deletion and insertion polymorphisms (Indel), copy number variation (CNV), microsatellite markers or short tandem repeats and structural variation. Somatic variant calling is the effort to identify variants present at low frequency in the DNA sample. Somatic variant calling is of interest in the context of cancer treatment. Cancer is caused by an accumulation of mutations in DNA. A DNA sample from a tumor is generally heterogeneous, including some normal cells, some cells at an early stage of cancer progression (with fewer mutations), and some late-stage cells (with more mutations). Because of this heterogeneity, when sequencing a tumor (e.g., from an FFPE sample), somatic mutations will often appear at a low frequency. For example, a SNV might be seen in only 10% of the reads covering a given base. A variant that is to be classified as somatic or germline by the variant classifier is also referred to herein as the "variant under test".

The term "noise" refers to a mistaken variant call resulting from one or more errors in the sequencing process and/or in the variant call application.

The term "variant frequency" represents the relative frequency of an allele (variant of a gene) at a particular locus in a population, expressed as a fraction or percentage. For example, the fraction or percentage may be the fraction of all chromosomes in the population that carry that allele. By way of example, sample variant frequency represents the relative frequency of an allele/variant at a particular locus/position along a genomic sequence of interest over a "population" corresponding to the number of reads and/or samples obtained for the genomic sequence of interest from an individual. As another example, a baseline variant frequency represents the relative frequency of an allele/variant at a particular locus/position along one or more baseline genomic sequences where the "population" corresponding to the number of reads and/or samples obtained for the one or more baseline genomic sequences from a population of normal individuals.

The term "variant allele frequency (VAF)" refers to the percentage of sequenced reads observed matching the variant divided by the overall coverage at the target position. VAF is a measure of the proportion of sequenced reads carrying the variant.

The terms "position", "designated position", and "locus" refer to a location or coordinate of one or more nucleotides within a sequence of nucleotides. The terms "position", "designated position", and "locus" also refer to a location or coordinate of one or more base pairs in a sequence of nucleotides.

The term "haplotype" refers to a combination of alleles at adjacent sites on a chromosome that are inherited together. A haplotype may be one locus, several loci, or an entire chromosome depending on the number of recombination events that have occurred between a given set of loci, if any occurred.

The term "threshold" herein refers to a numeric or non-numeric value that is used as a cutoff to characterize a sample, a nucleic acid, or portion thereof (e.g., a read). A threshold may be varied based upon empirical analysis. The threshold may be compared to a measured or calculated value to determine whether the source giving rise to such value suggests should be classified in a particular manner. Threshold values can be identified empirically or analytically. The choice of a threshold is dependent on the level of confidence that the user wishes to have to make the classification. The threshold may be chosen for a particular purpose (e.g., to balance sensitivity and selectivity). As used herein, the term "threshold" indicates a point at which a course of analysis may be changed and/or a point at which an action may be triggered. A threshold is not required to be a predetermined number. Instead, the threshold may be, for instance, a function that is based on a plurality of factors. The threshold may be adaptive to the circumstances. Moreover, a threshold may indicate an upper limit, a lower limit, or a range between limits.

In some implementations, a metric or score that is based on sequencing data may be compared to the threshold. As used herein, the terms "metric" or "score" may include values or results that were determined from the sequencing data or may include functions that are based on the values or results that were determined from the sequencing data. Like a threshold, the metric or score may be adaptive to the circumstances. For instance, the metric or score may be a normalized value. As an example of a score or metric, one or more implementations may use count scores when analyzing the data. A count score may be based on number of sample reads. The sample reads may have undergone one or more filtering stages such that the sample reads have at least one common characteristic or quality. For example, each of the sample reads that are used to determine a count score may have been aligned with a reference sequence or may be assigned as a potential allele. The number of sample reads having a common characteristic may be counted to determine a read count. Count scores may be based on the read count. In some implementations, the count score may be a value that is equal to the read count. In other implementations, the count score may be based on the read count and other information. For example, a count score may be based on the read count for a particular allele of a genetic locus and a total number of reads for the genetic locus. In some implementations, the count score may be based on the read count and previously-obtained data for the genetic locus. In some implementations, the count scores may be normalized scores between predetermined values. The count score may also be a function of read counts from other loci of a sample or a function of read counts from other samples that were concurrently run with the sample-of-interest. For instance, the count score may be a function of the read count of a particular allele and the read counts of other loci in the sample and/or the read counts from other samples. As one example, the read counts from other loci and/or the read counts from other samples may be used to normalize the count score for the particular allele.

The terms "coverage" or "fragment coverage" refer to a count or other measure of a number of sample reads for the same fragment of a sequence. A read count may represent a count of the number of reads that cover a corresponding fragment. Alternatively, the coverage may be determined by multiplying the read count by a designated factor that is based on historical knowledge, knowledge of the sample, knowledge of the locus, etc.

The term "read depth" (conventionally a number followed by "x") refers to the number of sequenced reads with overlapping alignment at the target position. This is often expressed as an average or percentage exceeding a cutoff over a set of intervals (such as exons, genes, or panels). For example, a clinical report might say that a panel average coverage is 1,105 × with 98% of targeted bases covered >100×.

The terms "base call quality score" or "Q score" refer to a PHRED-scaled probability ranging from 0-50 inversely proportional to the probability that a single sequenced base is correct. For example, a T base call with Q of 20 is considered likely correct with a probability of 99.99%. Any base call with Q<20 should be considered low quality, and any variant identified where a substantial proportion of sequenced reads supporting the variant are of low quality should be considered potentially false positive.

The terms "variant reads" or "variant read number" refer to the number of sequenced reads supporting the presence of the variant.

Regarding "strandedness" (or DNA strandedness), the genetic message in DNA can be represented as a string of the letters A, G, C, and T. For example, 5'-AGGACA-3'. Often, the sequence is written in the direction shown here, i.e., with the 5' end to the left and the 3' end to the right. DNA may sometimes occur as single-stranded molecule (as in certain viruses), but normally we find DNA as a double-stranded unit. It has a double helical structure with two antiparallel strands. In this case, the word "antiparallel" means that the two strands run in parallel, but have opposite polarity. The double-stranded DNA is held together by pairing between bases and the pairing is always such that adenine (A) pairs with thymine (T) and cytosine (C) pairs with guanine (G). This pairing is referred to as complementarity, and one strand of DNA is said to be the complement of the other. The double-stranded DNA may thus be represented as two strings, like this: 5'-AGGACA-3' and 3'-TCCTGT-5'. Note that the two strands have opposite polarity. Accordingly, the strandedness of the two DNA strands can be referred to as the reference strand and its complement, forward and reverse strands, top and bottom strands, sense and antisense strands, or Watson and Crick strands.

The reads alignment (also called reads mapping) is the process of figuring out where in the genome a sequence is from. Once the alignment is performed, the "mapping quality" or the "mapping quality score (MAPQ)" of a given read quantifies the probability that its position on the genome is correct. The mapping quality is encoded in the phred scale where P is the probability that the alignment is not correct. The probability is calculated as: $P=10^{(-MAPQ/10)}$, where MAPQ is the mapping quality. For example, a mapping quality of 40=10 to the power of −4, meaning that there is a 0.01% chance that the read was aligned incorrectly. The mapping quality is therefore associated with several alignment factors, such as the base quality of the read, the complexity of the reference genome, and the paired-end information. Regarding the first, if the base quality of the read is low, it means that the observed sequence might be wrong and thus its alignment is wrong. Regarding the second, the mappability refers to the complexity of the genome. Repeated regions are more difficult to map and reads falling in these regions usually get low mapping quality. In this context, the MAPQ reflects the fact that the reads are not uniquely aligned and that their real origin cannot be determined. Regarding the third, in case of paired-end sequencing data, concordant pairs are more likely to be well aligned. The higher is the mapping quality, the better is the alignment. A read aligned with a good mapping quality usually means that the read sequence was good and was aligned with few mismatches in a high mappability region. The MAPQ value can be used as a quality control of the alignment results. The proportion of reads aligned with an MAPQ higher than 20 is usually for downstream analysis.

As used herein, a "signal" refers to a detectable event such as an emission, preferably light emission, for example, in an image. Thus, in preferred implementations, a signal can represent any detectable light emission that is captured in an image (i.e., a "spot"). Thus, as used herein, "signal" can refer to both an actual emission from an analyte of the specimen, and can refer to a spurious emission that does not correlate to an actual analyte. Thus, a signal could arise from noise and could be later discarded as not representative of an actual analyte of a specimen.

As used herein, the term "clump" refers to a group of signals. In particular implementations, the signals are derived from different analytes. In a preferred implementation, a signal clump is a group of signals that cluster together. In a more preferred implementation, a signal clump represents a physical region covered by one amplified oligonucleotide. Each signal clump should be ideally observed as several signals (one per template cycle, and possibly more due to cross-talk). Accordingly, duplicate signals are detected where two (or more) signals are included in a template from the same clump of signals.

As used herein, terms such as "minimum," "maximum," "minimize," "maximize" and grammatical variants thereof can include values that are not the absolute maxima or minima. In some implementations, the values include near maximum and near minimum values. In other implementations, the values can include local maximum and/or local minimum values. In some implementations, the values include only absolute maximum or minimum values.

As used herein, "cross-talk" refers to the detection of signals in one image that are also detected in a separate image. In a preferred implementation, cross-talk can occur when an emitted signal is detected in two separate detection channels. For example, where an emitted signal occurs in one color, the emission spectrum of that signal may overlap with another emitted signal in another color. In a preferred implementation, fluorescent molecules used to indicate the presence of nucleotide bases A, C, G and T are detected in separate channels. However, because the emission spectra of A and C overlap, some of the C color signal may be detected during detection using the A color channel. Accordingly, cross-talk between the A and C signals allows signals from one color image to appear in the other color image. In some implementations, G and T cross-talk. In some implementations, the amount of cross-talk between channels is asymmetric. It will be appreciated that the amount of cross-talk between channels can be controlled by, among other things, the selection of signal molecules having an appropriate emission spectrum as well as selection of the size and wavelength range of the detection channel.

As used herein, "register", "registering", "registration" and like terms refer to any process to correlate signals in an image or data set from a first time point or perspective with signals in an image or data set from another time point or perspective. For example, registration can be used to align signals from a set of images to form a template. In another example, registration can be used to align signals from other images to a template. One signal may be directly or indirectly registered to another signal. For example, a signal from image "S" may be registered to image "G" directly. As another example, a signal from image "N" may be directly registered to image "G", or alternatively, the signal from image "N" may be registered to image "S", which has previously been registered to image "G". Thus, the signal from image "N" is indirectly registered to image "G".

As used herein, the term "fiducial" is intended to mean a distinguishable point of reference in or on an object. The point of reference can be, for example, a mark, second object, shape, edge, area, irregularity, channel, pit, post or the like. The point of reference can be present in an image of the object or in another data set derived from detecting the object. The point of reference can be specified by an x and/or y coordinate in a plane of the object. Alternatively or additionally, the point of reference can be specified by a z coordinate that is orthogonal to the xy plane, for example, being defined by the relative locations of the object and a detector. One or more coordinates for a point of reference can be specified relative to one or more other analytes of an object or of an image or other data set derived from the object.

As used herein, the term "optical signal" is intended to include, for example, fluorescent, luminescent, scatter, or absorption signals. Optical signals can be detected in the ultraviolet (UV) range (about 200 to 390 nm), visible (VIS)

range (about 391 to 770 nm), infrared (IR) range (about 0.771 to 25 microns), or other range of the electromagnetic spectrum. Optical signals can be detected in a way that excludes all or part of one or more of these ranges.

As used herein, the term "signal level" is intended to mean an amount or quantity of detected energy or coded information that has a desired or predefined characteristic. For example, an optical signal can be quantified by one or more of intensity, wavelength, energy, frequency, power, luminance or the like. Other signals can be quantified according to characteristics such as voltage, current, electric field strength, magnetic field strength, frequency, power, temperature, etc. Absence of signal is understood to be a signal level of zero or a signal level that is not meaningfully distinguished from noise.

As used herein, the term "simulate" is intended to mean creating a representation or model of a physical thing or action that predicts characteristics of the thing or action. The representation or model can in many cases be distinguishable from the thing or action. For example, the representation or model can be distinguishable from a thing with respect to one or more characteristic such as color, intensity of signals detected from all or part of the thing, size, or shape. In particular implementations, the representation or model can be idealized, exaggerated, muted, or incomplete when compared to the thing or action. Thus, in some implementations, a representation of model can be distinguishable from the thing or action that it represents, for example, with respect to at least one of the characteristics set forth above. The representation or model can be provided in a computer readable format or medium such as one or more of those set forth elsewhere herein.

As used herein, the term "specific signal" is intended to mean detected energy or coded information that is selectively observed over other energy or information such as background energy or information. For example, a specific signal can be an optical signal detected at a particular intensity, wavelength or color; an electrical signal detected at a particular frequency, power or field strength; or other signals known in the art pertaining to spectroscopy and analytical detection.

As used herein, the term "swath" is intended to mean a rectangular portion of an object. The swath can be an elongated strip that is scanned by relative movement between the object and a detector in a direction that is parallel to the longest dimension of the strip. Generally, the width of the rectangular portion or strip will be constant along its full length. Multiple swaths of an object can be parallel to each other. Multiple swaths of an object can be adjacent to each other, overlapping with each other, abutting each other, or separated from each other by an interstitial area.

As used herein, the term "variance" is intended to mean a difference between that which is expected and that which is observed or a difference between two or more observations. For example, variance can be the discrepancy between an expected value and a measured value. Variance can be represented using statistical functions such as standard deviation, the square of standard deviation, coefficient of variation or the like.

As used herein, the term "xy coordinates" is intended to mean information that specifies location, size, shape, and/or orientation in an xy plane. The information can be, for example, numerical coordinates in a Cartesian system. The coordinates can be provided relative to one or both of the x and y axes or can be provided relative to another location in the xy plane. For example, coordinates of a analyte of an object can specify the location of the analyte relative to location of a fiducial or other analyte of the object.

As used herein, the term "xy plane" is intended to mean a 2 dimensional area defined by straight line axes x and y. When used in reference to a detector and an object observed by the detector, the area can be further specified as being orthogonal to the direction of observation between the detector and object being detected.

As used herein, the term "z coordinate" is intended to mean information that specifies the location of a point, line or area along an axes that is orthogonal to an xy plane. In particular implementations, the z axis is orthogonal to an area of an object that is observed by a detector. For example, the direction of focus for an optical system may be specified along the z axis.

In some implementations, acquired signal data is transformed using an affine transformation. In some such implementations, template generation makes use of the fact that the affine transforms between color channels are consistent between runs. Because of this consistency, a set of default offsets can be used when determining the coordinates of the analytes in a specimen. For example, a default offsets file can contain the relative transformation (shift, scale, skew) for the different channels relative to one channel, such as the A channel In other implementations, however, the offsets between color channels drift during a run and/or between runs, making offset-driven template generation difficult. In such implementations, the methods and systems provided herein can utilize offset-less template generation, which is described further below.

In some aspects of the above implementations, the system can comprise a flow cell. In some aspects, the flow cell comprises lanes, or other configurations, of tiles, wherein at least some of the tiles comprise one or more arrays of analytes. In some aspects, the analytes comprise a plurality of molecules such as nucleic acids. In certain aspects, the flow cell is configured to deliver a labeled nucleotide base to an array of nucleic acids, thereby extending a primer hybridized to a nucleic acid within a analyte so as to produce a signal corresponding to a analyte comprising the nucleic acid. In preferred implementations, the nucleic acids within a analyte are identical or substantially identical to each other.

In some of the systems for image analysis described herein, each image in the set of images includes color signals, wherein a different color corresponds to a different nucleotide base. In some aspects, each image of the set of images comprises signals having a single color selected from at least four different colors. In some aspects, each image in the set of images comprises signals having a single color selected from four different colors. In some of the systems described herein, nucleic acids can be sequenced by providing four different labeled nucleotide bases to the array of molecules so as to produce four different images, each image comprising signals having a single color, wherein the signal color is different for each of the four different images, thereby producing a cycle of four color images that corresponds to the four possible nucleotides present at a particular position in the nucleic acid. In certain aspects, the system comprises a flow cell that is configured to deliver additional labeled nucleotide bases to the array of molecules, thereby producing a plurality of cycles of color images.

In preferred implementations, the methods provided herein can include determining whether a processor is actively acquiring data or whether the processor is in a low activity state. Acquiring and storing large numbers of high-quality images typically requires massive amounts of storage capacity. Additionally, once acquired and stored, the analysis of image data can become resource intensive and can interfere with processing capacity of other functions, such as ongoing acquisition and storage of additional image data. Accordingly, as used herein, the term low activity state refers to the processing capacity of a processor at a given time. In some implementations, a low activity state occurs when a processor is not acquiring and/or storing data. In some implementations, a low activity state occurs when some data acquisition and/or storage is taking place, but additional processing capacity remains such that image analysis can occur at the same time without interfering with other functions.

As used herein, "identifying a conflict" refers to identifying a situation where multiple processes compete for resources. In some such implementations, one process is given priority over another process. In some implementations, a conflict may relate to the need to give priority for allocation of time, processing capacity, storage capacity or any other resource for which priority is given. Thus, in some implementations, where processing time or capacity is to be distributed between two processes such as either analyzing a data set and acquiring and/or storing the data set, a conflict between the two processes exists and can be resolved by giving priority to one of the processes.

Also provided herein are systems for performing image analysis. The systems can include a processor; a storage capacity; and a program for image analysis, the program comprising instructions for processing a first data set for storage and the second data set for analysis, wherein the processing comprises acquiring and/or storing the first data set on the storage device and analyzing the second data set when the processor is not acquiring the first data set. In certain aspects, the program includes instructions for identifying at least one instance of a conflict between acquiring and/or storing the first data set and analyzing the second data set; and resolving the conflict in favor of acquiring and/or storing image data such that acquiring and/or storing the first data set is given priority. In certain aspects, the first data set comprises image files obtained from an optical imaging device. In certain aspects, the system further comprises an optical imaging device. In some aspects, the optical imaging device comprises a light source and a detection device.

As used herein, the term "program" refers to instructions or commands to perform a task or process. The term "program" can be used interchangeably with the term module. In certain implementations, a program can be a compilation of various instructions executed under the same set of commands. In other implementations, a program can refer to a discrete batch or file.

Set forth below are some of the surprising effects of utilizing the methods and systems for performing image analysis set forth herein. In some sequencing implementations, an important measure of a sequencing system's utility is its overall efficiency. For example, the amount of mappable data produced per day and the total cost of installing and running the instrument are important aspects of an economical sequencing solution. To reduce the time to generate mappable data and to increase the efficiency of the system, real-time base calling can be enabled on an instrument computer and can run in parallel with sequencing chemistry and imaging. This allows much of the data processing and analysis to be completed before the sequencing chemistry finishes. Additionally, it can reduce the storage required for intermediate data and limit the amount of data that needs to travel across the network.

While sequence output has increased, the data per run transferred from the systems provided herein to the network and to secondary analysis processing hardware has substantially decreased. By transforming data on the instrument computer (acquiring computer), network loads are dramatically reduced. Without these on-instrument, off-network data reduction techniques, the image output of a fleet of DNA sequencing instruments would cripple most networks.

The widespread adoption of the high-throughput DNA sequencing instruments has been driven in part by ease of use, support for a range of applications, and suitability for virtually any lab environment. The highly efficient algorithms presented herein allow significant analysis functionality to be added to a simple workstation that can control sequencing instruments. This reduction in the requirements for computational hardware has several practical benefits that will become even more important as sequencing output levels continue to increase. For example, by performing image analysis and base calling on a simple tower, heat production, laboratory footprint, and power consumption are kept to a minimum. In contrast, other commercial sequencing technologies have recently ramped up their computing infrastructure for primary analysis, with up to five times more processing power, leading to commensurate increases in heat output and power consumption. Thus, in some implementations, the computational efficiency of the methods and systems provided herein enables customers to increase their sequencing throughput while keeping server hardware expenses to a minimum.

Accordingly, in some implementations, the methods and/or systems presented herein act as a state machine, keeping track of the individual state of each specimen, and when it detects that a specimen is ready to advance to the next state, it does the appropriate processing and advances the specimen to that state. A more detailed example of how the state machine monitors a file system to determine when a specimen is ready to advance to the next state according to a preferred implementation is set forth in Example 1 below.

In preferred implementations, the methods and systems provided herein are multi-threaded and can work with a configurable number of threads. Thus, for example in the context of nucleic acid sequencing, the methods and systems provided herein are capable of working in the background during a live sequencing run for real-time analysis, or it can be run using a pre-existing set of image data for off-line analysis. In certain preferred implementations, the methods and systems handle multi-threading by giving each thread its own subset of specimen for which it is responsible. This minimizes the possibility of thread contention.

A method of the present disclosure can include a step of obtaining a target image of an object using a detection apparatus, wherein the image includes a repeating pattern of analytes on the object. Detection apparatus that are capable of high resolution imaging of surfaces are particularly useful. In particular implementations, the detection apparatus will have sufficient resolution to distinguish analytes at the densities, pitches, and/or analyte sizes set forth herein. Particularly useful are detection apparatus capable of obtaining images or image data from surfaces. Example detectors are those that are configured to maintain an object and detector in a static relationship while obtaining an area image. Scanning apparatus can also be used. For example, an apparatus that obtains sequential area images (e.g., so called 'step and shoot' detectors) can be used. Also useful are devices that continually scan a point or line over the surface of an object to accumulate data to construct an image of the surface. Point scanning detectors can be configured to scan a point (i.e., a small detection area) over the surface of an object via a raster motion in the x-y plane of the surface.

Line scanning detectors can be configured to scan a line along the y dimension of the surface of an object, the longest dimension of the line occurring along the x dimension. It will be understood that the detection device, object or both can be moved to achieve scanning detection. Detection apparatus that are particularly useful, for example in nucleic acid sequencing applications, are described in US Pat App. Pub. Nos. 2012/0270305 A1; 2013/0023422 A1; and 2013/0260372 A1; and U.S. Pat. Nos. 5,528,050; 5,719,391; 8,158,926 and 8,241,573, each of which is incorporated herein by reference.

The implementations disclosed herein may be implemented as a method, apparatus, system or article of manufacture using programming or engineering techniques to produce software, firmware, hardware, or any combination thereof. The term "article of manufacture" as used herein refers to code or logic implemented in hardware or computer readable media such as optical storage devices, and volatile or non-volatile memory devices. Such hardware may include, but is not limited to, field programmable gate arrays (FPGAs), coarse grained reconfigurable architectures (CGRAs), application-specific integrated circuits (ASICs), complex programmable logic devices (CPLDs), programmable logic arrays (PLAs), microprocessors, or other similar processing devices. In particular implementations, information or algorithms set forth herein are present in non-transient storage media.

In particular implementations, a computer implemented method set forth herein can occur in real time while multiple images of an object are being obtained. Such real time analysis is particularly useful for nucleic acid sequencing applications wherein an array of nucleic acids is subjected to repeated cycles of fluidic and detection steps. Analysis of the sequencing data can often be computationally intensive such that it can be beneficial to perform the methods set forth herein in real time or in the background while other data acquisition or analysis algorithms are in process. Example real time analysis methods that can be used with the present methods are those used for the MiSeq and HiSeq sequencing devices commercially available from Illumina, Inc. (San Diego, Calif.) and/or described in US Pat. App. Pub. No. 2012/0020537 A1, which is incorporated herein by reference.

An example data analysis system, formed by one or more programmed computers, with programming being stored on one or more machine readable media with code executed to carry out one or more steps of methods described herein. In one implementation, for example, the system includes an interface designed to permit networking of the system to one or more detection systems (e.g., optical imaging systems) that are configured to acquire data from target objects. The interface may receive and condition data, where appropriate. In particular implementations the detection system will output digital image data, for example, image data that is representative of individual picture elements or pixels that, together, form an image of an array or other object. A processor processes the received detection data in accordance with a one or more routines defined by processing code. The processing code may be stored in various types of memory circuitry.

In accordance with the presently contemplated implementations, the processing code executed on the detection data includes a data analysis routine designed to analyze the detection data to determine the locations and metadata of individual analytes visible or encoded in the data, as well as locations at which no analyte is detected (i.e., where there is no analyte, or where no meaningful signal was detected from an existing analyte). In particular implementations, analyte locations in an array will typically appear brighter than non-analyte locations due to the presence of fluorescing dyes attached to the imaged analytes. It will be understood that the analytes need not appear brighter than their surrounding area, for example, when a target for the probe at the analyte is not present in an array being detected. The color at which individual analytes appear may be a function of the dye employed as well as of the wavelength of the light used by the imaging system for imaging purposes. Analytes to which targets are not bound or that are otherwise devoid of a particular label can be identified according to other characteristics, such as their expected location in the microarray.

Once the data analysis routine has located individual analytes in the data, a value assignment may be carried out. In general, the value assignment will assign a digital value to each analyte based upon characteristics of the data represented by detector components (e.g., pixels) at the corresponding location. That is, for example when imaging data is processed, the value assignment routine may be designed to recognize that a specific color or wavelength of light was detected at a specific location, as indicated by a group or cluster of pixels at the location. In a typical DNA imaging application, for example, the four common nucleotides will be represented by four separate and distinguishable colors. Each color, then, may be assigned a value corresponding to that nucleotide.

As used herein, the terms "module", "system," or "system controller" may include a hardware and/or software system and circuitry that operates to perform one or more functions. For example, a module, system, or system controller may include a computer processor, controller, or other logic-based device that performs operations based on instructions stored on a tangible and non-transitory computer readable storage medium, such as a computer memory. Alternatively, a module, system, or system controller may include a hard-wired device that performs operations based on hard-wired logic and circuitry. The module, system, or system controller shown in the attached figures may represent the hardware and circuitry that operates based on software or hardwired instructions, the software that directs hardware to perform the operations, or a combination thereof. The module, system, or system controller can include or represent hardware circuits or circuitry that include and/or are connected with one or more processors, such as one or computer microprocessors.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are examples only, and are thus not limiting as to the types of memory usable for storage of a computer program.

In the molecular biology field, one of the processes for nucleic acid sequencing in use is sequencing-by-synthesis. The technique can be applied to massively parallel sequencing projects. For example, by using an automated platform, it is possible to carry out hundreds of thousands of sequencing reactions simultaneously. Thus, one of the implementations of the present invention relates to instruments and methods for acquiring, storing, and analyzing image data generated during nucleic acid sequencing.

Enormous gains in the amount of data that can be acquired and stored make streamlined image analysis methods even more beneficial. For example, the image analysis methods described herein permit both designers and end users to make efficient use of existing computer hardware. Accordingly, presented herein are methods and systems which reduce the computational burden of processing data in the face of rapidly increasing data output. For example, in the field of DNA sequencing, yields have scaled 15-fold over the course of a recent year, and can now reach hundreds of gigabases in a single run of a DNA sequencing device. If computational infrastructure requirements grew proportionately, large genome-scale experiments would remain out of reach to most researchers. Thus, the generation of more raw sequence data will increase the need for secondary analysis and data storage, making optimization of data transport and storage extremely valuable. Some implementations of the methods and systems presented herein can reduce the time, hardware, networking, and laboratory infrastructure requirements needed to produce usable sequence data.

The present disclosure describes various methods and systems for carrying out the methods. Examples of some of the methods are described as a series of steps. However, it should be understood that implementations are not limited to the particular steps and/or order of steps described herein. Steps may be omitted, steps may be modified, and/or other steps may be added. Moreover, steps described herein may be combined, steps may be performed simultaneously, steps may be performed concurrently, steps may be split into multiple sub-steps, steps may be performed in a different order, or steps (or a series of steps) may be re-performed in an iterative fashion. In addition, although different methods are set forth herein, it should be understood that the different methods (or steps of the different methods) may be combined in other implementations.

In some implementations, a processing unit, processor, module, or computing system that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

Moreover, the operations of the methods described herein can be sufficiently complex such that the operations cannot be mentally performed by an average human being or a person of ordinary skill in the art within a commercially reasonable time period. For example, the methods may rely on relatively complex computations such that such a person cannot complete the methods within a commercially reasonable time.

Throughout this application various publications, patents or patent applications have been referenced. The disclosures of these publications in their entireties are hereby incorporated by reference in this application in order to more fully describe the state of the art to which this invention pertains.

The term "comprising" is intended herein to be open-ended, including not only the recited elements, but further encompassing any additional elements.

As used herein, the term "each", when used in reference to a collection of items, is intended to identify an individual item in the collection but does not necessarily refer to every item in the collection. Exceptions can occur if explicit disclosure or context clearly dictates otherwise.

Although the invention has been described with reference to the examples provided above, it should be understood that various modifications can be made without departing from the invention.

The modules in this application can be implemented in hardware or software, and need not be divided up in precisely the same blocks as shown in the figures. Some can also be implemented on different processors or computers, or spread among a number of different processors or computers. In addition, it will be appreciated that some of the modules can be combined, operated in parallel or in a different sequence than that shown in the figures without affecting the functions achieved. Also as used herein, the term "module" can include "sub-modules", which themselves can be considered herein to constitute modules. The blocks in the figures designated as modules can also be thought of as flowchart steps in a method.

As used herein, the "identification" of an item of information does not necessarily require the direct specification of that item of information. Information can be "identified" in a field by simply referring to the actual information through one or more layers of indirection, or by identifying one or more items of different information which are together sufficient to determine the actual item of information. In addition, the term "specify" is used herein to mean the same as "identify".

As used herein, a given signal, event or value is "in dependence upon" a predecessor signal, event or value of the predecessor signal, event or value influenced by the given signal, event or value. If there is an intervening processing element, step or time period, the given signal, event or value can still be "in dependence upon" the predecessor signal, event or value. If the intervening processing element or step combines more than one signal, event or value, the signal output of the processing element or step is considered "in dependence upon" each of the signal, event or value inputs. If the given signal, event or value is the same as the predecessor signal, event or value, this is merely a degenerate case in which the given signal, event or value is still considered to be "in dependence upon" or "dependent on" or "based on" the predecessor signal, event or value. "Responsiveness" of a given signal, event or value upon another signal, event or value is defined similarly.

As used herein, "concurrently" or "in parallel" does not require exact simultaneity. It is sufficient if the evaluation of one of the individuals begins before the evaluation of another of the individuals completes.

Computer System

Figure 82:
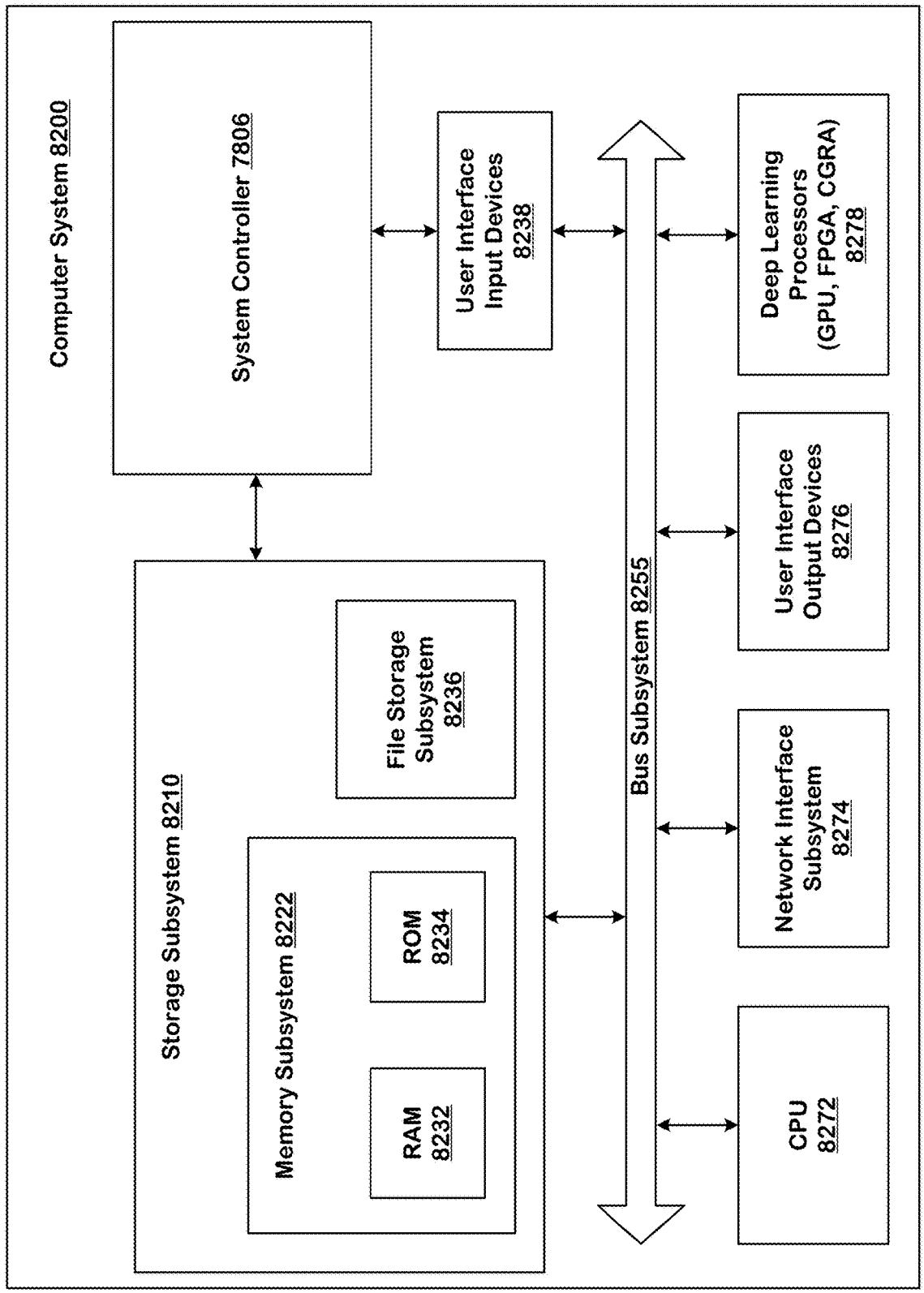
FIG. 82 is a computer system that can be used by the sequencing system of FIG. 78A to implement the technology disclosed herein.

FIG. 82 is a computer system 8200 that can be used by the sequencing system 800A to implement the technology disclosed herein. Computer system 8200 includes at least one central processing unit (CPU) 8272 that communicates with a number of peripheral devices via bus subsystem 8255. These peripheral devices can include a storage subsystem 8210 including, for example, memory devices and a file storage subsystem 8236, user interface input devices 8238, user interface output devices 8276, and a network interface subsystem 8274. The input and output devices allow user interaction with computer system 8200. Network interface subsystem 8274 provides an interface to outside networks, including an interface to corresponding interface devices in other computer systems.

In one implementation, the system controller 7806 is communicably linked to the storage subsystem 8210 and the user interface input devices 8238.

User interface input devices 8238 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 8200.

User interface output devices 8276 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 8200 to the user or to another machine or computer system.

Storage subsystem 8210 stores programming and data constructs that provide the functionality of some or all of the modules and methods described herein. These software modules are generally executed by deep learning processors 8278.

Deep learning processors 8278 can be graphics processing units (GPUs), field-programmable gate arrays (FPGAs), application-specific integrated circuits (ASICs), and/or coarse-grained reconfigurable architectures (CGRAs). Deep learning processors 8278 can be hosted by a deep learning cloud platform such as Google Cloud Platform™, Xilinx™, and Cirrascale™. Examples of deep learning processors 8278 include Google's Tensor Processing Unit (TPU)™, rackmount solutions like GX4 Rackmount Series™, GX82 Rackmount Series™, NVIDIA DGX-1™, Microsoft™ Stratix V FPGA™, Graphcore's Intelligent Processor Unit (IPU)™, Qualcomm's Zeroth Platform™ with Snapdragon Processors™, NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, Lambda GPU Server with Testa V100s™, and others.

Memory subsystem 8222 used in the storage subsystem 8210 can include a number of memories including a main random access memory (RAM) 8232 for storage of instructions and data during program execution and a read only memory (ROM) 8234 in which fixed instructions are stored. A file storage subsystem 8236 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 8236 in the storage subsystem 8210, or in other machines accessible by the processor.

Bus subsystem 8255 provides a mechanism for letting the various components and subsystems of computer system 8200 communicate with each other as intended. Although bus subsystem 8255 is shown schematically as a single bus, alternative implementations of the bus subsystem can use multiple busses.

Computer system 8200 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 8200 depicted in FIG. 82 is intended only as a specific example for purposes of illustrating the preferred implementations of the present invention. Many other configurations of computer system 8200 are possible having more or less components than the computer system depicted in FIG. 82.

Particular Implementations

We describe various implementations of neural network-based template generation and neural network-based base calling. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

Subpixel Base Calling

We disclose a computer-implemented method of determining metadata about analytes on a tile of a flow cell. The method includes accessing a series of image sets generated during a sequencing run, each image set in the series generated during a respective sequencing cycle of the sequencing run, each image in the series depicting the analytes and their surrounding background, and each image in the series having a plurality of subpixels. The method includes obtaining, from a base caller, a base call classifying each of the subpixels as one of four bases (A, C, T, and G), thereby producing a base call sequence for each of the subpixels across a plurality of sequencing cycles of the sequencing run. The method includes generating an analyte map that identifies the analytes as disjointed regions of contiguous subpixels which share a substantially matching base call sequence. The method includes determining spatial distribution of analytes, including their shapes and sizes based on the disjointed regions and storing the analyte map in memory for use as ground truth for training a classifier.

The method described in this section and other sections of the technology disclosed can include one or more of the following features and/or features described in connection with additional methods disclosed. In the interest of conciseness, the combinations of features disclosed in this application are not individually enumerated and are not repeated with each base set of features. The reader will understand how features identified in these implementations can readily be combined with sets of base features identified in other implementations.

In one implementation, the method includes identifying as background those subpixels in the analyte map that do not belong to any of the disjointed regions. In one implementation, the method includes obtaining, from the base caller, the base call classifying each of the subpixels as one of five bases (A, C, T, G, and N). In one implementation, the analyte map identifies analyte boundary portions between two contiguous subpixels whose base call sequences do not substantially match.

In one implementation, the method includes identifying origin subpixels at preliminary center coordinates of the analytes determined by the base caller, and breadth-first searching for substantially matching base call sequences by beginning with the origin subpixels and continuing with successively contiguous non-origin subpixels. In one implementation, the method includes, on an analyte-by-analyte basis, determining hyperlocated center coordinates of the analytes by calculating centers of mass of the disjointed regions of the analyte map as an average of coordinates of respective contiguous subpixels forming the disjointed regions, and storing the hyperlocated center coordinates of the analytes in the memory on the analyte-by-analyte basis for use as ground truth for training the classifier.

In one implementation, the method includes, on the analyte-by-analyte basis, identifying centers of mass subpixels in the disjointed regions of the analyte map at the hyperlocated center coordinates of the analytes, upsampling the analyte map using interpolation and storing the upsampled analyte map in the memory for use as ground truth for training the classifier, and, in the upsampled analyte map, on the analyte-by-analyte basis, assigning a value to each contiguous subpixel in the disjointed regions based on a decay factor that is proportional to distance of a contiguous subpixel from a center of mass subpixel in a disjointed region to which the contiguous subpixel belongs. In one implementation, the value is a intensity value normalized between zero and one. In one implementation, the method includes, in the upsampled analyte map, assigning a same predetermined value to all the subpixels identified as the background. In one implementation, the predetermined value is a zero intensity value.

In one implementation, the method includes generating a decay map from the upsampled analyte map that expresses the contiguous subpixels in the disjointed regions and the subpixels identified as the background based on their assigned values, and storing the decay map in the memory for use as ground truth for training the classifier. In one implementation, each subpixel in the decay map has a value normalized between zero and one. In one implementation, the method includes, in the upsampled analyte map, categorizing, on the analyte-by-analyte basis, the contiguous subpixels in the disjointed regions as analyte interior subpixels belonging to a same analyte, the centers of mass subpixels as analyte center subpixels, subpixels containing the analyte boundary portions as boundary subpixels, and the subpixels identified as the background as background subpixels, and storing the categorizations in the memory for use as ground truth for training the classifier.

In one implementation, the method includes, storing, on the analyte-by-analyte basis, coordinates of the analyte interior subpixels, the analyte center subpixels, the boundary subpixels, and the background subpixels in the memory for use as ground truth for training the classifier, downscaling the coordinates by a factor used to upsample the analyte map, and, storing, on the analyte-by-analyte basis, the downscaled coordinates in the memory for use as ground truth for training the classifier.

In one implementation, the method includes, in a binary ground truth data generated from the upsampled analyte map, using color coding to label the analyte center subpixels as belonging to an analyte center class and all other subpixels are belonging to a non-center class, and storing the binary ground truth data in the memory for use as ground truth for training the classifier. In one implementation, the method includes, in a ternary ground truth data generated from the upsampled analyte map, using color coding to label the background subpixels as belonging to a background class, the analyte center subpixels as belonging to an analyte center class, and the analyte interior subpixels as belonging to an analyte interior class, and storing the ternary ground truth data in the memory for use as ground truth for training the classifier.

In one implementation, the method includes generating analyte maps for a plurality of tiles of the flow cell, storing the analyte maps in memory and determining spatial distribution of analytes in the tiles based on the analyte maps, including their shapes and sizes, in the upsampled analyte maps of the analytes in the tiles, categorizing, on an analyte-by-analyte basis, subpixels as analyte interior subpixels belonging to a same analyte, analyte center subpixels, boundary subpixels, and background subpixels, storing the categorizations in the memory for use as ground truth for training the classifier, storing, on the analyte-by-analyte basis across the tiles, coordinates of the analyte interior subpixels, the analyte center subpixels, the boundary subpixels, and the background subpixels in the memory for use as ground truth for training the classifier, downscaling the coordinates by the factor used to upsample the analyte map, and, storing, on the analyte-by-analyte basis across the tiles, the downscaled coordinates in the memory for use as ground truth for training the classifier.

In one implementation, the base call sequences are substantially matching when a predetermined portion of base calls match on an ordinal position-wise basis. In one implementation, the base caller produces the base call sequences by interpolating intensity of the subpixels, including at least one of nearest neighbor intensity extraction, Gaussian based intensity extraction, intensity extraction based on average of 2×2 subpixel area, intensity extraction based on brightest of 2×2 subpixel area, intensity extraction based on average of 3×3 subpixel area, bilinear intensity extraction, bicubic intensity extraction, and/or intensity extraction based on weighted area coverage. In one implementation, the subpixels are identified to the base caller based on their integer or non-integer coordinates.

In one implementation, the method includes requiring that at least some of the disjointed regions have a predetermined minimum number of subpixels. In one implementation, the flow cell has at least one patterned surface with an array of wells that occupy the analytes. In such an implementation, the method includes, based on the determined shapes and sizes of the analytes, determining which ones of the wells are substantially occupied by at least one analyte, which ones of the wells are minimally occupied, and which ones of the wells are co-occupied by multiple analytes.

In one implementation, the flow cell has at least one nonpatterned surface and the analytes are unevenly scattered over the nonpatterned surface. In one implementation, the density of the analytes ranges from about 100,000 analytes/$mm^2$ to about 1,000,000 analytes/$mm^2$. In one implementation, the density of the analytes ranges from about 1,000,000 analytes/$mm^2$ to about 10,000,000 analytes/$mm^2$. In one implementation, the subpixels are quarter subpixels. In another implementation, the subpixels are half subpixels. In one implementation, the preliminary center coordinates of the analytes determined by the base caller are defined in a template image of the tile, and a pixel resolution, an image coordinate system, and measurement scales of the image coordinate system are same for the template image and the images. In one implementation, each image set has four images. In another implementation, each image set has two images. In yet another implementation, each image set has one image. In one implementation, the sequencing run utilizes four-channel chemistry. In another implementation, the sequencing run utilizes two-channel chemistry. In yet another implementation, the sequencing run utilizes one-channel chemistry.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

We disclose a computer-implemented method of determining metadata about analytes on a tile of a flow cell. The method includes accessing a set of images of the tile captured during a sequencing run and preliminary center coordinates of the analytes determined by a base caller. The method includes, for each image set, obtaining, from a base caller, a base call classifying, as one of four bases origin subpixels that contain the preliminary center coordinates and a predetermined neighborhood of contiguous subpixels that are successively contiguous to respective ones of the origin subpixels, thereby producing a base call sequence for each of the origin subpixels and for each of the predetermined neighborhood of contiguous subpixels. The method includes generating an analyte map that identifies the analytes as disjointed regions of contiguous subpixels that are successively contiguous to at least some of the respective ones of the origin subpixels and share a substantially matching base call sequence of the one of four bases with the at least some of the respective ones of the origin subpixels. The method includes storing the analyte map in memory and determining the shapes and the sizes of the analytes based on the disjointed regions in the analyte map.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the predetermined neighborhood of contiguous subpixels is a m×n subpixel patch centered at pixels containing the origin subpixels and the subpixel patch is 3×3 pixels. In one implementation, the predetermined neighborhood of contiguous subpixels is a n-connected subpixel neighborhood centered at pixels containing the origin subpixels. In one implementation, the method includes, identifying as background those subpixels in the analyte map that do not belong to any of the disjointed regions.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Training Data Generation

We disclose a computer-implemented method of generating training data for neural network-based template generation and base calling. The method includes accessing a multitude of images of a flow cell captured over a plurality of cycles of a sequencing run, the flow cell having a plurality of tiles and, in the multitude of images, each of the tiles having a sequence of image sets generated over the plurality of cycles, and each image in the sequence of image sets depicting intensity emissions of analytes and their surrounding background on a particular one of the tiles at a particular one the cycles. The method includes constructing a training set having a plurality of training examples, each training example corresponding to a particular one of the tiles and including image data from at least some image sets in the sequence of image sets of the particular one of the tiles. The method includes generating at least one ground truth data representation for each of the training examples, the ground truth data representation identifying at least one of spatial distribution of analytes and their surrounding background on the particular one of the tiles whose intensity emissions are depicted by the image data, including at least one of analyte shapes, analyte sizes, and/or analyte boundaries, and/or centers of the analytes.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the image data includes images in each of the at least some image sets in the sequence of image sets of the particular one of the tiles, and the images have a resolution of 1800×1800. In one implementation, the image data includes at least one image patch from each of the images, and the image patch covers a portion of the particular one of the tiles and has a resolution of 20×20. In one implementation, the image data includes an upsampled representation of the image patch, and the upsampled representation has a resolution of 80×80. In one implementation, the ground truth data representation has an upsampled resolution of 80×80.

In one implementation, multiple training examples correspond to a same particular one of the tiles and respectively include as image data different image patches from each image in each of at least some image sets in a sequence of image sets of the same particular one of the tiles, and at least some of the different image patches overlap with each other. In one implementation, the ground truth data representation identifies the analytes as disjoint regions of adjoining subpixels, the centers of the analytes as centers of mass subpixels within respective ones of the disjoint regions, and their surrounding background as subpixels that do not belong to any of the disjoint regions. In one implementation, the ground truth data representation uses color coding to identify each subpixel as either being a analyte center or a non-center. In one implementation, the ground truth data representation uses color coding to identify each subpixel as either being analyte interior, analyte center, or surrounding background.

In one implementation, the method includes, storing, in memory, the training examples in the training set and associated ground truth data representations as the training data for the neural network-based template generation and base calling. In one implementation, the method includes generating the training data for a variety of flow cells, sequencing instruments, sequencing protocols, sequencing chemistries, sequencing reagents, and analyte densities.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Metadata & Base Calls Generation

In one implementation, a method includes accessing sequencing images of analytes produced by a sequencer, generating training data from the sequencing images, and using the training data for training a neural network to generate metadata about the analytes. Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

In one implementation, a method includes accessing sequencing images of analytes produced by a sequencer, generating training data from the sequencing images, and using the training data for training a neural network to base call the analytes. Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Regression Model

We disclose a computer-implemented method of identifying analytes on a tile of a flow cell and related analyte metadata. The method includes processing input image data from a sequence of image sets through a neural network and generating an alternative representation of the input image data. Each image in the sequence of image sets covers the tile, and depicts intensity emissions of analytes on the tile and their surrounding background captured for a particular image channel at a particular one of a plurality of sequencing cycles of a sequencing run performed on the flow cell. The method includes processing the alternative representation through an output layer and generating an output that identifies analytes, whose intensity emissions are depicted by the input image data, as disjoint regions of adjoining subpixels, centers of the analytes as center subpixels at centers of mass of the respective ones of the disjoint regions, and their surrounding background as background subpixels not belonging to any of the disjoint regions.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the adjoining subpixels in the respective ones of the disjoint regions have intensity values weighted according to distance of an adjoining subpixel from a center subpixel in a disjoint region to which the adjoining subpixel belongs. In one implementation, the center subpixels have highest intensity values within the respective ones of the disjoint regions. In one implementation, the background subpixels all have a same lowest intensity value in the output. In one implementation, the output layer normalizes the intensity values between zero and one.

In one implementation, the method includes applying a peak locator to the output to find peak intensities in the output, determining location coordinates of the centers of the analytes based on the peak intensities, downscaling the location coordinates by an upsampling factor used to prepare the input image data, and storing the downscaled location coordinates in memory for use in base calling the analytes. In one implementation, the method includes categorizing the adjoining subpixels in the respective ones of the disjoint regions as analyte interior subpixels belonging to a same analyte, and storing the categorization and downscaled location coordinates of the analyte interior subpixels in the memory on an analyte-by-analyte basis for use in base calling the analytes. In one implementation, the method includes, on the analyte-by-analyte basis, determining distances of the analyte interior subpixels from respective ones of the centers of the analytes, and storing the distances in the memory on the analyte-by-analyte basis for use in base calling the analytes.

In one implementation, the method includes extracting intensities from the analyte interior subpixels in the respective ones of the disjoint regions, including using at least one of nearest neighbor intensity extraction, Gaussian based intensity extraction, intensity extraction based on average of 2×2 subpixel area, intensity extraction based on brightest of 2×2 subpixel area, intensity extraction based on average of 3×3 subpixel area, bilinear intensity extraction, bicubic intensity extraction, and/or intensity extraction based on weighted area coverage, and storing the intensities in the memory on the analyte-by-analyte basis for use in base calling the analytes.

In one implementation, the method includes based on the disjoint regions, determining, as part of the related analyte metadata, spatial distribution of the analytes, including at least one of analyte shapes, analyte sizes, and/or analyte boundaries, and storing the related analyte metadata in the memory on the analyte-by-analyte basis for use in base calling the analytes.

In one implementation, the input image data includes images in the sequence of image sets, and the images have a resolution of 3000×3000. In one implementation, the input image data includes at least one image patch from each of the images in the sequence of image sets, and the image patch covers a portion of the tile and has a resolution of 20×20. In one implementation, the input image data includes an upsampled representation of the image patch from each of the images in the sequence of image sets, and the upsampled representation has a resolution of 80×80. In one implementation, the output has an upsampled resolution of 80×80.

In one implementation, the neural network is a deep fully convolutional segmentation neural network with an encoder subnetwork and a corresponding decoder network, the encoder subnetwork includes a hierarchy of encoders, and the decoder subnetwork includes a hierarchy of decoders that map low resolution encoder feature maps to full input resolution feature maps. In one implementation, the density of the analytes ranges from about 100,000 analytes/$mm^2$ to about 1,000,000 analytes/$mm^2$. In another implementation, the density of the analytes ranges from about 1,000,000 analytes/$mm^2$ to about 10,000,000 analytes/$mm^2$.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Training Regression Model

We disclose a computer-implemented method of training a neural network to identify analytes and related analyte metadata. The method includes obtaining training data for training the neural network. The training data includes a plurality of training examples and corresponding ground truth data that should be generated by the neural network by processing the training examples. Each training example includes image data from a sequence of image sets. Each image in the sequence of image sets covers a tile of a flow cell and depicts intensity emissions of analytes on the tile and their surrounding background captured for a particular image channel at a particular one of a plurality of sequencing cycles of a sequencing run performed on the flow cell. Each ground truth data identifies analytes, whose intensity emissions are depicted by the image data of a corresponding training example, as disjoint regions of adjoining subpixels, centers of the analytes as center subpixels at centers of mass of the respective ones of the disjoint regions, and their surrounding background as background subpixels not belonging to any of the disjoint regions. The method includes using a gradient descent training technique to train the neural network and generating outputs for the training examples that progressively match the ground truth data, including iteratively optimizing a loss function that minimizes error between the outputs and the ground truth data, and updating parameters of the neural network based on the error.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes, upon error convergence after a final iteration, storing the updated parameters of the neural network in memory to be applied to further neural network-based template generation and base calling. In one implementation, in the ground truth data, the adjoining subpixels in the respective ones of the disjoint regions have intensity values weighted according to distance of an adjoining subpixel from a center subpixel in a disjoint region to which the adjoining subpixel belongs. In one implementation, in the ground truth data, the center subpixels have highest intensity values within the respective ones of the disjoint regions. In one implementation, in the ground truth data, the background subpixels all have a same lowest intensity value in the output. In one implementation, in the ground truth data, the intensity values are normalized between zero and one.

In one implementation, the loss function is mean squared error and the error is minimized on a subpixel-basis between the normalized intensity values of corresponding subpixels in the outputs and the ground truth data. In one implementation, the ground truth data identify, as part of the related analyte metadata, spatial distribution of the analytes, including at least one of analyte shapes, analyte sizes, and/or analyte boundaries. In one implementation, the image data includes images in the sequence of image sets, and the images have a resolution of 1800×1800. In one implementation, the image data includes at least one image patch from each of the images in the sequence of image sets, and the image patch covers a portion of the tile and has a resolution of 20×20. In one implementation, the image data includes an upsampled representation of the image patch from each of the images in the sequence of image sets, and the upsampled representation of the image patch has a resolution of 80×80.

In one implementation, in the training data, multiple training examples respectively include as image data different image patches from each image in a sequence of image sets of a same tile, and at least some of the different image patches overlap with each other. In one implementation, the ground truth data has an upsampled resolution of 80×80. In one implementation, the training data includes training examples for a plurality of tiles of the flow cell. In one implementation, the training data includes training examples for a variety of flow cells, sequencing instruments, sequencing protocols, sequencing chemistries, sequencing reagents, and analyte densities. In one implementation, the neural network is a deep fully convolutional segmentation neural network with an encoder subnetwork and a corresponding decoder network, the encoder subnetwork includes a hierarchy of encoders, and the decoder subnetwork includes a hierarchy of decoders that map low resolution encoder feature maps to full input resolution feature maps for subpixel-wise classification by a final classification layer.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Neural Network-Based Template Generator

We disclose a computer-implemented method of determining metadata about analytes on a flow cell. The method includes accessing image data that depicts intensity emissions of the analytes, processing the image data through one or more layers of a neural network and generating an alternative representation of the image data, and processing the alternative representation through an output layer and generating an output that identifies at least one of shapes and sizes of the analytes and/or centers of the analytes.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the image data further depicts intensity emissions of surrounding background of the analytes. In such an implementation, the method includes the output identifying spatial distribution of the analytes on the flow cell, including the surrounding background and boundaries between the analytes. In one implementation, the method includes determining center location coordinates of the analytes on the flow cell based on the output. In one implementation, the neural network is a convolutional neural network. In one implementation, the neural network is a recurrent neural network. In one implementation, the neural network is a deep fully convolutional segmentation neural network with an encoder subnetwork and a corresponding decoder network, followed by the output layer, the encoder subnetwork includes a hierarchy of encoders, and the decoder subnetwork includes a hierarchy of decoders that map low resolution encoder feature maps to full input resolution feature maps.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Binary Classification Model

We disclose a computer-implemented method of identifying analytes on a tile of a flow cell and related analyte metadata. The method includes processing input image data from a sequence of image sets through a neural network and generating an alternative representation of the image data. In one implementation, each image in the sequence of image sets covers the tile, and depicts intensity emissions of analytes on the tile and their surrounding background captured for a particular image channel at a particular one of a plurality of sequencing cycles of a sequencing run performed on the flow cell. The method includes processing the alternative representation through a classification layer and generating an output that identifies centers of analytes whose intensity emissions are depicted by the input image data. The output has a plurality of subpixels, and each subpixel in the plurality of subpixels is classified as either an analyte center or a non-center.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the classification layer assigns each subpixel in the output a first likelihood score of being the analyte center, and a second likelihood score of being the non-center. In one implementation, the first and second likelihood scores are determined based on a softmax function and exponentially normalized between zero and one. In one implementation, the first and second likelihood scores are determined based on a sigmoid function and normalized between zero and one. In one implementation, each subpixel in the output is classified as either the analyte center or the non-center based on which one of the first and second likelihood scores is higher than the other. In one implementation, each subpixel in the output is classified as either the analyte center or the non-center based on whether the first and second likelihood scores are above a predetermined threshold likelihood score. In one implementation, the output identifies the centers at centers of mass of respective ones of the analytes. In one implementation, in the output, subpixels classified as analyte centers are assigned a same first predetermined value, and subpixels classified as non-centers are all assigned a same second predetermined value. In one implementation, the first and second predetermined values are intensity values. In one implementation, the first and second predetermined values are continuous values.

In one implementation, the method includes determining location coordinates of subpixels classified as analyte centers, downscaling the location coordinates by an upsampling factor used to prepare the input image data, and storing the downscaled location coordinates in memory for use in base calling the analytes. In one implementation, the input image data includes images in the sequence of image sets, and the images have a resolution of 3000×3000. In one implementation, the input image data includes at least one image patch from each of the images in the sequence of image sets, and the image patch covers a portion of the tile and has a resolution of 20×20. In one implementation, the input image data includes an upsampled representation of the image patch from each of the images in the sequence of image sets, and the upsampled representation has a resolution of 80×80. In one implementation, the output has an upsampled resolution of 80×80.

In one implementation, the neural network is a deep fully convolutional segmentation neural network with an encoder subnetwork and a corresponding decoder network, followed by the classification layer, the encoder subnetwork includes a hierarchy of encoders, and the decoder subnetwork includes a hierarchy of decoders that map low resolution encoder feature maps to full input resolution feature maps for subpixel-wise classification by the classification layer. In one implementation, the density of the analytes ranges from about 100,000 analytes/mm$^2$ to about 1,000,000 analytes/mm$^2$. In another implementation, the density of the analytes ranges from about 1,000,000 analytes/mm$^2$ to about 10,000,000 analytes/mm$^2$.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Training Binary Classification Model

We disclose a computer-implemented method of training a neural network to identify analytes and related analyte metadata. The method includes obtaining training data for training the neural network. The training data includes a plurality of training examples and corresponding ground truth data that should be generated by the neural network by processing the training examples. Each training example includes image data from a sequence of image sets. Each image in the sequence of image sets covers a tile of a flow cell and depicts intensity emissions of analytes on the tile and their surrounding background captured for a particular image channel at a particular one of a plurality of sequencing cycles of a sequencing run performed on the flow cell. Each ground truth data identifies centers of analytes, whose intensity emissions are depicted by the image data of a corresponding training example. The ground truth data has a plurality of subpixels, and each subpixel in the plurality of subpixels is classified as either an analyte center or a non-center. The method includes using a gradient descent training technique to train the neural network and generating outputs for the training examples that progressively match the ground truth data, including iteratively optimizing a loss function that minimizes error between the outputs and the ground truth data, and updating parameters of the neural network based on the error.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes, upon error convergence after a final iteration, storing the updated parameters of the neural network in memory to be applied to further neural network-based template generation and base calling. In one implementation, in the ground truth data, subpixels classified as analyte centers are all assigned a same first predetermined class score, and subpixels classified as non-centers are all assigned a same second predetermined class score. In one implementation, in each output, each subpixel has a first prediction score of being the analyte center, and a second prediction score of being the non-center. In one implementation, the loss function is custom weighted binary cross entropy loss and the error is minimized on a subpixel-basis between the prediction scores and the class scores of corresponding subpixels in the outputs and the ground truth data. In one implementation, the ground truth data identifies the centers at centers of mass of respective ones of the analytes. In one implementation, in the ground truth data, subpixels classified as analyte centers are all assigned a same first predetermined value, and subpixels classified as non-centers are all assigned a same second predetermined value. In one implementation, the first and second predetermined values are intensity values. In another implementation, the first and second predetermined values are continuous values.

In one implementation, the ground truth data identify, as part of the related analyte metadata, spatial distribution of the analytes, including at least one of analyte shapes, analyte sizes, and/or analyte boundaries. In one implementation, the image data includes images in the sequence of image sets, and the images have a resolution of 1800×1800. In one implementation, the image data includes at least one image patch from each of the images in the sequence of image sets, and the image patch covers a portion of the tile and has a resolution of 20×20. In one implementation, the image data includes an upsampled representation of the image patch from each of the images in the sequence of image sets, and the upsampled representation of the image patch has a resolution of 80×80. In one implementation, in the training data, multiple training examples respectively include as image data different image patches from each image in a sequence of image sets of a same tile, and at least some of the different image patches overlap with each other. In one implementation, the ground truth data has an upsampled resolution of 80×80. In one implementation, the training data includes training examples for a plurality of tiles of the flow cell. In one implementation, the training data includes training examples for a variety of flow cells, sequencing instruments, sequencing protocols, sequencing chemistries, sequencing reagents, and analyte densities. In one implementation, the neural network is a deep fully convolutional segmentation neural network with an encoder subnetwork and a corresponding decoder network, followed by a classification layer, the encoder subnetwork includes a hierarchy of encoders, and the decoder subnetwork includes a hierarchy of decoders that map low resolution encoder feature maps to full input resolution feature maps for subpixel-wise classification by the classification layer.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Ternary Classification Model

We disclose a computer-implemented method of identifying analytes on a tile of a flow cell and related analyte metadata. The method includes processing input image data from a sequence of image sets through a neural network and generating an alternative representation of the image data. Each image in the sequence of image sets covers the tile, and depicts intensity emissions of analytes on the tile and their surrounding background captured for a particular image channel at a particular one of a plurality of sequencing cycles of a sequencing run performed on the flow cell. The method includes processing the alternative representation through a classification layer and generating an output that identifies spatial distribution of analytes and their surrounding background whose intensity emissions are depicted by the input image data, including at least one of analyte centers, analyte shapes, analyte sizes, and/or analyte boundaries. The output has a plurality of subpixels, and each subpixel in the plurality of subpixels is classified as either background, analyte center, or analyte interior.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the classification layer assigns each subpixel in the output a first likelihood score of being the background, a second likelihood score of being the analyte center, and a third likelihood score of being the analyte interior. In one implementation, the first, second, and third likelihood scores are determined based on a softmax function and exponentially normalized between zero and one. In one implementation, each subpixel in the output is classified as either the background, the analyte center, or the analyte interior based on which one among the first, second, and third likelihood scores is highest. In one implementation, each subpixel in the output is classified as either the background, the analyte center, or the analyte interior based on whether the first, second, and third likelihood scores are above a predetermined threshold likelihood score. In one implementation, the output identifies the analyte centers at centers of mass of respective ones of the analytes. In one implementation, in the output, subpixels classified as background are all assigned a same first predetermined value, subpixels classified as analyte centers are all assigned a same second predetermined value, and subpixels classified as analyte interior are all assigned a same third predetermined value. In one implementation, the first, second, and third predetermined values are intensity values. In one implementation, the first, second, and third predetermined values are continuous values.

In one implementation, the method includes determining location coordinates of subpixels classified as analyte centers on an analyte-by-analyte basis, downscaling the location coordinates by an upsampling factor used to prepare the input image data, and storing the downscaled location coordinates in memory on the analyte-by-analyte basis for use in base calling the analytes. In one implementation, the method includes determining location coordinates of subpixels classified as analyte interior on the analyte-by-analyte basis, downscaling the location coordinates by an upsampling factor used to prepare the input image data, and storing the downscaled location coordinates in memory on the analyte-by-analyte basis for use in base calling the analytes. In one implementation, the method includes, on the analyte-by-analyte basis, determining distances of the subpixels classified as analyte interior from respective ones of the subpixels classified as analyte centers, and storing the distances in the memory on the analyte-by-analyte basis for use in base calling the analytes. In one implementation, the method includes, on the analyte-by-analyte basis, extracting intensities from the subpixels classified as analyte interior, including using at least one of nearest neighbor intensity extraction, Gaussian based intensity extraction, intensity extraction based on average of 2×2 subpixel area, intensity extraction based on brightest of 2×2 subpixel area, intensity extraction based on average of 3×3 subpixel area, bilinear intensity extraction, bicubic intensity extraction, and/or intensity extraction based on weighted area coverage, and storing the intensities in the memory on the analyte-by-analyte basis for use in base calling the analytes.

In one implementation, the input image data includes images in the sequence of image sets, and the images have a resolution of 3000×3000. In one implementation, the input image data includes at least one image patch from each of the images in the sequence of image sets, and the image patch covers a portion of the tile and has a resolution of 20×20. In one implementation, the input image data includes an upsampled representation of the image patch from each of the images in the sequence of image sets, and the upsampled representation has a resolution of 80×80. In one implementation, the output has an upsampled resolution of 80×80. In one implementation, the neural network is a deep fully convolutional segmentation neural network with an encoder subnetwork and a corresponding decoder network, followed by the classification layer, the encoder subnetwork includes a hierarchy of encoders, and the decoder subnetwork includes a hierarchy of decoders that map low resolution encoder feature maps to full input resolution feature maps for subpixel-wise classification by the classification layer. In one implementation, the density of the analytes ranges from about 100,000 analytes/mm$^2$ to about 1,000,000 analytes/mm$^2$. In another implementation, the density of the analytes ranges from about 1,000,000 analytes/mm$^2$ to about 10,000,000 analytes/mm$^2$.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Training Ternary Classification Model

We disclose a computer-implemented method of training a neural network to identify analytes and related analyte metadata. The method includes obtaining training data for training the neural network. The training data includes a plurality of training examples and corresponding ground truth data that should be generated by the neural network by processing the training examples. Each training example includes image data from a sequence of image sets. Each image in the sequence of image sets covers a tile of a flow cell and depicts intensity emissions of analytes on the tile and their surrounding background captured for a particular image channel at a particular one of a plurality of sequencing cycles of a sequencing run performed on the flow cell. Each ground truth data identifies spatial distribution of analytes and their surrounding background whose intensity emissions are depicted by the input image data, including analyte centers, analyte shapes, analyte sizes, and analyte boundaries. The ground truth data has a plurality of subpixels, and each subpixel in the plurality of subpixels is classified as either background, analyte center, or analyte interior. The method includes using a gradient descent training technique to train the neural network and generating outputs for the training examples that progressively match the ground truth data, including iteratively optimizing a loss function that minimizes error between the outputs and the ground truth data, and updating parameters of the neural network based on the error.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes, upon error convergence after a final iteration, storing the updated parameters of the neural network in memory to be applied to further neural network-based template generation and base calling. In one implementation, in the ground truth data, subpixels classified as background are all assigned a same first predetermined class score, subpixels classified as analyte centers are all assigned a same second predetermined class score, and subpixels classified as analyte interior are all assigned a same third predetermined class score.

In one implementation, in each output, each subpixel has a first prediction score of being the background, a second prediction score of being the analyte center, and a third prediction score of being the analyte interior. In one implementation, the loss function is custom weighted ternary cross entropy loss and the error is minimized on a subpixel-basis between the prediction scores and the class scores of corresponding subpixels in the outputs and the ground truth data. In one implementation, the ground truth data identifies the analyte centers at centers of mass of respective ones of the analytes. In one implementation, in the ground truth data, subpixels classified as background are all assigned a same first predetermined value, subpixels classified as analyte centers are all assigned a same second predetermined value, and subpixels classified as analyte interior are all assigned a same third predetermined value. In one implementation, the first, second, and third predetermined values are intensity values. In one implementation, the first, second, and third predetermined values are continuous values. In one implementation, the image data includes images in the sequence of image sets, and the images have a resolution of 1800×1800. In one implementation, the image data includes images in the sequence of image sets, and the images have a resolution of 1800×1800.

In one implementation, the image data includes at least one image patch from each of the images in the sequence of image sets, and the image patch covers a portion of the tile and has a resolution of 20×20. In one implementation, the image data includes an upsampled representation of the image patch from each of the images in the sequence of image sets, and the upsampled representation of the image patch has a resolution of 80×80. In one implementation, in the training data, multiple training examples respectively include as image data different image patches from each image in a sequence of image sets of a same tile, and at least some of the different image patches overlap with each other. In one implementation, the ground truth data has an upsampled resolution of 80×80. In one implementation, the training data includes training examples for a plurality of tiles of the flow cell. In one implementation, the training data includes training examples for a variety of flow cells, sequencing instruments, sequencing protocols, sequencing chemistries, sequencing reagents, and analyte densities. In one implementation, the neural network is a deep fully convolutional segmentation neural network with an encoder subnetwork and a corresponding decoder network, followed by a classification layer, the encoder subnetwork includes a hierarchy of encoders, and the decoder subnetwork includes a hierarchy of decoders that map low resolution encoder feature maps to full input resolution feature maps for sub-pixel-wise classification by the classification layer.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Segmentation

We disclose a computer-implemented method of determining analyte metadata. The method includes processing input image data derived from a sequence of image sets through a neural network and generating an alternative representation of the input image data. The input image data has an array of units that depicts analytes and their surrounding background. The method includes processing the alternative representation through an output layer and generating an output value for each unit in the array. The method includes thresholding output values of the units and classifying a first subset of the units as background units depicting the surrounding background. The method includes locating peaks in the output values of the units and classifying a second subset of the units as center units containing centers of the analytes. The method includes applying a segmenter to the output values of the units and determining shapes of the analytes as non-overlapping regions of contiguous units separated by the background units and centered at the center units. The segmenter begins with the center units and determines, for each center unit, a group of successively contiguous units that depict a same analyte whose center is contained in the center unit.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the units are pixels. In another implementation, the units are subpixels. In yet another implementation, the units are superpixels. In one implementation, the output values are continuous values. In another implementation, the output values are softmax scores. In one implementation, the contiguous units in the respective ones of the non-overlapping regions have output values weighted according to distance of a contiguous unit from a center unit in a non-overlapping region to which the contiguous unit belongs. In one implementation, the center units have highest output values within the respective ones of the non-overlapping regions.

In one implementation, the non-overlapping regions have irregular contours and the units are subpixels. In such an implementation, the method includes determining analyte intensity of a given analyte by identifying subpixels that contribute to the analyte intensity of the given analyte based on a corresponding non-overlapping region of contiguous subpixels that identifies a shape of the given analyte, locating the identified subpixels in one or more optical, pixel-resolution images generated for one or more image channels at a current sequencing cycle, in each of the images, interpolating intensities of the identified subpixels, combining the interpolated intensities, and normalizing the combined interpolated intensities to produce a per-image analyte intensity for the given analyte in each of the images, and combining the per-image analyte intensity for each of the images to determine the analyte intensity of the given analyte at the current sequencing cycle. In one implementation, the normalizing is based on a normalization factor, and the normalization factor is a number of the identified subpixels. In one implementation, the method includes base calling the given analyte based on the analyte intensity at the current sequencing cycle.

In one implementation, the non-overlapping regions have irregular contours and the units are subpixels. In such an implementation, the method includes determining analyte intensity of a given analyte by identifying subpixels that contribute to the analyte intensity of the given analyte based on a corresponding non-overlapping region of contiguous subpixels that identifies a shape of the given analyte, locating the identified subpixels in one or more subpixel resolution images upsampled from corresponding optical, pixel-resolution images generated for one or more image channels at a current sequencing cycle, in each of the upsampled images, combining intensities of the identified subpixels and normalizing the combined intensities to produce a per-image analyte intensity for the given analyte in each of the upsampled images, and combining the per-image analyte intensity for each of the upsampled images to determine the analyte intensity of the given analyte at the current sequencing cycle. In one implementation, the normalizing is based on a normalization factor, and the normalization factor is a number of the identified subpixels. In one implementation, the method includes base calling the given analyte based on the analyte intensity at the current sequencing cycle.

In one implementation, each image in the sequence of image sets covers a tile, and depicts intensity emissions of analytes on a tile and their surrounding background captured for a particular image channel at a particular one of a plurality of sequencing cycles of a sequencing run performed on a flow cell. In one implementation, the input image data includes at least one image patch from each of the images in the sequence of image sets, and the image patch covers a portion of the tile and has a resolution of 20×20. In one implementation, the input image data includes an upsampled, subpixel resolution representation of the image patch from each of the images in the sequence of image sets, and the upsampled, subpixel representation has a resolution of 80×80.

In one implementation, the neural network is a convolutional neural network. In another implementation, the neural network is a recurrent neural network. In yet another implementation, the neural network is a residual neural network with residual bocks and residual connections. In yet further implementation, the neural network is a deep fully convolutional segmentation neural network with an encoder subnetwork and a corresponding decoder network, the encoder subnetwork includes a hierarchy of encoders, and the decoder subnetwork includes a hierarchy of decoders that map low resolution encoder feature maps to full input resolution feature maps.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Peak Detection

We disclose a computer-implemented method of determining analyte metadata. The method includes processing input image data derived from a sequence of image sets through a neural network and generating an alternative representation of the input image data. The input image data has an array of units that depicts analytes and their surrounding background. The method includes processing the alternative representation through an output layer and generating an output value for each unit in the array. The method includes thresholding output values of the units and classifying a first subset of the units as background units depicting the surrounding background. The method includes locating peaks in the output values of the units and classifying a second subset of the units as center units containing centers of the analytes.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the method includes applying a segmenter to the output values of the units and determining shapes of the analytes as non-overlapping regions of contiguous units separated by the background units and centered at the center units. The segmenter begins with the center units and determines, for each center unit, a group of successively contiguous units that depict a same analyte whose center is contained in the center unit.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Neural Network-Based Analyte Metadata Generator

In one implementation, a method includes processing image data through a neural network and generating an alternative representation of the image data. The image data depicts intensity emissions of analytes. The method includes processing the alternative representation through an output layer and generating an output that identifies metadata about the analytes, including at least one of spatial distribution of the analytes, shapes of the analytes, centers of the analytes, and/or boundaries between the analytes. Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Units-Based Regression Model

We disclose a computer-implemented method of identifying analytes on a tile of a flow cell and related analyte metadata. The method includes processing input image data from a sequence of image sets through a neural network and generating an alternative representation of the input image data. Each image in the sequence of image sets covers the tile, and depicts intensity emissions of analytes on the tile and their surrounding background captured for a particular image channel at a particular one of a plurality of sequencing cycles of a sequencing run performed on the flow cell. The method includes processing the alternative representation through an output layer and generating an output that identifies analytes, whose intensity emissions are depicted by the input image data, as disjoint regions of adjoining units, centers of the analytes as center units at centers of mass of the respective ones of the disjoint regions, and their surrounding background as background units not belonging to any of the disjoint regions.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the units are pixels. In another implementation, the units are subpixels. In yet another implementation, the units are superpixels. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Units-Based Binary Classification Model

We disclose a computer-implemented method of identifying analytes on a tile of a flow cell and related analyte metadata. The method includes processing input image data from a sequence of image sets through a neural network and generating an alternative representation of the image data. Each image in the sequence of image sets covers the tile, and depicts intensity emissions of analytes on the tile and their surrounding background captured for a particular image channel at a particular one of a plurality of sequencing cycles of a sequencing run performed on the flow cell. The method includes processing the alternative representation through a classification layer and generating an output that identifies centers of analytes whose intensity emissions are depicted by the input image data. The output has a plurality of units, and each unit in the plurality of units is classified as either an analyte center or a non-center.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the units are pixels. In another implementation, the units are subpixels. In yet another implementation, the units are superpixels. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

Units-Based Ternary Classification Model

We disclose a computer-implemented method of identifying analytes on a tile of a flow cell and related analyte metadata. The method includes processing input image data from a sequence of image sets through a neural network and generating an alternative representation of the image data. Each image in the sequence of image sets covers the tile, and depicts intensity emissions of analytes on the tile and their surrounding background captured for a particular image channel at a particular one of a plurality of sequencing cycles of a sequencing run performed on the flow cell. The method includes processing the alternative representation through a classification layer and generating an output that identifies spatial distribution of analytes and their surrounding background whose intensity emissions are depicted by the input image data, including at least one of analyte centers, analyte shapes, analyte sizes, and/or analyte boundaries. The output has a plurality of units, and each unit in the plurality of units is classified as either background, analyte center, or analyte interior.

Each of the features discussed in the particular implementation section for other implementations apply equally to this implementation. As indicated above, all the other features are not repeated here and should be considered repeated by reference. The reader will understand how features identified in these implementations can readily be combined with sets of base features identified in other implementations.

In one implementation, the units are pixels. In another implementation, the units are subpixels. In yet another implementation, the units are superpixels. Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

CLAUSES

We disclose the following clauses:

Clauses Set 1

1. A computer-implemented method of determining image regions indicative of analytes on a tile of a flow cell, the method comprising:

accessing a series of image sets generated during a sequencing run, each image set in the series generated during a respective sequencing cycle of the sequencing run, each image in the series depicting the analytes and their surrounding background, and each image in the series having a plurality of subpixels;

obtaining, from a base caller, a base call classifying each of the subpixels, thereby producing a base call sequence for each of the subpixels across a plurality of sequencing cycles of the sequencing run;

determining a plurality of disjointed regions of contiguous subpixels which share a substantially matching base call sequence; and generating an analyte map identifying the determined disjointed regions.

2. The computer-implemented method of clause 1, further including:

training a classifier based upon the determined plurality of disjointed regions of contiguous subpixels, the classifier being a neural network-based template generator for processing input image data to generate a decay map, a ternary map, or a binary map, representing one or more properties of each of a plurality of analytes represented in the input image data for base calling by a neural network-based base caller, preferably in order to increase the level of throughput in high-throughput nucleic acid sequencing technologies.

3. The computer-implemented method of any of clauses 1-2, further including:

generating the analyte map by identifying as background those subpixels that do not belong to any of the disjointed regions.

4. The computer-implemented method of any of clauses 1-3, wherein the analyte map identifies analyte boundary portions between two contiguous subpixels whose base call sequences do not substantially match.

5. The computer-implemented method of any of clauses 1-4, wherein the determining the plurality of disjointed regions of contiguous subpixels further includes:

identifying origin subpixels at preliminary center coordinates of the analytes determined by the base caller; and breadth-first searching for substantially matching base call sequences by beginning with the origin subpixels and continuing with successively contiguous non-origin subpixels.

6. The computer-implemented method of any of clauses 1-5, further including:

determining hyperlocated center coordinates of the analytes by calculating centers of mass of the disjointed regions of the analyte map as an average of coordinates of respective contiguous subpixels forming the disjointed regions; and storing the hyperlocated center coordinates of the analytes in the memory for use as ground truth for training the classifier.

7. The computer-implemented method of clause 6, further including:

identifying centers of mass subpixels in the disjointed regions of the analyte map at the hyperlocated center coordinates of the analytes;

upsampling the analyte map using interpolation and storing the upsampled analyte map in the memory for use as ground truth for training the classifier; and in the upsampled analyte map, assigning a value to each contiguous subpixel in the disjointed regions based on a decay factor that is proportional to distance of a contiguous subpixel from a center of mass subpixel in a disjointed region to which the contiguous subpixel belongs.

8. The computer-implemented method of clause 7, the method more preferably further including:

generating the decay map from the upsampled analyte map that expresses the contiguous subpixels in the disjointed regions and the subpixels identified as the background based on their assigned values; and storing the decay map in the memory for use as ground truth for training the classifier.

9. The computer-implemented method of clause 8, the method even more preferably further including:

in the upsampled analyte map, categorizing, on the analyte-by-analyte basis, the contiguous subpixels in the disjointed regions as analyte interior subpixels belonging to a same analyte, the centers of mass subpixels as analyte center subpixels, subpixels containing the analyte boundary portions as boundary subpixels, and the subpixels identified as the background as background subpixels; and storing the categorizations in the memory for use as ground truth for training the classifier.

10. The computer-implemented method of any of clauses 1-9, further including:

storing, on the analyte-by-analyte basis, coordinates of the analyte interior subpixels, the analyte center subpixels, the boundary subpixels, and the background subpixels in the memory for use as ground truth for training the classifier;

downscaling the coordinates by a factor used to upsample the analyte map; and storing, on the analyte-by-analyte basis, the downscaled coordinates in the memory for use as ground truth for training the classifier.

11. The computer-implemented method of any of clauses 1-10, further including:

in a binary ground truth data generated from the upsampled analyte map, using color coding to label the analyte center subpixels as belonging to an analyte center class and all other subpixels are belonging to a non-center class; and storing the binary ground truth data in the memory for use as ground truth for training the classifier.

12. The computer-implemented method of any of clauses 1-11, further including:

in a ternary ground truth data generated from the upsampled analyte map, using color coding to label the background subpixels as belonging to a background class, the analyte center subpixels as belonging to an analyte center class, and the analyte interior subpixels as belonging to an analyte interior class; and storing the ternary ground truth data in the memory for use as ground truth for training the classifier.

13. The computer-implemented method of any of clauses 1-12, further including:

generating analyte maps for a plurality of tiles of the flow cell;

storing the analyte maps in memory and determining spatial distribution of analytes in the tiles based on the analyte maps, including their shapes and sizes;

in the upsampled analyte maps of the analytes in the tiles, categorizing, on an analyte-by-analyte basis, subpixels as analyte interior subpixels belonging to a same analyte, analyte center subpixels, boundary subpixels, and background subpixels;

storing the categorizations in the memory for use as ground truth for training the classifier;

storing, on the analyte-by-analyte basis across the tiles, coordinates of the analyte interior subpixels, the analyte center subpixels, the boundary subpixels, and the background subpixels in the memory for use as ground truth for training the classifier;

downscaling the coordinates by the factor used to upsample the analyte map; and storing, on the analyte-by-analyte basis across the tiles, the downscaled coordinates in the memory for use as ground truth for training the classifier.

14. The computer-implemented method of any of clauses 1-13, wherein the base call sequences are substantially matching when a predetermined portion of base calls match on an ordinal position-wise basis.

15. The computer-implemented method of any of clauses 1-14, wherein the determining the plurality of disjointed regions of contiguous subpixels which share a substantially matching base call sequence is based upon a predetermined minimum number of subpixels for a disjointed region.

16. The computer-implemented method of any of clauses 1-15, wherein the flow cell has at least one patterned surface with an array of wells that occupy the analytes, further including:

based on the determined shapes and sizes of the analytes, determining which ones of the wells are substantially occupied by at least one analyte, which ones of the wells are minimally occupied, and which ones of the wells are co-occupied by multiple analytes.

17. A computer-implemented method of determining metadata about analytes on a tile of a flow cell, the method comprising:

accessing a set of images of the tile captured during a sequencing run and preliminary center coordinates of the analytes determined by a base caller;

for each image set, obtaining, from a base caller, a base call classifying, as one of four bases, origin subpixels that contain the preliminary center coordinates and a predetermined neighborhood of contiguous subpixels that are successively contiguous to respective ones of the origin subpixels, thereby producing a base call sequence for each of the origin subpixels and for each of the predetermined neighborhood of contiguous subpixels;

generating an analyte map that identifies the analytes as disjointed regions of contiguous subpixels that are successively contiguous to at least some of the respective ones of the origin subpixels and share a substantially matching base call sequence of the one of four bases with the at least some of the respective ones of the origin subpixels; and storing the analyte map in memory and determining the shapes and the sizes of the analytes based on the disjointed regions in the analyte map.

18. A computer-implemented method of generating training data for neural network-based template generation and base calling, the method comprising:

accessing a multitude of images of a flow cell captured over a plurality of cycles of a sequencing run, the flow cell having a plurality of tiles and, in the multitude of images, each of the tiles having a sequence of image sets generated over the plurality of cycles, and each image in the sequence of image sets depicting intensity emissions of analytes and their surrounding background on a particular one of the tiles at a particular one the cycles;

constructing a training set having a plurality of training examples, each training example corresponding to a particular one of the tiles and including image data from at least some image sets in the sequence of image sets of the particular one of the tiles; and generating at least one ground truth data representation for each of the training examples, the ground truth data representation identifying at least one property of analytes on the particular one of the tiles whose intensity emissions are depicted by the image data and being determined at least in part using the method of any of clauses 1-17.

19. The computer-implemented method of clause 18, wherein the at least one property of analytes is selected from the group consisting of: spatial distribution of analytes on the tile; analyte shape; analyte size; analyte boundary; and center of contiguous regions including a single analyte.

20. The computer-implemented method of any of clauses 18-19, wherein the image data includes images in each of the at least some image sets in the sequence of image sets of the particular one of the tiles.

21. The computer-implemented method of any of clauses 18-20, wherein the image data includes at least one image patch from each of the images.

22. The computer-implemented method of any of clauses 18-21, wherein the image data includes an upsampled representation of the image patch.

23. The computer-implemented method of any of clauses 18-22, wherein multiple training examples correspond to a same particular one of the tiles and respectively include as image data different image patches from each image in each of at least some image sets in a sequence of image sets of the same particular one of the tiles, and
wherein at least some of the different image patches overlap with each other.

24. The computer-implemented method of any of clauses 18-23, wherein the ground truth data representation identifies the analytes as disjoint regions of adjoining subpixels, the centers of the analytes as centers of mass subpixels within respective ones of the disjoint regions, and their surrounding background as subpixels that do not belong to any of the disjoint regions.

25. The computer-implemented method of any of clauses 18-24, further including:
storing, in memory, the training examples in the training set and associated ground truth data representations as the training data for the neural network-based template generation and base calling.

26. A computer-implemented method, including:
accessing sequencing images of analytes produced by a sequencer;
generating training data from the sequencing images; and
using the training data for training a neural network to generate metadata about the analytes.

27. A computer-implemented method, including:
accessing sequencing images of analytes produced by a sequencer;
generating training data from the sequencing images; and
using the training data for training a neural network to base call the analytes.

28. A computer-implemented method of determining image regions indicative of analytes on a tile of a flow cell, the method comprising:
accessing a series of image sets generated during a sequencing run, each image set in the series generated during a respective sequencing cycle of the sequencing run, each image in the series depicting the analytes and their surrounding background, and each image in the series having a plurality of subpixels;
obtaining, from a base caller, a base call classifying each of the subpixels, thereby producing a base call sequence for each of the subpixels across a plurality of sequencing cycles of the sequencing run; and
determining a plurality of disjointed regions of contiguous subpixels which share a substantially matching base call sequence.

Clauses Set 2

1. A computer-implemented method of generating ground truth training data to train a neural network-based template generator for cluster metadata determination task, the method comprising:
accessing a series of image sets generated during a sequencing run, each image set in the series generated during a respective sequencing cycle of the sequencing run, each image in the series depicting clusters and their surrounding background, each image in the series having pixels in a pixel domain, and each of the pixels is divided into a plurality of subpixels in a subpixel domain;
obtaining, from a base caller, a base call classifying each of the subpixels as one of four bases (A, C, T, and G), thereby producing a base call sequence for each of the subpixels across a plurality of sequencing cycles of the sequencing run;
generating a cluster map that identifies the clusters as disjointed regions of contiguous subpixels which share a substantially matching base call sequence;
determining cluster metadata based on the disjointed regions in the cluster map,
wherein the cluster metadata includes cluster centers, cluster shapes, cluster sizes, cluster background, and/or cluster boundaries; and
using the cluster metadata to generate ground truth training data for training a neural network-based template generator for cluster metadata determination task,
wherein the ground truth training data comprises a decay map, a ternary map, or a binary map,
wherein the neural network-based template generator is trained to produce the decay map, the ternary map, or the binary map as output based on the ground truth training data, and
wherein, upon execution of the cluster metadata determination task during inference, the cluster metadata is in turn determined from the decay map, the ternary map, or the binary map that are produced as the output by the trained neural network-based template generator.

2. The computer-implemented method of claim 1, further including:
using the cluster metadata derived from the decay map, the ternary map, or the binary map produced as the output by the neural network-based template generator for base calling by a neural network-based base caller, in order to increase throughput in high-throughput nucleic acid sequencing technologies.

3. The computer-implemented method of claim 1, further including:
generating the cluster map by identifying as background those subpixels that do not belong to any of the disjointed regions.

4. The computer-implemented method of claim 1, wherein the cluster map identifies cluster boundary portions between two contiguous subpixels whose base call sequences do not substantially match.

5. The computer-implemented method of claim 1, wherein the cluster map is generated based on:
identifying origin subpixels at preliminary center coordinates of the clusters determined by the base caller; and breadth-first searching for substantially matching base call sequences by beginning with the origin subpixels and continuing with successively contiguous non-origin subpixels.

6. The computer-implemented method of claim 1, further including:
determining hyperlocated center coordinates of the clusters by calculating centers of mass of the disjointed regions of the cluster map as an average of coordinates of respective contiguous subpixels forming the disjointed regions; and
storing the hyperlocated center coordinates of the clusters in the memory for use as the ground truth training data for training the neural network-based template generator.

7. The computer-implemented method of claim 6, further including:
identifying centers of mass subpixels in the disjointed regions of the cluster map at the hyperlocated center coordinates of the clusters;
upsampling the cluster map using interpolation and storing the upsampled cluster map in the memory for use as the ground truth training data for training the neural network-based template generator; and
in the upsampled cluster map, assigning a value to each contiguous subpixel in the disjointed regions based on a decay factor that is proportional to distance of a contiguous subpixel from a center of mass subpixel in a disjointed region to which the contiguous subpixel belongs.

8. The computer-implemented method of claim 7, further including:
generating the decay map from the upsampled cluster map that expresses the contiguous subpixels in the disjointed regions and the subpixels identified as the background based on their assigned values; and
storing the decay map in the memory for use as the ground truth training data for training the neural network-based template generator.

9. The computer-implemented method of claim 8, further including:
in the upsampled cluster map, categorizing, on the cluster-by-cluster basis, the contiguous subpixels in the disjointed regions as cluster interior subpixels belonging to a same cluster, the centers of mass subpixels as cluster center subpixels, subpixels containing the cluster boundary portions as boundary subpixels, and the subpixels identified as the background as background subpixels; and
storing the categorizations in the memory for use as the ground truth training data for training the neural network-based template generator.

10. The computer-implemented method of claim 9, further including:
storing, on the cluster-by-cluster basis, coordinates of the cluster interior subpixels, the cluster center subpixels, the boundary subpixels, and the background subpixels in the memory for use as the ground truth training data for training the neural network-based template generator;
downscaling the coordinates by a factor used to upsample the cluster map; and
storing, on the cluster-by-cluster basis, the downscaled coordinates in the memory for use as the ground truth training data for training the neural network-based template generator.

11. The computer-implemented method of claim 10, further including:
generating cluster maps for a plurality of tiles of the flow cell;
storing the cluster maps in memory and determining the cluster metadata of clusters in the tiles based on the cluster maps, including the cluster centers, the cluster shapes, the cluster sizes, the cluster background, and/or the cluster boundaries;
in the upsampled cluster maps of the clusters in the tiles, categorizing, on a cluster-by-cluster basis, subpixels as cluster interior subpixels belonging to a same cluster, cluster center subpixels, boundary subpixels, and background subpixels;
storing the categorizations in the memory for use as the ground truth training data for training the neural network-based template generator;
storing, on the cluster-by-cluster basis across the tiles, coordinates of the cluster interior subpixels, the cluster center subpixels, the boundary subpixels, and the background subpixels in the memory for use as the ground truth training data for training the neural network-based template generator;
downscaling the coordinates by the factor used to upsample the cluster map; and
storing, on the cluster-by-cluster basis across the tiles, the downscaled coordinates in the memory for use as the ground truth training data for training the neural network-based template generator.

12. The computer-implemented method of claim 11, wherein the base call sequences are substantially matching when a predetermined portion of base calls match on an ordinal position-wise basis.

13. The computer-implemented method of claim 1, wherein the cluster map is generated based upon a predetermined minimum number of subpixels for a disjointed region.

14. The computer-implemented method of claim 1, wherein the flow cell has at least one patterned surface with an array of wells that occupy the clusters, further including:
based on the determined shapes and sizes of the clusters, determining
which ones of the wells are substantially occupied by at least one cluster,
which ones of the wells are minimally occupied, and
which ones of the wells are co-occupied by multiple clusters.

15. A computer-implemented method of determining metadata about clusters on a tile of a flow cell, the method comprising:
accessing a set of images of the tile captured during a sequencing run and preliminary center coordinates of the clusters determined by a base caller;
for each image set, obtaining, from a base caller, a base call classifying, as one of four bases, origin subpixels that contain the preliminary center coordinates and
a predetermined neighborhood of contiguous subpixels that are successively contiguous to respective ones of the origin subpixels,
thereby producing a base call sequence for each of the origin subpixels and for each of the predetermined neighborhood of contiguous subpixels;
generating a cluster map that identifies the clusters as disjointed regions of contiguous subpixels that
are successively contiguous to at least some of the respective ones of the origin subpixels and
share a substantially matching base call sequence of the one of four bases with the at least some of the respective ones of the origin subpixels; and
storing the cluster map in memory and determining the shapes and the sizes of the clusters based on the disjointed regions in the cluster map.

16. A computer-implemented method of generating training data for neural network-based template generation and base calling, the method comprising:

accessing a multitude of images of a flow cell captured over a plurality of cycles of a sequencing run, the flow cell having a plurality of tiles and, in the multitude of images, each of the tiles having a sequence of image sets generated over the plurality of cycles, and each image in the sequence of image sets depicting intensity emissions of clusters and their surrounding background on a particular one of the tiles at a particular one the cycles;

constructing a training set having a plurality of training examples, each training example corresponding to a particular one of the tiles and including image data from at least some image sets in the sequence of image sets of the particular one of the tiles; and generating at least one ground truth data representation for each of the training examples, the ground truth data representation identifying at least one property of analytes on the particular one of the tiles whose intensity emissions are depicted by the image data.

17. The computer-implemented method of claim 16, wherein the at least one property of clusters is selected from the group consisting of: spatial distribution of clusters on the tile; cluster shape; cluster size; cluster boundary; and center of contiguous regions including a single cluster.

18. The computer-implemented method of claim 16, wherein the image data includes images in each of the at least some image sets in the sequence of image sets of the particular one of the tiles.

19. The computer-implemented method of claim 18, wherein the image data includes at least one image patch from each of the images.

20. The computer-implemented method of claim 19, wherein the image data includes an upsampled representation of the image patch.

21. The computer-implemented method of claim 16, wherein multiple training examples correspond to a same particular one of the tiles and respectively include as image data different image patches from each image in each of at least some image sets in a sequence of image sets of the same particular one of the tiles, and wherein at least some of the different image patches overlap with each other.

22. The computer-implemented method of claim 16, wherein the ground truth data representation identifies the clusters as disjoint regions of adjoining subpixels, the centers of the clusters as centers of mass subpixels within respective ones of the disjoint regions, and their surrounding background as subpixels that do not belong to any of the disjoint regions.

23. The computer-implemented method of claim 16, further including:

storing, in memory, the training examples in the training set and associated ground truth data representations as the training data for the neural network-based template generation and base calling.

24. A computer-implemented method, including:

accessing sequencing images of clusters produced by a sequencer;

generating training data from the sequencing images; and using the training data for training a neural network to generate metadata about the clusters.

25. A computer-implemented method, including:

accessing sequencing images of clusters produced by a sequencer;

generating training data from the sequencing images; and using the training data for training a neural network to base call the clusters.

26. A computer-implemented method of determining image regions indicative of analytes on a tile of a flow cell, the method comprising:

accessing a series of image sets generated during a sequencing run, each image set in the series generated during a respective sequencing cycle of the sequencing run, each image in the series depicting the analytes and their surrounding background, and each image in the series having a plurality of subpixels;

obtaining, from a base caller, a base call classifying each of the subpixels, thereby producing a base call sequence for each of the subpixels across a plurality of sequencing cycles of the sequencing run;

determining a plurality of disjointed regions of contiguous subpixels which share a substantially matching base call sequence; and generating a cluster map identifying the determined disjointed regions.

What is claimed is:

1. A computer-implemented method of generating ground truth training data to train a neural network-based template generator for cluster metadata determination task, the method comprising:

accessing a series of image sets generated during a sequencing run, each image set in the series generated during a respective sequencing cycle of the sequencing run, each image in the series depicting clusters and their surrounding background, each image in the series having pixels in a pixel domain, and each of the pixels is divided into a plurality of subpixels in a subpixel domain;

obtaining, from a base caller, a base call classifying each of the subpixels as one of four bases (A, C, T, and G), thereby producing a base call sequence for each of the sub pixels across a plurality of sequencing cycles of the sequencing run;

generating a cluster map that identifies the clusters as disjointed regions of contiguous subpixels which share a substantially matching base call sequence;

determining cluster metadata based on the disjointed regions in the cluster map,
  wherein the cluster metadata includes cluster centers, cluster shapes, cluster sizes, cluster background, and/or cluster boundaries; and using the cluster metadata to generate ground truth training data for training a neural network-based template generator for cluster metadata determination task,
  wherein the ground truth training data comprises a decay map, a ternary map, or a binary map,
  wherein the neural network-based template generator is trained to produce the decay map, the ternary map, or the binary map as output based on the ground truth training data, and
  wherein, upon execution of the cluster metadata determination task during inference, the cluster metadata is in turn determined from the decay map, the ternary map, or the binary map that are produced as the output by the trained neural network-based template generator.

2. The computer-implemented method of claim 1, further including:

using the cluster metadata derived from the decay map, the ternary map, or the binary map produced as the output by the neural network-based template generator for base calling by a neural network-based base caller, in order to increase through put in high-throughput nucleic acid sequencing technologies.

3. The computer-implemented method of claim 1, further including:
generating the cluster map by identifying as background those subpixels that do not belong to any of the disjointed regions.

4. The computer-implemented method of claim 1, wherein the cluster map identifies cluster boundary portions between two contiguous subpixels whose base call sequences do not substantially match.

5. The computer-implemented method of claim 1, wherein the cluster map is generated based on:
identifying origin subpixels at preliminary center coordinates of the clusters determined by the base caller; and
breadth-first searching for substantially matching base call sequences by beginning with the origin subpixels and continuing with successively contiguous non-origin subpixels.

6. The computer-implemented method of claim 1, further including:
determining hyperlocated center coordinates of the clusters by calculating centers of mass of the disjointed regions of the cluster map as an average of coordinates of respective contiguous subpixels forming the disjointed regions; and
storing the hyperlocated center coordinates of the clusters in the memory for use as the ground truth training data for training the neural network-based template generator.

7. The computer-implemented method of claim 6, further including:
identifying centers of mass subpixels in the disjointed regions of the cluster map at the hyperlocated center coordinates of the clusters;
upsampling the cluster map using interpolation and storing the upsampled cluster map in the memory for use as the ground truth training data for training the neural network-based template generator; and
in the upsampled cluster map, assigning a value to each contiguous subpixel in the disjointed regions based on a decay factor that is proportional to distance of a contiguous sub pixel from a center of mass subpixel in a disjointed region to which the contiguous subpixel belongs.

8. The computer-implemented method of claim 7, further including:
generating the decay map from the upsampled cluster map that expresses the contiguous subpixels in the disjointed regions and the sub pixels identified as the background based on their assigned values; and
storing the decay map in the memory for use as the ground truth training data for training the neural network-based template generator.

9. The computer-implemented method of claim 8, further including:
in the upsampled cluster map, categorizing, on the cluster-by-cluster basis, the contiguous subpixels in the disjointed regions as cluster interior subpixels belonging to a same cluster, the centers of mass subpixels as cluster center subpixels, subpixels containing the cluster boundary portions as boundary subpixels, and the subpixels identified as the background as background subpixels; and
storing the categorizations in the memory for use as the ground truth training data for training the neural network-based template generator.

10. The computer-implemented method of claim 9, further including:
storing, on the cluster-by-cluster basis, coordinates of the cluster interior subpixels, the cluster center subpixels, the boundary subpixels, and the background subpixels in the memory for use as the ground truth training data for training the neural network-based template generator;
downscaling the coordinates by a factor used to upsample the cluster map; and
storing, on the cluster-by-cluster basis, the downscaled coordinates in the memory for use as the ground truth training data for training the neural network-based template generator.

11. The computer-implemented method of claim 10, further including:
generating cluster maps for a plurality of tiles of the flow cell;
storing the cluster maps in memory and determining the cluster metadata of clusters in the tiles based on the cluster maps, including the cluster centers, the cluster shapes, the cluster sizes, the cluster background, and/or the cluster boundaries;
in the upsampled cluster maps of the clusters in the tiles, categorizing, on a cluster-by-cluster basis, sub pixels as cluster interior sub pixels belonging to a same cluster, cluster center subpixels, boundary subpixels, and background subpixels;
storing the categorizations in the memory for use as the ground truth training data for training the neural network-based template generator;
storing, on the cluster-by-cluster basis across the tiles, coordinates of the cluster interior subpixels, the cluster center subpixels, the boundary subpixels, and the background subpixels in the memory for use as the ground truth training data for training the neural network-based template generator;
downscaling the coordinates by the factor used to upsample the cluster map; and
storing, on the cluster-by-cluster basis across the tiles, the downscaled coordinates in the memory for use as the ground truth training data for training the neural network-based template generator.

12. The computer-implemented method of claim 11, wherein the base call sequences are substantially matching when a predetermined portion of base calls match on an ordinal position-wise basis.

13. The computer-implemented method of claim 1, wherein the cluster map is generated based upon a predetermined minimum number of subpixels for a disjointed region.

14. The computer-implemented method of claim 1, wherein the flow cell has at least one patterned surface with an array of wells that occupy the clusters, further including:
based on the determined shapes and sizes of the clusters, determining which ones of the wells are substantially occupied by at least one cluster,
which ones of the wells are minimally occupied, and
which ones of the wells are co-occupied by multiple clusters.

* * * * *